United States Patent
Vousden et al.

(10) Patent No.: US 11,072,652 B2
(45) Date of Patent: Jul. 27, 2021

(54) ILT7 BINDING MOLECULES AND METHODS OF USING THE SAME

(71) Applicant: Viela Bio, Inc., Gaithersburg, MD (US)

(72) Inventors: Katherine Ann Vousden, Cambridge (GB); Julie Ann Douthwaite, Cambridge (GB); Melissa Marie Damschroder, Gaithersburg, MD (US); Miguel Angel Sanjuan, Gaithersburg, MD (US)

(73) Assignee: Viela Bio, Inc., Gaithersburg, MD (US)

( * ) Notice: Subject to any disclaimer, the term of this patent is extended or adjusted under 35 U.S.C. 154(b) by 329 days.

(21) Appl. No.: 16/083,825

(22) PCT Filed: Mar. 9, 2017

(86) PCT No.: PCT/US2017/021616
§ 371 (c)(1),
(2) Date: Sep. 10, 2018

(87) PCT Pub. No.: WO2017/156298
PCT Pub. Date: Sep. 14, 2017

(65) Prior Publication Data
US 2020/0339673 A1    Oct. 29, 2020

Related U.S. Application Data

(60) Provisional application No. 62/306,125, filed on Mar. 10, 2016.

(51) Int. Cl.
| | | |
|---|---|---|
| *C07K 16/26* | (2006.01) | |
| *G01N 33/564* | (2006.01) | |
| *A61P 37/00* | (2006.01) | |
| *A61K 39/395* | (2006.01) | |
| *C12N 15/00* | (2006.01) | |
| *C12N 1/21* | (2006.01) | |
| *A61K 39/00* | (2006.01) | |

(52) U.S. Cl.
CPC ............. *C07K 16/26* (2013.01); *A61P 37/00* (2018.01); *G01N 33/564* (2013.01); *A61K 2039/505* (2013.01); *C07K 2317/21* (2013.01); *C07K 2317/24* (2013.01); *C07K 2317/33* (2013.01); *C07K 2317/41* (2013.01); *C07K 2317/52* (2013.01); *C07K 2317/565* (2013.01); *C07K 2317/622* (2013.01); *C07K 2317/732* (2013.01)

(58) Field of Classification Search
CPC ............. C07K 16/26; C07K 2317/21; C07K 2317/24; C07K 2317/33; C07K 2317/41; C07K 2317/52; C07K 2317/565; C07K 2317/622; C07K 2317/732; C07K 2317/30; C07K 2317/92; C07K 2319/00; C07K 16/2803; A61P 37/00; A61P 43/00; A61P 37/06; A61P 37/02; A61P 29/00; A61P 19/02; G01N 33/564; A61K 2039/505

See application file for complete search history.

(56) References Cited

U.S. PATENT DOCUMENTS

| | | |
|---|---|---|
| 2,096,948 A | 10/1937 | Gerrit |
| 4,683,195 A | 7/1987 | Mullis et al. |
| 4,741,900 A | 5/1988 | Alvarez et al. |
| 4,873,192 A | 10/1989 | Kunkel |
| 5,116,964 A | 5/1992 | Capon et al. |
| 5,122,464 A | 6/1992 | Wilson et al. |
| 5,223,409 A | 6/1993 | Ladner et al. |
| 5,225,538 A | 7/1993 | Capon et al. |
| 5,225,539 A | 7/1993 | Winter |
| 5,314,995 A | 5/1994 | Fell et al. |
| 5,403,484 A | 4/1995 | Ladner et al. |
| 5,427,908 A | 6/1995 | Dower et al. |
| 5,516,637 A | 5/1996 | Huang et al. |
| 5,571,698 A | 11/1996 | Ladner et al. |
| 5,580,717 A | 12/1996 | Dower et al. |
| 5,585,089 A | 12/1996 | Queen et al. |
| 5,658,727 A | 8/1997 | Barbas et al. |
| 5,693,761 A | 12/1997 | Queen et al. |
| 5,693,762 A | 12/1997 | Queen et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,821,047 A | 10/1998 | Garrard et al. |
| 5,859,205 A | 1/1999 | Adair et al. |
| 5,885,793 A | 3/1999 | Griffiths et al. |
| 5,892,019 A | 4/1999 | Schlom et al. |
| 5,939,598 A | 8/1999 | Kucherlapati et al. |

(Continued)

FOREIGN PATENT DOCUMENTS

| | | |
|---|---|---|
| AU | 2012244391 A1 | 11/2012 |
| EP | 0396387 A2 | 11/1990 |

(Continued)

OTHER PUBLICATIONS

Rudikoff et al., Proc. Natl. Acad. Sci. USA, 1982, 79(6):1979-1983. (Year: 1982).*
Paul, Fundamental Immunology, 3rd Edition, 1993, pp. 292-295. (Year: 1993).*
Colman, Research in Immunology, 1994, 145:33-36. (Year: 1994).*
Noel R. Rose, Prediction and Prevention of Autoimmune Disease in the 21st Century: A Review and Preview, American Journal of Epidemiology, vol. 183, Issue 5, Mar. 1, 2016, pp. 403-406 (Year: 2016).*
Viela Bio, A Phase 1 Study of MEDI7734 in Type I Interferon-Mediated Autoimmune Diseases, May 23, 2016, NCT02780674, https://clinicaltrials.gov/ct2/show/NCT02780674 (Year: 2016).*

(Continued)

*Primary Examiner* — Hong Sang
*Assistant Examiner* — Sung Min Yoon
(74) *Attorney, Agent, or Firm* — Cooley, LLP

(57) ABSTRACT

The present invention is directed to ILT7 binding molecules, e.g., anti-ILT7 antibodies, and methods for treating or preventing conditions and diseases associated with ILT7-expressing cells such as autoimmune diseases.

24 Claims, 27 Drawing Sheets

Figure 2:
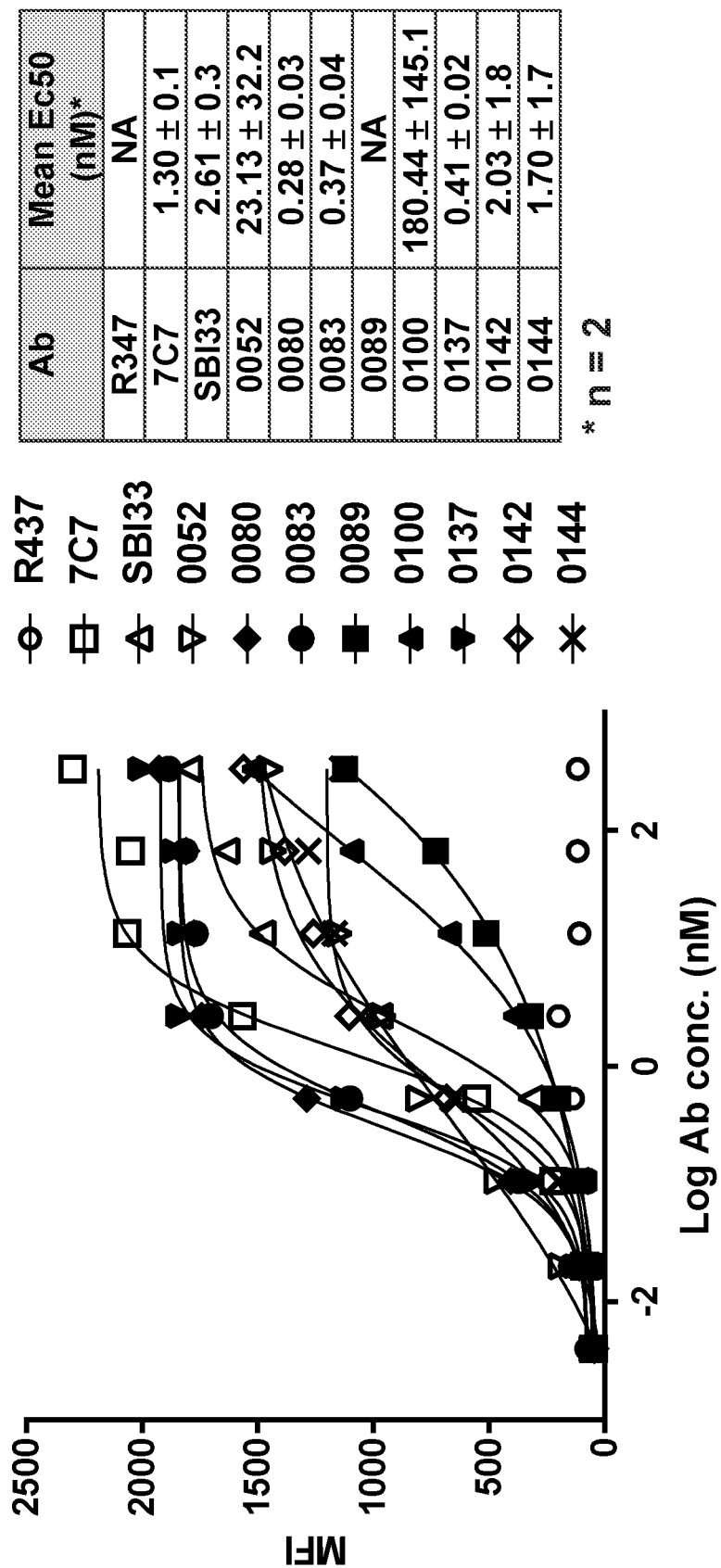

Specification includes a Sequence Listing.

(56) References Cited

U.S. PATENT DOCUMENTS

| | | | |
|---|---|---|---|
| 5,969,108 | A | 10/1999 | Mccafferty et al. |
| 6,172,197 | B1 | 1/2001 | Mccafferty et al. |
| 6,180,370 | B1 | 1/2001 | Queen et al. |
| 6,300,064 | B1 | 10/2001 | Knappik et al. |
| 6,521,404 | B1 | 2/2003 | Griffiths et al. |
| 6,544,731 | B1 | 4/2003 | Griffiths et al. |
| 6,555,313 | B1 | 4/2003 | Griffiths et al. |
| 6,582,915 | B1 | 6/2003 | Griffiths et al. |
| 6,593,081 | B1 | 7/2003 | Griffiths et al. |
| 6,653,068 | B2 | 11/2003 | Frisch et al. |
| 6,706,484 | B1 | 3/2004 | Knappik et al. |
| 6,737,056 | B1 | 5/2004 | Presta |
| 7,264,963 | B1 | 9/2007 | Knappik et al. |
| 8,605,807 | B1 | 12/2013 | Macrae |
| 8,901,036 | B2 | 12/2014 | Willms et al. |
| 8,912,624 | B2 | 12/2014 | Kakehata |
| 9,114,438 | B2 | 8/2015 | Hoinkis et al. |
| 9,208,495 | B2 | 12/2015 | Altberg et al. |
| 2002/0123057 | A1 | 9/2002 | Zauderer et al. |
| 2004/0132101 | A1 | 7/2004 | Lazar et al. |
| 2007/0025992 | A1 | 2/2007 | Takayama et al. |
| 2009/0280128 | A1 | 11/2009 | Kamogawa et al. |
| 2010/0070346 | A1 | 3/2010 | Davis |
| 2012/0316071 | A1 | 12/2012 | Smider et al. |
| 2016/0060326 | A1 | 3/2016 | Zhou et al. |

FOREIGN PATENT DOCUMENTS

| | | |
|---|---|---|
| RU | 2431638 C2 | 10/2011 |
| WO | 90/02809 A1 | 3/1990 |
| WO | 91/10737 A1 | 7/1991 |
| WO | 92/01047 A1 | 1/1992 |
| WO | 92/18619 A1 | 10/1992 |
| WO | 93/11236 A1 | 6/1993 |
| WO | 95/15982 A2 | 6/1995 |
| WO | 95/20401 A1 | 8/1995 |
| WO | 01/27160 A1 | 4/2001 |
| WO | WO-2006124269 A2 | 11/2006 |

OTHER PUBLICATIONS

International Search Report and Written Opinion dated Jun. 19, 2017 for International Application PCT/US2017/021616, (11 pages).

"Extended European Search Report issued in European Application No. 17764118.0", dated Oct. 28, 2019, 7 pages.

Cho et al. (Jan. 2008) "SAGE Library Screening Reveals ILT7 as a Specific Plasmacytoid Dendritic Cell Marker that Regulates Type I IFN Production", International Immunology, 20(1):155-164.

Acqua et al. (2005) "Antibody Humanization by Framework Shuffling", Methods, 36:43-60.

Ames et al. (1995) "Conversion of Murine Fabs Isolated from a Combinatorial Phage Display Library to Full Length Immunoglobulins", Journal of Immunological Methods, 184:177-186.

Aruffo et al. (Jun. 29, 1990) "CD44 is the Principal Cell Surface Receptor for Hyaluronate", Cell, 61(7):1303-1313.

Ashkenazi et al. (Dec. 1, 1991) "Protection against Endotoxic Shock by a Tumor Necrosis Factor Receptor Immunoadhesin", Proceedings of the National Academy of Sciences, 88(23):10535-10539.

Brinkman et al. (May 11, 1995) "Phage Display of Disulfide-Stabilized Fv Fragments", Journal of Immunological Methods, 182(1):41-50.

Burton et al. (1994) "Human Antibodies from Combinatorial Libraries", Advances in Immunology, 57:191-280.

Butler (1981) "The Amplified ELISA: Principles of and Applications for the Comparative Quantitation of Class and Subclass Antibodies and the Distribution of Antibodies and Antigens in Biochemical Separates", Methods in Enzymology, 73(Pt B):482-523.

Byrn et al. (Apr. 12, 1990) "Biological Properties of a CD4 Immunoadhesin", Nature, 344(6267):667-670.

Cao et al. (May 30, 2006) "Plasmacytoid Dendritic Cell-Specific Receptor ILT7-Fcεriγ Inhibits Toll-Like Receptor-Induced Interferon Production", Journal of Experimental Medicine, 203 (6): 1399-1405.

Capon et al. (Feb. 9, 1989) "Designing CD4 Immunoadhesins for AIDS Therapy", Nature, 337(6207):525-531.

Chapman (Jun. 17, 2002) "PEGylated Antibodies and Antibody Fragments for Improved Therapy: A Review", Advanced Drug Delivery Reviews, 54(4):531-545.

Chothia et al. (Aug. 20, 1987) "Canonical Structures for the Hypervariable Regions of Immunoglobulins", Journal of Molecular Biology, 196(4):901-917.

Cockett et al. (Jul. 1990) "High Level Expression of Tissue Inhibitor of Metalloproteinases in Chinese Hamster Ovary Cells Using Glutamine Synthetase Gene Amplification", Biotechnology, 8(7):662-667.

Colberre-Garapin et al. (Jul. 25, 1981) "A New Dominant Hybrid Selective Marker for Higher Eukaryotic Cells", Journal of Molecular Biology, 150(1):1-14.

Crouse et al. (Feb. 1983) "Expression and Amplification of Engineered Mouse Dihydrofolate Reductase Minigenes", Molecular and Cellular Biology, 3(2):257-266.

Dashivets et al. (2016) "Oxidation in the Complementarity-Determining Regions Differentially Influences the Properties of Therapeutic Antibodies", MAbs, 8(8):1525-1535.

Dayhoff et al. (1978) "A Model of Evolutionary Change in Proteins", Atlas of Protein Sequence and Structure, Chapter 22, 345-352.

Foecking et al. (1986) "Powerful and Versatile Enhancer-Promoter Unit for Mammalian Expression Vectors", Gene, 45(1):101-105.

Foote et al. (Mar. 20, 1992,) "Antibody Framework Residues Affecting the Conformation of the Hypervariable Loops", Journal of Molecular Biology, 224(2):487-499.

Gascoigne et al. (1987) "Secretion of a Chimeric T-Cell Receptor-Immunoglobulin Protein", Proceedings of the National Academy of Sciences of the United States of America, 84:2936-2940.

Gentz et al. (1989) "Bioassay for Trans-Activation Using Purified Human Immunodeficiency Virus Tat-Encoded Protein: Trans-Activation Requires Mrna Synthesis", Proceedings of the National Academy of Sciences of the United States of America, February, 86(3): 821-824.

Hamers-Casterman et al. (1993) "Naturally Occurring Antibodies Devoid of Light Chains", Nature, 363:446-448.

Heeke et al. (1989) "Expression of Human Asparagine Synthetase in *Escherichia coli*", Journal of Biological Chemistry, Apr. 5, 264(10):5503-5509.

Hoogenboom et al. (Sep. 20, 1992) "By-Passing immunisation: Human Antibodies from Synthetic Repertoires of Germline VH Gene Segments Rearranged in Vitro", Journal of Molecular Biology, 227(2):381-388.

Inouye et al. (May 10, 1985) "Up-Promoter Mutations in the Lpp Gene of *Escherichia coli*", Nucleic Acids Research, 13(9): 3101-3110.

Jalkanen et al. (1987) "Cell Surface Proteoglycan of Mouse Mammary Epithelial Cells is Shed by Cleavage of its Matrix-Binding Ectodomain from its Membrane-Associated Domain", Journal of Cell Biology, 105:3087-3096.

Jalkanen et al. (1985) "Heparan Sulfate Proteoglycans from Mouse Mammary Epithelial Cells: Localization on the Cell Surface with a Monoclonal Antibody", Journal of Cell Biology, 101(3):976-984.

Jones et al. (Jan. 1977) "Proteinase Mutants of *Saccharomyces cerevisiae*", Genetics, 85(1):23-33.

Jones et al. (May 29, 1986) "Replacing the Complementarity-Determining Regions in a Human Antibody with those from a Mouse", Nature, 321(6069):522-525.

Kettleborough et al. (Apr. 1994) "Isolation of Tumor Cell-Specific Single-Chain Fv from Immunized Mice Using Phage-Antibody Libraries and the Re-Construction of Whole Antibodies from these Antibody Fragments", European Journal of Immunology, 24(4):952-958.

Kingsman et al. (Oct. 1979) "Replication in *Saccharomyces cerevisiae* of Plasmid pBR313 Carrying DNA from the Yeast Trpl Region", Gene, 7(2):141-152.

Kunkel et al. (1987) "Rapid and Efficient Site-Specific Mutagenesis Without Phenotypic Selection", Methods in Enzymology, 154:367-382.

(56) References Cited

OTHER PUBLICATIONS

Kunkel (Jan. 1985) "Rapid and Efficient Site-Specific Mutagenesis Without Phenotypic Selection", PNAS, 82:488-492.
Lefranc et al. (Jan. 2003) "IMGT Unique Numbering for Immunoglobulin and T Cell Receptor Variable Domains and Ig Superfamily V-Like Domains", Developmental & Comparative Immunology, 27(1):55-77.
Leong et al. (Nov. 2001) "Adapting Pharmacokinetic Properties of a Humanized Anti-Interleukin-8 Antibody for Therapeutic Applications using Site-Specific Pegylation", Cytokine, 16(3):106-119.
Lesslauer et al. (Nov. 1991) "Recombinant Soluble Tumor Necrosis Factor Receptor Proteins Protect Mice from Lipopolysaccharide-Induced Lethality", European Journal of Immunology, 21(11):2883-2886.
Linsley et al. (Mar. 1, 1991) "Binding of the B Cell Activation Antigen B7 to CD28 Costimulates T Cell Proliferation and Interleukin 2 mRNA Accumulation", Journal of Experimental Medicine, 173(3):721-730.
Linsley et al. (Sep. 1, 1991) "CTLA-4 is a Second Receptor for the B Cell Activation Antigen B7", Journal of Experimental Medicine, 174(3):561-569.
Lloyd et al. (Oct. 29, 2008) "Modelling the Human Immune Response: Performance of a 1011 Human Antibody Repertoire Against a Broad Panel of Therapeutically Relevant Antigens", Protein Engineering, Design and Selection, 22(3):159-168.
Lonberg et al. (1995) "Human Antibodies from Transgenic Mice", International Reviews of Immunology, 13(1):65-93.
Lowy et al. (Dec. 1980) "Isolation of Transforming DNA: Cloning the Hamster APRT Gene", Cell, 22(3):817-823.
Mach et al. (Jan. 1992) "Statistical Determination of the Average Values of the Extinction Coefficients of Tryptophan and Tyrosine in Native Proteins", Analytical Biochemistry, 200(1):74-80.
Maggio, (1980) "Enzyme-Immunoassay", CRC Press, Inc., 30 pages.
Malleret et al. (2008) "Effect of Sivmac Infection on Plasmacytoid and CD1c + Myeloid Dendritic Cells in Cynomolgus Macaques", Immunology,124: 223-233.
Peppel et al., "A Tumor Necrosis Factor (TNF) Receptor-Igg Heavy Chain Chimeric Protein as a Bivalent Antagonist of TNF Activity", Journal of Experimental Medicine, Dec. 1, 1991, 174(6):1483-1489.
Persic et al., "An Integrated Vector System for the Eukaryotic Expression of Antibodies or their Fragments After Selection from Phage Display Libraries", Gene, Mar. 10, 1997, 187(1):9-18.
Presta Leonard G., "Antibody Engineering", Current Opinion in Structural Biology, 1992, 2(4):593-596.
Rattan et al., "Protein Synthesis, Posttranslational Modifications, and Aging", Annals of the New York Academy of Sciences, Nov. 1992, 663:48-62.
Riechmann et al., "Reshaping Human Antibodies for Therapy", Nature, Mar. 24, 1988, 332(6162):323-327.
Rothe et al., "The Human Combinatorial Antibody Library HuCAL GOLD Combines Diversification of All Six Cdrs According to the Natural Immune System with a Novel Display Method for Efficient Selection of High-Affinity Antibodies", Journal of Molecular Biology, Feb. 29, 2008, 376(4):1182-1200.
Marks et al. (Dec. 5, 1991) "By-Passing Immunization: Human Antibodies from V-Gene Libraries Displayed on Phage", Journal of Molecular Biology, 222(3):581-597.
McCafferty et al. (May-Jun. 1994) "Selection and Rapid Purification of Murine Antibody Fragments that Bind a Transition-State Analog by Phage Display", Biotechnology and Applied Biochemistry, May-Jun. 1994, 47(2-3):157-173.
Morgan et al. (1993) "Human Gene Therapy", Annual Review of Biochemistry, 62:191-217.
Mulligan et al. (Apr. 1981) "Selection for Animal Cells that Express the *Escherichia coli* Gene Coding for Xanthine-Guanine Phosphoribosyltransferase", Proceedings of the National Academy of Sciences of the United States of America, 78(4): 2072-2076.
Mulligan RC (May 14, 1993) "The Basic Science of Gene Therapy", Science, 260(5110):926-932.

Ohare et al. (Mar. 1981) "Transformation of Mouse Fibroblasts to Methotrexate Resistance by a Recombinant Plasmid Expressing a Prokaryotic Dihydrofolate Reductase", Proceedings of the National Academy of Sciences of the United States of America, 78(3): 1527-1531.
Ohtsuka et al. (May 25, 2004) "NFAM1, an Immunoreceptor Tyrosine-Based Activation Motif-Bearing Molecule that Regulates B Cell Development and Signaling", Proceedings of the National Academy of Sciences of the United States of America, 101(21):8126-8131.
Orlando et al. (Jan. 2003) "Modification of Proteins and Low Molecular Weight Substances with Hydroxyethyl Starch (HES)", Inaugural Dissertation: Justus-Liebig university of Giessen, 191 Pages.
Osbourn et al. (Sep. 1996) "Generation of a Panel of Related Human ScFv Antibodies With High Affinities for Human CEA", Immunotechnology, 2(3):181-196.
Roux et al. (1998) "Comparisons of the Ability of Human IgG3 Hinge Mutants, IgM, IgE, and IgA2, to Form Small Immune Complexes: A Role for Flexibility and Geometry", Journal of Immunology,161:4083-4090.
Ruther et al. (1983) "Easy Identification of Cdna Clones", The EMBO Journal, 2(10):1791-1794.
Safdari et al. (Aug. 2, 2013) "Antibody Humanization Methods—A Review and Update", Biotechnology and Genetic Engineering Reviews, 29(2):175-186.
Santerre et al. (Oct. 1984) "Expression of Prokaryotic Genes for Hygromycin B and G418 Resistance as Dominant-Selection Markers in Mouse L Cells", Gene, 30(1-3):147-156.
Seifter et al. (1990) "Analysis for Protein Modifications and Nonprotein Cofactors", Methods in Enzymology, 182:626-646.
Sheets et al. (May 26, 1998) "Efficient Construction of a Large Nonimmune Phage Antibody Library: The Production of High-Affinity Human Single-Chain Antibodies to Protein Antigens", Proceedings of the National Academy of Sciences, 95(11):6157-6162.
Smith et al. (1981) "Comparison of Biosequences", Advances in Applied Mathematics, 2(4):482-489.
Stamenkovic et al. (1991) "The B Lymphocyte Adhesion Molecule CD22 Interacts with Leukocyte Common Antigen CD45RO on T Cells and A2-6 Sialyltransferase, CD75, on B Cells", Cell, 66:1133-1144.
Stinchcomb et al. (Nov. 1, 1979) "Isolation and Characterisation of a Yeast Chromosomal Replicator", Nature, 282(5734):39-43.
Szybalska et al. (1962) "Genetics of Human Cell Lines, IV. DNA-Mediated Heritable Transformation of a Biochemical Trait", Proceedings of the National Academy of Sciences, 48(12):2026-2034.
Thorpe et al. (1982) "The Preparation and Cytotoxic Properties of Antibody-Toxin Conjugates", Immunological Reviews, 62:119-158.
Tolstoshev Paul (Apr. 1993) "Gene Therapy, Concepts, Current Trials and Future Directions", Annual Review of Pharmacology and Toxicology, 33:573-596.
Traunecker et al. (May 4, 1989) "Highly Efficient Neutralization of HIV with Recombinant CD4-Immunoglobulin Molecules", Nature, 339(6219):68-70.
Tschumper et al. (Jul. 1980) "Sequence of a Yeast DNA Fragment Containing a Chromosomal Replicator and the TRP1 Gene", Gene, 10(2):157-166.
UniProt (Oct. 3, 2003) "Leukocyte Immunoglobulin-like Receptor Subfamily A Member 4", UniProtKB-P59901, 11 pages.
Vaughan et al. (Mar. 1996) "Human Antibodies with Sub-Nanomolar Affinities Isolated from a Large Non-Immunized Phage Display Library", Nature Biotechnology, 14(3):309-314.
Verhoeyen et al. (Mar. 25, 1988) "Reshaping Human Antibodies: Grafting an Antilysozyme Activity", Science, 239(4847):1534-1536.
Watson et al. (1990) "A Homing Receptor-IgG Chimera as a Probe for Adhesive Ligands of Lymph Node High Endothelial Venules", Journal of Cell Biology,110(6):2221-2229.
Watson et al. (1991) "Neutrophil Influx into an Inflammatory Site Inhibited by a Soluble Homing Receptor-IgG Chimaera", Nature, 349:164-167.

(56) References Cited

OTHER PUBLICATIONS

Weir et al. (Aug. 1, 2002) "Formatting Antibody Fragments to Mediate Specific Therapeutic Functions", Biochemical Society Transactions, 30(4): 512-516.

Wigler et al. (May 1977) "Transfer of Purified Herpes Virus Thymidine Kinase Gene to Cultured Mouse Cells", Cell, 11(1):223-232.

Wilson et al. (Jul. 1984) "The Structure of an Antigenic Determinant in a Protein", Cell, 37(3):767-778.

Wu et al. (Aug. 1, 1970) "An Analysis of the Sequences of the Variable Regions of Bence Jones Proteins and Myeloma Light Chains and their Implications for Antibody Complementarity", Journal of Experimental Medicine, 132(2):211-250.

Wu et al. (Jan. 1991) "Delivery Systems for Gene Therapy", Biotherapy, 3:87-95.

Zettlmeissl et al. (Jun. 1990) "Expression and Characterization of Human CD4:immunoglobulin Fusion Proteins", DNA and Cell Biology, 9(5):347-353.

Zurfluh et al. (Jan. 1, 1980) "Auxin-Induced Changes in the Patterns of Protein Synthesis in Soybean Hypocotyl", Proceedings of the National Academy of Sciences of the United States of America, 77(1) 357-361.

Werth et al., Targeting Plasmacytoid Dendritic Cells Improves Cutaneous Lupus Erythematosus Skin Lesions and Reduces Type I Interferon Levels: Results of a Phase 1 Study of VIB7734 [abstract]. Arthritis Rheumatol. 2020; 72 (suppl 10). https://acrabstracts.org/abstract/targeting-plasmacytoid-dendritic-cells-improves-cutaneous-lupus-erythematosus-skin-lesions-and-reduces-type-i-interferon-levels-results-of-a-phase-1-study-of-vib7734/.

\* cited by examiner

Alignment VH:

| | | |
|---|---|---|
| #28-VH | QVQLQQSGAELVKPGASVKMSCKAFGYTFTTYPIEWMKQNHGKSLEWIGNFHPYNDDTKY | 60 |
| 10D10-VH | EVQLVESGGGVVQPGRSLRLSCAASGFTFSTYPIEWVRQAPGQGLEWIGNFHLYNDDTKY | 60 |
| 7C7-VH | EVQLVESGGGVVQPGRSLRLSCAASGFTFSITPIEWVRQAPGQGLEWIGNFHPYNDDTKY | 60 |
| #28-VH | NEKFKGKAKLTVEKSSSTVYLELSRLTSDDSAVYYCARGDDYGMDYWGQGTSVTVSS | 117 |
| 10D10-VH | NEKFKGRVTMTTDTSTSTVYMELSSLRSEDTAVYYCTRGDDYGMDYWGQGTLVTVSS | 117 |
| 7C7-VH | NEKFKGRVTMTTDTSTSTVYMELSSLRSEDTAVYYCTRGDDYGLDYWGQGTLVTVSS | 117 |

Figure 1A

Alignment VL:

| | | |
|---|---|---|
| #28-VL | DIVMTQSQKFMSTSVGDRVSITCKASQNVRTAVAWYQQKPGQSPKALIYLASNRHTGVPD | 60 |
| 10D10-VL | NIQMTQSPSSLSASVGDRVTITCKASQNVRTAVAWYQQKPGKAPKRLIYLASNRHTGVPS | 60 |
| 7C7-VL | NIQMTQSPSSLSASVGDRVTITCQASQNVRTAVAWYQQKPGKAPKRLIYLASNRHTGVPS | 60 |
| #28-VL | RFTGSGSGTDFTLTISNVQSEDLADYFCLQHWNYPFTFGSGTKLEIK | 107 |
| 10D10-VL | RFSGSGSGTDFTLTISSLQSEDFATYYCLQHWNYPFTFGPGTKLEIK | 107 |
| 7C7-VL | RFSGSGSGTDFTLTISSLQSEDFATYYCLQHWNYPFTFGPGTKLEIK | 107 |

Figure 1B

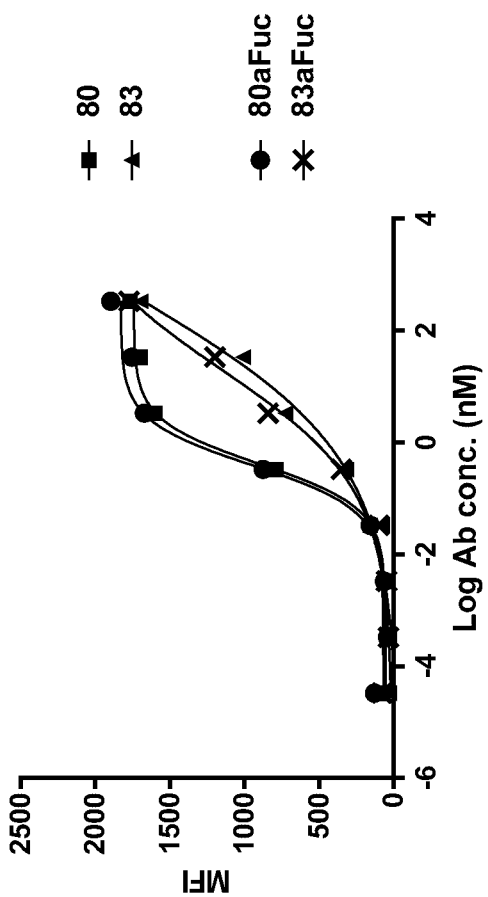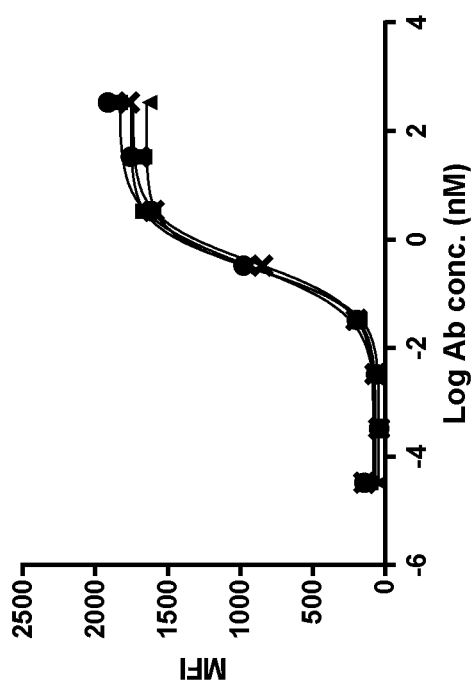
Figure 7

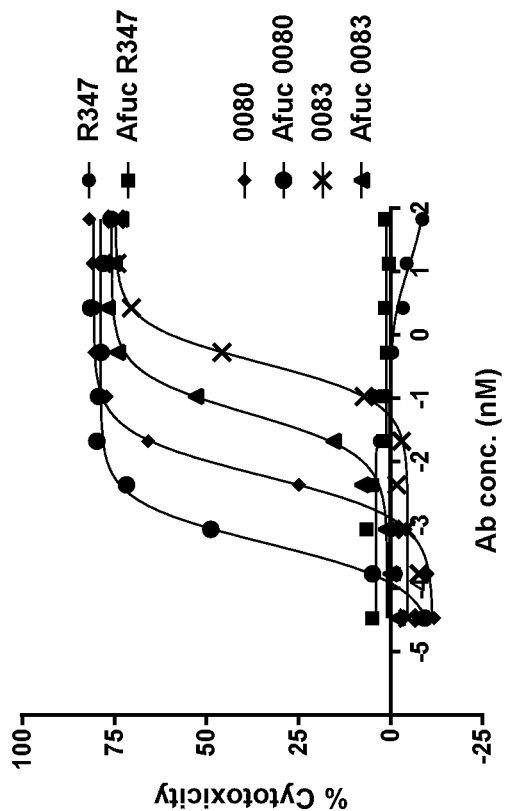
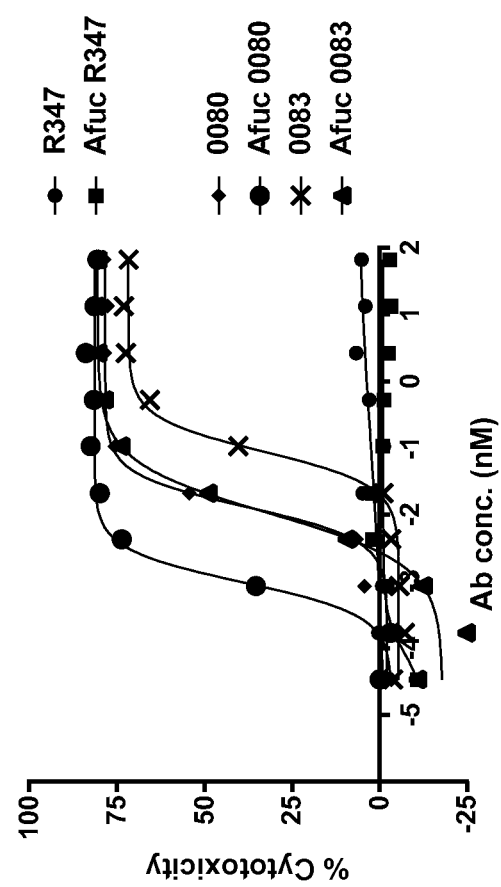
Figure 8

Heavy chain sequence alignment

|  | FW 1 | CDR 1 | FW 2 | CDR 2 |
|---|---|---|---|---|
| ILT70080    | QVQLVQSGAEVKAPGTSVKVSCKASGDSFRNYAVS----WVRQAPGQGLEWMGAMMP-------SFGTREHSQQFNG |
| ILT70080.1  | QVQLVQSGAEVKAPGTSVKVSCKASGDSFRNYAVS----WVRQAPGQGLEWMGAMMP-------SFGTREHSQQFQG |
| ILT70080.2  | QVQLVQSGAEVKPPGSSVKVSCKASGDSFRNYAVS----WVRQAPGQGLEWMGAMMP-------SFGTREHSQQFQG |
| ILT70080.3  | QVQLVQSGAEVKKPGSSVKVSCKASGDSFRNYAVS----WVRQAPGQGLEWMGAMMP-------SFGTREHSQQFQG |
| ILT70080.4  | QVQLVQSGAEVKAPGTSVKVSCKASGDSFRNYAVS----WVRQAPGQGLEWMGAMMP-------SFGTREHSQQFQG |
| ILT70080.5  | QVQLVQSGAEVKKPGSSVKVSCKASGDSFRNYAVS----WVRQAPGQGLEWMGAMMP-------SFGTREHSQQFQG |
| ILT70080.6  | QVQLVQSGAEVKKPGSSVKVSCKASGDSFRNYAVS----WVRQAPGQGLEWMGAMMP-------SFGTREHSQQFQG |
| ILT70080.7  | QVQLVQSGAEVKKPGSSVKVSCKASGDSFRNYAVS----WVRQAPGQGLEWMGAMMP-------SFGTREHSQQFQG |
| IGHV1-69*01 | QVQLVQSGAEVKKPGSSVKVSCKASGGTFSSYAIS----WVRQAPGQGLEWMGGIIP-------IFGTANYAQKFQG |

|  | FW 3 | CDR 3 | FW 4 |
|---|---|---|---|
| ILT70080    | RVTLSADESTSTAYLELSSL--RYDDTAVYYCAGSRDYNAYHFWTGPP-------DFWGRGTLVTVSS |
| ILT70080.1  | RVTLTADESTSTAYMELSSL--RSEDTAVYYCAGSRDYNAYHFWTGPP-------DFWGRGTLVTVSS |
| ILT70080.2  | RVTLSADESTSTAYMELSSL--RSEDTAVYYCAGSRDYNAYHFWTGPP-------DFWGRGTLVTVSS |
| ILT70080.3  | RVTLSADESTSTAYMELSSL--RSEDTAVYYCAGSRDYNAYHFWTGPP-------DFWGRGTLVTVSS |
| ILT70080.4  | RVTLSADESTSTAYMELSSL--RSEDTAVYYCAGSRDYNAYHFWTGPP-------DFWGRGTLVTVSS |
| ILT70080.5  | RVTLTADESTSTAYMELSSL--RSEDTAVYYCAGSRDYNAYHFWTGPP-------DFWGRGTLVTVSS |
| ILT70080.6  | RVTLTADESTSTAYMELSSL--RSEDTAVYYCAGSRDYNAYHFWTGPP-------DFWGRGTLVTVSS |
| ILT70080.7  | RVTLTADESTSTAYMELSSL--RSEDTAVYYCAGSRDYNAYHFWTGPP-------DFWGRGTLVTVSS |
| IGHV1-69*01 | RVTITADESTSTAYMELSSL--RSEDTAVYYCAR............................... |

Figure 9A

Light chain sequence alignment

FW 1, CDR 1, FW 2, CDR 2

```
                  FW 1                                    CDR 1                        FW 2                              CDR 2
             *    ■
ILT70080     SYELTQPPS-VSVAPGKTAKISCGGDS------VGSTSVHWYQQKPGQAPVMVMFYN------SDRPS
ILT70080.1   SYVLTQPPS-VSVAPGKTARITCGGDS------VGSTSVHWYQQKPGQAPVMVMFYN------SDRPS
ILT70080.2   SYVLTQPPS-VSVAPGKTARITCGGDS------VGSTSVHWYQQKPGQAPVMVMFYN------SDRPS
ILT70080.3   SYVLTQPPS-VSVAPGKTARITCGGDS------VGSTSVHWYQQKPGQAPVMVMFYN------SDRPS
ILT70080.4   SYELTQPPS-VSVAPGKTAKISCGGDS------VGSTSVHWYQQKPGQAPVMVMFYN------SDRPS
ILT70080.5   SYVLTQPPS-VSVAPGKTARITCGGDS------VGSTSVHWYQQKPGQAPVMVMFYN------SDRPS
ILT70080.6   SYVLTQPPS-VSVAPGKTARITCGGDS------VGSTSVHWYQQKPGQAPVIVIYN------SDRPS
ILT70080.7   SYVLTQPPS-VSVAPGKTARITCGGDS------VGSTSVHWYQQKPGQAPVIVMFYN------SDRPS
IGLV3-21*01  SYVLTQPPS-VSVAPGKTARITCGGNN------IGSKSVHWYQQKPGQAPVIVIYYD------SDRPS
```

FW 3, CDR 3, FW 4

```
                      FW 3                                 CDR 3                         FW 4
             *    ■■ ■
ILT70080     GIPERFSGSISG--NTATLTISRVEAGDEADYYCQVWDTSSDH-------PEFGGGTKLTV--L
ILT70080.1   GIPERFSGSISG--NTATLTISRVEAGDEADYYCQVWDTSSDH-------PEFGGGTKLTV--L
ILT70080.2   GIPERFSGSISG--NTATLTISRVEAGDEADYYCQVWDTSSDH-------PEFGGGTKLTV--L
ILT70080.3   GIPERFSGSISG--NTATLTISRVEAGDEADYYCQVWDTSSDH-------PEFGGGTKLTV--L
ILT70080.4   GIPERFSGSISG--NTATLTISRVEAGDEADYYCQVWDTSSDH-------PEFGGGTKLTV--L
ILT70080.5   GIPERFSGSNSG--NTATLTISRVEAGDEADYYCQVWDTSSDH-------PEFGGGTKLTV--L
ILT70080.6   GIPERFSGSNSG--NTATLTISRVEAGDEADYYCQVWDTSSDH-------PEFGGGTKLTV--L
ILT70080.7   GIPERFSGSNSG--NTATLTISRVEAGDEADYYCQVWDTSSDH-------PEFGGGTKLTV--L
IGLV3-21*01  GIPERFSGSNSG--NTATLTISRVEAGDEADYYCQVWD..................
```

Figure 9B

Heavy chain sequence alignment

FW 1 — CDR 1 — FW 2 — CDR 2

| | FW 1 | CDR 1 | FW 2 | CDR 2 |
|---|---|---|---|---|
| ILT70083 | EVQLLESGGGLVQPGGSLRLSCAASGFTFS | SYAMS | WVRQAPGKGLEWVSAISG | SGGSTYYADSVKG |
| ILT70083.1 | EVQLLESGGGLVQPGGSLRLSCAASGFTFS | SYAMS | WVRQAPGKGLEWVSAISG | SGGSTYYADSVKG |
| ILT70083.2 | EVQLLESGGGLVQPGGSLRLSCAASGFTFS | SYAMS | WVRQAPGKGLEWVSAISG | SGGSTYYADSVKG |
| ILT70083.3 | EVQLLESGGGLVQPGGSLRLSCAASGFTFS | SYAMS | WVRQAPGKGLEWVSAISG | SGGSTYYADSVKG |
| ILT70083.4 | EVQLLESGGGLVQPGGSLRLSCAASGFTFS | SYAMS | WVRQAPGKGLEWVSAISG | SGGSTYYADSVKG |
| ILT70083.5 | EVQLLESGGGLVQPGGSLRLSCAASGFTFS | SYAMS | WVRQAPGKGLEWVSAISG | SGGSTYYADSVKG |
| ILT70083.6 | EVQLLESGGGLVQPGGSLRLSCAASGFTFS | SYAMS | WVRQAPGKGLEWVSAISG | SGGSTYYADSVKG |
| ILT70083.7 | EVQLLESGGGLVQPGGSLRLSCAASGFTFS | SYAMS | WVRQAPGKGLEWVSAISG | SGGSTYYADSVKG |
| ILT70083.8 | EVQLLESGGGLVQPGGSLRLSCAASGFTFS | SYAMS | WVRQAPGKGLEWVSAISG | SGGSTYYADSVKG |
| ILT70083.9 | EVQLLESGGGLVQPGGSLRLSCAASGFTFS | SYAMS | WVRQAPGKGLEWVSAISG | SGGSTYYADSVKG |
| IGHV3-23*01 | EVQLLESGGGLVQPGGSLRLSCAASGFTFS | SYAMS | WVRQAPGKGLEWVSAISG | SGGSTYYADSVKG |

FW 3 — CDR 3 — FW 4

| | FW 3 | CDR 3 | FW 4 |
|---|---|---|---|
| ILT70083 | WFTISRDNSKNTLYLQMNSL--RAEDTAVYYCAR | RTYYYDSDGHSDVF | DIWGRGTLVTVSS |
| ILT70083.1 | WFTISRDNSKNTLYLQMNSL--RAEDTAVYYCAR | RTYYYDSDGHSDVF | DIWGRGTLVTVSS |
| ILT70083.2 | WFTISRDNSKNTLYLQMNSL--RAEDTAVYYCAR | RTYYYDSDGHSDVF | DIWGRGTLVTVSS |
| ILT70083.3 | WFTISRDNSKNTLYLQMNSL--RAEDTAVYYCAR | RTYYYDSDGHSDVF | DIWGRGTLVTVSS |
| ILT70083.4 | WFTISRDNSKNTLYLQMNSL--RAEDTAVYYCAR | RTYYYDSDGHSDVF | DIWGRGTLVTVSS |
| ILT70083.5 | RFTISRDNSKNTLYLQMNSL--RAEDTAVYYCAR | RTYYYDSDGHSDVF | DIWGRGTLVTVSS |
| ILT70083.6 | RFTISRDNSKNTLYLQMNSL--RAEDTAVYYCAR | RTYYYDSDGHSDVF | DIWGRGTLVTVSS |
| ILT70083.7 | RFTISRDNSKNTLYLQMNSL--RAEDTAVYYCAR | RTYYYDSDGHSDVF | DIWGRGTLVTVSS |
| ILT70083.8 | RFTISRDNSKNTLYLQMNSL--RAEDTAVYYCAR | RTYYYDSDGHSDVF | DIWGRGTLVTVSS |
| ILT70083.9 | RFTISRDNSKNTLYLQMNSL--RAEDTAVYYCAR | RTYYYDSDGHSDVF | DIWGRGTLVTVSS |
| IGHV3-23*01 | RFTISRDNSKNTLYLQMNSL--RAEDTAVYYCA | | |

Figure 10A

Light chain sequence alignment

|  | FW 1 | CDR 1 | FW 2 | CDR 2 |
|---|---|---|---|---|
| ILT70083   | QSVVTQPPS-VSAAPGQKVTISCSGSASN------ | IGSNFVSWYQQLPGRAPKLLIYDN----- | -DKRDL |
| ILT70083.1 | QSVVTQPPS-VSAAPGQKVTISCSGSASN------ | IGSNFVSWYQQLPGTAPKLLIYDN----- | -DKRDL |
| ILT70083.2 | QSVITQPPS-VSAAPGQKVTISCSGSASN------ | IGSNFVSWYQQLPGTAPKLLIYDN----- | -DKRDL |
| ILT70083.3 | QSVVTQPPS-VSAAPGQKVTISCSGSASN------ | IGSNFVSWYQQLPGTAPKLLIYDN----- | -DKRDL |
| ILT70083.4 | QSVVTQPPS-VSAAPGQKVTISCSGSASN------ | IGSNFVSWYQQLPGTAPKLLIYDN----- | -DKRDL |
| ILT70083.5 | QSVVTQPPS-VSAAPGQKVTISCSGSASN------ | IGSNFVSWYQQLPGRAPKLLIYDN----- | -DKRDL |
| ILT70083.6 | QSVVTQPPS-VSAAPGQKVTISCSGSASN------ | IGSNFVSWYQQLPGTAPKLLIYDN----- | -DKRDL |
| ILT70083.7 | QSVITQPPS-VSAAPGQKVTISCSGSASN------ | IGSNFVSWYQQLPGTAPKLLIYDN----- | -DKRDL |
| ILT70083.8 | QSVITQPPS-VSAAPGQKVTISCSGSASN------ | IGSNFVSWYQQLPGTAPKLLIYDN----- | -DKRDL |
| ILT70083.9 | QSVITQPPS-VSAAPGQKVTISCSGSASN------ | IGSNFVSWYQQLPGTAPKLLIYDN----- | -DKRDL |
| IGLV1-51*01 | QSVLTQPPS-VSAAPGQKVTISCSGSSSN------ | IGNNYVSWYQQLPGTAPKLLIYDN----- | -NKRPS |

|  | FW 3 | CDR 3 | FW 4 |
|---|---|---|---|
| ILT70083   | GIPDRFSASISS--TSAALAITGLQTEDEADYYCGTWDTSLTV------GVFGGGTKLTV----L |
| ILT70083.1 | GIPDRFSASISS--TSATLGITGLQTGDEADYYCGTWDTSLTV------GVFGGGTKLTV----L |
| ILT70083.2 | GIPDRFSASISS--TSATLGITGLQTGDEADYYCGTWDTSLTV------GVFGGGTKLTV----L |
| ILT70083.3 | GIPDRFSGSKSG--TSATLGITGLQTGDEADYYCGTWDTSLTV------GVFGGGTKLTV----L |
| ILT70083.4 | GIPDRFSGSKSG--TSATLGITGLQTGDEADYYCGTWDTSLTV------GVFGGGTKLTV----L |
| ILT70083.5 | GIPDRFSASISS--TSAALAITGLQTEDEADYYCGTWDTSLTV------GVFGGGTKLTV----L |
| ILT70083.6 | GIPDRFSASISS--TSATLGITGLQTGDEADYYCGTWDTSLTV------GVFGGGTKLTV----L |
| ILT70083.7 | GIPDRFSASISS--TSATLGITGLQTGDEADYYCGTWDTSLTV------GVFGGGTKLTV----L |
| ILT70083.8 | GIPDRFSGSKSG--TSATLGITGLQTGDEADYYCGTWDTSLTV------GVFGGGTKLTV----L |
| ILT70083.9 | GIPDRFSGSKSG--TSATLGITGLQTGDEADYYCGTWDTSLTV------GVFGGGTKLTV----L |
| IGLV1-51*01 | GIPDRFSGSKSG--TSATLGITGLQTGDEADYYCGTWD............................ |

Figure 10B

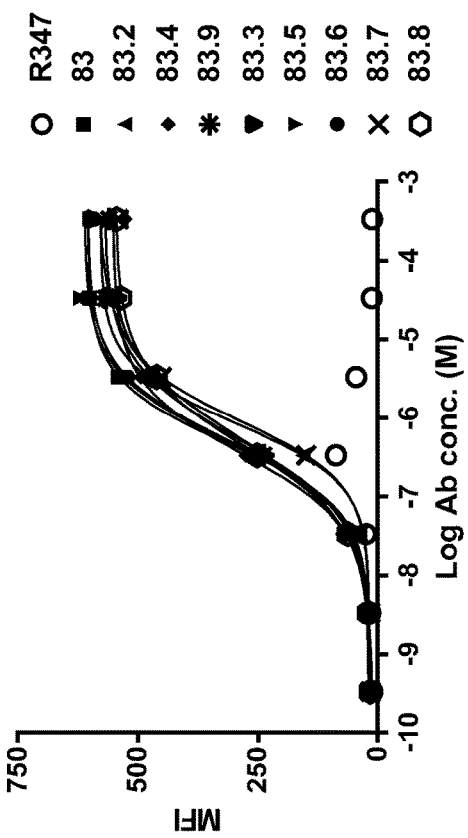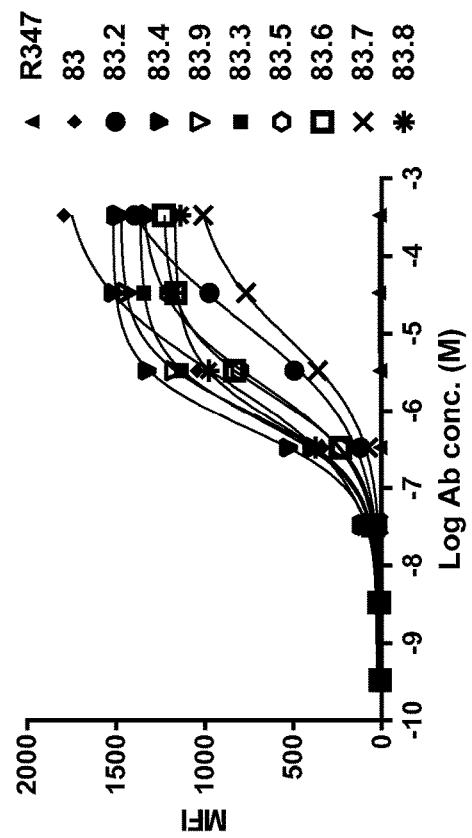
Figure 12

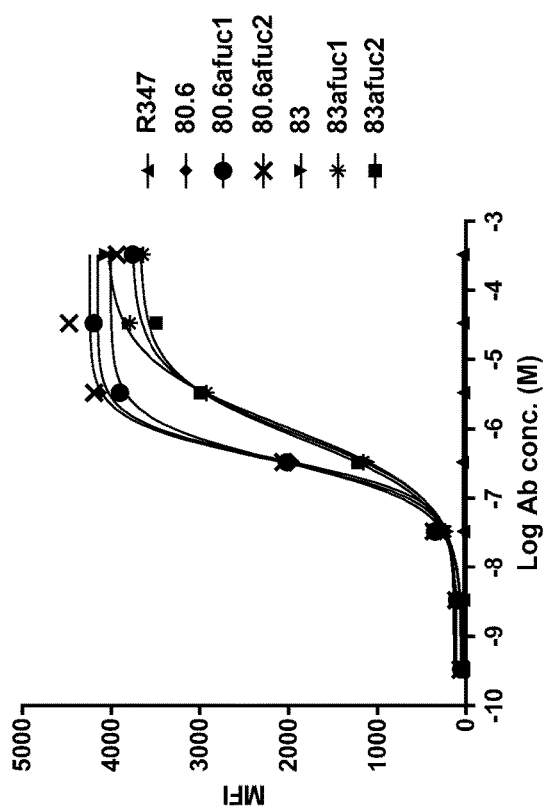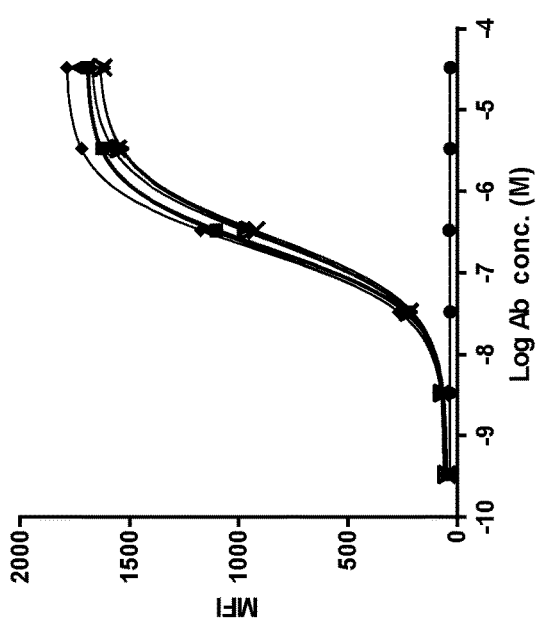
Figure 15

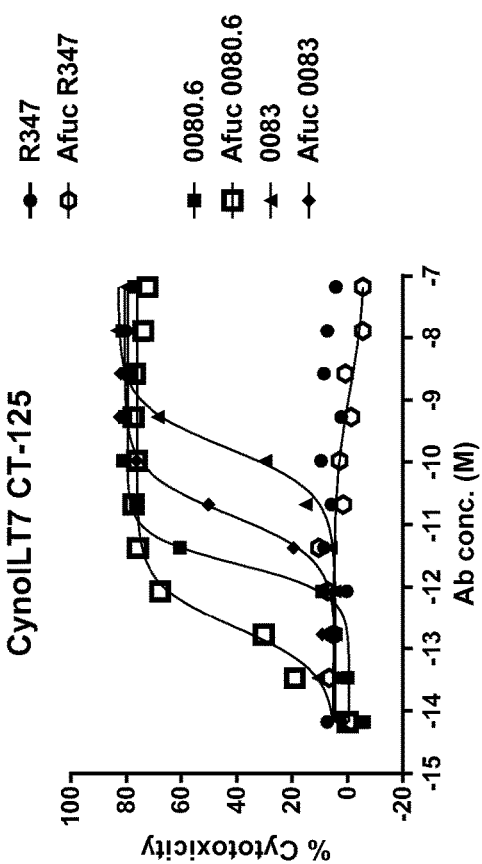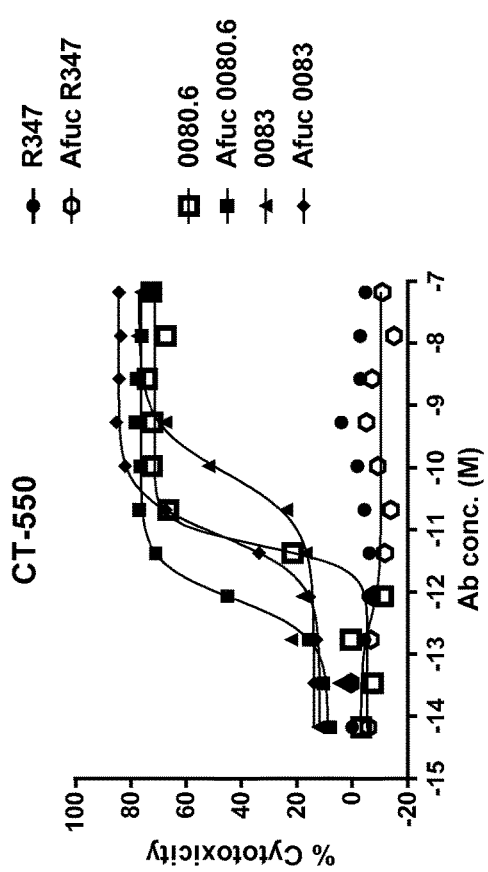
Figure 16

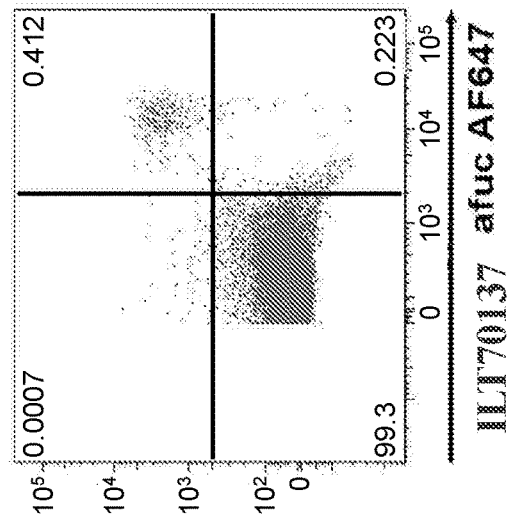
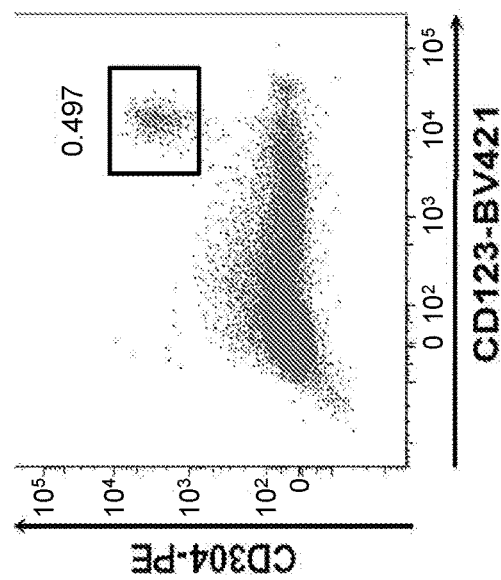
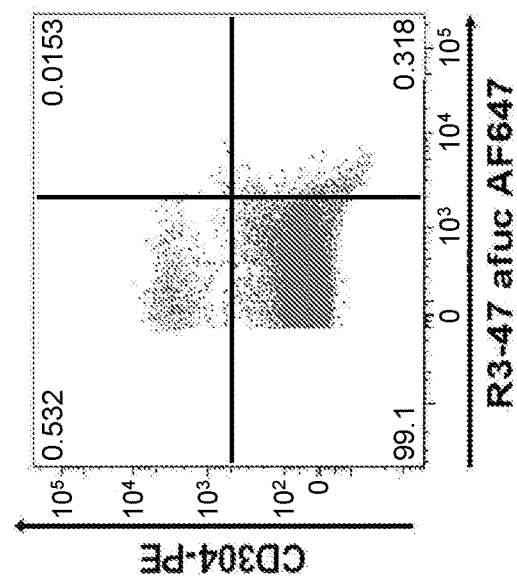
Figure 21

US 11,072,652 B2

ILT7 BINDING MOLECULES AND METHODS OF USING THE SAME

CROSS-REFERENCE TO RELATED APPLICATION

This application is a U.S. National Stage entry filed under 35 U.S.C. § 371 of International Application PCT/US17/21616 filed on Mar. 9, 2017, and claims the benefit of and priority to U.S. Provisional Application for Patent Ser. No. 62/306,125 filed Mar. 10, 2016, the entire contents of each of which are incorporated by reference herein in its entirety.

REFERENCE TO SEQUENCE LISTING SUBMITTED ELECTRONICALLY

The content of the electronically submitted sequence listing in an ASCII text file (Name 054493-506N01US_SL.txt; Size: 148,542 bytes; and Date of Creation: Dec. 17, 2020) is incorporated herein by reference in its entirety.

BACKGROUND OF THE INVENTION

Plasmacytoid dendritic cells (pDCs) are a distinct population of dendritic cells (DC) in the peripheral blood and secondary lymphoid organs that make up only about 0.1 to 0.5% of peripheral blood mononuclear cells (PBMC). However, these cells are particularly important regulators of the immune system because they are the main source of Type-I interferon (IFN). Type-I IFNs promote the function of NK cells, B cells, T cells, and myeloid dendritic cells. These IFNs are important in initial immune responses and have antiviral and antitumor activity. However, pDCs and Type-I IFNs are also thought to play a role in the development of autoimmune diseases such as systemic lupus erythematosus, chronic rheumatism, and psoriasis. Therefore, understanding how to regulate the molecular pathways involved in IFN release is useful for controlling immune responses and treating and preventing disease.

pDCs release IFN in response to nucleic acids that are sensed by Toll-like receptors (TLRs) TLR7 and TLR9 expressed on the surface of the pDCs. The TLR-induced response is regulated by receptors containing immunoreceptor tyrosine-based activation motifs (ITAMs). Immunoglobulin-Like transcript-7 (ILT7), also called LIRA4, LILRA4, or CD85g, is one such receptor.

ILT7 is a member of the immunoglobulin-like transcript (ILT) or leukocyte immunoglobulin-like receptor (LIR) gene family. ILT7 is selectively expressed on the surface of human plasmacytoid dendrite cells (pDCs) and is not on myeloid dendritic cells or other peripheral blood leukocytes. Cao et al., *J. Exp. Medicine* 6:1399-1405 (2006). ILT7 contains four immunoglobulin-like extracellular domains and a transmembrane domain. The extracellular portion is important for interacting with the ILT7 ligand, bone marrow stromal cell antigen 2 (BST2), and the transmembrane domain of ILT7 contains a positively charged residue that allows it to complex with FcεRIγ. It has been postulated that the BST2-ILT7 interaction negatively regulates the innate immune function of pDCs, potentially as a mechanism of negative feed back. In addition, in vitro antibody cross-linking of ILT7 has been shown to negatively regulate the production of IFN-alpha and TNF-alpha by pDCs. Therefore, antibodies and other ILT7 binding molecules that are useful for neutralizing ILT7 and regulating pDC activity and IFN release are needed, for example, for treating and preventing diseases such as autoimmune diseases.

FIELD OF THE INVENTION

The invention relates to ILT7 binding molecules, e.g., anti-ILT7 antibodies and antigen-binding fragments, variants, or derivatives thereof, methods of using the antibodies and fragments, and methods for treating or preventing autoimmune diseases and conditions associated with ILT7-expressing cells.

BRIEF SUMMARY OF THE INVENTION

Provided herein are ILT7 binding molecules, e.g., anti-ILT7 antibodies and antigen-binding fragments thereof.

In one instance, an isolated ILT7 binding protein is an ILT7 binding protein that can bind to the same ILT7 epitope as an antibody comprising a heavy chain variable region (VH) of SEQ ID NO:202 and a light chain variable region (VL) of SEQ ID NO:207.

In one instance, an isolated ILT7 binding protein is an ILT7 binding protein that competitively inhibits the binding to ILT7 of an antibody comprising a VH of SEQ ID NO:202 and a VL of SEQ ID NO:207

In one instance, an isolated ILT7 binding protein is an ILT7 binding protein comprising Complementarity-Determining Regions (CDRs) HCDR1, HDR2, HCDR3, LCDR1, LCDR2, and LCDR3 comprising the sequences of SEQ ID NOs: 203, 204, 205, 208, 209, and 210, respectively.

In one instance, the ILT7 binding protein comprises a VH at least 85%, 90%, 95%, 96%, 97%, 98% or 99% identical to SEQ ID NO:202 and/or a VL at least 85%, 90%, 95%, 96%, 97%, 98% or 99% identical to SEQ ID NO:207.

In one instance, the ILT7 binding protein comprises a VH comprising SEQ ID NO:202 and a VL comprising SEQ ID NO:207.

In one instance, an isolated ILT7 binding protein is an ILT7 binding protein comprising a VH comprising SEQ ID NO:202.

In one instance, an isolated ILT7 binding protein is an ILT7 binding protein comprising a VH comprising SEQ ID NO:207.

In one instance, an isolated ILT7 binding protein is an ILT7 binding protein that can bind to the same ILT7 epitope as an antibody comprising a VH and a VL selected from the group consisting of SEQ ID NO:12 and SEQ ID NO:17, respectively SEQ ID NO:22 and SEQ ID NO:27, respectively; SEQ ID NO:32 and SEQ ID NO:37, respectively; SEQ ID NO:42 and SEQ ID NO:47, respectively; SEQ ID NO:52 and SEQ ID NO:57, respectively; SEQ ID NO:62 and SEQ ID NO:67, respectively; SEQ ID NO:72 and SEQ ID NO:77, respectively; SEQ ID NO:82 and SEQ ID NO:87, respectively; SEQ ID NO:92 and SEQ ID NO:97, respectively; SEQ ID NO:102 and SEQ ID NO:107, respectively; SEQ ID NO:112 and SEQ ID NO:117, respectively; SEQ ID NO:122 and SEQ ID NO:127, respectively; SEQ ID NO:132 and SEQ ID NO:137, respectively; SEQ ID NO:142 and SEQ ID NO:147, respectively; SEQ ID NO:152 and SEQ ID NO:157, respectively; SEQ ID NO:162 and SEQ ID NO:167, respectively; SEQ ID NO:172 and SEQ ID NO:177, respectively; SEQ ID NO:182 and SEQ ID NO:187, respectively; SEQ ID NO:192 and SEQ ID NO:197, respectively; SEQ ID NO:212 and SEQ ID NO:217, respectively; SEQ ID NO:222 and SEQ ID NO:227, respectively; SEQ ID NO:232 and SEQ ID NO:237, respectively; and SEQ ID NO:242 and SEQ ID NO:247, respectively.

In one instance, an isolated ILT7 binding protein is an ILT7 binding protein that competitively inhibits the binding to ILT7 of an antibody comprising a VH and VL selected from the group consisting of SEQ ID NO:12 and SEQ ID NO:17, respectively SEQ ID NO:22 and SEQ ID NO:27, respectively; SEQ ID NO:32 and SEQ ID NO:37, respectively; SEQ ID NO:42 and SEQ ID NO:47, respectively; SEQ ID NO:52 and SEQ ID NO:57, respectively; SEQ ID NO:62 and SEQ ID NO:67, respectively; SEQ ID NO:72 and SEQ ID NO:77, respectively; SEQ ID NO:82 and SEQ ID NO:87, respectively; SEQ ID NO:92 and SEQ ID NO:97, respectively; SEQ ID NO:102 and SEQ ID NO:107, respectively; SEQ ID NO:112 and SEQ ID NO:117, respectively; SEQ ID NO:122 and SEQ ID NO:127, respectively; SEQ ID NO:132 and SEQ ID NO:137, respectively; SEQ ID NO:142 and SEQ ID NO:147, respectively; SEQ ID NO:152 and SEQ ID NO:157, respectively; SEQ ID NO:162 and SEQ ID NO:167, respectively; SEQ ID NO:172 and SEQ ID NO:177, respectively; SEQ ID NO:182 and SEQ ID NO:187, respectively; SEQ ID NO:192 and SEQ ID NO:197, respectively; SEQ ID NO:212 and SEQ ID NO:217, respectively; SEQ ID NO:222 and SEQ ID NO:227, respectively; SEQ ID NO:232 and SEQ ID NO:237, respectively; and SEQ ID NO:242 and SEQ ID NO:247, respectively.

In one instance, an isolated ILT7 binding protein is an ILT7 binding protein comprising CDRs: HCDR1, HDR2, HCDR3, LCDR1, LCDR2, and LCDR3 selected from the group consisting of SEQ ID NOs: 13, 14, 15, 18, 19, and 20, respectively; SEQ ID NOs: 23, 24, 25, 28, 29, and 30, respectively; SEQ ID NOs: 33, 34, 35, 38, 39, and 40, respectively; SEQ ID NOs: 103, 104, 105, 108, 109, and 110, respectively; SEQ ID NOs: 213, 214, 215, 218, 219, and 220, respectively; SEQ ID NOs: 223, 224, 225, 228, 229, and 230, respectively; SEQ ID NOs: 233, 234, 235, 238, 239, and 240, respectively; and SEQ ID NOs: 243, 244, 245, 248, 249, and 250; respectively.

In one instance, the ILT7 binding protein comprises a VH and a VL at least 85%, 90%, 95%, 96%, 97%, 98% or 99% identical to: SEQ ID NO:12 and SEQ ID NO:17, respectively; SEQ ID NO:22 and SEQ ID NO:27, respectively; SEQ ID NO:32 and SEQ ID NO:37, respectively; SEQ ID NO:42 and SEQ ID NO:47, respectively; SEQ ID NO:52 and SEQ ID NO:57, respectively; SEQ ID NO:62 and SEQ ID NO:67, respectively; SEQ ID NO:72 and SEQ ID NO:77, respectively; SEQ ID NO:82 and SEQ ID NO:87, respectively; SEQ ID NO:92 and SEQ ID NO:97, respectively; SEQ ID NO:102 and SEQ ID NO:107, respectively; SEQ ID NO:112 and SEQ ID NO:117, respectively; SEQ ID NO:122 and SEQ ID NO:127, respectively; SEQ ID NO:132 and SEQ ID NO:137, respectively; SEQ ID NO:142 and SEQ ID NO:147, respectively; SEQ ID NO:152 and SEQ ID NO:157, respectively; SEQ ID NO:162 and SEQ ID NO:167, respectively; SEQ ID NO:172 and SEQ ID NO:177, respectively; SEQ ID NO:182 and SEQ ID NO:187, respectively; SEQ ID NO:192 and SEQ ID NO:197, respectively; SEQ ID NO:212 and SEQ ID NO:217, respectively; SEQ ID NO:222 and SEQ ID NO:227, respectively; SEQ ID NO:232 and SEQ ID NO:237, respectively; or SEQ ID NO:242 and SEQ ID NO:247, respectively.

In one instance, the VH and VL comprise SEQ ID NO:12 and SEQ ID NO:17, respectively; SEQ ID NO:22 and SEQ ID NO:27, respectively; SEQ ID NO:32 and SEQ ID NO:37, respectively; SEQ ID NO:42 and SEQ ID NO:47, respectively; SEQ ID NO:52 and SEQ ID NO:57, respectively; SEQ ID NO:62 and SEQ ID NO:67, respectively; SEQ ID NO:72 and SEQ ID NO:77, respectively; SEQ ID NO:82 and SEQ ID NO:87, respectively; SEQ ID NO:92 and SEQ ID NO:97, respectively; SEQ ID NO:102 and SEQ ID NO:107, respectively; SEQ ID NO:112 and SEQ ID NO:117, respectively; SEQ ID NO:122 and SEQ ID NO:127, respectively; SEQ ID NO:132 and SEQ ID NO:137, respectively; SEQ ID NO:142 and SEQ ID NO:147, respectively; SEQ ID NO:152 and SEQ ID NO:157, respectively; SEQ ID NO:162 and SEQ ID NO:167, respectively; SEQ ID NO:172 and SEQ ID NO:177, respectively; SEQ ID NO:182 and SEQ ID NO:187, respectively; SEQ ID NO:192 and SEQ ID NO:197, respectively; SEQ ID NO:212 and SEQ ID NO:217, respectively; SEQ ID NO:222 and SEQ ID NO:227, respectively; SEQ ID NO:232 and SEQ ID NO:237, respectively; or SEQ ID NO:242 and SEQ ID NO:247, respectively.

In one instance, an isolated ILT7 binding protein comprises a VH comprising SEQ ID NO: 12, 22, 32, 42, 52, 62, 72, 82, 92, 102, 112, 122, 132, 142, 152, 162, 172, 182, 192, 212, 222, 232, or 242.

In one instance, an isolated ILT7 binding protein comprises a VL comprising SEQ ID NO: 17, 27, 37, 47, 57, 67, 77, 87, 97, 107, 117, 127, 137, 147, 157, 167, 177, 187, 197, 217, 227, 237, or 247.

In one instance, the ILT7 binding protein comprises an antibody or antigen-binding fragment thereof. In one instance, the antibody or antigen-binding fragment thereof is afucosylated.

In one instance, the ILT7 binding protein binds to the Ig1 region of ILT7. In one instance, the ILT7 binding protein binds to the Ig2 region of ILT7.

In one instance, the ILT7 binding protein binds to human and cynomolgus ILT7.

In one instance, the ILT7 binding protein suppresses interferon (IFN) alpha release from peripheral blood mononuclear cells (PBMCs). In one instance, the ILT7 binding protein has ADCC activity against plasmacytoid dendritic cells (pDCs) in PMBCs.

In one instance, the ILT7 binding protein comprises a murine, human, chimeric, humanized, or resurfaced antibody or antigen-binding fragment thereof.

In one instance, the ILT7 binding protein comprises an antibody, Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

In one instance, the ILT7 binding protein comprises a monoclonal antibody or an antigen binding fragment thereof.

In one instance, the ILT7 binding protein comprises a heavy chain immunoglobulin constant domain selected from the group consisting of: (a) an IgA constant domain; (b) an IgD constant domain; (c) an IgE constant domain; (d) an IgG1 constant domain; (e) an IgG2 constant domain; (f) an IgG3 constant domain; (g) an IgG4 constant domain; and (h) an IgM constant domain.

In one instance, the ILT7 binding protein comprises a light chain immunoglobulin constant domain selected from the group consisting of: (a) an Ig kappa constant domain; and (b) an Ig lambda constant domain.

In one instance, the ILT7 binding protein comprises a human IgG1 constant domain and a human lambda constant domain.

In one instance, provided herein is a host cell producing the ILT7 binding molecule.

In one instance, provided herein is an isolated polynucleotide comprising a nucleic acid encoding a VH, wherein the VH comprises an amino acid sequence at least 85%, 90%, 95% identical, or identical to the VH of SEQ ID NO: 202, 12, 22, 32, 42, 52, 62, 72, 82, 92, 102, 112, 122, 132, 142, 152, 162, 172, 182, 192, 212, 222, 232, or 242. In one instance, the polynucleotide comprises a sequence at least 85%, 90%, 95% identical, or identical to SEQ ID NO:201, 11, 21, 31, 41, 51, 61, 71, 81, 91, 101, 111, 121, 131, 141, 151, 161, 171, 181, 191, 211, 221, 231, or 241.

In one instance, provided herein is an isolated polynucleotide comprising a nucleic acid encoding a VL, wherein the VL comprises an amino acid sequence at least 85%, 90%, 95% identical, or identical to the VL of 207, 17, 27, 47, 57, 67, 77, 87, 97, 107, 117, 127, 137, 147, 157, 167, 177, 187, 197, 217, 227, 237, or 247. In one instance, the polynucleotide comprises a sequence at least 85%, 90%, 95% identical, or identical to SEQ ID NO: 206, 16, 26, 36, 46, 56, 66, 76, 86, 96, 106, 116, 126, 136, 146, 156, 166, 176, 186, 196, 216, 226, 236, or 246.

In one instance, the nucleic acid is operably linked to a control sequence. In one instance, an antibody or antigen-binding fragment thereof comprising the VH or the VL encoded by the nucleic acid can specifically bind to ILT7.

In one instance, a polynucleotide encodes an ILT7 binding molecule provided herein.

In one instance, provided herein is a vector comprising the polynucleotide.

In one instance, provided herein is a polypeptide encoded by the polynucleotide.

In one instance, provided herein is a host cell transformed with a polynucleotide provided herein (e.g., a polynucleotide comprising a nucleic acid encoding a VH and a polynucleotide comprising a nucleic acid encoding a VL).

In one instance, provided herein is a host cell comprising a polynucleotide provided herein (e.g., a polynucleotide comprising a nucleic acid encoding a VH and a polynucleotide comprising a nucleic acid encoding a VL), a vector provided herein, or a polypeptide provided herein. In one instance, the host cell is a mammalian host cell. In one instance, the host cell is a NS0 murine myeloma cell, a PER.C6® human cell, or a Chinese hamster ovary (CHO) cells. In one instance, the host cell lacks the enzyme α-1, 6-fucosyltransferase.

In one instance, provided herein is a method of producing an anti-ILT7 binding molecule, comprising culturing a host cell provided herein and recovering said binding molecule. In one instance, provided herein is an anti-ILT7 binding molecule, produced by the method.

In one instance, provided herein is a method for detecting ILT7 expression in a sample comprising (a) contacting the sample with an ILT7 binding molecule provided herein and (b) detecting binding of the binding molecule in the sample.

In one instance, provided herein is a method for detecting plasmacytoid dendritic cells comprising (a) contacting a sample containing cells with an ILT7 binding molecule provided herein and (b) detecting binding of the binding molecule in the sample.

In one instance, provided herein is a pharmaceutical composition comprising (a) an ILT7 binding molecule provided herein, a polynucleotide provided herein, a vector provided herein, a polypeptide provided herein, or a host cell provided herein and (b) a carrier.

In one instance, provided herein is a method for decreasing IFN-alpha release from a plasmacytoid dendritic cell, comprising contacting a plasmacytoid dendritic cell with an ILT7 binding molecule provided herein, a polynucleotide provided herein, a vector provided herein, a polypeptide provided herein, a host cell provided herein, or a pharmaceutical composition provided herein.

In one instance, provided herein is a method for treating a human subject with an autoimmune disease comprising administering to the subject an effective amount of an ILT7 binding molecule provided herein, a polynucleotide provided herein, a vector provided herein, a polypeptide provided herein, a host cell provided herein, or a pharmaceutical composition provided herein.

In one instance, provided herein is a method for preventing an autoimmune disease in a human subject comprising administering to the subject an effective amount of an ILT7 binding molecule provided herein, a polynucleotide provided herein, a vector provided herein, a polypeptide provided herein, a host cell provided herein, or a pharmaceutical composition provided herein. In one instance, the autoimmune disease is systemic lupus erythematosus. In one instance, the autoimmune disease is chronic rheumatism.

BRIEF DESCRIPTION OF THE DRAWINGS/FIGURES

FIGS. 1A and 1B: show the variable heavy chain (1A) and variable light chain (1B) sequence alignments of the SBI28 (#28), 10D10, and 7C7 antibodies. Shading indicates CDR sequences. Open boxes represent mutations introduced in 10D10 to generate 7C7. FIG. 1A discloses SEQ ID NOS 2, 293, and 12 and FIG. 1B discloses SEQ ID NOS 7, 294, and 17, respectively, in order of appearance.

FIG. 2: shows the binding of ILT7 antibodies and negative control antibody (R437) to CT-550 cells expressing human ILT7 as determined by flow cytometry. SBI33 refers to the anti-ILT7 antibody ILT7#33 as provided in U.S. Published Application No. 2009/0280128.

Figure 3:
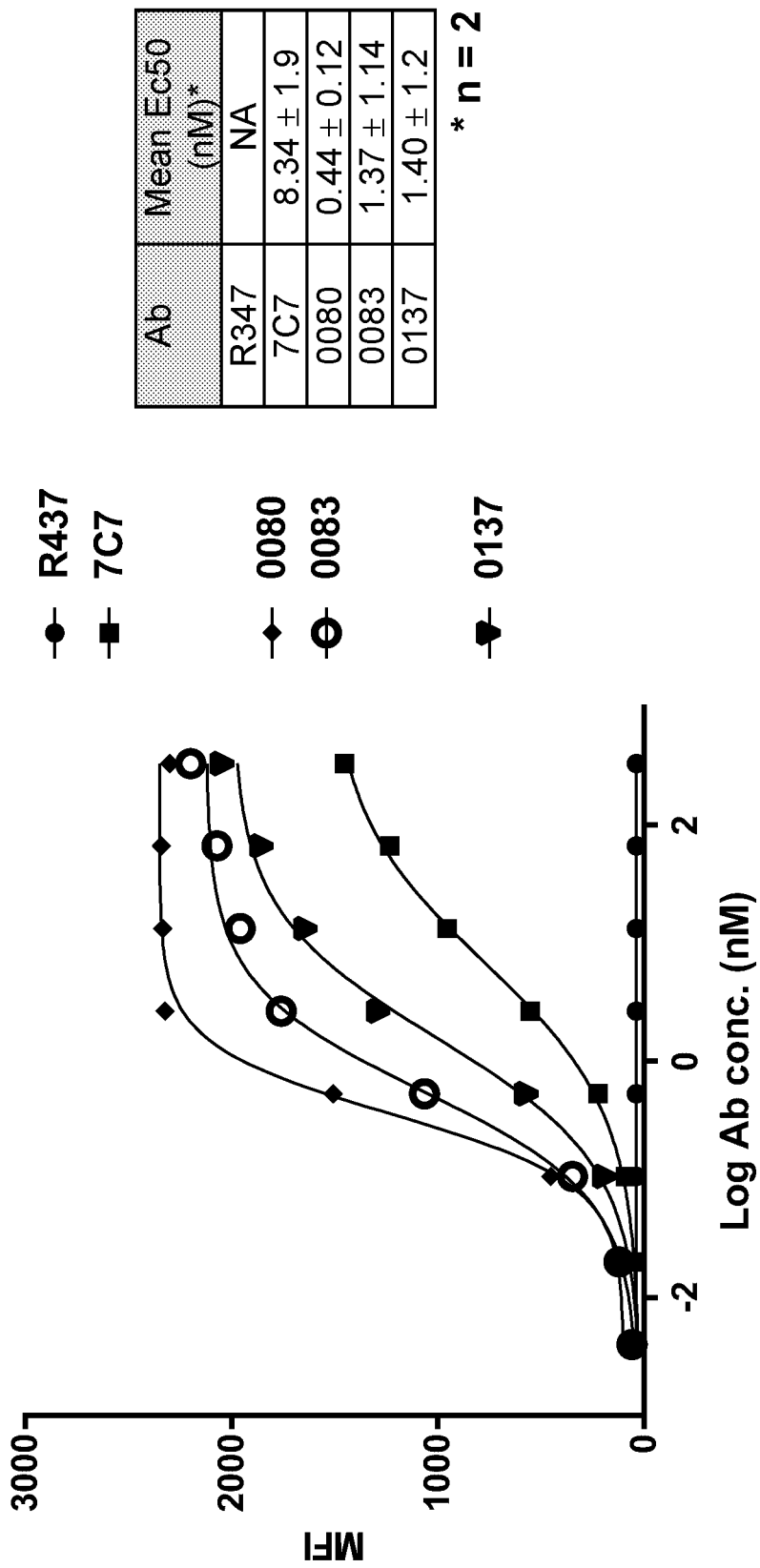

FIG. 3: shows the binding of ILT7 antibodies and negative control antibody (R437) to CT-125 cells expressing cynomolgus ILT7 as determined by flow cytometry.

Figure 4:
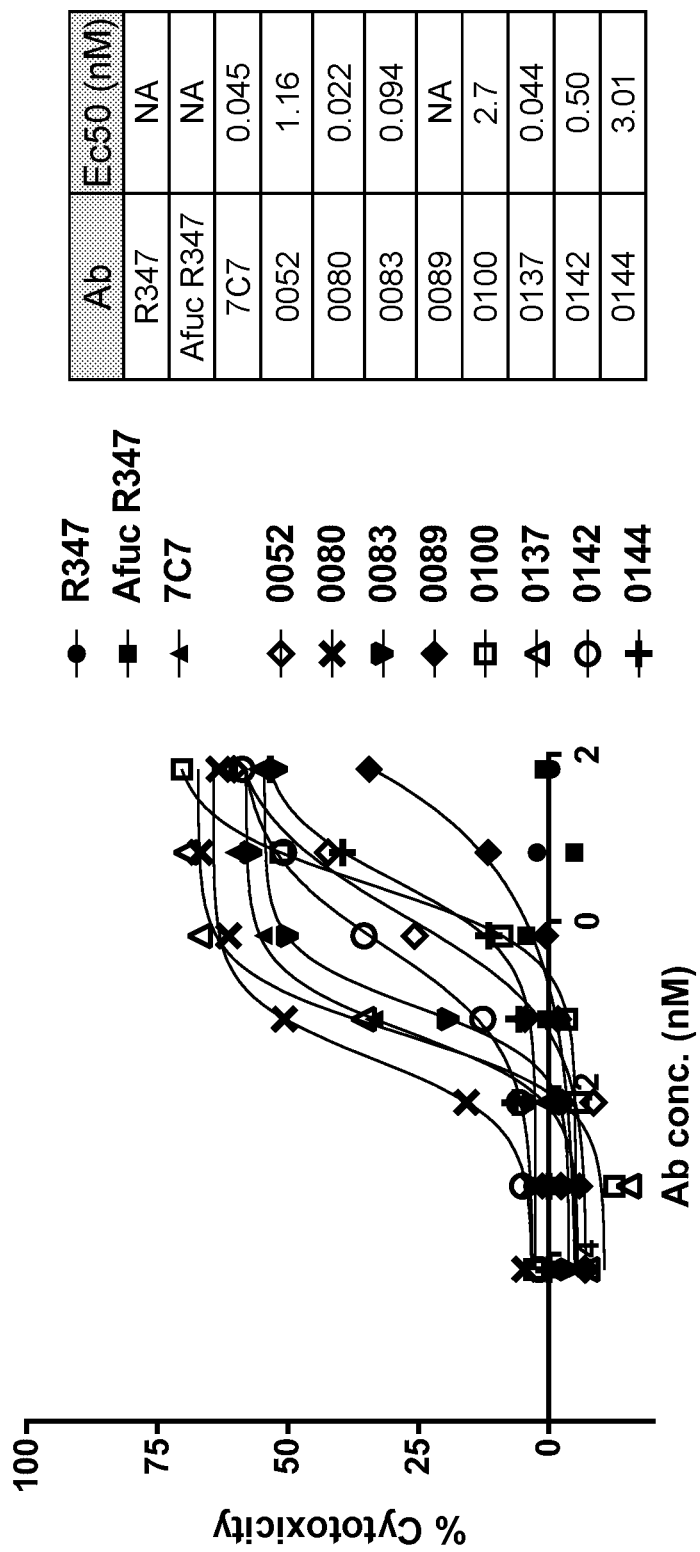

FIG. 4: shows the ADCC potency of ILT7 antibodies and negative control antibody (R437) against human ILT7-expressing cells.

Figure 5:
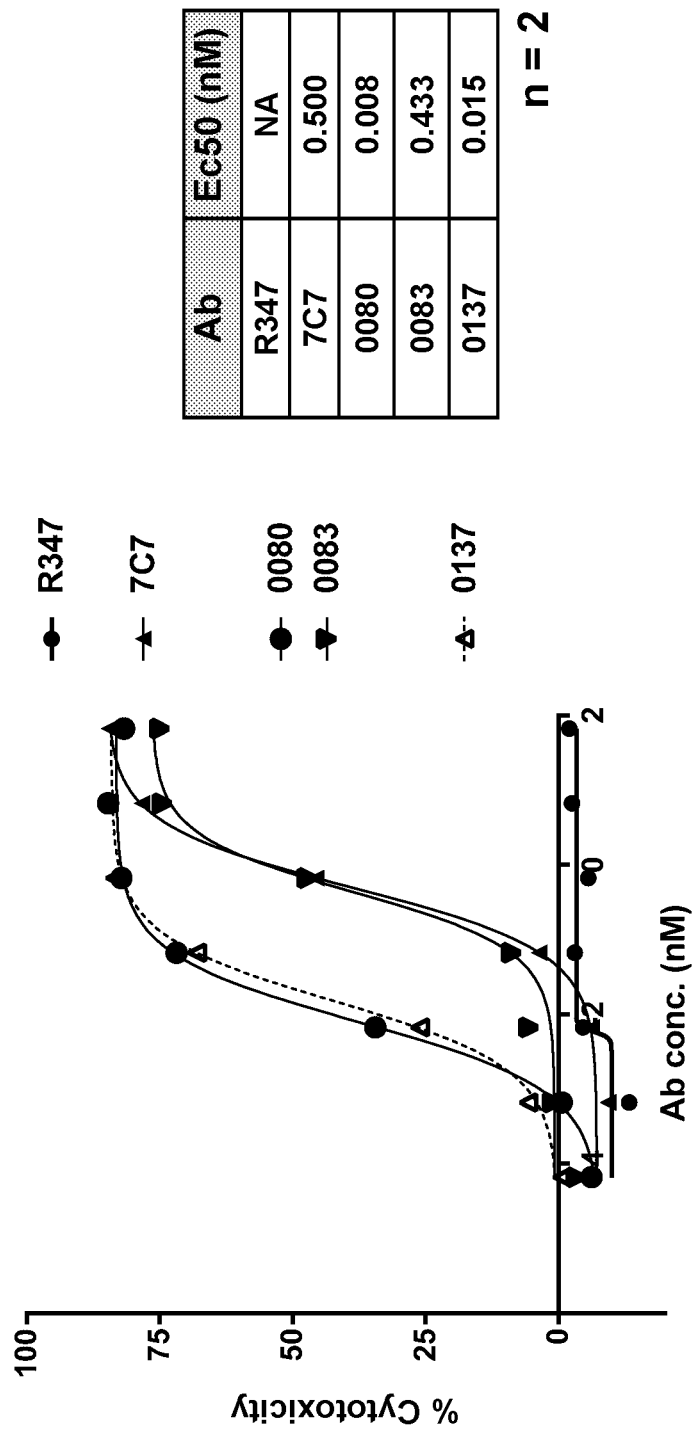

FIG. 5: shows the ADCC potency of ILT7 antibodies and negative control antibody (R437) against cynomolgus ILT7-expressing cells.

Figure 6A:
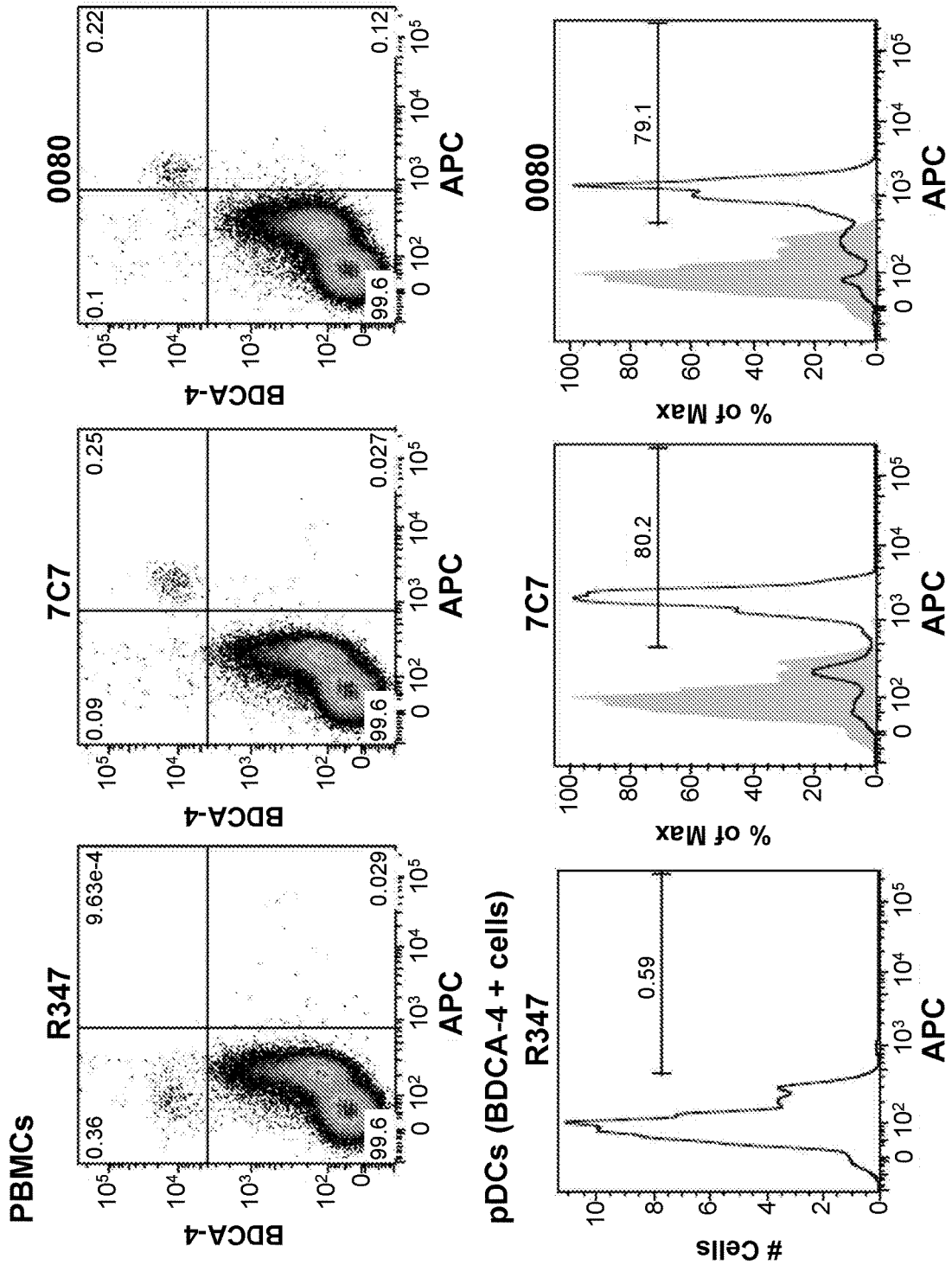
Figure 6B:
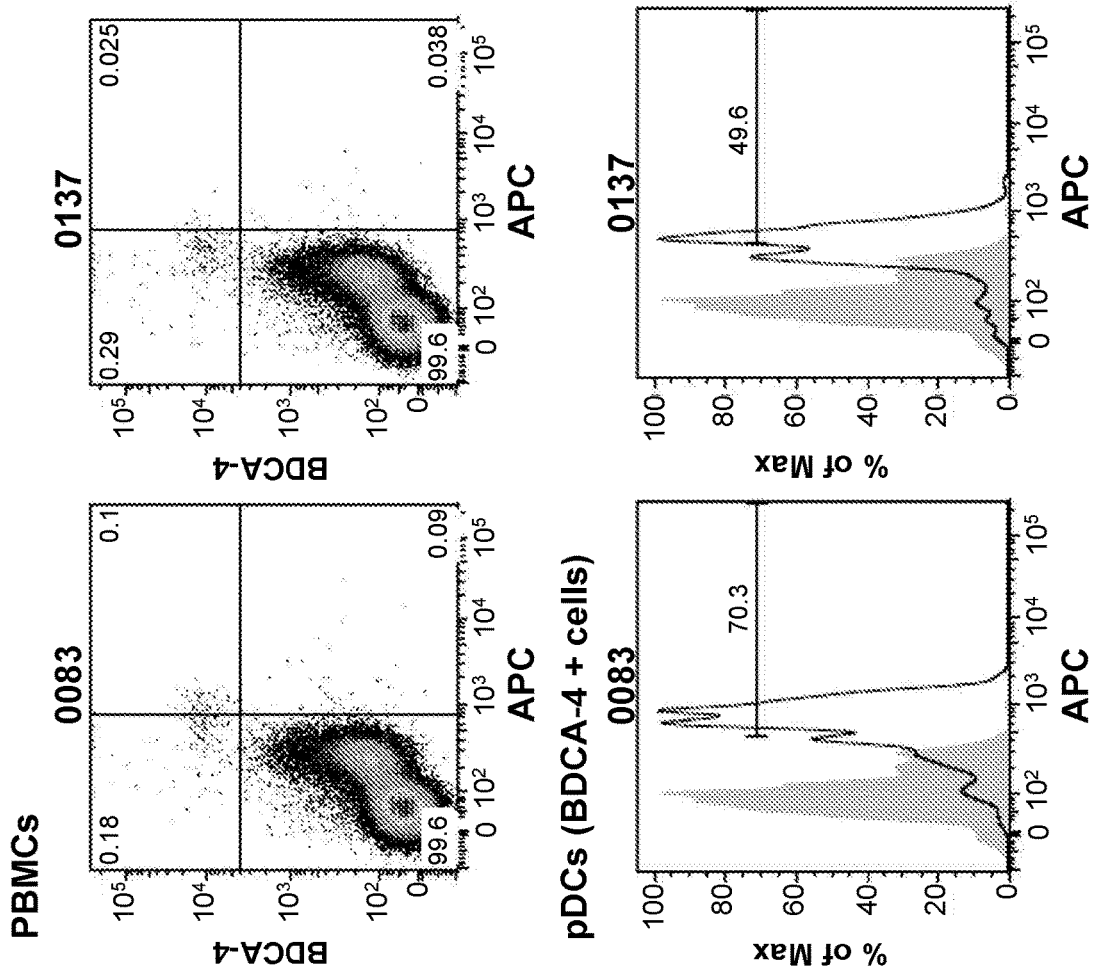

FIGS. 6A and 6B: show the binding of ILT7 antibodies and negative control antibody (R437) to plasmacytoid dendritic cells (pDCs) in peripheral blood mononuclear cells (PBMCs).

FIG. 7: shows the binding of afucosylated ILT7 antibodies and their parent antibodies to CT-550 cells expressing human (left panel) and cynomolgus (right panel) ILT7 as determined by flow cytometry.

FIG. 8: shows the ADCC potency of afucosylated ILT7 antibodies and their parent antibodies against human (left panel) and cynomolgus (right panel) ILT7-expressing cells.

FIGS. 9A and 9B: show the variable heavy chain (9A) and variable light chain (9B) sequence alignments of seven ILT70080 variants. The closest germline sequences (IGHV1-69*1 and IGLV3-21*01) are also shown in the alignments. FIG. 9A discloses SEQ ID NOS 22, 32, 42, 52, 62, 72, 82, 92, and 295 and FIG. 9B discloses SEQ ID NOS 27, 37, 47, 57, 67, 77, 87, 97, and 296, respectively, in order of appearance.

FIGS. 10A and 10B: show the variable heavy chain (10A) and variable light chain (10B) sequence alignments of nine ILT70083 variants. The closest germline sequences (IGHV3-23*01 and IGLV1-51*01) are also shown in the alignments. FIG. 10A discloses SEQ ID NOS 102, 112, 122, 132, 142, 152, 162, 172, 182, 192, and 297 and FIG. 10B discloses SEQ ID NOS 107, 117, 127, 137, 147, 157, 167, 177, 187, 197, and 298, respectively, in order of appearance.

Figure 11:
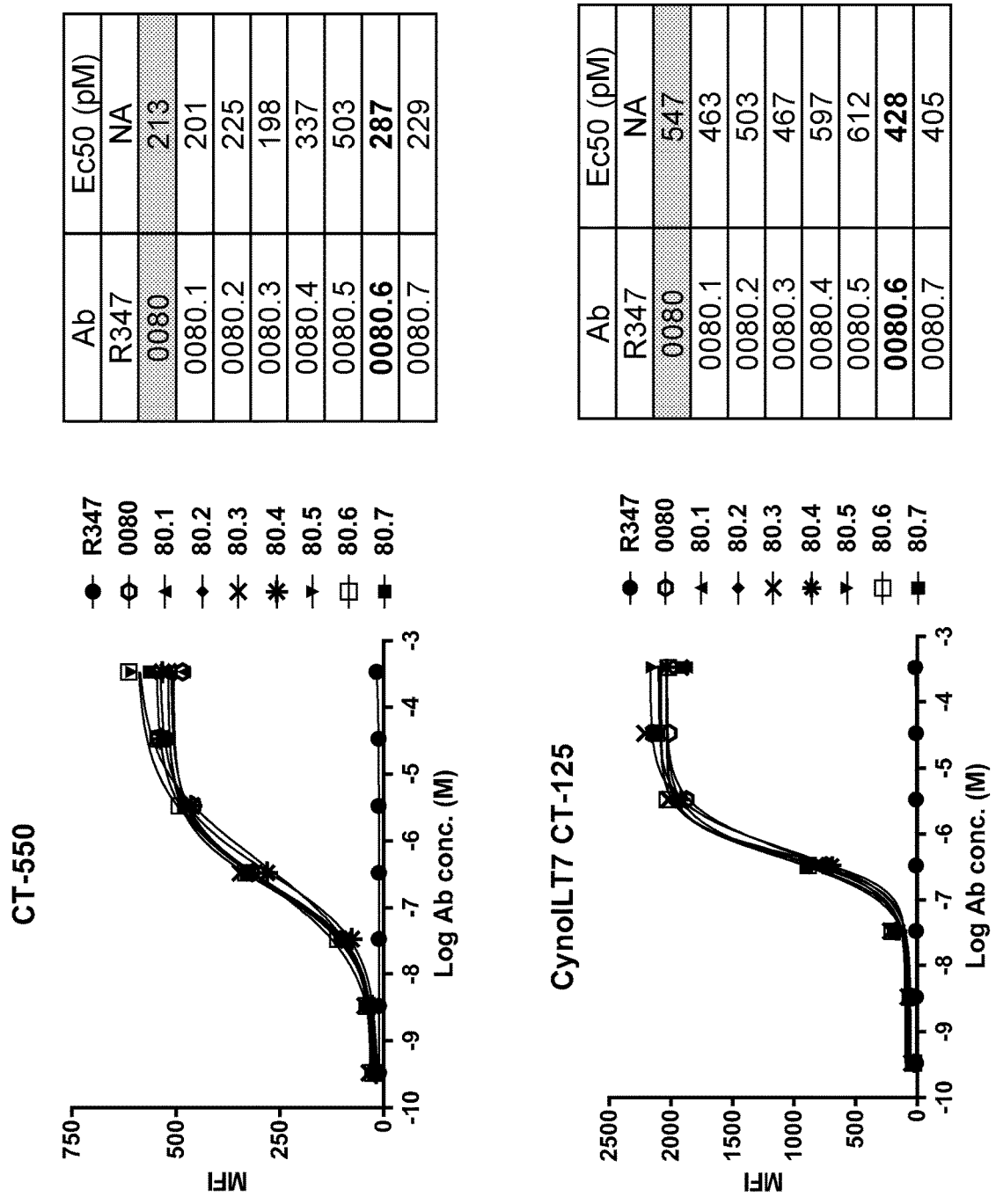

FIG. 11: shows the binding of ILT70080 variants to cells expressing human ILT7 (CT-550; top panel) and cells expressing cynomolgus ILT7 (CT-125; bottom panel).

FIG. 12: shows the binding of ILT70083 variants to cells expressing human ILT7 (top panel) or cynomolgus ILT7 (bottom panel).

Figure 13:
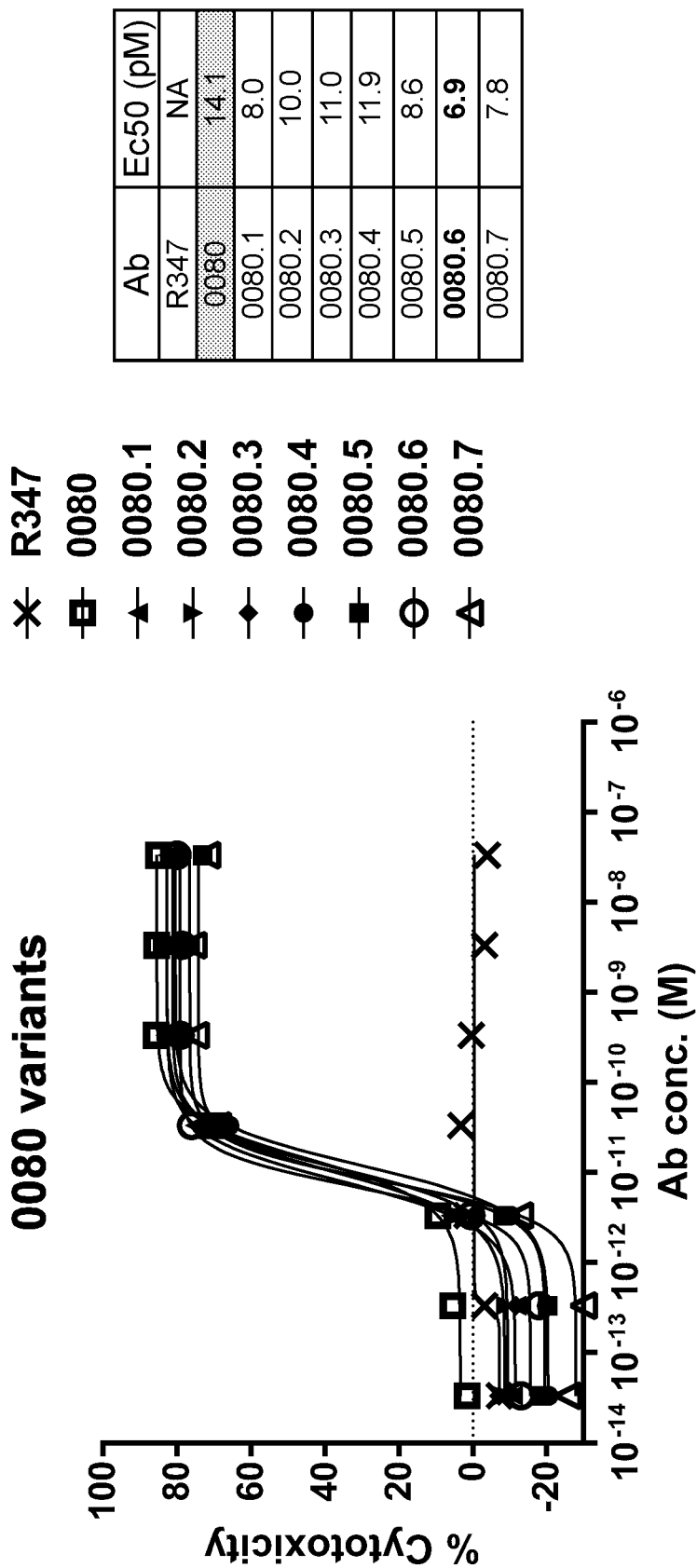

FIG. 13: shows the ADCC potency of ILT70080 variant antibodies against human ILT7-expressing cells.

Figure 14:
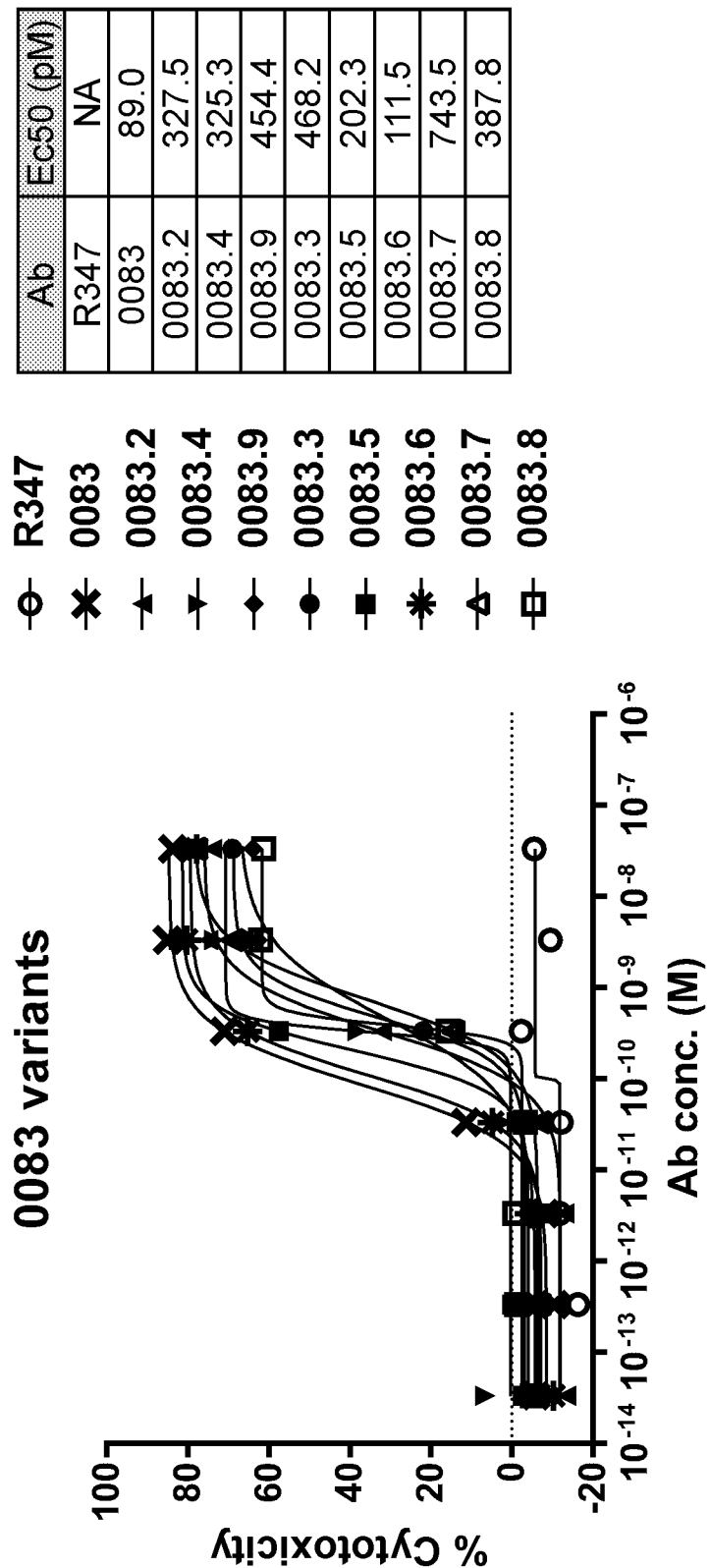

FIG. 14: shows the ADCC potency of ILT70083 variant antibodies against human ILT7-expressing cells.

FIG. 15: shows the binding of afucosylated ILT70080.6 and ILT70083 antibodies to human (left panel) and cynomolgus (right panel) ILT7-expressing cells.

FIG. 16: shows the ADCC activity of afucosylated ILT70080.6 and ILT70083 antibodies on human (left panel) and cynomolgus (right panel) ILT7-expressing cells.

Figure 17:
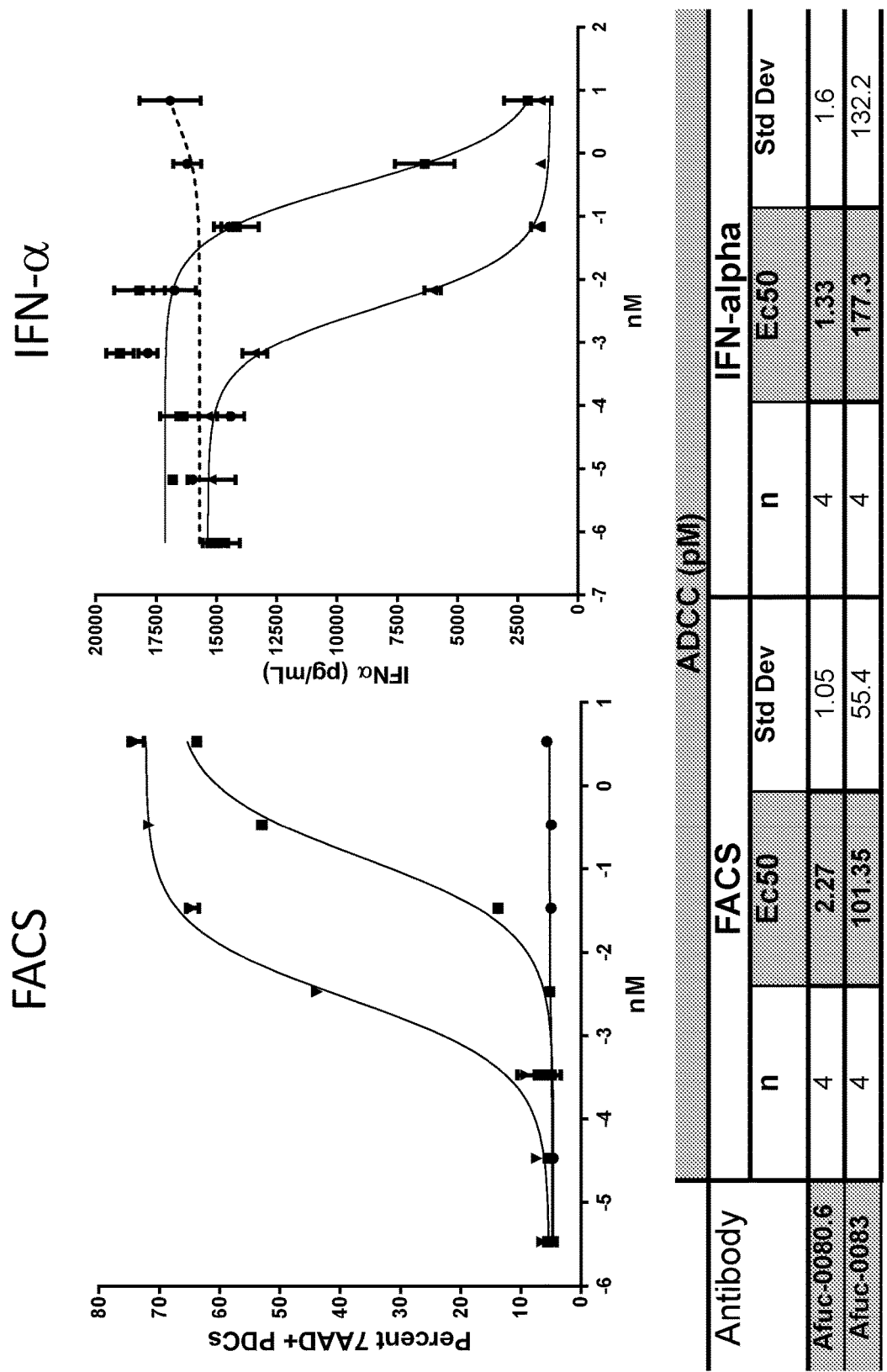

FIG. 17: shows the cytotoxicity (left) and IFN-α secretion (right) of human PBMCs exposed to afucosylated ILT70080.6 and ILT70083 antibodies.

Figure 18:
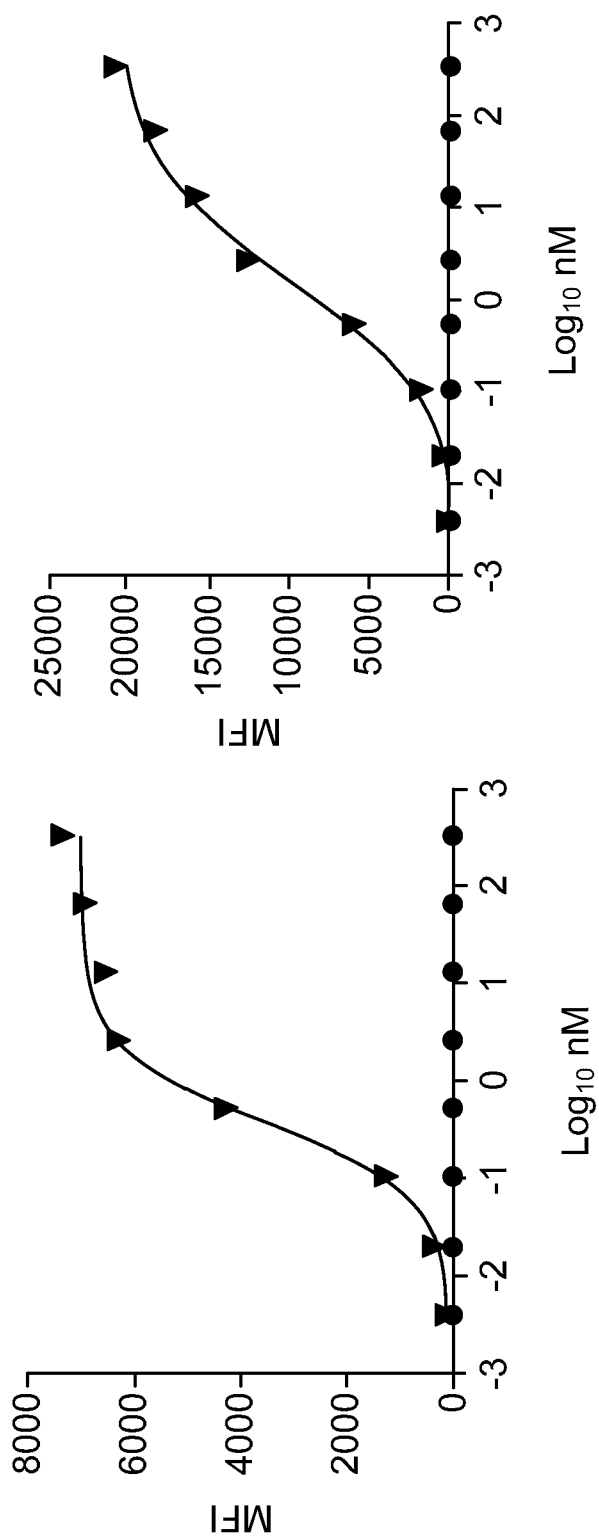

FIG. 18: shows binding of afucosylated ILT70137 to cells expressing human ILT7 (left panel) or cynomolgus ILT7 (right panel). The circles denote afucosylated ILT70137, and the triangles denote control.

Figure 19:
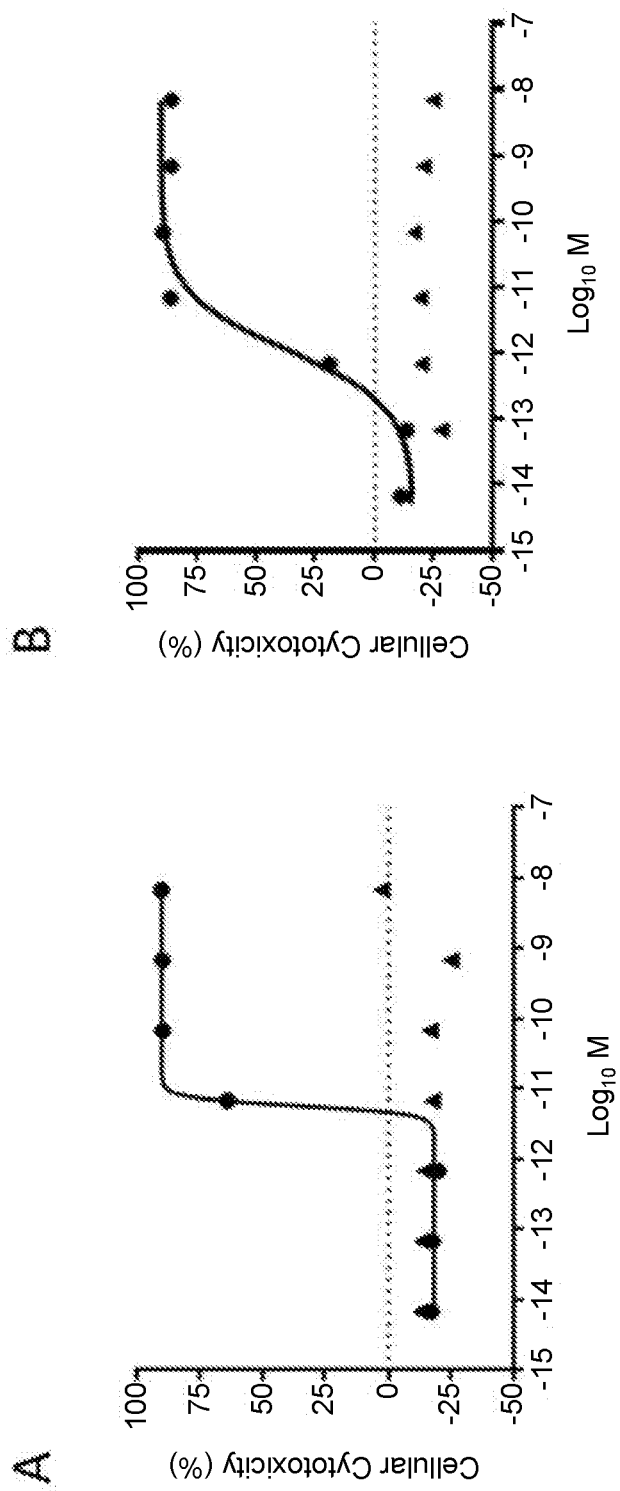

FIG. 19: shows ADCC activity of afucosylated ILT70137 on cells expressing human ILT7 (left panel) or cynomolgus ILT7 (right panel). The triangles denote afucosylated ILT70137, and the circles denote control.

Figure 20:
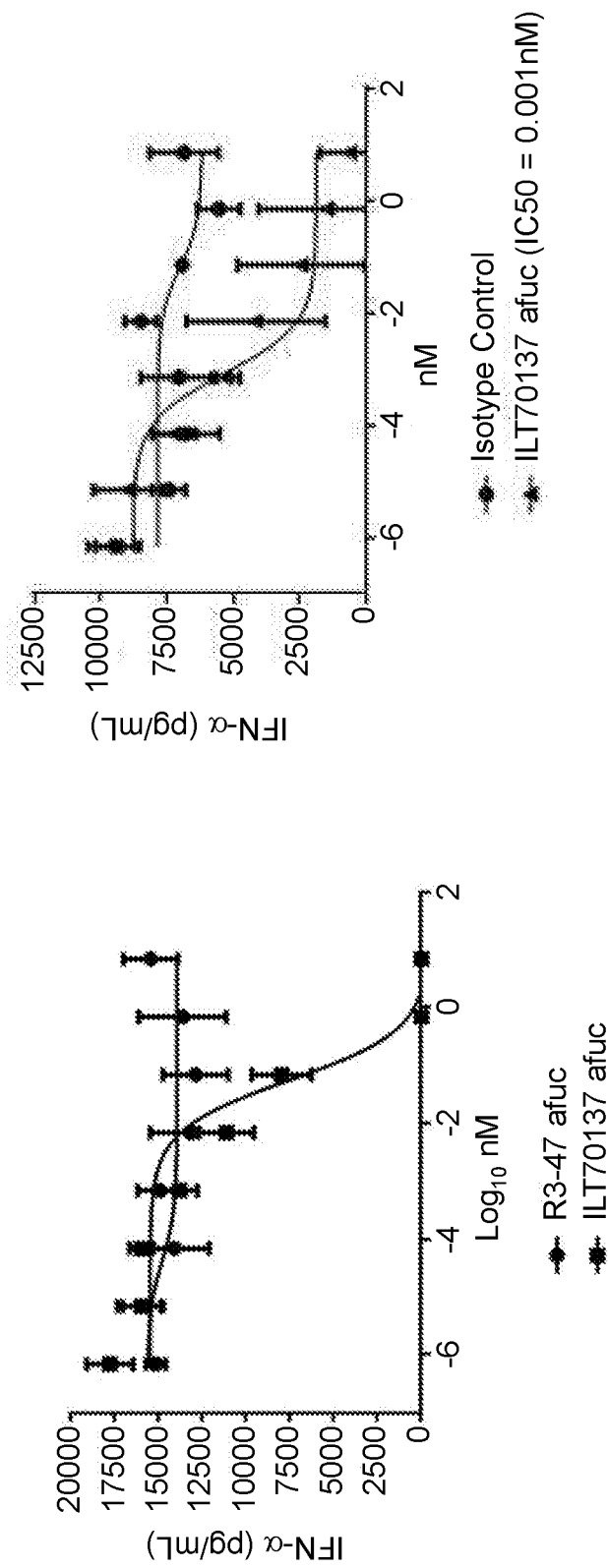

FIG. 20: shows ADCC activity of of afucosylated ILT70137 by measuring the inhibition of IFN-alpha production as an indirect assessment of the ability of the antibody to induce ADCC of peripheral blood mononuclear cells (PBMCs) in vitro.

FIG. 21: shows binding of afucosylated ILT70137 to human primary plasmacytoid dendritic cells (pDCs).

Figure 22:
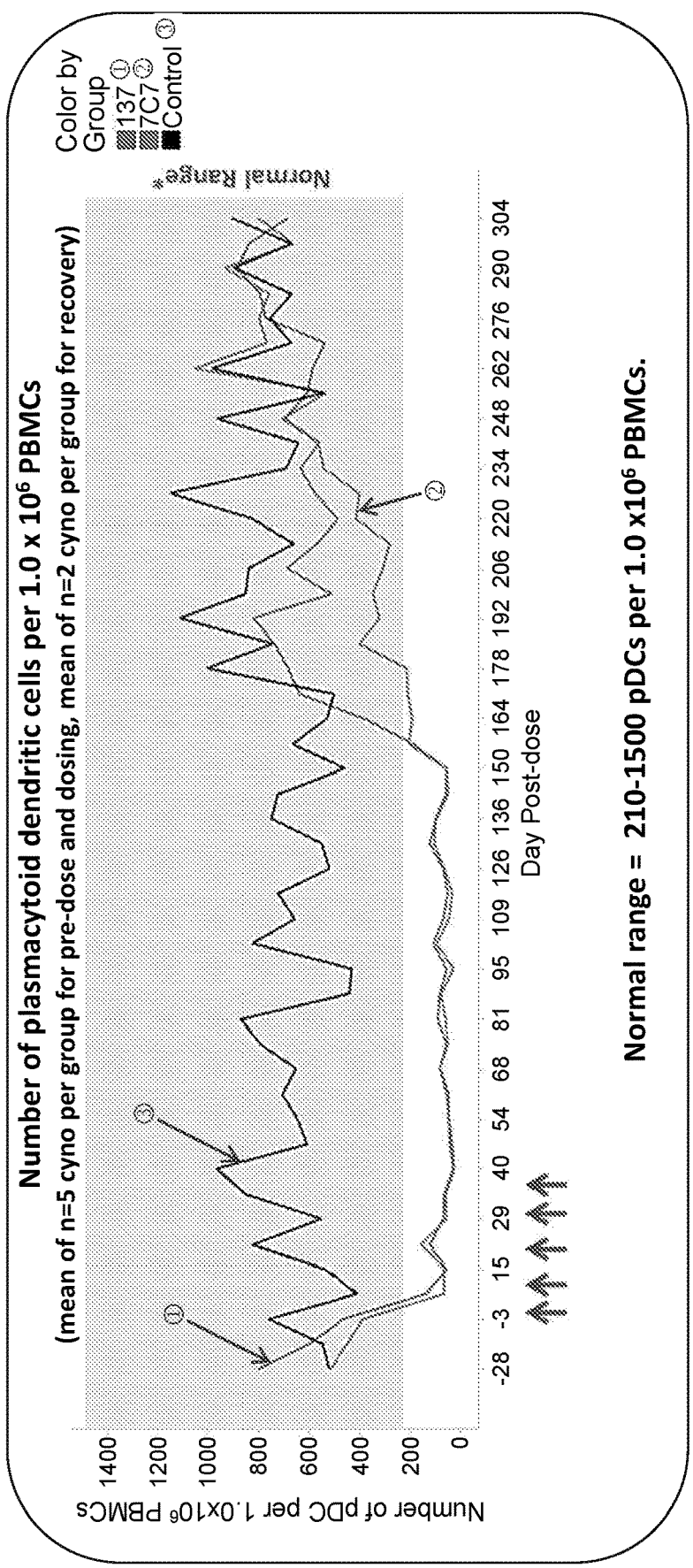

FIG. 22: shows pDC depletion in cynomolgus monkeys treated with afucosylated 7C7 or afucosylated ILT70137. Arrows at the bottom of the graph indicate time points of antibody administration.

Figure 23:
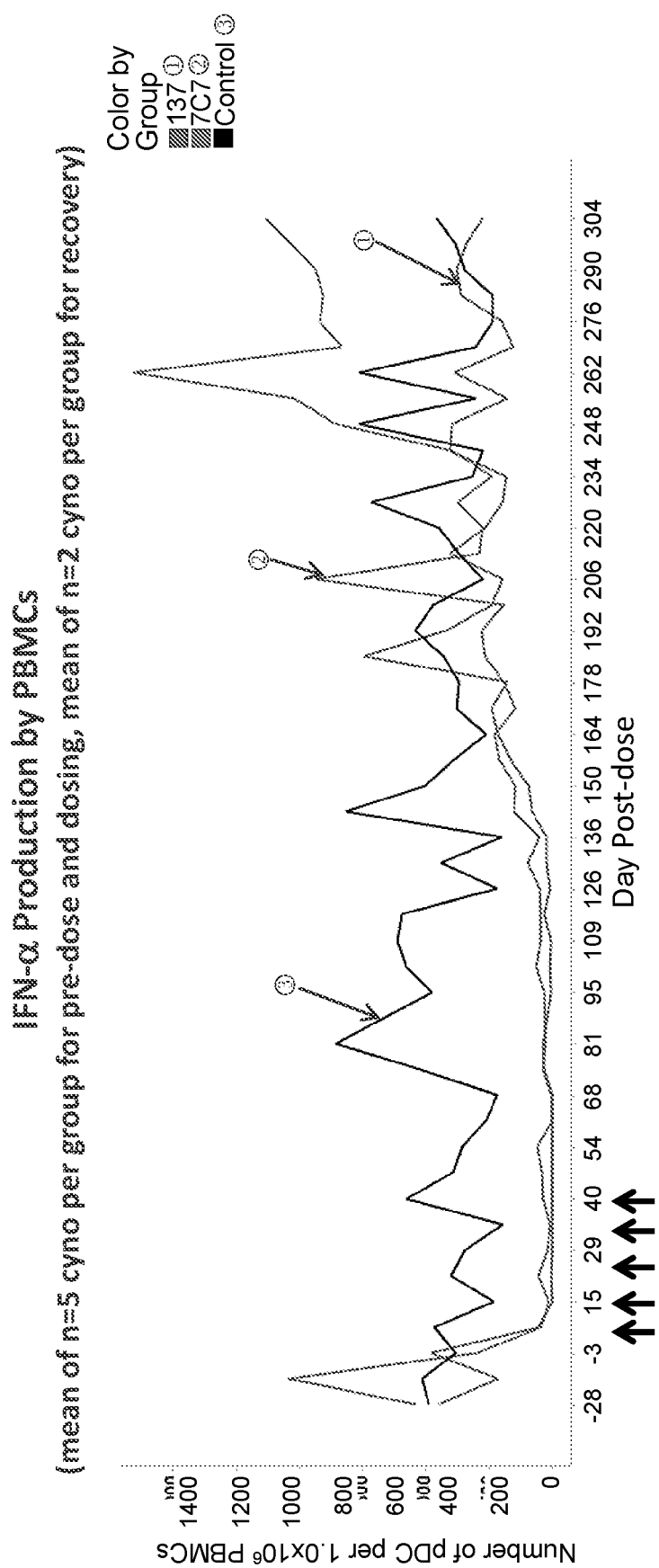

FIG. 23: shows IFNα production after treatment with afucosylated 7C7 or afucosylated ILT70137. Arrows at the bottom of the graph indicate time points of antibody administration.

DETAILED DESCRIPTION OF THE INVENTION

I. Definitions

It is to be noted that the term "a" or "an" entity refers to one or more of that entity; for example, "an anti-ILT7 antibody" is understood to represent one or more anti-ILT7 antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. It can be generated in any manner, including by chemical synthesis.

A polypeptide of the invention can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purpose of the invention, as are native or recombinant polypeptides that have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative," and "analog" when referring to anti-ILT7 antibodies or antibody polypeptides of the present invention include any polypeptides that retain at least some of the antigen-binding properties of the corresponding antibody or antibody polypeptide of the invention. Fragments of polypeptides of the present invention include proteolytic fragments, as well as deletion fragments, in addition to specific antibody fragments discussed elsewhere herein. Variants of anti-ILT7 antibodies and antibody polypeptides of the present invention include fragments as described above, and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions, or additions. Variant polypeptides can also be referred to herein as "polypeptide analogs." As used herein a "derivative" of an anti-ILT7 antibody or antibody polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine. Derivatives of anti-ILT7 antibodies and antibody polypeptides of the present invention, can include polypeptides that have been altered so as to exhibit additional features not found on the reference antibody or antibody polypeptide of the invention.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-ILT7 binding molecule, e.g., an antibody or antigen binding fragment thereof, contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can be or can include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid of the invention can encode heterologous coding regions, either fused or unfused to a nucleic acid encoding an anti-ILT7 antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention can be associated with additional coding regions that encode secretory or signal peptides, which direct the secretion of a polypeptide encoded by a polynucleotide of the present invention. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

A "binding molecule" or "antigen binding molecule" of the present invention refers in its broadest sense to a molecule that specifically binds an antigenic determinant. In one embodiment, the binding molecule specifically binds to ILT7, e.g., full length ILT7 or mature ILT7. In another embodiment, a binding molecule of the invention is an antibody or an antigen-binding fragment thereof. In another embodiment, a binding molecule of the invention comprises at least one heavy or light chain CDR of a reference antibody molecule. In another embodiment, a binding molecule of the invention comprises at least two CDRs from one or more reference antibody molecules. In another embodiment, a binding molecule of the invention comprises at least three CDRs from one or more reference antibody molecules. In another embodiment, a binding molecule of the invention comprises at least four CDRs from one or more reference antibody molecules. In another embodiment, a binding molecule of the invention comprises at least five CDRs from one or more reference antibody molecules. In another embodiment, a binding molecule of the invention comprises at least six CDRs from one or more reference antibody molecules. In certain embodiments, the reference antibody molecule is 7C7, ILT70080, ILT70080.1-ILT70080.7, ILT70083, ILT70083.1-ILT70083.9, ILT70089, ILT70100, ILT70137, ILT70142, ILT70144, or ILT70052.

The present invention is directed to certain anti-ILT7 antibodies, or antigen-binding fragments, variants, or derivatives thereof. The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" or "antibody fragment thereof" refers to a portion of an intact antibody. An "antigen-binding fragment" or "antigen-binding fragment thereof" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, scFvs, and single chain antibodies.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. Completely human antibodies are particularly desirable for therapeutic treatment of human patients.

Human antibodies can be made by variety of methods known in the art including phage display methods using antibody libraries derived from human immunoglobulin sequences as described in Vaughan et al., *Nat. Biotech.* 14:309-314 (1996), Sheets et al., *Proc. Nat'l. Acad. Sci.* 95:6157-6162 (1998), Hoogenboom and Winter, *J. Mol. Biol.* 227:381 (1992), and Marks et al., *J. Mol. Biol.* 222:581 (1991)). Additional examples of phage display methods that can be used to make and use antibodies include those disclosed in Rothe et al., *J. Mol. Biol.,* 376:1182 (2008), Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 6,172,197; 5,885,793, 6,521,404; 6,544,731; 6,555,313; 6,582,915; 6,593,081; 6,300,064; 6,653,068; 6,706,484; 7,264,963; 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

In addition, as known in the art, human antibodies can be produced using transgenic mice which are incapable of expressing functional endogenous immunoglobulins, but which can express human immunoglobulin genes. For an overview of this technology, see Lonberg and Huszar, *Int. Rev. Immunol.* 13:65-93 (1995).

Further techniques available in the art of antibody engineering have made it possible to isolate human antibodies or fragments thereof. For example, human hybridomas can be made as described by Kontermann and Sefan. Antibody Engineering, Springer Laboratory Manuals (2001). Fully human antibodies can likewise be produced by various display technologies, e.g., phage display or other viral display systems. In phage display methods, functional antibody domains are displayed on the surface of phage particles which carry the polynucleotide sequences encoding them. For example, DNA sequences encoding VH and VL regions are amplified from animal cDNA libraries (e.g., human or murine cDNA libraries of lymphoid tissues) or synthetic cDNA libraries. In certain embodiments, the DNA encoding the VH and VL regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13, and the VH or VL regions are usually recombinantly fused to either the phage gene III or gene VIII. Phage expressing an antigen binding domain that binds to an antigen of interest (i.e., ILT7) can be selected or identified with antigen, e.g., using labeled antigen or antigen bound or captured to a solid surface or bead.

"Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or antigen-binding fragments, variants, or derivatives thereof immunospecifically bind to a ILT7 polypeptide or fragment or variant thereof. Standard techniques known to those of skill in the art can be used to introduce mutations in the nucleotide sequence encoding a human anti-ILT7 antibody, including, but not limited to, site-directed mutagenesis and PCR-mediated mutagenesis which result in amino acid substitutions. The variants (including derivatives) can encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitutions, discussed further below. Alternatively, mutations can be introduced randomly along all or part of the coding sequence, such as by saturation mutagenesis, and the resultant mutants can be screened for biological activity to identify mutants that retain activity (e.g., the ability to bind a ILT7 polypeptide, e.g., human, primate, murine, or any combination of human, primate and murine ILT7). Such variants (or derivatives thereof) of "human" or "fully human" antibodies can also be referred to as human or fully human antibodies that are "optimized" or "optimized for antigen binding" and include antibodies that have improved affinity to antigen.

Basic immunoglobulin structures in vertebrate systems are relatively well understood. See, e.g., Harlow et al. (1988) Antibodies: A Laboratory Manual (2nd ed.; Cold Spring Harbor Laboratory Press).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. While the following discussion will generally be directed to the IgG class of immunoglobulin molecules, all immunoglobulin classes are clearly within the scope of the present invention. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (x, X). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

The base of the antibody "Y" is called the Fc (Fragment, crystallizable) region, and is composed of two heavy chains that contribute two or three constant domains depending on the class of the antibody. Thus, the Fc region binds to a specific class of Fc receptors, and other immune molecules, such as complement proteins. Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule can consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. IMGT (ImMunoGeneTics) also provides a numbering system for the immunoglobulin variable regions, including the CDRs. See e.g., Lefranc, M. P. et al., *Dev. Comp. Immunol.* 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. The appropriate amino acid residues that encompass the CDRs as defined by each of the above cited references are set forth below in Table 1 as a comparison. The exact residue numbers that encompass a particular CDR can vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia | IMGT |
|---|---|---|---|
| VH CDR1 | 31-35 | 26-32 | 26-35 |
| VH CDR2 | 50-65 | 52-58 | 51-57 |
| VH CDR3 | 95-102 | 95-102 | 93-102 |
| VL CDR1 | 24-34 | 26-32 | 27-32 |
| VL CDR2 | 50-56 | 50-52 | 50-52 |
| VL CDR3 | 89-97 | 91-96 | 89-97 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest."

Antibodies or antigen-binding fragments, variants, or derivatives thereof of the invention include, but are not limited to, polyclonal, monoclonal, mouse, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-ILT7 antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

In certain anti-ILT7 antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical.

The heavy chain portions of a binding molecule for use in the diagnostic and treatment methods disclosed herein can be derived from different immunoglobulin molecules. For example, a heavy chain portion of a polypeptide can comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. The light chain portion can comprise at least one of a VL or CL domain.

Anti-ILT7 antibodies, or antigen-binding fragments, variants, or derivatives thereof disclosed herein can be described or specified in terms of the epitope(s) or portion(s) of an antigen, e.g., a target polypeptide disclosed herein (e.g., full length or mature ILT7) that they recognize or specifically bind. The portion of a target polypeptide that specifically interacts with the antigen binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide can be or can include non-polypeptide elements, e.g., an epitope can include a carbohydrate side chain.

The minimum size of a peptide or polypeptide epitope for an antibody is thought to be about four to five amino acids. Peptide or polypeptide epitopes can contain at least seven, at least nine, or at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-ILT7 antibodies of the present invention can contain a sequence of at least 4, at least 5, at least 6, at least 7, at least 8, at least 9, at least 10, at least 15, at least 20, at least 25, or between about 15 to about 30 contiguous or non-contiguous amino acids of ILT7.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody can cross-react with the related epitope.

By way of non-limiting example, an antibody can be considered to bind a first epitope preferentially if it binds said first epitope with a dissociation constant ($K_D$) that is less than the antibody's $K_D$ for the second epitope. In another non-limiting example, an antibody can be considered to bind a first antigen preferentially if it binds the first epitope with an affinity that is at least one order of magnitude less than the antibody's $K_D$ for the second epitope. In another non-limiting example, an antibody can be considered to bind a first epitope preferentially if it binds the first epitope with an affinity that is at least two orders of magnitude less than the antibody's $K_D$ for the second epitope.

In another non-limiting example, an antibody can be considered to bind a first epitope preferentially if it binds the first epitope with an off rate (k(off)) that is less than the antibody's k(off) for the second epitope. In another non-limiting example, an antibody can be considered to bind a first epitope preferentially if it binds the first epitope with an affinity that is at least one order of magnitude less than the antibody's k(off) for the second epitope. In another non-limiting example, an antibody can be considered to bind a first epitope preferentially if it binds the first epitope with an affinity that is at least two orders of magnitude less than the antibody's k(off) for the second epitope. An antibody or antigen-binding fragment, variant, or derivative thereof disclosed herein can be said to bind a target polypeptide disclosed herein (e.g., ILT7, e.g., human, primate, murine, or any combination of human, primate and murine ILT7) or a fragment or variant thereof with an off rate (k(off)) of less than or equal to $5 \times 10^{-2}$ sec-1, $10^{-2}$ sec-1, $5 \times 10^{-3}$ sec$^{-1}$ or $10^{-3}$ sec$^{-1}$. An antibody of the invention can be said to bind a target polypeptide disclosed herein (e.g., ILT7, e.g., human, primate, murine, or any combination of human, primate and murine ILT7) or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative thereof disclosed herein can be said to bind a target polypeptide disclosed herein (e.g., ILT7, e.g., human, primate, murine, or any combination of human, primate and murine ILT7) or a fragment or variant thereof with an on rate (k(on)) of greater than or equal to $10^3$ $M^{-1}$ sec$^{-1}$, $5 \times 10^3$ $M^{-1}$ sec$^{-1}$, $10^4$ $M^{-1}$ sec$^{-1}$ or $5 \times 10^4$ $M^{-1}$ sec$^{-1}$. An antibody of the invention can bind a target polypeptide disclosed herein (e.g., ILT7, e.g., human, primate, murine, or any combination of human, primate and murine ILT7) or a fragment or variant thereof with an on rate (k(on)) greater than or equal to $10^5$ $M^{-1}$ sec$^{-1}$, $5 \times 10^5$ $M^{-1}$ sec$^{-1}$, $10^6$ $M^{-1}$ sec$^{-1}$, or $5 \times 10^6$ $M^{-1}$ sec$^{-1}$ or $10^7$ $M^{-1}$ sec$^{-1}$.

An antibody is said to competitively inhibit binding of a reference antibody to a given epitope if it preferentially binds to that epitope or an overlapping epitope to the extent that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-ILT7 antibodies or antigen-binding fragments, variants, or derivatives thereof of the invention can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, can actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

Anti-ILT7 binding molecules, e.g., antibodies or antigen-binding fragments, variants or derivatives thereof of the invention can also be described or specified in terms of their binding affinity to a polypeptide of the invention, e.g., ILT7, e.g., human, primate, murine, or any combination of human, primate and murine ILT7. Useful binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-4}$ M, $10^{-4}$ M, $5\times10^{-7}$ M, $10^{-7}$M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In some embodiments, the antibody binds to human ILT7 with a dissociation constant or Kd less than 1 nM. In some embodiments, the antibody binds to cynomolgus ILT7 with a dissociation constant or Kd less than 5 nM. In some embodiments, the antibody binds to human ILT7 with a dissociation constant or Kd less than 1 nM and binds to cynomolgus ILT7 with a dissociation constant or Kd less than 5 nM.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al.). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which can be intact, partial or modified in accordance with the instant invention) is obtained from a second species. In certain embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class or from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody can comprise solely residues of human origin, in which case these framework regions of the humanized antibody are referred to as "fully human framework regions." Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the ILT7 antigen. A human framework region that has been engineered in this manner would thus comprise a mixture of human and donor framework residues, and is referred to herein as a "partially human framework region."

For example, humanization of an anti-ILT7 antibody can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent or mutant rodent anti-ILT7 CDRs or CDR sequences into the corresponding sequences of a human antibody. See also U.S. Pat. Nos. 5,225,539; 5,585,089; 5,693,761; 5,693,762; 5,859,205; herein incorporated by reference. The resulting humanized anti-ILT7 antibody would comprise at least one rodent or mutant rodent CDR within the fully human framework regions of the variable domain of the heavy and/or light chain of the humanized antibody. In some instances, residues within the framework regions of one or more variable domains of the humanized anti-ILT7 antibody are replaced by corresponding non-human (for example, rodent) residues (see, for example, U.S. Pat. Nos. 5,585,089; 5,693,761; 5,693,762; and 6,180,370), in which case the resulting humanized anti-ILT7 antibody would comprise partially human framework regions within the variable domain of the heavy and/or light chain.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* 331:522-525 (1986); Riechmann et al., *Nature* 332:323-329 (1988); and Presta, *Curr. Op. Struct. Biol.* 2:593-596 (1992); herein incorporated by reference. Accordingly, such "humanized" antibodies can include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

As used herein, the terms "linked," "fused," or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of an autoimmune condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of an anti-ILT7 antibody" and "an animal in need of treatment" includes subjects, such as mammalian subjects, that would benefit from administration of an anti-ILT7 antibody used, e.g., for detection of an anti-ILT7 polypeptide (e.g., for a diagnostic procedure) and/or from treatment, i.e., palliation or prevention of a disease, with an anti-ILT7 antibody.

II. ILT7

As used herein, the terms "ILT7" and "ILT7 polypeptide" are used interchangably. In certain embodiments, ILT7 is full length. In another embodiment, ILT7 is mature ILT7 (amino acids 24-499). In other embodiments, ILT7 can include a full length ILT7, a fragment thereof, or a ILT7 variant polypeptide, wherein the fragment of ILT7 or ILT7 variant polypeptide retains some or all functional properties of active ILT7.

Full length human ILT7 is a 499 amino acid protein (Accession No. P59901), containing a signal peptide (amino acids 1-23), an extracellular domain (amino acids 24-446), a transmembrane domain (amino acids 447-467), and a cytoplasmic domain (amino acids 468-499). The extracellular domain includes four immunoglobulin-like C2 domains (amino acids 24-118, 123-213, 224-313, and 324-413). ILT7 is a member of the immunoglobulin-like transcript (ILT) or leukocyte immunoglobulin-like receptor (LIR) gene family. The sequence of cynomolgus ILT7 is provided as SEQ ID NO:292:

```
                                         (SEQ ID NO: 292)
PRTHMQAENLLKPILWAEPGPVIIWKKPVTIWCQGTLEAQEYRLDKEGNS

ISRHMLKTLESENKAKFSIPSMMWEHAGRYHCYYQSPAGWSEPSDPLELV

VTAYSRPSLSALPSPVVTSGVNVTLRCASRLGLGRFTLIEEGDHRLSWTL

DSHQHNHGKFQALFPVGPLTFSNRGTFRCYGYENNTPYVWSEPSDPLQLL

VSGVSRKPSLLTLQGPVVAPGDNLTLQCGSDVGYIRYALYKEGGDGLPQR

PGQQSQAGLSQASFTLNPVRGSHGGQYRCYGAHNVSSKWSAPSDPLDILI

AGQIPDRPSLSVQLGPTVASGEKVTLLCQSWGPMFTFLLAKEGAAHPPLR
```

-continued

LRSTYRAQQYQAEFPMSPVTSAHAGTYRCYGSRSSDPYLLSHSSEPLELV

VSEATETLNPAQNKSDSKTAPHLQDYTVENLIRMGIAGLVLVFLGILLFE

AQQSQRSPTRCSQEVNSREDNAPFRVVEPWEQI.

ILT7 is selectively expressed on a subset of peripheral blood mononuclear cells (PBMCs) called plasmacytoid dendritic cells (pDCs). pDCs are the main source of the immunomodulatory molecule interferon (IFN)-alpha, and ILT7 plays a role in regulating the release of IFN-alpha from these cells.

III. Anti-ILT7 Binding Molecules

In certain embodiments, the ILT-7 binding molecules provided herein are antibodies or antigen-binding fragments thereof that contain sequences and/or properties of ILT7-binding antibodies provided herein. The SEQ ID NOs of sequences of ILT7 antibodies are provided in Table 2.

TABLE 2

ILT7 Antibody Sequence SEQ ID NOs

| Antibody | VH PN | VH PP | VH CDR1 | VH CDR2 | VH CDR3 | VL PN | VL PP | VL CDR1 | VL CDR2 | VL CDR2 |
|---|---|---|---|---|---|---|---|---|---|---|
| SBI28 | 1 | 2 | 3 | 4 | 5 | 6 | 7 | 8 | 9 | 10 |
| 7C7 | 11 | 12 | 13 | 14 | 15 | 16 | 17 | 18 | 19 | 20 |
| ILT70080 | 21 | 22 | 23 | 24 | 25 | 26 | 27 | 28 | 29 | 30 |
| ILT70080.1 | 31 | 32 | 33 | 34 | 35 | 36 | 37 | 38 | 39 | 40 |
| ILT70080.2 | 41 | 42 | 43 | 44 | 45 | 46 | 47 | 48 | 49 | 50 |
| ILT70080.3 | 51 | 52 | 53 | 54 | 55 | 56 | 57 | 58 | 59 | 60 |
| ILT70080.4 | 61 | 62 | 63 | 64 | 65 | 66 | 67 | 68 | 69 | 70 |
| ILT70080.5 | 71 | 72 | 73 | 74 | 75 | 76 | 77 | 78 | 79 | 80 |
| ILT70080.6 | 81 | 82 | 83 | 84 | 85 | 86 | 87 | 88 | 89 | 90 |
| ILT70080.7 | 91 | 92 | 93 | 94 | 95 | 96 | 97 | 98 | 99 | 100 |
| ILT70083 | 101 | 102 | 103 | 104 | 105 | 106 | 107 | 108 | 109 | 110 |
| ILT70083.1 | 111 | 112 | 113 | 114 | 115 | 116 | 117 | 118 | 119 | 120 |
| ILT70083.2 | 121 | 122 | 123 | 124 | 125 | 126 | 127 | 128 | 129 | 130 |
| ILT70083.3 | 131 | 132 | 133 | 134 | 135 | 136 | 137 | 138 | 139 | 140 |
| ILT70083.4 | 141 | 142 | 143 | 144 | 145 | 146 | 147 | 148 | 149 | 150 |
| ILT70083.5 | 151 | 152 | 153 | 154 | 155 | 156 | 157 | 158 | 159 | 160 |
| ILT70083.6 | 161 | 162 | 163 | 164 | 165 | 166 | 167 | 168 | 169 | 170 |
| ILT70083.7 | 171 | 172 | 173 | 174 | 175 | 176 | 177 | 178 | 179 | 180 |
| ILT70083.8 | 181 | 182 | 183 | 184 | 185 | 186 | 187 | 188 | 189 | 190 |
| ILT70083.9 | 191 | 192 | 193 | 194 | 195 | 196 | 197 | 198 | 199 | 200 |
| ILT70137 | 201 | 202 | 203 | 204 | 205 | 206 | 207 | 208 | 209 | 210 |
| ILT70052 | 211 | 212 | 213 | 214 | 215 | 216 | 217 | 218 | 219 | 220 |
| ILT70100 | 221 | 222 | 223 | 224 | 225 | 226 | 227 | 228 | 229 | 230 |
| ILT70142 | 231 | 232 | 233 | 234 | 235 | 236 | 237 | 238 | 239 | 240 |
| ILT70144 | 241 | 242 | 243 | 244 | 245 | 246 | 247 | 248 | 249 | 250 |
| ILT70019 | 251 | 252 | 253 | 254 | 255 | 256 | 257 | 258 | 259 | 260 |
| ILT70028 | 261 | 262 | 263 | 264 | 265 | 266 | 267 | 268 | 269 | 270 |
| ILT70076 | 271 | 272 | 273 | 274 | 275 | 276 | 277 | 278 | 279 | 280 |
| ILT70089 | 281 | 282 | 283 | 284 | 285 | 286 | 287 | 288 | 289 | 290 |

In certain embodiments, the binding molecules, e.g., antibodies or antigen-binding fragments, variants, or derivatives thereof, of the invention, e.g., antibodies 7C7, ILT70080, ILT70080.1-ILT70080.7, ILT70083, ILT70083.1-ILT70083.9, ILT70089, ILT70100, ILT70137, ILT70142, ILT70144, and ILT70052, bind to ILT7 and inhibit IFN-alpha release from plasmacytoid dendritic cells.

In certain embodiments, the antibodies of the invention comprise anti-ILT7 antibodies or antigen-binding fragments, variants, or derivatives thereof that bind to ILT7, e.g., antibodies 7C7, ILT70080, ILT70080.1-ILT70080.7, ILT70083, ILT70083.1-ILT70083.9, ILT70089, ILT70100, ILT70137, ILT70142, and ILT70052. In certain embodiments the anti-ILT7 antibodies bind human, primate, murine, or any combination of human, primate and murine ILT7.

In one embodiment, the present invention provides an isolated binding molecule, e.g., an antibody or antigen-binding fragment, variant, or derivative thereof, which specifically binds to the same ILT7 epitope as antibody 7C7, ILT70080, ILT70080.1-ILT70080.7, ILT70083, ILT70083.1-ILT70083.9, ILT70089, ILT70100, ILT70137, ILT70142, ILT70144, or ILT70052. In another embodiment, the present invention provides an isolated binding molecule, e.g., an antibody or antigen-binding fragment, variant, or derivative thereof, which specifically binds to the same ILT7 epitope as an antibody comprising the VH and VL of 7C7, ILT70080, ILT70080.1-ILT70080.7, ILT70083, ILT70083.1-ILT70083.9, ILT70089, ILT70100, ILT70137, ILT70142, ILT70144, or ILT70052. In another embodiment, the present invention provides an isolated binding molecule, e.g., an antibody or antigen-binding fragment, variant, or derivative thereof, which specifically binds to the same ILT7 epitope as an antibody comprising the VH or VL of 7C7, ILT70080, ILT70080.1-ILT70080.7, ILT70083, ILT70083.1-ILT70083.9, ILT70089, ILT70100, ILT70137, ILT70142, ILT70144, or ILT70052.

In another embodiment, the present invention provides an isolated binding molecule, e.g., an antibody or antigen-binding fragment, variant, or derivative thereof, which specifically binds to ILT7, and competitively inhibits antibody 7C7, ILT70080, ILT70080.1-ILT70080.7, ILT70083, ILT70083.1-ILT70083.9, ILT70089, ILT70100, ILT70137, ILT70142, ILT70144, or ILT70052 from specifically binding to ILT7, e.g., human, primate, murine, or any combination of human, primate, and murine ILT7. In another embodiment, the present invention provides an isolated binding molecule, e.g., an antibody or antigen-binding fragment, variant, or derivative thereof, which specifically binds to ILT7, and competitively inhibits an antibody comprising the VH and VL of 7C7, ILT70080, ILT70080.1-ILT70080.7, ILT70083, ILT70083.1-ILT70083.9, ILT70089, ILT70100, ILT70137, ILT70142, ILT70144, or ILT70052 from specifically binding to ILT7, e.g., human, primate, murine, or any combination of human, primate, and murine ILT7. In another embodiment, the present invention provides an isolated binding molecule, e.g., an antibody or antigen-binding fragment, variant, or derivative thereof, which specifically binds to ILT7, and competitively inhibits an antibody comprising the VH or VL of 7C7, ILT70080, ILT70080.1-ILT70080.7, ILT70083, ILT70083.1-ILT70083.9, ILT70089, ILT70100, ILT70137, ILT70142, ILT70144, or ILT70052 from specifically binding to ILT7, e.g., human, primate, murine, or any combination of human, primate, and murine ILT7.

In certain embodiments, the binding molecule of the invention has an amino acid sequence that has at least 80%, 85%, 88%, 89%, 90%, 91%, 92%, 93%, 94%, or 95% sequence identity to the amino acid sequence for the reference anti-ILT7 antibody molecule. In a further embodiment, the binding molecule shares at least 96%, 97%, 98%, 99%, or 100% sequence identity to the reference antibody. In certain embodiments, the reference antibody is 7C7, ILT70080, ILT70080.1-ILT70080.7, ILT70083, ILT70083.1-ILT70083.9, ILT70089, ILT70100, ILT70137, ILT70142, ILT70144, or ILT70052.

In another embodiment, the present invention provides an isolated antibody or antigen-binding fragment, variant, or derivative thereof comprising, consisting essentially of, or consisting of a VH domain that has an amino acid sequence that is at least 80%, 85%, 90%, 91%, 92%, 93%, 94%, 95%, 96%, 97%, 98%, 99%, or 100% identical to a VH amino acid sequence of SEQ ID NOs: 22, 42, 52, 62, 72, 82, 92, 102, 112, 122, 132, 142, 152, 162, 172, 182, 192, 202, 212, 222, 232, 242, 252, and 262, wherein the antibody or antigen-binding fragment, variant, or derivative thereof comprising the VH domain specifically or preferentially binds to ILT7. In a further embodiment, and the antibody or antigen-binding fragment variant or derivative thereof inhibits IFN-alpha release from plasmacytoid dendritic cells.

In a further embodiment, the present invention includes an isolated antibody or antigen-binding fragment, variant, or derivative thereof comprising, consisting essentially of, or consisting of a VL domain that has an amino acid sequence that is at least 80%, 85%, 90%, 91%, 92%, 93%, 94%, 95%, 96%, 97%, 98%, 99%, or 100% identical to a VL amino acid sequence of SEQ ID NOs: 27, 47, 57, 67, 77, 87, 97, 107, 117, 127, 137, 147, 157, 167, 177, 187, 197, 207, 217, 227, 237, 247, 257, or 267, wherein the antibody or antigen-binding fragment, variant, or derivative thereof comprising the VL domain specifically or preferentially binds to ILT7. In a further embodiment, and the antibody or antigen-binding fragment, variant, or derivative thereof inhibits IFN-alpha release from plasmacytoid dendritic cells.

In a further embodiment, the present invention includes an isolated antibody or antigen-binding fragment, variant, or derivative thereof comprising, consisting essentially of, or consisting of a VH domain and a VL domain that have amino acid sequences that are at least 80%, 85%, 90%, 91%, 92%, 93%, 94%, 95%, 96%, 97%, 98%, 99%, or 100% identical to the VH and VL sequences of SEQ ID NOs: 22 and 27; 42 and 47; 52 and 57; 62 and 67; 72 and 77; 82 and 87; 92 and 97; 102 and 107; 112 and 117; 122 and 127; 132 and 137; 142 and 147; 152 and 157; 162 and 167; 172 and 177; 182 and 187; 192 and 197; 202 and 207; 212 and 217; 222 and 227; 232 and 237; 242 and 247; 252 and 257; or 262 and 267; respectively wherein the antibody or antigen-binding fragment, variant, or derivative thereof comprising the VH and VL domains specifically or preferentially binds to ILT7. In a further embodiment, and the antibody or antigen-binding fragment, variant, or derivative thereof inhibits IFN-alpha release from plasmacytoid dendritic cells.

In a further embodiment, the present invention includes an isolated antibody or antigen-binding fragment, variant, or derivative thereof comprising, consisting essentially of, or consisting of a VH domain and a VL domain that have the VH-CDR1, VH-CDR2, VH-CDR3, VL-CDR1, VL-CDR2, and VL-CDR3 sequences of SEQ ID NOs: 23, 24, 25, 28, 29, and 30; 43, 44, 45, 48, 49, and 50; 53, 54, 55, 58, 59, and 60; 63, 64, 65, 68, 69, and 70; 73, 74, 74, 78, 79, and 80; 83, 84, 85, 88, 89, and 90; 93, 94, 95, 98, 99, and 100; 103, 104, 105, 108, 109, and 110; 113, 114, 115, 118, 119, and 120; 123, 124, 125, 128, 129, and 130; 133, 134, 135, 138, 139, and 140; 143, 144, 145, 148, 149, and 150; 153, 154, 155, 158, 159, and 160; 163, 164, 165, 168, 169, and 170; 173, 174, 175, 178, 179, and 180; 183, 184, 185, 188, 189, and 190; 193, 194, 195, 198, 199, and 200; 203, 204, 205, 208, 209, and 210; 213, 214, 215, 218, 219, and 220; 223, 224, 225, 228, 229, and 230; 233, 234, 235, 238, 239, and 240; 243, 244, 245, 248, 249, and 250; 253, 254, 255, 258, 259, and 260; 263, 264, 265, 268, 269, and 270; respectively, wherein the antibody or antigen-binding fragment, variant, or derivative thereof comprising the VH and VL domains specifically or preferentially binds to ILT7. In a further embodiment, and the antibody or antigen-binding fragment, variant, or derivative thereof inhibits IFN-alpha release from plasmacytoid dendritic cells.

Suitable biologically active variants of the anti-ILT7 antibodies of the invention can be used in the methods of the present invention. Such variants will retain the desired binding properties of the parent anti-ILT7 antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest can be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, can be beneficial. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of an anti-ILT7 binding molecule, e.g., an antibody or antigen-binding fragment, variant, or derivative thereof, modifications are made such that variants continue to possess the desired properties, e.g., being capable of specifically binding to a ILT7, and in certain embodiments being able to inhibit IFN-alpha release. Obviously, any mutations made in the DNA encoding the variant polypeptide must not place the sequence out of reading frame. In some embodiment, any mutations made in the DNA will not create complementary regions that could produce secondary mRNA structure.

Methods for measuring the binding specificity of an anti-ILT7 binding molecule, e.g., an antibody or antigen-binding fragment, variant, or derivative thereof, include, but are not limited to, standard competitive binding assays, cytotoxicity assays, IFN release assays, ELISA assays, and the like.

When discussed herein whether any particular polypeptide, including the constant regions, CDRs, VH domains, or VL domains disclosed herein, is at least 65%, 70%, 75%, 80%, 85%, 90%, 91%, 92%, 93%, 94%, 95%, 96%, 97%, 98%, 99%, or even 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity can be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant can, for example, differ from a reference anti-ILT7 antibody (e.g., 7C7, ILT70080, ILT70080.1-ILT70080.7, ILT70083, ILT70083.1-ILT70083.9, ILT70089, ILT70100, ILT70137, ILT70142, ILT70144, or ILT70052) by as few as 1 to 15 amino acid residues, as few as 1 to 10 amino acid residues, such as 6-10, as few as 5, as few as 4, 3, 2, or even 1 amino acid residue.

The precise chemical structure of a polypeptide capable of specifically binding ILT7 and retaining the desired activity depends on a number of factors. As ionizable amino and carboxyl groups are present in the molecule, a particular polypeptide can be obtained as an acidic or basic salt, or in neutral form. All such preparations that retain their biological activity when placed in suitable environmental conditions are included in the definition of anti-ILT7 antibodies as used herein. Further, the primary amino acid sequence of the polypeptide can be augmented by derivatization using sugar moieties (glycosylation) or by other supplementary molecules such as lipids, phosphate, acetyl groups and the like. It can also be augmented by conjugation with saccharides. Certain aspects of such augmentation are accomplished through post-translational processing systems of the producing host; other such modifications can be introduced in vitro. In any event, such modifications are included in the definition of an anti-ILT7 antibody used herein so long as the desired properties of the anti-ILT7 antibody are not destroyed. It is expected that such modifications can quantitatively or qualitatively affect the activity, either by enhancing or diminishing the activity of the polypeptide, in the various assays. Further, individual amino acid residues in the chain can be modified by oxidation, reduction, or other derivatization, and the polypeptide can be cleaved to obtain fragments that retain activity. Such alterations that do not destroy the desired properties (e.g., binding specificity for ILT7, binding affinity, and associated activity, e.g., ability to inhibit the ILT7-driven cytokine release from mast cells, endothelial cells and proliferation of TF-1 cells) do not remove the polypeptide sequence from the definition of anti-ILT7 antibodies of interest as used herein.

The art provides substantial guidance regarding the preparation and use of polypeptide variants. In preparing variants of an anti-ILT7 binding molecule, e.g., an antibody or antigen-binding fragment, variant, or derivative thereof, one of skill in the art can readily determine which modifications to the native protein's nucleotide or amino acid sequence will result in a variant that is suitable for use as a therapeutically active component of a pharmaceutical composition used in the methods of the present invention.

The constant region of an anti-ILT7 antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-ILT7 antibodies, the Fc portion can be mutated to decrease effector function using techniques known in the art. For example, the deletion or inactivation (through point mutations or other means) of a constant region domain can reduce Fc receptor binding of the circulating modified antibody. In other cases it can be that constant region modifications consistent with the instant invention moderate complement binding and thus reduce the serum half life and nonspecific association of a conjugated cytotoxin. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as biodistribution and serum half-life, can easily be measured and quantified using well known immunological techniques without undue experimentation.

Certain ILT7 antibodies provided herein are afucosylated. Antibodies lacking core fucose residues from the Fc N-glycans exhibit strong ADCC at lower concentrations with much higher efficacy compared to fucosylated counterparts, and they can evade the inhibitory effect of serum immunoglobulin G (IgG) on ADCC through its high binding to gamma receptor IIIa (Fc FcγRIIIa).

Anti-ILT7 antibodies of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-ILT7 polypeptide).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to immunospecifically bind at least one epitope of a ILT7 polypeptide) can be determined using techniques described herein or by routinely modifying techniques known in the art.

In certain embodiments, the anti-ILT7 antibodies of the invention comprise at least one optimized complementarity-determining region (CDR). By "optimized CDR" is intended that the CDR has been modified and optimized sequences selected based on the sustained or improved binding affinity and/or anti-ILT7 activity that is imparted to an anti-ILT7 antibody comprising the optimized CDR. "Anti-ILT7 activity" can include, e.g., activity which modulates one or more of the following activities associated with ILT7, e.g., ILT7-driven interferon release from plasmacytoid dendritic cells, cytotoxicity to ILT7-expressing cells, or any other activity association with ILT7. Anti-ILT7 activity can also be attributed to a decrease in incidence or severity of diseases associated with ILT7 expression, including, but not limited to, certain types of autoimmune conditions, e.g., systemic lupus erythematosus, chronic rheumatism, and psoriasis. The modifications can involve replacement of amino acid residues within the CDR such that an anti-ILT7 antibody retains specificity for the ILT7 antigen and has improved binding affinity and/or improved anti-ILT7 activity.

IV. Polynucleotides Encoding Anti-ILT7 Antibodies

The present invention also provides for nucleic acid molecules encoding anti-ILT7 antibodies of the invention, or antigen-binding fragments, variants, or derivatives thereof.

In a further embodiment, the present invention includes an isolated polynucleotide comprising, consisting essentially of, or consisting of a nucleic acid encoding a VH domain that has an amino acid sequence that is at least 80%, 85%, 90%, 91%, 92%, 93%, 94%, 95%, 96%, 97%, 98%, 99%, or 100% identical to a reference VH domain polypeptide sequence comprising SEQ ID NOs: 12, 22, 32, 42, 52, 62, 72, 82, 92, 102, 112, 122, 132, 142, 152, 162, 172, 182, 192, 202, 212, 222, 232, or 242, wherein the anti-ILT7 antibody comprising the encoded VH domain specifically or preferentially binds to ILT7. In certain embodiments, the polynucleotide encodes an antibody or antigen-binding fragment, variant, or derivative thereof that inhibits IFN-alpha release from plasmacytoid dendritic cells.

In a further embodiment, the present invention includes an isolated polynucleotide comprising, consisting essentially of, or consisting of a nucleic acid encoding a VL domain that has an amino acid sequence that is at least 80%, 85%, 90%, 91%, 92%, 93%, 94%, 95%, 96%, 97%, 98%, 99%, or 100% identical to a reference VL domain polypeptide sequence comprising SEQ ID NOs: 17, 27, 37, 47, 57, 67, 77, 87, 97, 107, 117, 127, 137, 147, 157, 167, 177, 187, 197, 207, 217, 227, 237, or 247, wherein the anti-ILT7 antibody comprising the encoded VL domain specifically or preferentially binds to ILT7. In certain embodiments, the polynucleotide encodes an antibody or antigen-binding fragment, variant, or derivative thereof that inhibits IFN-alpha release from plasmacytoid dendritic cells.

Any of the polynucleotides described above can further include additional nucleic acids, encoding, e.g., a signal peptide to direct secretion of the encoded polypeptide, antibody constant regions as described herein, or other heterologous polypeptides as described herein. Also, as described in more detail elsewhere herein, the present invention includes compositions comprising one or more of the polynucleotides described above.

In one embodiment, the invention includes compositions comprising a first polynucleotide and second polynucleotide wherein said first polynucleotide encodes a VH domain as described herein and wherein said second polynucleotide encodes a VL domain as described herein. Specifically a composition can comprise, consist essentially of, or consist of a VH domain-encoding polynucleotide, as set forth in SEQ ID NO: 11, 21, 31, 41, 51, 61, 71, 81, 91, 101, 111, 121, 131, 141, 151, 161, 171, 181, 191, 201, 211, 221, 231, or 241 and a VL domain-encoding polynucleotide as set forth in SEQ ID NO: 16, 26, 36, 46, 56, 66, 76, 86, 96, 106, 116, 126, 136, 146, 156, 166, 176, 186, 196, 206, 216, 226, 236, or 246. A composition can also comprise, consist essentially of, or consist of a VH domain-encoding polynucleotide that encodes the sequence set forth in SEQ ID NO: 12, 22, 32, 42, 52, 62, 72, 82, 92, 102, 112, 122, 132, 142, 152, 162, 172, 182, 192, 202, 212, 222, 232, or 242, and a VL domain-encoding polynucleotide that encodes the sequence set forth in SEQ ID NO: 17, 27, 37, 47, 57, 67, 77, 87, 97, 107, 117, 127, 137, 147, 157, 167, 177, 187, 197, 207, 217, 227, 237, 247, 257, or 267. In some embodiments, the VH domain-encoding polypeptide and the VL domain-encoding polypeptide are on the same vector. In some embodiments, the VH domain-encoding polypeptide and the VL domain-encoding polypeptide are on different vectors.

The present invention also includes fragments of the polynucleotides of the invention, as described elsewhere. Additionally polynucleotides that encode fusion polypeptides, Fab fragments, and other derivatives, as described herein, are also contemplated by the invention.

The polynucleotides can be produced or manufactured by any method known in the art. For example, if the nucleotide sequence of the antibody is known, a polynucleotide encoding the antibody can be assembled from chemically synthesized oligonucleotides (e.g., as described in Kutmeier et al., *Bio Techniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-ILT7 antibody, or antigen-binding fragment, variant, or derivative thereof of the invention, can be generated from nucleic acid from a suitable source. If a clone containing a nucleic acid encoding a particular antibody is not available, but the sequence of the antibody molecule is known, a nucleic acid encoding the antibody can be chemically synthesized or obtained from a suitable source (e.g., an antibody cDNA library, or a cDNA library generated from, or nucleic acid, e.g., poly A+RNA, isolated from, any tissue or cells expressing the antibody or other anti-ILT7 antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-ILT7 antibody. Amplified nucleic acids generated by PCR can then be cloned into replicable cloning vectors using any method well known in the art.

Once the nucleotide sequence and corresponding amino acid sequence of the anti-ILT7 antibody, or antigen-binding fragment, variant, or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al. (1990) Molecular Cloning, A Laboratory Manual (2nd ed.; Cold Spring Harbor Laboratory, Cold Spring Harbor, N.Y.) and Ausubel et al., eds. (1998) Current Protocols in Molecular Biology (John Wiley & Sons, NY), which are both incorporated by reference herein in their entireties), to generate antibodies having a different amino acid sequence, for example to create amino acid substitutions, deletions, and/or insertions.

A polynucleotide encoding an anti-ILT7 binding molecule, e.g., an antibody, or antigen-binding fragment, variant, or derivative thereof, can be composed of any polyribonucleotide or polydeoxyribonucleotide, which can be unmodified RNA or DNA or modified RNA or DNA. For example, a polynucleotide encoding anti-ILT7 antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide encoding an anti-ILT7 binding molecule, e.g., an antibody, or antigen-binding fragment, variant, or derivative thereof can be composed of triple-stranded regions comprising RNA or DNA or both RNA and DNA. A polynucleotide encoding an anti-ILT7 binding molecule, e.g., antibody, or antigen-binding fragment, variant, or derivative thereof, can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. Conservative amino acid substitutions can be made at one or more non-essential amino acid residues.

V. Fusion Proteins and Antibody Conjugates

As discussed in more detail elsewhere herein, anti-ILT7 binding molecules, e.g., antibodies of the invention, or antigen-binding fragments, variants, or derivatives thereof, can further be recombinantly fused to a heterologous polypeptide at the N- or C-terminus or chemically conjugated (including covalent and non-covalent conjugations) to polypeptides or other compositions. For example, anti-ILT7 antibodies can be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Anti-ILT7 antibodies of the invention, or antigen-binding fragments, variants, or derivatives thereof, can include derivatives that are modified, i.e., by the covalent attachment of any type of molecule to the antibody such that covalent attachment does not prevent the antibody from binding to ILT7. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

Anti-ILT7 binding molecules, e.g., antibodies of the invention, or antigen-binding fragments, variants, or derivatives thereof, can be composed of amino acids joined to each other by peptide bonds or modified peptide bonds, i.e., peptide isosteres, and can contain amino acids other than the 20 gene-encoded amino acids. For example, anti-ILT7 antibodies can be modified by natural processes, such as post-translational processing, or by chemical modification techniques that are well known in the art. Such modifications are well described in basic texts and in more detailed monographs, as well as in a voluminous research literature. Modifications can occur anywhere in the anti-ILT7 binding molecule, including the peptide backbone, the amino acid side-chains and the amino or carboxyl termini, or on moieties such as carbohydrates. It will be appreciated that the same type of modification can be present in the same or varying degrees at several sites in a given anti-ILT7 binding molecule. Also, a given anti-ILT7 binding molecule can contain many types of modifications. Anti-ILT7 binding molecules can be branched, for example, as a result of ubiquitination, and they can be cyclic, with or without branching. Cyclic, branched, and branched cyclic anti-ILT7 binding molecule can result from posttranslational natural processes or can be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, T. E. Creighton, W. H. Freeman and Company, NY; 2nd ed. (1993); Johnson, ed. (1983) Posttranslational Covalent Modification of Proteins (Academic Press, NY), pgs. 1-12; Seifter et al., *Meth. Enzymol.* 182:626-646 (1990); Rattan et al., *Ann. NY Acad. Sci.* 663:48-62 (1992)).

The present invention also provides for fusion proteins comprising an anti-ILT7 antibody, or antigen-binding fragment, variant, or derivative thereof, and a heterologous polypeptide. The heterologous polypeptide to which the antibody is fused can be useful for function or is useful to target the anti-ILT7 polypeptide expressing cells.

In one embodiment, a fusion protein of the invention comprises, consists essentially of, or consists of, a polypeptide having the amino acid sequence of any one or more of the VH domains of an antibody of the invention or the amino acid sequence of any one or more of the VL domains of an antibody of the invention or fragments, variants, or derivatives thereof, and a heterologous polypeptide sequence.

In another embodiment, a fusion protein for use in the diagnostic and treatment methods disclosed herein comprises, consists essentially of, or consists of a polypeptide having the amino acid sequence of any one, two, three of the CDRs of the VH domain of an anti-ILT7 antibody, or fragments, variants, or derivatives thereof, or the amino acid sequence of any one, two, three of the CDRs of the VL domain an anti-ILT7 antibody, or fragments, variants, or derivatives thereof, and a heterologous polypeptide sequence. In one embodiment, a fusion protein comprises a polypeptide having the amino acid sequence of at least one VH domain of an anti-ILT7 antibody of the invention and the amino acid sequence of at least one VL domain of an anti-ILT7 antibody of the invention or fragments, derivatives or variants thereof, and a heterologous polypeptide sequence. In some embodiments, the VH and VL domains of the fusion protein correspond to a single source antibody (or scFv or Fab fragment) that specifically binds at least one epitope of ILT7. In yet another embodiment, a fusion protein for use in the diagnostic and treatment methods disclosed herein comprises a polypeptide having the amino acid sequence of any one, two, three or more of the CDRs of the VH domain of an anti-ILT7 antibody and the amino acid sequence of any one, two, three or more of the CDRs of the VL domain of an anti-ILT7 antibody, or fragments or variants thereof, and a heterologous polypeptide sequence. In some embodiments, two, three, four, five, six, or more of the CDR(s) of the VH domain or VL domain correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., *Proc. Natl. Acad Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349:164-167 (1991)); CD44 (Aruffo et al., *Cell* 61:1303-1313 (1990)); CD28 and B7 (Linsley et al., *J. Exp. Med* 173:721-730 (1991)); CTLA-4 (Lisley et al., *J. Exp. Med* 174:561-569 (1991)); CD22 (Stamenkovic et al., *Cell* 66:1133-1144 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med* 174:1483-1489 (1991)); and IgE receptor a (Ridgway and Gorman, J. Cell. Biol. Vol. 115, Abstract No. 1448 (1991)).

As discussed elsewhere herein, anti-ILT7 binding molecules, e.g., antibodies of the invention, or antigen-binding fragments, variants, or derivatives thereof, can be fused to heterologous polypeptides to increase the in vivo half life of the polypeptides or for use in immunoassays using methods known in the art. For example, in one embodiment, PEG can be conjugated to the anti-ILT7 antibodies of the invention to increase their half-life in vivo. See Leong et al., *Cytokine* 16:106 (2001); Adv. in Drug Deliv. Rev. 54:531 (2002); or Weir et al., *Biochem. Soc. Transactions* 30:512 (2002).

Moreover, anti-ILT7 binding molecules, e.g., antibodies of the invention, or antigen-binding fragments, variants, or derivatives thereof, can be fused to marker sequences, such as a peptide to facilitate their purification or detection. In some embodiments, the marker amino acid sequence is a hexa-histidine peptide (SEQ ID NO: 299), such as the tag provided in a pQE vector (QIAGEN, Inc., 9259 Eton Avenue, Chatsworth, Calif., 91311), among others, many of which are commercially available. As described in Gentz et al., *Proc. Natl. Acad Sci. USA* 86:821-824 (1989), for instance, hexa-histidine (SEQ ID NO: 299) provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,116,964 and 5,225,538). The precise site at which the fusion is made can be selected empirically to optimize the secretion or binding characteristics of the fusion protein. DNA encoding the fusion protein is then transfected into a host cell for expression.

Anti-ILT7 binding molecules, e.g., antibodies of the present invention, or antigen-binding fragments, variants, or derivatives thereof, can be used in non-conjugated form or can be conjugated to at least one of a variety of molecules, e.g., to improve the therapeutic properties of the molecule, to facilitate target detection, or for imaging or therapy of the patient. Anti-ILT7 binding molecules, e.g., antibodies of the invention, or antigen-binding fragments, variants, or derivatives thereof, can be labeled or conjugated either before or after purification, or when purification is performed.

In particular, anti-ILT7 antibodies of the invention, or antigen-binding fragments, variants, or derivatives thereof, can be conjugated to therapeutic agents, prodrugs, peptides, proteins, enzymes, viruses, lipids, biological response modifiers, pharmaceutical agents, or PEG.

Those skilled in the art will appreciate that conjugates can also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker can be prepared in the presence of a coupling agent, e.g., those listed herein, or by reaction with an isothiocyanate, such as fluorescein-isothiocyanate. Conjugates of the anti-ILT7 antibodies of the invention, or antigen-binding fragments, variants, or derivatives thereof, are prepared in an analogous manner.

The present invention further encompasses anti-ILT7 binding molecules, e.g., antibodies of the invention, or antigen-binding fragments, variants, or derivatives thereof, conjugated to a diagnostic or therapeutic agent. The anti-ILT7 antibodies, including antigen-binding fragments, variants, and derivatives thereof, can be used diagnostically to, for example, monitor the development or progression of a disease as part of a clinical testing procedure to, e.g., determine the efficacy of a given treatment and/or prevention regimen. For example, detection can be facilitated by coupling the anti-ILT7 antibody, or antigen-binding fragment, variant, or derivative thereof, to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$, $^{111}$In, $^{90}$Y, or $^{99}$Tc.

An anti-ILT7 binding molecule, e.g., an antibody, or antigen-binding fragment, variant, or derivative thereof, also can be detectably labeled by coupling it to a chemiluminescent compound. The presence of the chemiluminescent-tagged anti-ILT7 binding molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an anti-ILT7 antibody, or antigen-binding fragment, variant, or derivative thereof, can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md.; Diagnostic Horizons 2:1-7 (1978); Voller et al., J. Clin. Pathol. 31:507-520 (1978); Butler, Meth. Enzymol. 73:482-523 (1981); Maggio, ed. (1980) Enzyme Immunoassay, CRC Press, Boca Raton, Fla.; Ishikawa et al., eds. (1981) Enzyme Immunoassay (Kgaku Shoin, Tokyo). The enzyme, which is bound to the anti-ILT7 antibody will react with an appropriate substrate, such as a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection can also be accomplished by visual comparison of the extent of enzymatic reaction of a substrate in comparison with similarly prepared standards.

Detection may also be accomplished using any of a variety of other immunoassays. For example, by radioactively labeling the anti-ILT7 binding molecule, e.g., antibody, or antigen-binding fragment, variant, or derivative thereof, it is possible to detect the binding molecule through the use of a radioimmunoassay (RIA) (see, for example, Weintraub (March, 1986) Principles of Radioimmunoassays, Seventh Training Course on Radioligand Assay Techniques (The Endocrine Society), which is incorporated by reference herein). The radioactive isotope can be detected by means including, but not limited to, a gamma counter, a scintillation counter, or autoradiography.

An anti-ILT7 binding molecule, e.g., antibody, or antigen-binding fragment, variant, or derivative thereof, can also be detectably labeled using fluorescence emitting metals such as 152Eu, or others of the lanthanide series. These metals can be attached to the binding molecule using such metal chelating groups as diethylenetriaminepentacetic acid (DTPA) or ethylenediaminetetraacetic acid (EDTA).

Techniques for conjugating various moieties to an antibody (e.g., an anti-ILT7 antibody), or antigen-binding fragment, variant, or derivative thereof, are well known, see, e.g., Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-56; Hellstrom et al. (1987) "Antibodies for Drug Delivery," in Controlled Drug Delivery, ed. Robinson et al. (2nd ed.; Marcel Dekker, Inc.), pp. 623-53); Thorpe (1985) "Antibody Carriers of Cytotoxic Agents in Cancer Therapy: A Review," in Monoclonal Antibodies '84: Biological and Clinical Applications, ed. Pinchera et al., pp. 475-506; "Analysis, Results, and Future Prospective of the Therapeutic Use of Radiolabeled Antibody in Cancer Therapy," in Monoclonal Antibodies for Cancer Detection and Therapy, ed. Baldwin et al., Academic Press, pp. 303-16 (1985); and Thorpe et al. (1982) "The Preparation and Cytotoxic Properties of Antibody-Toxin Conjugates," Immunol. Rev. 62:119-58.

VI. Expression of Antibody Polypeptides

DNA sequences that encode the light and the heavy chains of the antibody can be made, either simultaneously or separately, using reverse transcriptase and DNA polymerase in accordance with well known methods. PCR can be initiated by consensus constant region primers or by more specific primers based on the published heavy and light chain DNA and amino acid sequences. As discussed above, PCR also can be used to isolate DNA clones encoding the antibody light and heavy chains. In this case, the libraries can be screened by consensus primers or larger homologous probes, such as mouse constant region probes.

DNA, typically plasmid DNA, can be isolated from the cells using techniques known in the art, restriction mapped and sequenced in accordance with standard, well known techniques set forth in detail, e.g., in the foregoing references relating to recombinant DNA techniques. Of course, the DNA can be synthetic according to the present invention at any point during the isolation process or subsequent analysis.

Following manipulation of the isolated genetic material to provide anti-ILT7 antibodies, or antigen-binding fragments, variants, or derivatives thereof, of the invention, the polynucleotides encoding the anti-ILT7 antibodies are typically inserted in an expression vector for introduction into host cells that can be used to produce the desired quantity of anti-ILT7 antibody.

Recombinant expression of an antibody, or fragment, variant, or derivative thereof, e.g., a heavy or light chain of an antibody that binds to a target molecule described herein, e.g., ILT7, requires construction of an expression vector containing a polynucleotide that encodes the antibody. Once a polynucleotide encoding an antibody molecule or a heavy or light chain of an antibody, or portion thereof (e.g., containing the heavy or light chain variable domain), of the invention has been obtained, the vector for the production of the antibody molecule can be produced by recombinant DNA technology using techniques well known in the art. Thus, methods for preparing a protein by expressing a polynucleotide containing an antibody encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors can include the nucleotide sequence encoding the constant region of the antibody molecule (see, e.g., PCT Publication WO 86/05807; PCT Publication WO 89/01036; and U.S. Pat. No. 5,122,464) and the variable domain of the antibody can be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors can easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems can be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells that have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements can also be needed for optimal synthesis of mRNA. These elements can include signal sequences, splice signals, as well as transcriptional promoters, enhancers, and termination signals.

In some embodiments, the cloned variable region genes are inserted into an expression vector along with the heavy and light chain constant region genes (e.g., human) synthesized as discussed above. Of course, any expression vector that is capable of eliciting expression in eukaryotic cells can be used in the present invention. Examples of suitable vectors include, but are not limited to plasmids pcDNA3, pHCMV/Zeo, pCR3.1, pEF 1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those that express suitably high levels if immunoglobulin heavy and light chains is routine experimentation that can be carried out, for example, by robotic systems.

More generally, once the vector or DNA sequence encoding a monomeric subunit of the anti-ILT7 antibody has been prepared, the expression vector can be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in Vectors, ed. Rodriguez and Denhardt (Butterworths, Boston, Mass.), Chapter 24.2, pp. 470-472. Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques, and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In some embodiments for the expression of double-chained antibodies, vectors encoding both the heavy and light chains can be co-expressed in the host cell for expression of the entire immunoglobulin molecule, as detailed below.

As used herein, "host cells" refers to cells that harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" can mean either from spun down whole cells, or from the cell culture containing both the medium and the suspended cells.

A variety of host-expression vector systems can be utilized to express antibody molecules for use in the methods described herein. Such host-expression systems represent vehicles by which the coding sequences of interest can be produced and subsequently purified, but also represent cells that can, when transformed or transfected with the appropriate nucleotide coding sequences, express an antibody molecule of the invention in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli* or eukaryotic cells, especially for the expression of whole recombinant antibody molecule, are used for the expression of a recombinant antibody molecule. For example, mammalian cells such as Chinese hamster ovary cells (CHO), in conjunction with vectors comprising, e.g., the major intermediate early gene promoter element from human cytomegalovirus are an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to determine particular host cell lines that are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain can be chosen that modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used.

For long-term, high-yield production of recombinant proteins, stable expression is useful. For example, cell lines that stably express the antibody molecule can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the antibody molecule.

A number of selection systems can be used, including, but not limited to, the herpes simplex virus thymidine kinase (Wigler et al., *Cell* 11:223 (1977)), hypoxanthine-guanine phosphoribosyltransferase (Szybalska and Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad Sci. USA* 78:1527 (1981)); gpt, which confers resistance to mycophenolic acid (Mulligan and Berg, *Proc. Natl. Acad. Sci. USA* 78:2072 (1981)); neo, which confers resistance to the aminoglycoside G-418 Clinical Pharmacy 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); TIB TECH 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (1993) Current Protocols in Molecular Biology (John Wiley & Sons, NY); Kriegler (1990) "Gene Transfer and Expression" in A Laboratory Manual (Stockton Press, NY); Dracopoli et al. (eds) (1994) Current Protocols in Human Genetics (John Wiley & Sons, NY) Chapters 12 and 13; Colberre-Garapin et al. (1981) J. Mol. Biol. 150:1, which are incorporated by reference herein in their entireties.

The expression levels of an antibody molecule can be increased by vector amplification (for a review, see Bebbington and Hentschel (1987) "The Use of Vectors Based on Gene Amplification for the Expression of Cloned Genes in Mammalian Cells in DNA Cloning" (Academic Press, NY) Vol. 3. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding anti-ILT7 antibodies, or antigen-binding fragments, variants, or derivatives thereof of the invention can also be expressed in non-mammalian cells such as insect, bacteria or yeast or plant cells. Bacteria that readily take up nucleic acids include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO 02/096948A2).

In bacterial systems, a number of expression vectors can be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., *EMBO J.* 2:1791 (1983)), in which the antibody coding sequence can be ligated individually into the vector in frame with the lacZ coding region so that a fusion protein is produced; pIN vectors (Inouye and Inouye, *Nucleic Acids Res.* 13:3101-3109 (1985); Van Heeke and Schuster, *J. Biol. Chem.* 24:5503-5509 (1989)); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes can also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., *Nature* 282:39 (1979); Kingsman et al., *Gene* 7:141 (1979); Tschemper et al., *Gene* 10:157 (1980)) is commonly used. This plasmid already contains the TRP1 gene, which provides a selection marker for a mutant strain of yeast lacking the ability to grow in tryptophan, for example ATCC No. 44076 or PEP4-1 (Jones, Genetics 85:12 (1977)). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

Once a binding molecule of the invention has been recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a beneficial method for increasing the affinity of antibodies of the invention is disclosed in U.S. Patent Application Publication No. 2002 0123057 A1.

VII. Treatment Methods Using Therapeutic Anti-ILT7 Binding Molecules

Methods of the invention are directed to the use of anti-ILT7 binding molecules, e.g., antibodies, including antigen-binding fragments, variants, and derivatives thereof, to treat patients having a disease associated with ILT7 expression or ILT7-expressing cells. By "ILT7-expressing cell" is intended cells expressing ILT7 antigen. Methods for detecting ILT7 expression in cells are well known in the art and include, but are not limited to, PCR techniques, immunohistochemistry, flow cytometry, Western blot, ELISA, and the like.

Though the following discussion refers to diagnostic methods and treatment of various diseases and disorders with an anti-ILT7 antibody of the invention, the methods described herein are also applicable to the antigen-binding fragments, variants, and derivatives of these anti-ILT7 antibodies that retain the desired properties of the anti-ILT7 antibodies of the invention, e.g., capable of specifically binding ILT7 and neutralizing ILT7 pathogenic activity.

In one embodiment, treatment includes the application or administration of an anti-ILT7 binding molecule, e.g., an antibody or antigen binding fragment, variant, or derivative thereof of the current invention to a subject or patient, or application or administration of the anti-ILT7 binding molecule to an isolated tissue or cell line from a subject or patient, where the subject or patient has a disease, a symptom of a disease, or a predisposition toward a disease. In another embodiment, treatment is also intended to include the application or administration of a pharmaceutical composition comprising the anti-ILT7 binding molecule, e.g., an antibody or antigen binding fragment, variant, or derivative thereof of the current invention to a subject or patient, or application or administration of a pharmaceutical composition comprising the anti-ILT7 binding molecule to an isolated tissue or cell line from a subject or patient, who has a disease, a symptom of a disease, or a predisposition toward a disease.

The anti-ILT7 binding molecules, e.g., antibodies or antigen-binding fragments, variants, or derivatives thereof of the present invention are useful for the treatment of various autoimmune conditions. For example, therapy with at least one anti-ILT7 antibody causes a physiological response, for example, a reduction in interferon, that is beneficial with respect to treatment of disease states associated with ILT7-expressing cells in a human.

In one embodiment, the invention relates to anti-ILT7 binding molecules, e.g., antibodies or antigen-binding fragments, variants, or derivatives thereof for use as a medicament, in particular for use in the treatment or prophylaxis of an autoimmune condition or disease. Examples of autoimmune diseases include, but are not limited to: myositis, diabetes, Hashimoto's disease, autoimmune adrenal insufficiency, pure red cell anemia, multiple sclerosis, rheumatoid carditis, systemic lupus erythematosus, psoriasis, rheumatoid arthritis, chronic inflammation, Sjogren's syndrome, polymyositis, dermatomyositis, inclusion body myositis, juvenile myositis, and scleroderma.

In accordance with the methods of the present invention, at least one anti-ILT7 binding molecule, e.g., an antibody or antigen binding fragment, variant, or derivative thereof as defined elsewhere herein is used to promote a positive therapeutic response with respect to an autoimmune response. By "positive therapeutic response" with respect to autoimmune treatment is intended an improvement in the disease in association with the activity of these binding molecules, e.g., antibodies or antigen-binding fragments, variants, or derivatives thereof, and/or an improvement in the symptoms associated with the disease. That is, a decrease in interferon-alpha levels, a decrease in the number or activity of plasmacytoid dendritic cells, or a decrease in one or more symptoms associated with the disease can be observed. Thus, for example, an improvement in the disease can be characterized as a complete response. By "complete response" is intended an absence of clinically detectable disease with normalization of any previously test results. Such a response must persist for at least one month following treatment according to the methods of the invention. Alternatively, an improvement in the disease can be categorized as being a partial response.

The anti-ILT7 binding molecules, e.g., antibodies or antigen binding fragments, variants, or derivatives thereof described herein can also find use in the treatment of autoimmune diseases and deficiencies or disorders of the immune system that are associated with ILT7 expressing cells. Autoimmune diseases are characterized by cellular, tissue and/or organ injury caused by an immunologic reaction of the subject to its own cells, tissues and/or organs. In one embodiment, the autoimmune disease is systemic lupus erythematosus.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-ILT7 binding molecule, e.g., an antibody or antigen-binding fragment, variant, or derivative thereof, can experience the beneficial effect of an improvement in the symptoms associated with the disease.

A further embodiment of the invention is the use of anti-ILT7 binding molecules, e.g., antibodies or antigen-binding fragments, variants, or derivatives thereof, for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

VIII. Pharmaceutical Compositions and Administration Methods

Methods of preparing and administering anti-ILT7 binding molecules, e.g., antibodies, or antigen-binding fragments, variants, or derivatives thereof, provided herein to a subject in need thereof are well known to or are readily determined by those skilled in the art.

As discussed herein, anti-ILT7 binding molecules, e.g., antibodies, or antigen-binding fragments, variants, or derivatives thereof, provided herein can be administered in a pharmaceutically effective amount for the in vivo treatment of ILT7-expressing cell-mediated diseases such as certain types autoimmune diseases. In this regard, it will be appreciated that the disclosed binding molecules of the invention will be formulated so as to facilitate administration and promote stability of the active agent. Pharmaceutical compositions in accordance with the present invention can comprise a pharmaceutically acceptable, non-toxic, sterile carrier. For the purposes of the instant application, a pharmaceutically effective amount of an anti-ILT7 binding molecule, e.g., an antibody, or antigen-binding fragment, variant, or derivative thereof, conjugated or unconjugated, shall be held to mean an amount sufficient to achieve effective binding to a target and to achieve a benefit, e.g., to ameliorate symptoms of a disease or condition or to detect a substance or a cell.

Pharmaceutical compositions suitable for injectable should be sterile and should be fluid to the extent that easy syringability exists. It should be stable under the conditions of manufacture and storage and will beneficially be preserved against the contaminating action of microorganisms, such as bacteria and fungi. Prevention of the action of microorganisms can be achieved by various antibacterial and antifungal agents. Suitable formulations for use in the therapeutic methods disclosed herein are described in Remington's Pharmaceutical Sciences (Mack Publishing Co.) 16th ed. (1980).

In keeping with the scope of the present disclosure, anti-ILT7 antibodies, or antigen-binding fragments, variants, or derivatives thereof of the invention can be administered to a human or other animal in accordance with the aforementioned methods of treatment in an amount sufficient to produce a therapeutic effect. The anti-ILT7 antibodies, or antigen-binding fragments, variants, or derivatives thereof of the invention can be administered to such human or other animal in a conventional dosage form prepared by combining the antibody or antigen-binding fragment, variant, or derivative thereof of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-ILT7 binding molecules, e.g., antibodies, or antigen-binding fragments, variants, or derivatives thereof, of the invention can prove to be particularly effective.

By "therapeutically effective dose or amount" or "effective amount" is intended an amount of anti-ILT7 binding molecule, e.g., antibody or antigen binding fragment, variant, or derivative thereof, that when administered brings about a positive therapeutic response with respect to treatment of a patient with a disease or condition to be treated.

Therapeutically effective doses of the compositions of the present invention, for treatment of ILT7-expressing cell-mediated diseases such as certain types of autoimmune diseases including e.g., systemic lupus erythematosus, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated to optimize safety and efficacy.

The present invention also provides for the use of an anti-ILT7 binding molecule, e.g., an antibody or antigen-binding fragment, variant, or derivative thereof, in the manufacture of a medicament for treating an autoimmune disease, including, e.g., systemic lupus erythematosus.

IX. Diagnostics

The invention further provides a diagnostic method useful during diagnosis of ILT7-expressing cell-mediated diseases such as certain types of autoimmune diseases including, e.g., systemic lupus erythematosus, which involves measuring the expression level of ILT7 protein or transcript in tissue or other cells or body fluid from an individual and comparing the measured expression level with a standard ILT7 expression level in normal tissue or body fluid, whereby an increase in the expression level compared to the standard is indicative of a disorder.

The anti-ILT7 antibodies of the invention and antigen-binding fragments, variants, and derivatives thereof, can be used to assay ILT7 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting ILT7 protein expression include immunoassays, such as the enzyme linked immunosorbent assay (ELISA), immunoprecipitation, or Western blotting. Suitable assays are described in more detail elsewhere herein.

By "assaying the expression level of ILT7 polypeptide" is intended qualitatively or quantitatively measuring or estimating the level of ILT7 polypeptide in a first biological sample either directly (e.g., by determining or estimating absolute protein level) or relatively (e.g., by comparing to the disease associated polypeptide level in a second biological sample). ILT7 polypeptide expression level in the first biological sample can be measured or estimated and compared to a standard ILT7 polypeptide level, the standard being taken from a second biological sample obtained from an individual not having the disorder or being determined by averaging levels from a population of individuals not having the disorder. As will be appreciated in the art, once the "standard" ILT7 polypeptide level is known, it can be used repeatedly as a standard for comparison.

By "biological sample" is intended any biological sample obtained from an individual, cell line, tissue culture, or other source of cells potentially expressing ILT7. Methods for obtaining tissue biopsies and body fluids from mammals are well known in the art.

X. Immunoassays

Anti-ILT7 binding molecules, e.g., antibodies, or antigen-binding fragments, variants, or derivatives thereof of the invention can be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety). Exemplary immunoassays are described briefly below (but are not intended by way of limitation).

Anti-ILT7 antibodies, or antigen-binding fragments, variants, or derivatives thereof of the invention, additionally, can be employed histologically, as in immunofluorescence, immunoelectron microscopy or non-immunological assays, for in situ detection of ILT7 protein or conserved variants or peptide fragments thereof. In situ detection can be accomplished by removing a histological specimen from a patient, and applying thereto a labeled anti-ILT7 antibody, or antigen-binding fragment, variant, or derivative thereof, e.g., applied by overlaying the labeled antibody (or fragment) onto a biological sample. Through the use of such a procedure, it is possible to determine not only the presence of ILT7 protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for ILT7 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to ILT7 or conserved variants or peptide fragments thereof, and detecting the bound antibody by any of a number of techniques well known in the art.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled anti-ILT7 antibody, or antigen-binding fragment, variant, or derivative thereof. The solid phase support can then be washed with the buffer a second time to remove unbound antibody. Optionally the antibody is subsequently labeled. The amount of bound label on solid support can then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Exemplary supports include polystyrene beads. Those skilled in the art will know many other suitable carriers for binding antibody or antigen, or will be able to ascertain the same by use of routine experimentation.

The binding activity of a given lot of anti-ILT7 antibody, or antigen-binding fragment, variant, or derivative thereof can be determined according to well known methods. Those skilled in the art will be able to determine operative and optimal assay conditions for each determination by employing routine experimentation.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon resonance (SPR) as performed on BIACORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BIAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to bind the first Mab, followed by addition of antigen and second MAb sequentially. The sensorgrams will reveal: (1) how much of the antigen binds to first Mab, (2) to what extent the second MAb binds to the surface-attached antigen, (3) if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides that interfere with binding of a given MAb are assumed to be structurally related to the epitope defined by that MAb.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Materials and Methods

Biological Samples

Human peripheral blood from normal healthy volunteers was obtained through MedImmune Blood Donor Program, with written informed consent and approval from the IRB. Peripheral blood mononuclear cells (PBMC) were isolated from fresh whole blood using Vacutainer CPT cell preparation tubes with sodium citrate (Becton Dickinson Biosciences, NJ, USA). Tubes were spun at 17000 g for 25 min, 22° C., with minimal braking. After the spin, the serum was removed, and the cellular buffy coat was transferred to conical 50 mL tubes (BD Biosciences). Purified cells were washed twice with sterile phosphate buffered saline (PBS) (Invitrogen Life Technologies, CA, USA) at 350 g for 10 minutes at 22° C. Cells were resuspended in PBS or RPMI 1640 media supplemented with 10% fetal bovine serum (Invitrogen) and were filtered using BD Falcon 5 mL tubes with cell strainer caps (BD Biosciences). Cell densities were determined using a Vi-Cell XR® cell counter (Beckman Coulter, Calif., USA).

Cynomolgus peripheral blood from healthy animals was obtained from Bioqual (Bioqual, Inc. MD, USA), in accordance with the guidelines of the National Institutes of Health for care and use of primates. Cynomolgus PBMCs were either isolated using Vacutainer CPT cell preparation tubes with sodium citrate (as described above) or with Histopaque 10771 (Sigma-Aldrich, Mo., USA). Briefly, fresh whole blood was adjusted to 50× the initial blood volume with sterile PBS. Then, 25 mL of diluted blood was overlaid onto 10 mL of 90% Histopaque 10771 (Sigma Aldrich) and samples were spun at 400 g for 20 min at room temperature with minimal braking. Cellular disc was removed and transferred to a new 50 mL conical tube. Purified cells were washed twice with sterile PBS at 350 g for 10 minutes at 22° C. Cells were resuspended in PBS or RPMI 1640 media supplemented with 10% fetal bovine serum, filtered, and counted as described above.

Cells

CT-125 and CT-550 cells were obtained from Dr. Yong-Jun Liu (University of Texas M. D. Anderson Cancer Center, Houston, Tex., USA). CT-125 cells were generated by transducing 2B4 murine T-cell hybridoma with untagged mouse FcεR1γ and a NFAT-GFP reporter gene and CT-550 cells were generated by transducing CT-125 cells with HA-tagged human ILT7 (Ohtsuka M. et al., PNAS 101: 8126-8131 (2004); Cao W. et al., JEM 203: pp 1399-1405 (2006)). CT-125 Cyno ILT7 stable cell line was generated by transfecting CT-125 cells with cynomolgus monkey ILT7 gene cloned into a pME18X plasmid vector. CT cells were cultured in RPMI 1640 supplemented with 10% fetal bovine serum (FBS) and 1× penicillin/streptomycin (all from Invitrogen Life Technologies).

KC1333 cells were obtained from Biowa (Biowa, NJ, USA). KC1333 cells were cultured in Advance RPMI 1640 supplemented with 10% FBS, 4 mM L-Glutamine, 0.2 μg/mL Geneticin (all from Invitrogen), and 18.3 pg/mL of recombinant human IL-2 (PeproTech, NJ, USA).

Antibodies and Reagents

Anti-ILT7 humanized antibody variants, anti-ILT7 clone 7C7 (7C7), and humanized isotype control R347 were generated at MedImmune. Allophycocyanin (APC) conjugated anti-ILT7 humanized antibody variants, 7C7, and isotype control R347 were generated using APC monoclonal antibody labeling kits (Thermo Fisher Scientific, IL, USA). R-Phycoerythrin (PE) and FITC-labeled anti-human BDCA-2 antibody (clone AC144), R-PE anti-human BDCA-4 (clone AD5-17F6), and Human FcR Blocking Reagent were from Miltenyi Biotech, CA, USA. Anti-human CD123 (clone 7G3) conjugated to either R-PE, FITC or APC, Alexa Fluor 488 anti-human CD8 (clone RPA-T8), Alexa Fluor 488 anti-human CD3 (clone SP34-2), FITC anti-human CD14 (clone M5E2), FITC anti-human CD20 (clone 2H7) and PerCP-Cy 5.5 anti-human HLA-DR (clone G46-6) were obtained from BD Biosciences. Pacific Blue anti-human CD56 antibody (clone MEM-188) was obtained from BioLegend, CA, USA. DyLight 649-labeled anti-human IgG and human whole IgG were from Jackson Immunoresearch, PA, USA.

Whole blood staining was done using BD FACS Lysing Solution (BD Biosciences). 7-AAD was obtained from Invitrogen. Human male AB plasma was from Sigma-Aldrich. Recombinant human IL-2 was from R&D Systems, MN, USA, and recombinant human interferon β (IFN-β) was from PBL Biomedical, NJ, USA. CpG A ODN 2216 was from InvivoGen, CA, USA.

Labeling of Human and Cynomolgus Recombinant IL 77

Proteins were biotinylated via free amines using EZ link Sulfo-NHS-LC-Biotin (Thermo/Pierce, product: 21335). The reagent was dissolved in anhydrous dimethylformamide, and the PBS based protein solutions were adjusted to pH ~8 with 1 M $NaHCO_3$ in D-PBS.

Label incorporations were assessed by MALDI-TOF mass spectrometry in all cases, and unreacted reagents were cleared by buffer exchange using D-PBS equilibrated disposable Sephadex G25 columns. For biotinylations the final protein concentrations were determined by 280 nm absorbance using extinction coefficients calculated from amino acid sequences.

ELISA Binding Assay

Single-chain Fv fragments were displayed on phage particles and tested in a binding assay to determine cross-reactivity and specificity to a panel of recombinant antigens. Phage-displayed scFv supernatant samples were generated in 96-well deep well plates as follows. 5 µl of culture from each well of a 96-well master plate was transferred into a Greiner deep well culture plate containing 500 µl of 2TYAG (2TY+100 µg/ml ampicillin+2% glucose) media and incubated for 5 hours at 37° C., 280 rpm. K07 M13 helper phage (diluted to $1.5 \times 10^{11}$ pfu/ml in 2TYAG) was then added at 100 µl/well and the plate incubated at 37° C., 150 rpm to allow infection. The plate was spun down at 3200 rpm for 10 minutes and the supernatant removed. Bacterial pellets were resuspended in 500 µl/well 2TYAK (2TY+100 µg/ml ampicillin+50 µg/ml kanamycin) and the plate incubated overnight at 25° C., 280 rpm. In the morning, 500 µl of 6% (w/v) skimmed milk powder in 2xPBS was added to each well and the plate incubated for 1 hour at room temperature. The plate was then centrifuged at 3200 rpm for 10 minutes and the blocked phage-displayed scFv supernatants were used directly in ELISA experiments.

For EC50 determinations, typically purified IgGs were diluted 3-fold in 3% (w/v) dried-milk powder in PBS (PBS-M), to give 11 concentration points. 96-well Greiner polypropylene plates (Greiner, 650201) were used for dilution preparation. Generally, each dilution was prepared in duplicate. IgG dilutions were allowed to block in PBS-M for 1 hour at room temperature before being used directly in ELISA experiments.

The IL-T7 binding assays were plate-based ELISAs performed essentially as follows. Not all antigens were used in every experiment, but typically a human, a mouse, and a cynomolgus IL-T7 antigen was tested. Relevant control antigens (bovine insulin plus IL-4Rα FLAG®His, if appropriate) were also used to test for non-specific binding. With the exception of bovine insulin, all antigens were biotinylated and all were generated using bacterial expression. IL-T7 antigens were biotinylated via free sulfhydryl groups using EZ link Biotin-BMCC (Perbio/Pierce 21900). The method for generation of IL-4Rα FLAG® His, which was used as a control antigen, is described in WO/2010/070346. IL-4Rα FLAG®His was biotinylated via free amines using EZ link Sulfo-NHS-LC-Biotin (Perbio/Pierce, 21335).

Streptavidin plates (Thermo Scientific, AB-1226) were coated with biotinylated antigen at 0.5 µg/ml in PBS and incubated overnight at 4° C. Plates were washed 3× with PBS and blocked with 300 µl/well blocking buffer (PBS-M) for 1 hour. Plates were washed 1× with PBS and blocked samples added, 50 µl/well for 1 hour at room temperature. Plates were washed 3× with PBS-T (PBS+1% (v/v) Tween-20) and detection reagents [anti-human IgG HRP (Sigma, A0170) or anti-M13-HRP antibody (Amersham, 27-9421-01) for detection of IgG or phage-displayed scFv, respectively] at 1:5000 dilutions were added at 50 µl/well in PBS-M for 1 hour at room temperature. Plates were washed 3× with PBS-T and developed with TMB, 50 µl/well (Sigma, T0440). The reaction was quenched with 50 µl/well 0.1M $H_2SO_4$ before reading on an EnVision™ plate reader, or similar equipment, at 450 nm.

Dose response curves were plotted for IgG titrations using Prism (Graphpad) curve-fitting software. Phage-displayed scFv were considered to bind the IL-T7 antigen if the absorbance 450 nm was >0.5, and <0.1-0.2 for the same sample on controls (insulin and IL-4Rα Flag®His). Single-chain Fv fragments were displayed on phage particles and tested as unpurified preparations in a single point ELISA screen.

Fluorescence Microvolume Assay Technology (FMAT) Cell Binding Assay

This homogeneous assay assessed the binding of crude scFv supernatant samples or purified IgG to Chinese Hamster Ovary (CHO) cells expressing either human or cynomolgus ILT7 in a 384-well (Costar 3655) format. ScFv or Ab binding to cells was detected using a mouse anti-His/goat anti-mouse Alexafluor®-647 labelled antibody (Molecular Probes A21236) mix, or goat anti-human Alexafluor®-647 labelled antibody (Molecular Probes A21445) respectively. Plates were read on the Applied Biosystems Cellular Detection system 8200 reader. The Helium neon excitation laser was focused within 100 µm depth of the bottom of the well, scanning an area 1 $mm^2$. The cells settled at the bottom of the well, and upon laser excitation at 633 nm, those beads with fluorophore bound (where the local concentration of fluorophore is relatively high compared to unbound fluorophore) emitted a signal at 650-685 nm that was measured using photomultiplier tube-1 (PMT1). Unbound fluorophore in solution was outside the excitation depth or at a relatively low local concentration, and thus did not emit a significant signal. The presence of scFv or IgG samples binding to the cells at the bottom of the well caused an increase in Alexafluor-labeled detection antibody within the excitation depth. This was measured as an increase in fluorescence.

In these experiments, the assay buffer was PBS (Gibco 14190-094) containing 0.1% BSA (Sigma A9576-50 ml), 0.1% Tween-20 (Sigma P2287), and 0.01% sodium azide. To create the ScFv detection mix, mouse anti-His and anti-mouse AF647 antibodies were mixed at 1 ug/ml and 2 ug/ml respectively in assay buffer. To create the IgG detection mix, anti-human AF647 antibody was prepared at 2 ug/ml in assay buffer.

The cells used were CHO-K1 cells expressing either human or cynomolgus ILT7 that were cultured using standard tissue culture techniques. Cells were grown to approximately 80% confluence in F-10 (Gibco, 22390-025)+10% FCS (SAFC Biosciences, 13068C)+0.5 mg/ml Zeocin (Invitrogen, R250-01), washed with PBS, detached with accutase (PAA, L11-007), and resuspended in PBS at $1.5 \times 10$ cells/ml.

Crude scFv supernatant samples were generated in 96 deep well plates. A 5 µl culture from each well of a 96-well master plate was transferred into a Greiner deep well culture plate containing 900 µl of 2TY (1.6% tryptone, 1% yeast extract, 0.5% NaCl, pH 7.0)+100 µg/ml ampicillin+0.1% glucose media and incubated for 5 hours at 37° C., 280 rpm. 10 mM IPTG in TY was then added at 100 µl/well, and the block was incubated overnight at 30° C., 280 rpm. In the morning, the block was spun down at 3200 rpm for 15 minutes. For high-throughput screening, scFv supernatants from the deep well block were transferred directly to the assay plate for the dilution required of 20%.

To test wells of a 384-well clear bottomed non-binding surface black Costar plate the following were added: 10 µl sample (IgG or ScFv), 10 µl detection antibody or antibody mix, and 30 µl cells. Negative controls used in these experiments typically involved addition of isotype (IgG) or irrelevant (ScFv) controls, or assay buffer in place of experimental sample. The plates were sealed and incubated for four hours at room temperature in the dark and then read on the Applied Biosystems Cellular Detection System 8200 reader. Data was typically analyzed with the Velocity algorithm, with gating set as color ratio <0.4, size 15-30, and min count 20. Hits from the crude scFv supernatant samples were defined as showing 50% or greater inhibition of signal compared to the total binding control wells. Dose response curves were plotted for purified IgG titrations using Prism (Graphpad) curve-fitting software.

For $IC_{50}$ determinations, typically purified IgGs were diluted 2-fold in assay buffer from 500 nM to give 11 concentration points. 96-well Greiner polypropylene (Greiner, 650201) plates were used for dilution preparation. Generally each dilution was prepared in duplicate. Alternatively, IgG testing was performed at a single concentration taken from the range 500 nM-0.2 nM.

Assessment of Antibody Binding on Cell Lines by Flow Cytometry

Binding of anti-ILT7 variants and isotype controls on human and cynomolgus ILT7 was assessed by flow cytometry analysis using CT-550 and cynoILT7 CT-125 cells respectively. CT-125 cells were used as control. Cells were resuspended in Blocking Buffer (PBS supplemented with 10% FBS) at a concentration of 5 million cells per mL and transferred into a round-bottom 96-well plates (BD Falcon™ Clear Microtest Plate, BD Biosciences) at 100 µL per well. Anti-ILT7 variants and control antibodies were added onto the cells for 30 min at 4° C. on a plate shaker. Cells were washed three times with PBS and resuspended in Blocking Buffer (100 µL/well). Human IgG binding on cell surface was detected using a secondary anti-human IgG antibody conjugated to DyLight 649 (1 in 1000 dilution). Cells were incubated in the dark for 30 min at 4° C. on a plate shaker. Cells were washed three times with PBS and surface fluorescence was acquired using LSRII Flow Cytometry System and FACSDiva Software (both from BD Biosciences).

Assessment of Antibody Binding on Whole Blood and PBMCs by Flow Cytometry

Binding of APC-labeled anti-ILT7 antibodies and isotype controls on human and cynomolgus whole blood was assessed by flow cytometry analysis. Whole blood was transferred into 50 mL conical tubes, 1 mL per tube. APC-labeled antibodies were added directly into whole blood. Anti-BDCA-2-PE and anti-CD123-PE antibodies were used as plasmacytoid dendritic cell (pDC)-specific markers in human whole blood staining and cynomolgus whole blood staining, respectively. The whole blood was incubated with the antibodies for 30 min at 4° C. in the dark on a plate shaker. Blood was treated with BD FACS Lysing Solution following the manufacturer's instructions. Cells were washed, and antibody binding was assessed by flow cytometry using LSRII Flow Cytometry System and FACSDiva Software.

For PBMC staining, PBMCs were first washed with PBS and resuspended in a cold PBS-based blocking buffer containing 50% human male AB plasma, 20 µg/mL human IgG and 200 µL/mL of Human FcR Blocking Reagent for 15 min at 4° C. on a plate shaker. After 15 min, APC-labeled anti-ILT7 variants or APC-labeled isotype control antibody were added directly into the blocking solution. Anti-BDCA-2-PE and anti-BDCA-4-PE antibodies were alternatively used as pDC-specific marker for human PBMC staining. In cynomolgus PBMCs, pDCs are defined as HLA-DR$^+$, Lineage$^-$, CD11c$^-$ and CD123$^{high}$ (Malleret et al., Immunology 124: 223-233 (2008)). Therefore, anti-HLA-DR PerCP-Cy5.5, Lineage-FITC (CD3, CD8, CD20 and CD14 antibodies) and anti-CD123-PE antibodies were used as a pDC-specific marker for cynomolgus PBMC staining. PBMCs were incubated for 30 min 4° C. in the dark on a plate shaker. Cells were washed and antibody binding was assessed by flow cytometry using LSRII Flow Cytometry System and FACSDiva Software.

Assessment of Antibody Potency by Antibody-Dependent Cell-Mediated Cytotoxicity (ADCC) Assay Using Cell Lines The potency of the anti-ILT7 antibodies was determined using an ADCC in vitro cell-based assay. KC1333 cells (effectors) and CT cells (targets) were co-cultured at a 5:1 ratio ($2.5 \times 10^5$ KC1333 for $0.5 \times 10^5$ CT cells) in round-bottom 96-well plates. Cells were co-cultured in presence of anti-ILT7 antibodies or isotype control for 16 hours in RPMI 1640 culture media supplemented with 10% FBS at 37° C., 5% $CO_2$. Cells were then washed and transferred into blocking buffer (PBS-10% FBS). KC1333 cells were detected using Pacific-Blue-anti-CD56 antibody. Dead cells were detected using 7-AAD. Target cell viability was assessed by flow cytometry using LSRII Flow Cytometry System and FACSDiva Software. The percentage of cytotoxicity was obtained by applying the following formula: percentage cytotoxicity=100−(number of live targets/number of live target at baseline)×100.

Assessment of Antibody Potency by ADCC Assay Using Human PBMCs

Human PBMCs were washed with PBS and resuspended in RPMI media supplemented with 10% FBS and 200 ng/mL recombinant human IL-2 at a concentration of $5.0 \times 10^6$ cells per mL. PBMCs were seeded in duplicate in round bottom 96-well plates, 100 µl per well. 10-fold serial dilutions of anti-ILT7 antibodies and control antibodies were prepared, and 100 µL of antibody solutions were added to appropriate wells for final concentrations of 33.85 nM-3.385 fM. Cells were incubated for 6 hours at 37° C., 5% $CO_2$. Following incubations, cells were washed twice in 250 µL cold PBS. Cells were resuspended in 100 µL of cold PBS-based blocking buffer containing 50% human male AB plasma, 20 µg/mL human IgG and 200 µL/mL of Human FcR Blocking Reagent for 15 min at 4° C. Following blocking step, 100 µL of cold blocking buffer containing FITC-anti-human BDCA2 and APC-anti-human CD123 antibodies was added to appropriate wells. Plates were incubated, gently shaking for 30 minutes at 4° C. After incubation, cells were washed twice in 250 µL cold PBS with final resuspension in 200 µL cold PBS. 50 µL of cold 7-AAD (Invitrogen) solution was added to all wells, and 7-AAD positive plasmacytoid dendritic cells were evaluated using LSRII Flow Cytometry System and FACSDiva Software.

IFNα Secretion Assays with Human PBMCs

Human PBMCs were washed with PBS and seeded in duplicate in round bottom, 96-well plates at a final density of 150,000-156,000 cells per well in RPMI media supplemented with 10% FBS and 200 ng/mL recombinant human IL-2. 10-fold serial dilutions of anti-ILT7 antibodies and control antibodies were prepared, and 100 µL of antibody solutions were added to appropriate wells for final concentrations of 6.77 nM-0.677 fM. Cells and antibodies were incubated for 9.5-10 hours at 37° C., 5% $CO_2$. Following incubations, 50 uL of ODN2216 (Invitrogen™) was added to appropriate wells for a final concentration of 0.5 µM, and plates were further incubated for an additional 16 hours at 37° C., 5% $CO_2$. Following incubations, plates were spun at 350 g for 10 minutes, supernatants were carefully removed, and IFNα was quantitated using a multisubtype IFNα ELISA kit (PBL Biomedical).

IFNα Secretion Assays with Cynomolgus Monkey PBMCs

Cynomolgus PBMCs were washed with PBS and resuspended in RPMI 1640 supplemented with 10% FBS, 220 ng/mL recombinant human IL-2, and 500 IU/mL recombinant human IFN-β. Maximum numbers of cells were added to appropriate wells with densities ranging from 314,000-818,000 cells per well. 10-fold serial dilutions of anti-ILT7 antibodies and control antibodies were prepared, and 100 µL of antibody solutions were added to appropriate wells for final concentrations of 33.85 nM-3.385 fM. Cells and antibodies were incubated for 9.5-10 hours at 37° C., 5% $CO_2$. Following incubations, 50 µL of ODN2216 (Invitrogen™) was added to appropriate wells for a final concentration of 0.5 M, and plates were further incubated for an additional 16 hours at 37° C., 5% $CO_2$. Following incubations, plates were spun at 350 g for 10 minutes, supernatants were carefully removed, and supernatant IFNα was quantitated using a rhesus/cynomolgus monkey IFNα ELISA kit (PBL Biomedical).

Statistical Analysis $EC_{50}$ and $IC_{50}$ curves for binding, ADCC, and cytokine secretion assays were generated using GraphPad Prims 5 software (GraphPad Software, CA, USA).

Example 1

Generation of Humanized ILT7 Antibodies from Murine Antibody SB128

Murine mAb SBI28 (SBI28 refers to the anti-ILT7 antibody ILT7#28 provided in U.S. Published Application No. 2009/0280128) was humanized by framework shuffling (Dall'Acqua et al., Methods 36:43-60 (2005)). Using this method, murine mAb SBI28 was humanized by synthesizing a combinatorial library comprised of its six CDRs fused in-frame to a pool of individual human germline frameworks. Human framework genes were selected from the publicly available pool of antibody germline genes. These universal framework primer pools include 46 human germline kappa chain genes, 5 human germline Jk sequences, 44 human germline heavy chain genes, and 6 human germline JH sequences. Primer banks were designed to encode each framework of each germline gene. Antibody-specific CDR primers were also synthesized with degenerate ends which overlap with the framework pools. The SBI28 framework shuffled library was constructed by pairing the variable heavy chain framework-shuffled sub-library with the variable light chain framework-shuffled sub-library. The framework-shuffled sub-libraries were assembled sequentially using the PCR by overlap extension. A first fusion-PCR was carried out to synthesize each individual human germline framework fused in-frame with a portion of the corresponding CDRs. A second "assembly-PCR" was then carried out using fusion-PCR product as template to amplify the full length VH and VL sub-libraries. The SBI28 framework-shuffled library was cloned into a M13-based Fab expression vector using Kunkel method hybridization mutagenesis. Approximately 1300 clones from the SBI28 framework-shuffled library were screened on CHO cells expressing recombinant ILT7CHO-cell using the MesoScale Discovery (MSD) assay. One humanized variant, 10D10, bound with 3-fold lower affinity to human ILT7 when compared to its chimeric parent ("SBI28ch") as measured by surface Plasmon Resonance (SPR) on ProteOn. SBI28ch refers to the anti-ILT7 antibody ILT7#28 as provided in U.S. Published Application No. 2009/0280128 which is herein incorporated by reference in its entirety.

Affinity optimization of 10D10 was initiated to improve its binding affinity to human and cynomolgus ILT7. 10D10 was first cloned into a M13-based ScFv expression vector for parsimonious mutagenesis. In this method, each individual amino acid of all 6 CDRs was randomly mutated using two separate libraries (NSS and NWS) per residue position. A total of 12 independent libraries were constructed for 6 CDRs using Kunkel method hybridization mutagenesis. (Kunkel, T. A., et al. Methods Enzymol. 154: 367 (1987)) The screening of the synthesized libraries consisted of a single-point ELISA designed to capture limiting concentrations of secreted ScFv from bacterial culture media to normalize the scFv concentration in each well. Labeled ILT7 antigen bound to the captured ScFv, and the signal strength of this interaction correlated with the relative binding affinity. Approximately 2,000 to 3,000 clones were screened. To further engineer a variant with improved affinity, all beneficial single amino acid changes were encoded together creating a small and focused combinatorial library. In this step, 14 individual positive hits at 9 positions in the 6 CDRs were encoded simultaneously to build the combinatorial scFv library. Briefly, degenerate primers were designed that encoded all beneficial amino acid changes as well as the parental residue at the same position. This combinatorial library was screened with a single point capture ELISA as previously described. Approximately 1,200 clones were screened. The variable regions of the affinity-improved variant 7C7 was individually cloned into the mammalian expression pOE vector and expressed transiently in HEK293 cells. The secreted, soluble human IgGs were purified directly from the conditioned media. Purified IgGs were assayed for binding to rILT7 using ProteOn and FACS. In the ProteOn experiment, the affinity optimized antibody 7C7 showed about 60-fold KD improvement over SBI28ch. By FACs, where binding to recombinant human and cyno ILT7 expressed on CHO cells was measured, 7C7 exhibited 2.2-fold and 14-fold better EC50 to human and cynomolgus ILT7, respectively, compared to SBI28ch. Alignments of the VH and VL sequences of SBI28, 10D10, and 7C7 are provided in FIGS. 1A and 1B, respectively.

Example 2

Generation of Human ILT7 Antibodies from Human Library

In addition to humanizing a murine anti-ILT7 antibody (as described above in Example 1), human antibodies were generated using a library of human sequences. Pursing multiple strategies for generating anti-ILT7 antibodies maximizes the chances of generating anti-ILT7 antibodies with distinct traits, so that the ideal antibody for a particular purpose can be selected.

2.1 Selections

A large single chain Fv (scFv) human antibody library produced using individual heavy chain variable region and light chain variable regions derived from bone marrow from adult naïve donors that were cloned into a phagemid vector based on filamentous phage M13 was used for selections (Hutchings, C., "Generation of Naïve Human Antibody Libraries" in Antibody Engineering, Dubel. Berlin, Springer Laboratory Manuals: p. 93 (2001); Lloyd et al., *Protein Eng. Des. Sel.* 22(3):159-68 (2009)). ILT7-specific scFv antibodies were isolated from the phage display library in a series of repeated selection cycles on recombinant human and/or cynomolgus ILT7 essentially as previously described in Vaughan et al. (*Nat. Biotechnol.* 14(3):309-14 (1996)). In brief, the scFv-phage particles were incubated with biotinylated recombinant ILT7 in solution (biotinylated via free amines using EZ link Sulfo-NHS-LC-Biotin (Thermo/Pierce, product: 21335)). Typically, scFv-phage particles were incubated with 100 nM biotinylated recombinant ILT7 for 1 hour. ScFv bound to antigen were then captured on streptavidin-coated paramagnetic beads (Dynabeads® M-280) following manufacturer's recommendations. Unbound phage was washed away in a series of wash cycles using PBS-Tween. The phage particles retained on the antigen were eluted, infected into bacteria, and rescued for the next round of selection. Typically three rounds of selection were performed in this way.

2.2 Identification of ILT7 Specific Binders by Phage ELISA scFvs were displayed on phage particles and tested in a binding assay to determine cross-reactivity and specificity to recombinant antigens. The detailed assay method is provided in the Materials and Methods section. Approximately 2100 separate data points were generated from the binding assay, and identified hits, i.e., scFv clones that showed binding to recombinant ILT7, were subjected to DNA sequencing (Osbourn et al., *Immunotechnology* 2(3):181-96 (1996); Vaughan et al., *Nat. Biotechnol.* 14(3):309-14 (1996)).

2.3 Identification of ILT7 Binders by FMAT

Unique scFvs were expressed in the bacterial periplasm and screened for their binding activity in a Fluorescence Microvolume Assay Technology (FMAT) binding assay. Binding of scFvs to ILT7 expressed on the cell surface was detected using a goat anti-mouse Alexafluor-647 labeled antibody. The detailed assay method is provided in the Materials and Methods section.

2.4 Reformatting of scFv to IgG1

The most potent scFv binders were converted to whole immunoglobulin G1 (IgG1) antibody format essentially as described by Persic et al (Gene 187(1):9-18 (1997)) with the following modifications. An OriP fragment was included in the expression vectors to facilitate use with CHO-transient cells and to allow episomal replication. The VH domain was cloned into a vector (pEU1.3) containing the human heavy chain constant domains and regulatory elements to express whole IgG1 heavy chain in mammalian cells. Similarly, the VL domain was cloned into a vector (pEU4.4) for the expression of the human light chain (lambda) constant domains and regulatory elements to express whole IgG light chain in mammalian cells. To obtain IgGs, the heavy and light chain IgG expressing vectors were transfected into CHO-transient mammalian cells. IgGs were expressed and secreted into the medium. Harvests were pooled and filtered prior to purification. Then IgG was purified using Protein A chromatography. Culture supernatants were loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralized by the addition of Tris-HCl (pH 9.0). The eluted material was buffer exchanged into PBS using Nap10 columns (Amersham, #17-0854-02), and the concentration of IgG was determined spectrophotometrically using an extinction coefficient based on the amino acid sequence of the IgG (Mach et al., *Anal. Biochem.* 200(1): 74-80 (1992)).

2.5 Binding Assay for IgGs

Species cross-reactivity of anti-ILT7 antibodies was determined using FMAT binding assay. The detailed assay method is provided in the Materials and Methods section. The following 11 antibodies were identified as antibodies that successfully bound to both human and cynomolgus ILT7 in the FMAT screening assay: ILT70019, ILT70028, ILT70052, ILT70076, ILT70080, ILT70083, ILT70089, ILT70100, ILT70137, ILT70142, and ILT70144.

Example 3

ILT7 Antibodies Bind to ILT7-Expressing Cells

In order to determine the binding $EC_{50}$ of ILT70019, ILT70028, ILT70052, ILT70076, ILT70080, ILT70083, ILT70089, ILT70100, ILT70137, ILT70142 and ILT70144 on cells expressing human ILT7, the candidates were screened for binding on CT-550 cells by flow cytometry. ILT70080 ($EC_{50}$=0.28 nM), ILT70083 ($EC_{50}$=0.37 nM), ILT70137 ($EC_{50}$=0.41 nM), ILT70144, ILT70142, ILT70052, and ILT70100 bound to human ILT7-expressing cells. Candidates ILT70019, ILT70028, and ILT70076 did not bind human ILT7-expressing cells. The anti-ILT7 antibodies 7C7 (7C7 is described above in Example 1) and SBI33 (SBI33 refers to the anti-ILT7 antibody ILT7#33 provided in U.S. Published Application No. 2009/0280128) were used as positive controls. Isotype control R347 was used as a negative control and did not show any binding on ILT7-expressing cells. The graph shown in FIG. 2 represents the mean results from two independent experiments, and the table shown in FIG. 2 shows the average $EC_{50}$.

In order to determine the binding $EC_{50}$ of the variants on cells expressing cynomolgus ILT7, the antibodies were screened for binding on CynoILT7 CT-125 cells by flow cytometry. ILT70052 ($EC_{50}$=0.35 nM), ILT70080 ($EC_{50}$=0.44 nM), ILT70083 ($EC_{50}$=1.37 nM), ILT70137 ($EC_{50}$=1.40 nM), ILT70100 ($EC_{50}$=1.63 nM) and ILT70144 ($EC_{50}$=7.81 nM), ILT70142, and ILT70089 were positive for binding on human ILT7. ILT70019, ILT70028, and ILT70076 did not bind cynomolgus ILT7-expressing cells. Isotype control R347 did not show any binding on ILT7-expressing cells. The graph in FIG. 3 represents the mean results from two independent experiments, and the table in FIG. 3 show the average $EC_{50}$.

Thus, all of ILT70052, ILT70080, ILT70083, ILT70100, ILT70137, ILT70142 and ILT70144 bind to cells expressing either cynomolgus ILT7 or human ILT7. Particularly low $EC_{50}$ values were obtained with cells expressing both cynomolgus and human ILT7 using, ILT70080, ILT70083, and ILT70137.

Example 4

ADCC Potency of ILT7 Antibodies

Anti-ILT7 antibodies were tested for ADCC potency against human ILT7-expressing cell lines using an in-vitro cell-based assay. Cells expressing human ILT7 (target cells) were plated in a proportion of 1:5 with the natural killer (NK) cell line KC1333 (effector cells) in the presence of anti-ILT7 variants or isotype control for 18 hours. During flow cytometry analysis, KC1333 cells were gated out using the NK marker CD56 (Biolegend #304624), and 7-AAD was used to distinguish viable from dead cells. Using this method, the percentage of live target cells was calculated and compared to the baseline (no antibody control). Cytotoxicity was calculated using the following formula:

Percent cytotoxicity=100−(Number of live targets/ Number of live targets is no antibody control)× 100

ILT70080 had the greatest ADCC potency against human ILT7-expressing cells ($EC_{50}$=0.022 nM), followed by ILT70137 ($EC_{50}$=0.044 nM) and ILT70083 ($EC_{50}$=0.094 nM). ILT70142, ILT70052, ILT70100 and ILT70144 also displayed ADCC activity (FIG. 4). Isotype control R347 and an afucosylated version of R347 ("Afuc R347") did not display any ADCC activity with human ILT7-expressing cells.

Anti-ILT7 antibodies were also tested for ADCC potency against cynomolgus ILT7-expressing cells using the in-vitro cell-based activity. ILT70080 had the greatest ADCC potency against cynomolgus ILT7-expressing cells ($EC_{50}$=0.008 nM), followed by ILT70137 ($EC_{50}$=0.015 nM), ILT70142 ($EC_{50}$=0.058 nM), ILT70052 ($EC_{50}$=0.073 nM), ILT70144 ($EC_{50}$=0.123), ILT70100 ($EC_{50}$=0.188 nM) and ILT70083 ($EC_{50}$=0.433 nM). ILT70089 also displayed ADCC activity. Positive control 7C7 displayed ADCC, and isotype (negative) control R347 did not display any ADCC with cynomolgus ILT7-expressing cells. The graph and table in FIG. 5 are representative of two independent experiments.

Thus, ILT70080 and ILT70137 showed the greatest ADCC activity in both cynomolgus and human ILT-7 expressing cells.

Example 5

Binding of ILT7 Antibodies to PBMCs

The binding of anti-ILT7 antibodies ILT70080, ILT70083, and ILT70137 on human PBMCs was assessed by flow cytometry using an antibody concentration of 2.5 μg/ml. ITL70080, ILT70083, and ILT70137 bound to specifically to pDCs (BDCA-4$^+$ cells) (FIGS. 6A and B). Binding was negative with the isotype control R347.

The binding of anti-ILT7 antibodies ILT70080, ILT70083, and ILT70137 on cynomolgus PBMCs was also assessed by flow cytometry. ITL70080 and ILT70083 bound specifically to pDCs (HLA-DR$^+$, Lineage$^-$, CD123$^{high}$ cells).

Example 6

Effect of ILT7 Antibodies on IFN-Alpha Secretion

Anti-ILT7 variants were tested for ADCC potency in human and cynomolgus PBMCs as described above. IFNα secretion in the supernatant of PBMCs cultured with anti-ILT7 antibodies and CpG-A was measured by ELISA. ILT70080, ILT70083, and ILT70137 all suppressed IFNα response to CpG-A in human and cynomolgus PBMCs. ILT70080 had the greatest suppressive effect on the IFNα response.

Example 7

Afucosylation of ILT70080 and ILT70083 Antibodies

IgG1 antibodies contain two sites for N-linked oligosaccharides in the Fc region, and these sites are heavily fucosylated in human antibodies. Antibody-dependent cellular cytotoxicity (ADCC) is mediated by the binding of lymphocyte receptors to antibody Fc regions, and this is affected by the amount of fucosylation. Increases in ADCC have been observed with decreased fucosylation. Therefore, afucosylated versions of ILT7 were generated and analyzed.

7.1 Generation of the Afucosylated Version of Anti-ILT7 Antibodies

ILT70080 and ILT70083 IgG$_1$ were expressed in a CHO cell line that lacks the enzyme α-1,6-fucosyltransferase. Expression in this cell line results in an antibody which lacks the α-1,6 fucose moiety on the N-glycan at Asn-297 of the heavy chain.

7.2 Testing of Afucosylated ILT70080 and ILT70083 Anti ILT7 Antibodies

A binding assay with afucosylated and parental ILT70080 and ILT70083 antibodies on ILT7-expressing cells was performed to assess whether afucosylation impacted the binding $EC_{50}$ of the antibodies. The parental and the afucosylated antibodies showed similar binding on both human and cynomolgus ILT7-expressing cells (FIG. 7).

ADCC potency of afucosylated ILT70080 and ILT70083 antibodies was tested on human and cynomolgus ILT7-expressing cells using the in-vitro cell-based assay described above (Example 3). Afucosylation increased ADCC potency for all the candidates tested (FIG. 8). A ten-fold increase in potency was observed for ILT70080 antibody upon afucosylation in both human and cynomolgus assays (from $EC_{50}$=0.013 nM to $EC_{50}$=0.001 nM, and from $EC_{50}$=0.006 nM to $EC_{50}$=0.00051 nM, respectively), while a 6 to 7-fold increase was observed for ILT70083 (from $EC_{50}$=0.089 nM to $EC_{50}$=0.0105 nM, and from $EC_{50}$=0.36 nM to $EC_{50}$=0.057 nM, respectively). Afucosylated isotype control R347 did not display any ADCC with ILT7-expressing cells.

The binding of afucosylated anti-ILT7 antibodies ILT70080 and ILT70083 on human PBMCs was assessed by flow cytometry. Afucosylated variants ITL70080 and ILT70083 bound specifically to pDCs (BDCA-2$^+$ cells). Binding was negative with the isotype control R347.

The binding of afucosylated anti-ILT7 variants ILT70080 and ILT70083 on cynomolgus PBMCs was also assessed by flow cytometry. Afucosylated variants ITL70080 and ILT70083 bound specifically to pDCs (HLA-DR$^+$ Lineage CD123$^{high}$). Binding was negative with the isotype control R347.

Example 8

Engineering of ILT70080 and ILT70083 Antibodies 8.1 Engineering of ILT70080

The amino acid sequences of ILT70080 VH and VL were aligned to the known human germline sequences in the VBASE database (Althaus H-H, Müller W and Tomlinson I: V BASE; http://vbase.mrc-cpe.cam.ac.uk/), and the closest germline sequence was identified by sequence similarity. For the VH domain this was VH1-69 (DP-10), and for the VL domain it was Vlambda3-h. Seven residues in the frameworks (FWs) of each of the VH domain (A13K, T16S, L69I*, S70T, L80M, Y84S and D85E) and VL domain (E3V, K20R, S22T, M46L*, M48I*, F50Y* and I66N*) were selected for reversion to the closest germline sequence. The mutations marked with an asterisk are at positions classified as Vernier residues (Foote, J. et al. J. Mol. Biol. 224: 487 (1992)) and are typically left unchanged. However, from analysis of both Kabat (Wu, T. T. and Kabat E. A. J. Exp. Med. 132:211-250 (1970)) and IMGT (Lefranc, M.-P. et al. Dev. Comp. Immunol. 27: 55-77 (2003)) classification of CDRs, these positions were considered to offer an additional opportunity to further reduce immunogenicity with a low risk of altering the binding properties of the parent antibody. Additionally, a heavy chain N64Q mutagenesis was performed within the VH CDR2 (Kabat-defined) sequence, to remove a potential deamidation (NG) site at this position. Mutagenesis was performed on ILT70080 scFv sequence in pCantab6 (McCafferty et al., Appl Biochem Biotech 47:157 (1994)) using standard molecular biology techniques. Different mutagenic oligonucleotide combinations were utilized in multiple mutagenesis reactions to generate libraries of sequences containing different combinations of FW mutations. Panels of ILT70080 scFv variants were then tested for retention of binding to human ILT7 as crude periplasmic extracts in an FMAT cell-binding assay as described above.

Seven ILT70080 variants were generated as IgG. See FIGS. 9A and 9B for VH and VL sequence alignments, respectively.

8.2 Engineering of ILT70083

Germlining of ILT70083 was also performed. The closest germline sequences identified were VH3-23 (DP-47) and Vlambda1-b (DPL-5) for VH and VL sequences, respectively. One FW residue was selected for mutagenesis in the VH domain (W66R), and eight FW residues were selected in the VL domain, again including selected Vernier positions (V4L*, R42T, A64G*, I66K*, S68G*, A72T, A74G and E81G). ILT70083 variants containing different combinations of mutations were generated directly on the pEU vectors containing separate VH and VL chains, using standard molecular biology techniques. ILT70083 VH and VL chains were then co-transfected in different combinations to generate nine ILT70083 IgG1 variants. See FIGS. 10A and 10B for VH and VL alignments, respectively.

8.3 Testing of Engineered Antibodies

The resultant IgG1s were tested to confirm that the sequence changes incorporated into ILT70080 and ILT70083 had not adversely impacted the binding of the parent antibody to cells expressing human ILT7 (CT-550 cells) or cynomolgus ILT7 (CT-125 cells). The variants were screened for binding by flow cytometry. All ILT70080 variants had a binding similar to the parental ILT70080 antibody to human and cynomolgus ILT7 ($EC_{50}$=0.213 nM and 0.547 nM, respectively). See FIG. 11. The binding of ILT70083 variants was also similar the parental antibody for human ILT7 ($EC_{50}$=0.464 nM). See FIG. 12. However, five ILT70083 variants (ILT70083.4, ILT70083.9, ILT70083.3, ILT70083.6, and ILT70083.8) had improved binding capacity compared to the parental antibody for cynomolgus ILT7. See FIG. 12.

Engineered ILT70080 and ILT70083 antibodies were tested for ADCC potency against human ILT7-expressing cell lines using an in-vitro cell-based assay. All ILT70080 variants had an increased ADCC potency compared to the parental antibody ($EC_{50}$<14.1 pM). See FIG. 13. The two candidates with the lowest $EC_{50}$ were ILT70080.6 ($EC_{50}$=6.9 pM) and ILT70080.1 ($EC_{50}$=8.0 pM). The $EC_{50}$ values for the other ILT70080 variants were as follows: ILT70080.1 $EC_{50}$=10.0 pM; ILT70080.3 $EC_{50}$=11.0 pM; ILT70080.4 $EC_{50}$=11.9 pM; ILT70080.5 $EC_{50}$=8.6 pM; and ILT70080.7 $EC_{50}$=7.8 pM. All ILT70083 variants were found to have a decreased potency compared to the parental antibody ($EC_{50}$>89.0 pM). See FIG. 14.

Example 9

Afucosylation of Engineered ILT70080 and ILT70083 Antibodies

Anfucosylated version of ILT70080.6 was generated. Afucosylation of the ILT70080.6 antibody did not affect its binding to either human or cynomolgus ILT7-expressing cells. The binding $EC_{50}$ of afucosylated ILT70080.6 on human and cynomolgus ILT7-expressing cells was 152.3 pM and 366.2 pM, respectively. See FIG. 15. The tables in FIG. 15 provide the mean results of three independent binding experiments measuring mean fluorescence intensity (MFI).

The ADCC activity of afucosylated versions of ILT70080.6 and ILT70083 (see Example 7 above) was also assessed. Afucosylation of ILT70080.6 improved its ADCC potency against both human and cynomolgus ILT7-expressing cells by about 10-fold. See FIG. 16. The $EC_{50}$ of afucosylated ILT0080.6 was 1.12 pM against human ILT7-expressing cells and 0.44 pM against cynomolgus ILT7-expressing cells. The tables in FIG. 16 provide the mean results of three independent ADCC assays measuring cytotoxicity.

Afucosylated ILT70080.6 and ILT70083 were tested for ADCC potency in human PBMCs. Cytotoxicity of the antibodies was assessed by flow cytometry and CpG A-mediated IFNα secretion in the supernatant was measured by ELISA. The results are shown in FIG. 17. In cynomolgus PBMCs, the EC50 values for IFNα secretion using afucosylated ILT70080.6 and ILT70083 antibodies were 58 pM and 5216 pM, respectively.

In human whole blood and PBMCs, afucosylated ILT70080.6 and ILT70083 antibodies were found to bind specifically to BDCA-2 positive cells. Binding of both antibodies was restricted to human pDC at all concentration tested (0.1-5.0 µg/mL).

In cynomolgus whole blood, afucosylated ILT70080.6 and ILT70083 antibodies were found to bind to pDCs (HLA-DR$^+$ Lineage$^-$ CD123$^{high}$ cells) at all concentrations tested (0.5-2.5 µg/ml).

Example 10

Afucosylation of ILT70137 Antibody

An afucosylated version of the ILT70137 antibody was made as described above in Example 7 for the ILT70080 and ILT70083 antibodies.

10.1 Binding to Soluble Recombinant Human ILT7

BIAcore (surface plasmon resonance) was used to measure the kinetic rate ($k_{on}$, $k_{off}$) constants for the binding of afucosylated IgG1 ILT70137 to human ILT7 protein using an IgG-capture assay format. The binding of each concentration of a two-fold dilution series of the ILT7 protein was recorded after first capturing IgG onto the sensor chip surface, followed by either the ILT7 protein or instrument buffer. In between each pair of injections, the IgG capture surface was regenerated. Individual association and dissociation rate constants were then calculated from the resulting binding curves using the Biaevaluation software available through the vendor's software employing a 1:1 fitting model, which included a term to correct for mass transport limited binding, should it be detected. From a high-resolution BIAcore plot of the data, the association rate constant and dissociation rate constants for the binding of ILT7 protein to afucosylated IgG$_1$ ILT70137 was determined to be $1.855 \times 10^5$ M$^{-1}$ s$^{-1}$. This same plot was also used to determine the corresponding dissociation rate constant for this interaction, which measured $3.175 \times 10^{-2}$ s$^{-1}$. From these rate constants, the K$_D$ was then calculated from the quotient of k$_{off}$/k$_{on}$ to be 171 nM. These results are summarized in Table 3, below. The individual errors for k$_{on}$ and k$_{off}$ were low, and the overall fit to the data was good as judged by Chi2 values of ~1% of the calculated R. (maximum response). Taken together, this suggests that the use of the one-site binding model to fit the data was appropriate. The evaluation did not indicate the binding was mass transport limited, so the measured association rate constants are considered valid.

TABLE 3

Summary of Kinetic Rate Constant and KD Data for the Binding of Human ILT7 Protein to Afucosylated IgG$_1$ ILT70137

| Interaction | k$_{on}$ (×10$^5$ M$^{-1}$s$^{-1}$) | k$_{off}$(×10$^{-2}$ s$^{-1}$) | K$_D$ (nM) |
| --- | --- | --- | --- |
| huILT7/Afuc IgG$_1$ ILT70137 | 1.855 | 3.175 | 171 |

K$_{on}$ = association rate constant; K$_{off}$ = dissociation rate constant; K$_D$ = equilibrium binding constant.

10.2 Binding to ILT7-Expressing Cell Lines

Binding of afucosylated ILT70137 to ILT7 was determined using cell lines stably expressing human or cynomolgus monkey ILT7. The mean fluorescence intensity of cell-bound antibodies was assessed by flow cytometry. Cells were incubated with increasing concentrations of test antibody ranging from 0.004 to 333.3 nM for 30 minutes at 4° C. After incubation, cells were washed with cold PBS and incubated for 30 minutes at 4° C. with an anti-human-Alexa Fluor 647 antibody. Fluorescent intensity was then determined by FACS and EC$_{50}$ values were calculated using a non-linear fit equation in GraphPad Prism 6 software.

The results are shown in FIG. 18. Afucosylated ILT70137 was found to bind recombinant human and cynomolgus monkey ILT7-expressing cells in a dose-dependent manner. No significant binding was observed with isotype controls. The average afucosylated ILT70137 half maximal effective concentration (EC$_{50}$) was 0.303 nM for binding to human ILT7-expressing and 2.148 nM for cynomolgus monkey ILT7-expressing cells.

10.3 ADCC Activity on ILT7-Expressing Cell Lines

The potential of afucosylated ILT70137 to induce ADCC was measured by a fluorescence-activated cell sorting (FACS) assay on target cells that express human or cynomolgus monkey ILT7. Target cells were co-cultured with effector NK cells line KC1333 at a ratio of 1:5 in the presence of increasing concentrations of afucosylated ILT70137 or an isotype control (ranging from 0-6.66×10$^{-9}$ M). For assessment of target cell viability by flow cytometry, KC1333 were gated out using CD56, and dead cells were gated out using 7-amino-actinomycin D (7-AAD) viability stain. The viable target cells were defined as CD56 negative, 7-AAD negative. The percentage of cytotoxicity was calculated using the following formula: % Cytotoxicity=100-(percentage of live target cells/percentage of live targets in No Antibody controls)×100. Half-maximal effective concentration values (EC$_{50}$) values were calculated using a non-linear fit equation in GraphPad Prism 6 software. x-axis: antibody concentration.

The results are shown in FIG. 19. Afucosylated ILT70137 induced ADCC on cells expressing ILT7 in a dose-dependent manner with an EC$_{50}$ of 4.19 pM on cells expressing human ILT-7 and 1.89 pM for cells expressing cynomolgus monkey ILT7.

10.4 ADCC Activity on Primary Plasmacytoid Dendritic Cells

IFN-α secretion in response to a Toll-like receptor 9 (TLR9) agonist is largely due to plasmacytoid dendritic cells (pDCs) in the peripheral blood mononuclear cell (PBMC) preparation. Therefore, the potential of afucosylated ILT70137 to induce ADCC of primary pDCs was indirectly measured by assessing its ability to block the secretion of IFN-α in PBMCs. In these assays, purified PBMCs were plated in 96-well, round bottom plates in media supplemented with 10% fetal bovine serum and 200 ng/mL recombinant human IL-2. Serial dilutions of afucosylated ILT70137 and the control antibodies were added to appropriate wells in duplicate and incubated for 9.5 hours. After incubation, 50 μL of the TLR9 agonist ODN2216 was added to each well for a final concentration of 0.5 μM. IFN-α was quantitated in supernatants using a multisubtype IFN-α ELISA kit, and is presented as pg/mL of supernatant in FIG. 20. The IC50 of ADCC was calculated using a non-linear fit equation in GraphPad Prism v5.01 software.

Afucosylated ILT70137 reduced TLR9-mediated secretion of IFN-α in PBMCs in a dose-dependent manner with a half-maximal inhibitory concentration (IC$_{50}$) of 0.048 nM. These results indicate that afucosylated ILT70137 effectively depletes naturally occurring primary human pDCs in PBMCs.

10.5 Binding to Primary Plasmacytoid Dendritic Cells

The specificity of afucosylated ILT70137 to human primary plasmacytoid dendritic cells (pDCs) was assessed by FACS in peripheral blood mononuclear cells (PBMCs). PBMCs were isolated from human donors. In order to properly identify this dendritic cell subset, the markers CD123 (expressed on pDCs and basophils) and CD304 (unique to pDCs) were first utilized. The pDCs were CD123+CD304+ double positive, and CD304 staining was sufficient to identify pDCs. See FIG. 21 (upper panel). Afucosylated ILT70137 bound only to CD304 positive cells, indicating that it binds uniquely to pDCs. See FIG. 21 (lower right panel). No significant binding to this population was observed with the human IgG1 isotype afucosylated control antibody R3-47. See FIG. 21 (lower left panel).

Example 11

In Vivo Activity of ILT7 Antibodies

Three anti-ILT7 antibodies were administered to male cynomolgus monkeys: afucosylated 7C7, afucosylated ILT70080.6, and afucosylated IgG1 ILT70137. All three antibodies were active in depleting plasmacytoid dendritic cells (pDCs).

Administration of afucosylated ILT70080.6 was generally well tolerated. However, the following pathological findings were observed: decreased neutrophil count, vascular leukocytosis, an increase in glomerular matrix, and vascular/perivascular inflammation. In addition, the appearance of antibodies against the afucosylated ILT70080.6 antibody (anti-drug antibodies) was associated with increased clearance of the afucosylated ILT70080.6.

In another study, the toxicokinetics of afucosylated 7C7 and afucosylated ILT70137 were studied. In this study 5 equivalent doses of the antibodies were administered to cynomolgus monkeys by infusion. Following administration, exposure was comparable between afucosylated 7C7 and afucosylated ILT70137 at steady state. In addition, as shown in FIG. 22, a specific and reversible depletion of pDCs was achieved using either antibody. The pDC depletion lead to an ex-vivo inhibition of IFNα production. See FIG. 23.

However, the pathology of animals treated with afucosylated 7C7 and afucosylated ILT70137 was different. Increased spleen weights were observed in some animals treated with afucosylated 7C7. Microscopic findings were also observed in some animals treated with afucosylated 7C7. In particular, red pulp and macrophage hypertrophy/hyperplasia were observed in spleens. Kupffer cell hypertrophy/hyperplasia was observed in livers. In addition, immunohistochemistry showed human IgG/7C7 and monkey IgG-containing granular deposits associated with hypertrophied/hyperplastic Kupffer cells in liver and red pup macrophages in spleen. These observations are consistent with exaggerated physiological clearance of immune complexes containing drug (7C7) and anti-drug antibodies (ADA). In contrast, no changes in organ weights and no macroscopic or microscopic findings were observed with afucosylated afucosylated ILT70137.

In addition, while neutrophil counts dropped below 1 E3/μl for two monkeys treated with the afucosylated 7C7 antibody, no significant changes in neutrophil count were observed in monkeys treated with control or afucosylated afucosylated ILT70137.

Thus, while all three antibodies depleted pDCs in vivo, the superior safety and lack of anti-drug antibodies after administration of afucosylated afucosylated ILT70137 is surprisingly advantageous.

Example 12

Epitope Mapping

In order to determine the epitope bound by the ILT7 antibodies, chimeric polypeptides containing ILT7 and ILT1 polypeptides were constructed, and the binding of ILT7 antibodies to these constructs was tested. ILT1 (Accession Number Q8N149) was selected to construct chimeric variants because it has the same modular structure as ILT7 and shares 65% identity with ILT7, but is not recognized by ILT7 monoclonal antibodies. The chimeric polypeptides were generated by replacing the extracellular Ig domains of ILT7 with ILT1 counterparts. All of these constructs contained an N-terminal Flag tag. The results demonstrated that ILT70080 and ILT70083 bind to the Ig1 domain of ILT7. In contrast, the 7C7 antibody binds to the Ig2 domain of ILT7.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An anti-Immunoglobulin-like transcript-7 (ILT7) antibody comprising Complementarity-Determining Regions (CDRs) HCDR1, HCDR2, HCDR3, LCDR1, LCDR2, and LCDR3, wherein the HCDR1, HCDR2, HCDR3, LCDR1, LCDR2, and LCDR3 comprise the amino acid sequences of SEQ ID NOs:203, 204, 205, 208, 209, and 210, respectively.

2. The anti-ILT7 antibody of claim 1, wherein the antibody comprises a heavy chain variable region (VH) and a light chain variable region (VL), wherein the VH and VL regions comprise an amino acid sequence at least 95% identical to SEQ ID NO:202 and SEQ ID NO:207, respectively.

3. The anti-ILT7 antibody of claim 2, wherein the VH and VL regions comprise the amino acid sequence of SEQ ID NO:202 and SEQ ID NO:207, respectively.

4. The anti-ILT7 antibody according to claim 1, wherein the antibody comprises a heavy chain immunoglobulin constant domain selected from the group consisting of an IgA constant domain, an IgD constant domain, an IgE constant domain, an IgG1 constant domain, an IgG2 constant domain, an IgG3 constant domain, an IgG4 constant domain, and an IgM constant domain.

5. The anti-ILT7 antibody of claim 4, wherein the antibody comprises an IgG1 constant domain.

6. The anti-ILT7 antibody according to claim 1, wherein the antibody comprises a light chain immunoglobulin constant domain selected from the group consisting of an Ig kappa constant domain and an Ig lambda constant domain.

7. The anti-ILT7 antibody of claim 6, wherein the antibody comprises a lambda constant domain.

8. The anti-ILT7 antibody according to claim 1, wherein the antibody is a monoclonal antibody.

9. The anti-ILT7 antibody according to claim 1, wherein the antibody is a human, chimeric, or resurfaced antibody.

10. The anti-ILT7 antibody of claim 9, wherein the antibody is a human antibody.

11. The anti-ILT7 antibody according to claim 1, wherein the antibody is afucosylated.

12. The anti-ILT7 antibody according to claim 1, wherein the antibody specifically binds to human and cynomolgus ILT7.

13. An afucosylated, human, monoclonal anti-ILT7 antibody comprising:
   i. Complementarity-Determining Regions (CDRs) HCDR1, HCDR2, HCDR3, LCDR1, LCDR2, and LCDR3;
   ii. a human IgG1 constant domain; and
   iii. a human lambda constant domain,
wherein the HCDR1, HCDR2, HCDR3, LCDR1, LCDR2, and LCDR3 comprise the amino acid sequences of SEQ ID NOs:203, 204, 205, 208, 209, and 210, respectively.

14. A polynucleotide comprising a nucleic acid encoding the anti-ILT7 antibody of claim 1.

15. A isolated host cell comprising the polynucleotide of claim 14.

16. A method of producing an anti-ILT7 antibody, comprising culturing the isolated host cell of claim 15, and recovering said antibody.

17. A method for detecting ILT7 expression in a sample comprising (a) contacting said sample with the anti-ILT7 antibody of claim 1 and (b) detecting binding of said antibody in said sample.

18. A method for decreasing interferon (IFN)-alpha release from a plasmacytoid dendritic cell (pDC), comprising contacting a pDC with the anti-ILT7 antibody of claim 1.

19. A method for treating a human subject with an autoimmune disease comprising administering to the subject an effective amount the anti-ILT7 antibody of claim 1.

20. The method of claim 19, wherein the autoimmune disease is selected from the group consisting of: myositis, diabetes, Hashimoto's disease, autoimmune adrenal insufficiency, pure red cell anemia, multiple sclerosis, rheumatoid carditis, systemic lupus erythematosus, psoriasis, rheumatoid arthritis, chronic inflammation, Sjogren's syndrome, polymyositis, dermatomyositis, inclusion body myositis, juvenile myositis, and scleroderma.

21. The method of claim 20, wherein the autoimmune disease is systemic lupus erythematosus.

22. An afucosylated IgG1 human monoclonal anti-ILT7 antibody comprising a heavy chain variable region (VH) and a light chain variable region (VL), wherein the heavy chain variable region comprises the amino acid of SEQ ID NO:202 and the light chain variable region comprises the amino acid of SEQ ID NO:207.

23. The anti-ILT7 antibody of claim 22, wherein the antibody comprises a human IgG1 constant domain; and a human lambda constant domain.

24. A pharmaceutical composition comprising the afucosylated IgG1 human monoclonal anti-ILT7 antibody of claim 22.

* * * * *

SEQUENCE LISTING

```
<160> NUMBER OF SEQ ID NOS: 299

<210> SEQ ID NO 1
<211> LENGTH: 351
<212> TYPE: DNA
<213> ORGANISM: Artificial Sequence
<220> FEATURE:
<223> OTHER INFORMATION: SBI28 VH

<400> SEQUENCE: 1
caggttcagc tgcagcagtc tggggctgag ctggtgaagc ctggggcctc agtgaagatg      60
tcctgcaagg cttttggcta caccttcact acctatccaa tagagtggat gaagcagaat     120
catgggaaga gcctagagtg gattggaaat tttcatcctt acaatgatga tactaagtac     180
aatgaaaaat tcaagggcaa ggccaaattg actgtagaaa aatcctctag cacagtctac     240
ttggagctca gccgattaac atctgatgac tctgctgttt attactgtgc aaggggggat     300
gattacggga tggactactg gggtcaagga acctcagtca ccgtctcctc a              351

<210> SEQ ID NO 2
<211> LENGTH: 117
<212> TYPE: PRT
<213> ORGANISM: Artificial Sequence
<220> FEATURE:
<223> OTHER INFORMATION: SBI28 VH

<400> SEQUENCE: 2
```

Gln Val Gln Leu Gln Gln Ser Gly Ala Glu Leu Val Lys Pro Gly Ala
1               5                   10                  15

Ser Val Lys Met Ser Cys Lys Ala Phe Gly Tyr Thr Phe Thr Thr Tyr
            20                  25                  30

Pro Ile Glu Trp Met Lys Gln Asn His Gly Lys Ser Leu Glu Trp Ile
        35                  40                  45

Gly Asn Phe His Pro Tyr Asn Asp Asp Thr Lys Tyr Asn Glu Lys Phe
50                  55                  60

Lys Gly Lys Ala Lys Leu Thr Val Glu Lys Ser Ser Thr Val Tyr
65                  70                  75                  80

Leu Glu Leu Ser Arg Leu Thr Ser Asp Asp Ser Ala Val Tyr Tyr Cys
                85                  90                  95

Ala Arg Gly Asp Asp Tyr Gly Met Asp Tyr Trp Gly Gln Gly Thr Ser
            100                 105                 110

Val Thr Val Ser Ser
        115

<210> SEQ ID NO 3
<211> LENGTH: 5
<212> TYPE: PRT
<213> ORGANISM: Artificial Sequence
<220> FEATURE:
<223> OTHER INFORMATION: SBI28 VHCDR1

<400> SEQUENCE: 3

Thr Tyr Pro Ile Glu
1               5

<210> SEQ ID NO 4
<211> LENGTH: 17
<212> TYPE: PRT
<213> ORGANISM: Artificial Sequence
<220> FEATURE:
<223> OTHER INFORMATION: SBI28 VHCDR2

<400> SEQUENCE: 4

Asn Phe His Pro Tyr Asn Asp Asp Thr Lys Tyr Asn Glu Lys Phe Lys
1               5                   10                  15

Gly

<210> SEQ ID NO 5
<211> LENGTH: 8
<212> TYPE: PRT
<213> ORGANISM: Artificial Sequence
<220> FEATURE:
<223> OTHER INFORMATION: SBI28 VHCDR3

<400> SEQUENCE: 5

Gly Asp Asp Tyr Gly Met Asp Tyr
1               5

<210> SEQ ID NO 6
<211> LENGTH: 321
<212> TYPE: DNA
<213> ORGANISM: Artificial Sequence
<220> FEATURE:
<223> OTHER INFORMATION: SBI28 VL

<400> SEQUENCE: 6
gacattgtga tgacccagtc tcaaaaattc atgtccacat cagtaggaga cagggtcagc      60
atcacctgca aggccagtca gaatgttcgt actgctgtag cctggtatca acagaaacca     120

```
gggcagtctc ctaaagcact gatttacttg gcatccaacc ggcacactgg agtccctgat    180
cgcttcacag gcagtggatc tgggacagat tcactctca ccattagcaa tgtgcaatct    240
gaagacctgg cagattattt ctgtctgcaa cattggaatt atccattcac gttcggctcg    300
gggacaaagt tggaaataaa a                                             321
```

```
<210> SEQ ID NO 7
<211> LENGTH: 107
<212> TYPE: PRT
<213> ORGANISM: Artificial Sequence
<220> FEATURE:
<223> OTHER INFORMATION: SBI28 VL

<400> SEQUENCE: 7

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Phe
                85                  90                  95

Thr Phe Gly Ser Gly Thr Lys Leu Glu Ile Lys
            100                 105

<210> SEQ ID NO 8
<211> LENGTH: 11
<212> TYPE: PRT
<213> ORGANISM: Artificial Sequence
<220> FEATURE:
<223> OTHER INFORMATION: SBI28 VLCDR1

<400> SEQUENCE: 8

Lys Ala Ser Gln Asn Val Arg Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: SBI28 VLCDR2

<400> SEQUENCE: 9

Leu Ala Ser Asn Arg His Thr
1               5

<210> SEQ ID NO 10
<211> LENGTH: 9
<212> TYPE: PRT
<213> ORGANISM: Artificial Sequence
<220> FEATURE:
<223> OTHER INFORMATION: SBI28 VLCDR3

<400> SEQUENCE: 10

Leu Gln His Trp Asn Tyr Pro Phe Thr
1               5
```

<210> SEQ ID NO 11
<211> LENGTH: 351
<212> TYPE: DNA
<213> ORGANISM: Artificial Sequence
<220> FEATURE:
<223> OTHER INFORMATION: 7C7 VH

<400> SEQUENCE: 11

```
gaggtgcagc tggtggagtc tgggggaggc gtagtacagc ctgggagatc cctgagactc    60
tcctgtgcag cctctggatt cacctttagc atctacccca tcgagtgggt gcgacaggct   120
cctggacagg gcctggaatg gatcggcaac ttccacccct acaacgacga caccaagtac   180
aacgagaagt tcaagggcag agtcaccatg accacagaca catccacgag cacagtgtac   240
atggagctga gcagcctgag atctgaggac acggccgtgt attactgtac gagaggcgac   300
gactacggcc tggactattg gggccagggc accctcgtga ccgtgtcctc t            351
```

<210> SEQ ID NO 12
<211> LENGTH: 117
<212> TYPE: PRT
<213> ORGANISM: Artificial Sequence
<220> FEATURE:
<223> OTHER INFORMATION: 7C7 VH

<400> SEQUENCE: 12

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ile Tyr
            20                  25                  30

Pro Ile Glu Trp Val Arg Gln Ala Pro Gly Gln Gly Leu Glu Trp Ile
        35                  40                  45

Gly Asn Phe His Pro Tyr Asn Asp Asp Thr Lys Tyr Asn Glu Lys Phe
    50                  55                  60

Lys Gly Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Asp Asp Tyr Gly Leu Asp Tyr Trp Gly Gln Gly Thr Leu
            100                 105                 110

Val Thr Val Ser Ser
        115

<210> SEQ ID NO 13
<211> LENGTH: 5
<212> TYPE: PRT
<213> ORGANISM: Artificial Sequence
<220> FEATURE:
<223> OTHER INFORMATION: 7C7 VHCDR1

<400> SEQUENCE: 13

Ile Tyr Pro Ile Glu
1               5

<210> SEQ ID NO 14
<211> LENGTH: 17
<212> TYPE: PRT
<213> ORGANISM: Artificial Sequence
<220> FEATURE:
<223> OTHER INFORMATION: 7C7 VHCDR2

<400> SEQUENCE: 14

Asn Phe His Pro Tyr Asn Asp Asp Thr Lys Tyr Asn Glu Lys Phe Lys

<210> SEQ ID NO 15
<211> LENGTH: 8
<212> TYPE: PRT
<213> ORGANISM: Artificial Sequence
<220> FEATURE:
<223> OTHER INFORMATION: 7C7 VHCDR3

<400> SEQUENCE: 15

Gly Asp Asp Tyr Gly Leu Asp Tyr
1               5

<210> SEQ ID NO 16
<211> LENGTH: 321
<212> TYPE: DNA
<213> ORGANISM: Artificial Sequence
<220> FEATURE:
<223> OTHER INFORMATION: 7C7 VL

<400> SEQUENCE: 16
aatattcaga tgacccagag cccgagcagc ctgagcgcaa gcgttggtga tcgtgttacc        60
attacctgtg acgccagcca gaatgttcgt accgcagttg catggtatca gcagaaaccg       120
ggtaaagcac cgaaacgtct gatttatctg gcaagtaatc gtcataccgg tgttccgagc       180
cgttttagcg gtagcggttc tggcaccgat tttaccctga ccattagcag cctgcagagc       240
gaagattttg ccacctatta ttgtctgcag cattggaatt atccgtttac ctttggtccg       300
ggtacaaaac tggaaattaa a                                                 321

<210> SEQ ID NO 17
<211> LENGTH: 107
<212> TYPE: PRT
<213> ORGANISM: Artificial Sequence
<220> FEATURE:
<223> OTHER INFORMATION: 7C7 VL

<400> SEQUENCE: 17

Asn Ile Gln Met Thr Gln Ser Pro Ser Ser Leu Ser Ala Ser Val Gly
1               5                   10                  15

Asp Arg Val Thr Ile Thr Cys Asp Ala Ser Gln Asn Val Arg Thr Ala
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Leu Gln His Trp Asn Tyr Pro Phe
                85                  90                  95

Thr Phe Gly Pro Gly Thr Lys Leu Glu Ile Lys
            100                 105

<210> SEQ ID NO 18
<211> LENGTH: 11
<212> TYPE: PRT
<213> ORGANISM: Artificial Sequence
<220> FEATURE:
<223> OTHER INFORMATION: 7C7 VLCDR1

<400> SEQUENCE: 18

Asp Ala Ser Gln Asn Val Arg Thr Ala Val Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: 7C7 VLCDR2

<400> SEQUENCE: 19

Leu Ala Ser Asn Arg His Thr
1               5

<210> SEQ ID NO 20
<211> LENGTH: 9
<212> TYPE: PRT
<213> ORGANISM: Artificial Sequence
<220> FEATURE:
<223> OTHER INFORMATION: 7C7 VLCDR3

<400> SEQUENCE: 20

Leu Gln His Trp Asn Tyr Pro Phe Thr
1               5

<210> SEQ ID NO 21
<211> LENGTH: 375
<212> TYPE: DNA
<213> ORGANISM: Artificial Sequence
<220> FEATURE:
<223> OTHER INFORMATION: ILT70080 VH

<400> SEQUENCE: 21
caggtgcagc tggtgcaatc tgggctgag gtgaaggcgc ctgggacttc ggtgaaagtc     60
tcctgcaagg catctggaga cagcttcagg aactatgctg tcagttgggt gcgacaggcc    120
ccaggacaag gtcttgagtg gatgggagcg atgatgccta gttttggaac aagggagcac    180
tcacagcagt tcaacggcag agtcacccTT ccgcggacg aatccacgag cacagcctac    240
ttggaactga gcagtctaag atatgacgac acggccgtct attactgtgc gggtagtcgg    300
gactacaatg cttaccattt ttggactggt cccccTGact tctggggccg aggaaccctg    360
gtcaccgtct cgagt                                                    375

<210> SEQ ID NO 22
<211> LENGTH: 125
<212> TYPE: PRT
<213> ORGANISM: Artificial Sequence
<220> FEATURE:
<223> OTHER INFORMATION: ILT70080 VH

<400> SEQUENCE: 22

Gln Val Gln Leu Val Gln Ser Gly Ala Glu Val Lys Ala Pro Gly Thr
1               5                   10                  15

Ser Val Lys Val Ser Cys Lys Ala Ser Gly Asp Ser Phe Arg Asn Tyr
            20                  25                  30

Ala Val Ser Trp Val Arg Gln Ala Pro Gly Gln Gly Leu Glu Trp Met
        35                  40                  45

Gly Ala Met Met Pro Ser Phe Gly Thr Arg Glu His Ser Gln Gln Phe
    50                  55                  60

Asn Gly Arg Val Thr Leu Ser Ala Asp Glu Ser Thr Ser Thr Ala Tyr
65                  70                  75                  80

-continued

```
Leu Glu Leu Ser Ser Leu Arg Tyr Asp Asp Thr Ala Val Tyr Tyr Cys
                85                  90                  95

Ala Gly Ser Arg Asp Tyr Asn Ala Tyr His Phe Trp Thr Gly Pro Pro
            100                 105                 110

Asp Phe Trp Gly Arg Gly Thr Leu Val Thr Val Ser Ser
        115                 120                 125

<210> SEQ ID NO 23
<211> LENGTH: 5
<212> TYPE: PRT
<213> ORGANISM: Artificial Sequence
<220> FEATURE:
<223> OTHER INFORMATION: ILT70080 VHCDR1

<400> SEQUENCE: 23

Asn Tyr Ala Val Ser
1               5

<210> SEQ ID NO 24
<211> LENGTH: 17
<212> TYPE: PRT
<213> ORGANISM: Artificial Sequence
<220> FEATURE:
<223> OTHER INFORMATION: ILT70080 VHCDR2

<400> SEQUENCE: 24

Ala Met Met Pro Ser Phe Gly Thr Arg Glu His Ser Gln Gln Phe Asn
1               5                   10                  15

Gly

<210> SEQ ID NO 25
<211> LENGTH: 16
<212> TYPE: PRT
<213> ORGANISM: Artificial Sequence
<220> FEATURE:
<223> OTHER INFORMATION: ILT70080 VHCDR3

<400> SEQUENCE: 25

Ser Arg Asp Tyr Asn Ala Tyr His Phe Trp Thr Gly Pro Pro Asp Phe
1               5                   10                  15

<210> SEQ ID NO 26
<211> LENGTH: 324
<212> TYPE: DNA
<213> ORGANISM: Artificial Sequence
<220> FEATURE:
<223> OTHER INFORMATION: ILT70080 VL

<400> SEQUENCE: 26
tcctatgagc tgactcagcc accctcagtg tcagtggccc caggaaagac ggccaagatt      60
tcctgtgggg gagacagcgt tggcagtaca agtgtccact ggtaccagca gaagccgggc     120
caggcccctg tgatggtcat gttttataac agtgaccggc cctcagggat ccctgagcga     180
ttctctggct ccatctctgg gaacacggcc accctgacca tcagcagggt cgaagccggg     240
gatgaggccg actattactg tcaggtgtgg gatactagta gtgatcatcc ggagttcggc     300
ggagggacca agctgaccgt ccta                                            324

<210> SEQ ID NO 27
<211> LENGTH: 108
<212> TYPE: PRT
<213> ORGANISM: Artificial Sequence
<220> FEATURE:
<223> OTHER INFORMATION: ILT70080 VL
```

-continued

<400> SEQUENCE: 27

Ser Tyr Glu Leu Thr Gln Pro Pro Ser Val Ser Val Ala Pro Gly Lys
1               5                   10                  15

Thr Ala Lys Ile Ser Cys Gly Gly Asp Ser Val Gly Ser Thr Ser Val
            20                  25                  30

His Trp Tyr Gln Gln Lys Pro Gly Gln Ala Pro Val Met Val Met Phe
        35                  40                  45

Tyr Asn Ser Asp Arg Pro Ser Gly Ile Pro Glu Arg Phe Ser Gly Ser
    50                  55                  60

Ile Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Pro Glu Phe Gly Gly Gly Thr Lys Leu Thr Val Leu
            100                 105

<210> SEQ ID NO 28
<211> LENGTH: 11
<212> TYPE: PRT
<213> ORGANISM: Artificial Sequence
<220> FEATURE:
<223> OTHER INFORMATION: ILT70080 VLCDR1

<400> SEQUENCE: 28

Gly Gly Asp Ser Val Gly Ser Thr Ser Val His
1               5                   10

<210> SEQ ID NO 29
<211> LENGTH: 7
<212> TYPE: PRT
<213> ORGANISM: Artificial Sequence
<220> FEATURE:
<223> OTHER INFORMATION: ILT70080 VLCDR2

<400> SEQUENCE: 29

Tyr Asn Ser Asp Arg Pro Ser
1               5

<210> SEQ ID NO 30
<211> LENGTH: 11
<212> TYPE: PRT
<213> ORGANISM: Artificial Sequence
<220> FEATURE:
<223> OTHER INFORMATION: ILT70080 VLCDR3

<400> SEQUENCE: 30

Gln Val Trp Asp Thr Ser Ser Asp His Pro Glu
1               5                   10

<210> SEQ ID NO 31
<211> LENGTH: 375
<212> TYPE: DNA
<213> ORGANISM: Artificial Sequence
<220> FEATURE:
<223> OTHER INFORMATION: ILT70080.1 VH

<400> SEQUENCE: 31
caggtgcagc tggtgcaatc tggggctgag gtgaagaagc ctgggtcttc ggtgaaagtc      60
tcctgcaagg catctggaga cagcttcagg aactatgctg tcagttgggt gcgacaggcc     120
ccaggacaag gtcttgagtg gatgggagcg atgatgccta gttttggaac aagggagcac     180

-continued

```
tcacagcagt tccagggcag agtcaccctt accgcggacg aatccacgag cacagcctac      240
atggaactga gcagtctaag atctgaggac acggccgtct attactgtgc gggtagtcgg      300
gactacaatg cttaccattt ttggactggt ccccctgact tctggggccg aggaaccctg      360
gtcaccgtct cctca                                                        375
```

```
<210> SEQ ID NO 32
<211> LENGTH: 125
<212> TYPE: PRT
<213> ORGANISM: Artificial Sequence
<220> FEATURE:
<223> OTHER INFORMATION: ILT70080.1 VH

<400> SEQUENCE: 32
```

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ser Phe Arg Asn Tyr
            20                  25                  30

Ala Val Ser Trp Val Arg Gln Ala Pro Gly Gln Gly Leu Glu Trp Met
        35                  40                  45

Gly Ala Met Met Pro Ser Phe Gly Thr Arg Glu His Ser Gln Gln Phe
    50                  55                  60

Gln Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ser Arg Asp Tyr Asn Ala Tyr His Phe Trp Thr Gly Pro Pro
            100                 105                 110

Asp Phe Trp Gly Arg Gly Thr Leu Val Thr Val Ser Ser
        115                 120                 125

```
<210> SEQ ID NO 33
<211> LENGTH: 5
<212> TYPE: PRT
<213> ORGANISM: Artificial Sequence
<220> FEATURE:
<223> OTHER INFORMATION: ILT70080.1 VHCDR1

<400> SEQUENCE: 33
```

Asn Tyr Ala Val Ser
1               5

```
<210> SEQ ID NO 34
<211> LENGTH: 17
<212> TYPE: PRT
<213> ORGANISM: Artificial Sequence
<220> FEATURE:
<223> OTHER INFORMATION: ILT70080.1 VHCDR2

<400> SEQUENCE: 34
```

Ala Met Met Pro Ser Phe Gly Thr Arg Glu His Ser Gln Gln Phe Gln
1               5                   10                  15

Gly

```
<210> SEQ ID NO 35
<211> LENGTH: 16
<212> TYPE: PRT
<213> ORGANISM: Artificial Sequence
<220> FEATURE:
<223> OTHER INFORMATION: ILT70080.1 VHCDR3

<400> SEQUENCE: 35
```

Ser Arg Asp Tyr Asn Ala Tyr His Phe Trp Thr Gly Pro Pro Asp Phe
1               5                   10                  15

<210> SEQ ID NO 36
<211> LENGTH: 324
<212> TYPE: DNA
<213> ORGANISM: Artificial Sequence
<220> FEATURE:
<223> OTHER INFORMATION: ILT70080.1 VL

<400> SEQUENCE: 36

```
tcctatgtgc tgactcagcc accctcagtg tcagtggccc caggaaagac ggccaggatt    60
acctgtgggg agacagcgt tggcagtaca agtgtccact ggtaccagca gaagccgggc   120
caggcccctg tgatggtcat gttttataac agtgaccggc cctcagggat ccctgagcga   180
ttctctggct ccatctctgg gaacacggcc accctgacca tcagcagggt cgaagccggg   240
gatgaggccg actattactg tcaggtgtgg gatactagta gtgatcatcc ggagttcggc   300
ggagggacca agctgaccgt ccta                                          324
```

<210> SEQ ID NO 37
<211> LENGTH: 108
<212> TYPE: PRT
<213> ORGANISM: Artificial Sequence
<220> FEATURE:
<223> OTHER INFORMATION: ILT70080.1 VL

<400> SEQUENCE: 37

Ser Tyr Val Leu Thr Gln Pro Pro Ser Val Ser Val Ala Pro Gly Lys
1               5                   10                  15

Thr Ala Arg Ile Thr Cys Gly Gly Asp Ser Val Gly Ser Thr Ser Val
            20                  25                  30

His Trp Tyr Gln Gln Lys Pro Gly Gln Ala Pro Val Met Val Met Phe
        35                  40                  45

Tyr Asn Ser Asp Arg Pro Ser Gly Ile Pro Glu Arg Phe Ser Gly Ser
    50                  55                  60

Ile Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Pro Glu Phe Gly Gly Gly Thr Lys Leu Thr Val Leu
            100                 105

<210> SEQ ID NO 38
<211> LENGTH: 11
<212> TYPE: PRT
<213> ORGANISM: Artificial Sequence
<220> FEATURE:
<223> OTHER INFORMATION: ILT70080.1 VLCDR1

<400> SEQUENCE: 38

Gly Gly Asp Ser Val Gly Ser Thr Ser Val His
1               5                   10

<210> SEQ ID NO 39
<211> LENGTH: 7
<212> TYPE: PRT
<213> ORGANISM: Artificial Sequence
<220> FEATURE:
<223> OTHER INFORMATION: ILT70080.1 VLCDR2

<400> SEQUENCE: 39

Tyr Asn Ser Asp Arg Pro Ser
1               5

<210> SEQ ID NO 40
<211> LENGTH: 11
<212> TYPE: PRT
<213> ORGANISM: Artificial Sequence
<220> FEATURE:
<223> OTHER INFORMATION: ILT70080.1 VLCDR3

<400> SEQUENCE: 40

Gln Val Trp Asp Thr Ser Ser Asp His Pro Glu
1               5                   10

<210> SEQ ID NO 41
<211> LENGTH: 375
<212> TYPE: DNA
<213> ORGANISM: Artificial Sequence
<220> FEATURE:
<223> OTHER INFORMATION: ILT70080.2 VH

<400> SEQUENCE: 41

```
caggtgcagc tggtgcaatc tggggctgag gtgaagaagc ctgggtcttc ggtgaaagtc     60
tcctgcaagg catctggaga cagcttcagg aactatgctg tcagttgggt gcgacaggcc    120
ccaggacaag gtcttgagtg gatgggagcg atgatgccta gttttggaac aagggagcac    180
tcacagcagt tccagggcag agtcacccct tccgcggacg aatccacgag cacagcctac    240
atggaactga gcagtctaag atctgaggac acggccgtct attactgtgc gggtagtcgg    300
gactacaatg cttaccattt ttggactggt ccccctgact ctggggccg aggaaccctg    360
gtcaccgtct cctca                                                    375
```

<210> SEQ ID NO 42
<211> LENGTH: 125
<212> TYPE: PRT
<213> ORGANISM: Artificial Sequence
<220> FEATURE:
<223> OTHER INFORMATION: ILT70080.2 VH

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ser Phe Arg Asn Tyr
            20                  25                  30

Ala Val Ser Trp Val Arg Gln Ala Pro Gly Gln Gly Leu Glu Trp Met
        35                  40                  45

Gly Ala Met Met Pro Ser Phe Gly Thr Arg Glu His Ser Gln Gln Phe
    50                  55                  60

Gln Gly Arg Val Thr Leu Ser Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ser Arg Asp Tyr Asn Ala Tyr His Phe Trp Thr Gly Pro Pro
            100                 105                 110

Asp Phe Trp Gly Arg Gly Thr Leu Val Thr Val Ser Ser
        115                 120                 125

<210> SEQ ID NO 43
<211> LENGTH: 5
<212> TYPE: PRT

```
<213> ORGANISM: Artificial Sequence
<220> FEATURE:
<223> OTHER INFORMATION: ILT70080.2 VHCDR1

<400> SEQUENCE: 43

Asn Tyr Ala Val Ser
1               5

<210> SEQ ID NO 44
<211> LENGTH: 17
<212> TYPE: PRT
<213> ORGANISM: Artificial Sequence
<220> FEATURE:
<223> OTHER INFORMATION: ILT70080.2 VHCDR2

<400> SEQUENCE: 44

Ala Met Met Pro Ser Phe Gly Thr Arg Glu His Ser Gln Gln Phe Gln
1               5                   10                  15

Gly

<210> SEQ ID NO 45
<211> LENGTH: 16
<212> TYPE: PRT
<213> ORGANISM: Artificial Sequence
<220> FEATURE:
<223> OTHER INFORMATION: ILT70080.2 VHCDR3

<400> SEQUENCE: 45

Ser Arg Asp Tyr Asn Ala Tyr His Phe Trp Thr Gly Pro Pro Asp Phe
1               5                   10                  15

<210> SEQ ID NO 46
<211> LENGTH: 324
<212> TYPE: DNA
<213> ORGANISM: Artificial Sequence
<220> FEATURE:
<223> OTHER INFORMATION: ILT70080.2 VL

<400> SEQUENCE: 46
tcctatgtgc tgactcagcc accctcagtg tcagtggccc caggaaagac ggccaggatt      60
acctgtgggg gagacagcgt tggcagtaca agtgtccact ggtaccagca gaagccgggc     120
caggcccctg tgatggtcat gttttataac agtgaccggc cctcagggat ccctgagcga     180
ttctctggct ccatctctgg gaacacggcc accctgacca tcagcagggt cgaagccggg     240
gatgaggccg actattactg tcaggtgtgg gatactagta gtgatcatcc ggagttcggc     300
ggagggacca agctgaccgt ccta                                            324

<210> SEQ ID NO 47
<211> LENGTH: 108
<212> TYPE: PRT
<213> ORGANISM: Artificial Sequence
<220> FEATURE:
<223> OTHER INFORMATION: ILT70080.2 VL

<400> SEQUENCE: 47

Ser Tyr Val Leu Thr Gln Pro Pro Ser Val Ser Val Ala Pro Gly Lys
1               5                   10                  15

Thr Ala Arg Ile Thr Cys Gly Gly Asp Ser Val Gly Ser Thr Ser Val
                20                  25                  30

His Trp Tyr Gln Gln Lys Pro Gly Gln Ala Pro Val Met Val Met Phe
            35                  40                  45

Tyr Asn Ser Asp Arg Pro Ser Gly Ile Pro Glu Arg Phe Ser Gly Ser
```

```
            50                  55                  60
Ile Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Thr Ser Ser Asp His
                 85                  90                  95

Pro Glu Phe Gly Gly Gly Thr Lys Leu Thr Val Leu
            100                 105
```

<210> SEQ ID NO 48
<211> LENGTH: 11
<212> TYPE: PRT
<213> ORGANISM: Artificial Sequence
<220> FEATURE:
<223> OTHER INFORMATION: ILT70080.2 VLCDR1

<400> SEQUENCE: 48

```
Gly Gly Asp Ser Val Gly Ser Thr Ser Val His
 1               5                  10
```

<210> SEQ ID NO 49
<211> LENGTH: 7
<212> TYPE: PRT
<213> ORGANISM: Artificial Sequence
<220> FEATURE:
<223> OTHER INFORMATION: ILT70080.2 VLCDR2

<400> SEQUENCE: 49

```
Tyr Asn Ser Asp Arg Pro Ser
 1               5
```

<210> SEQ ID NO 50
<211> LENGTH: 11
<212> TYPE: PRT
<213> ORGANISM: Artificial Sequence
<220> FEATURE:
<223> OTHER INFORMATION: ILT70080.2 VLCDR3

<400> SEQUENCE: 50

```
Gln Val Trp Asp Thr Ser Ser Asp His Pro Glu
 1               5                  10
```

<210> SEQ ID NO 51
<211> LENGTH: 375
<212> TYPE: DNA
<213> ORGANISM: Artificial Sequence
<220> FEATURE:
<223> OTHER INFORMATION: ILT70080.3 VH

<400> SEQUENCE: 51

```
caggtgcagc tggtgcaatc tggggctgag gtgaaggcgc tgggacttc ggtgaaagtc      60 tcctgcaagg catctggaga cagcttcagg aactatgctg tcagttgggt gcgacaggcc     120
ccaggacaag gtcttgagtg gatgggagcg atgatgccta gttttggaac aagggagcac     180
tcacagcagt tccagggcag agtcacccct tccgcggacg aatccacgag cacagcctac     240
atggaactga gcagtctaag atctgaggac acggccgtct attactgtgc gggtagtcgg     300
gactacaatg cttaccattt ttggactggt cccctgact tctggggccg aggaaccctg      360
gtcaccgtct cctca                                                     375
```

<210> SEQ ID NO 52
<211> LENGTH: 125
<212> TYPE: PRT
<213> ORGANISM: Artificial Sequence

<220> FEATURE:
<223> OTHER INFORMATION: ILT70080.3 VH

<400> SEQUENCE: 52

Gln Val Gln Leu Val Gln Ser Gly Ala Glu Val Lys Ala Pro Gly Thr
1               5                   10                  15

Ser Val Lys Val Ser Cys Lys Ala Ser Gly Asp Ser Phe Arg Asn Tyr
            20                  25                  30

Ala Val Ser Trp Val Arg Gln Ala Pro Gly Gln Gly Leu Glu Trp Met
        35                  40                  45

Gly Ala Met Met Pro Ser Phe Gly Thr Arg Glu His Ser Gln Gln Phe
    50                  55                  60

Gln Gly Arg Val Thr Leu Ser Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ser Arg Asp Tyr Asn Ala Tyr His Phe Trp Thr Gly Pro Pro
            100                 105                 110

Asp Phe Trp Gly Arg Gly Thr Leu Val Thr Val Ser Ser
        115                 120                 125

<210> SEQ ID NO 53
<211> LENGTH: 5
<212> TYPE: PRT
<213> ORGANISM: Artificial Sequence
<220> FEATURE:
<223> OTHER INFORMATION: ILT70080.3 VHCDR1

<400> SEQUENCE: 53

Asn Tyr Ala Val Ser
1               5

<210> SEQ ID NO 54
<211> LENGTH: 17
<212> TYPE: PRT
<213> ORGANISM: Artificial Sequence
<220> FEATURE:
<223> OTHER INFORMATION: ILT70080.3 VHCDR2

<400> SEQUENCE: 54

Ala Met Met Pro Ser Phe Gly Thr Arg Glu His Ser Gln Gln Phe Gln
1               5                   10                  15

Gly

<210> SEQ ID NO 55
<211> LENGTH: 16
<212> TYPE: PRT
<213> ORGANISM: Artificial Sequence
<220> FEATURE:
<223> OTHER INFORMATION: ILT70080.3 VHCDR3

<400> SEQUENCE: 55

Ser Arg Asp Tyr Asn Ala Tyr His Phe Trp Thr Gly Pro Pro Asp Phe
1               5                   10                  15

<210> SEQ ID NO 56
<211> LENGTH: 324
<212> TYPE: DNA
<213> ORGANISM: Artificial Sequence
<220> FEATURE:
<223> OTHER INFORMATION: ILT70080.3 VL

<400> SEQUENCE: 56

```
tcctatgtgc tgactcagcc accctcagtg tcagtggccc caggaaagac ggccaggatt    60
acctgtgggg gagacagcgt tggcagtaca agtgtccact ggtaccagca gaagccgggc   120
caggcccctg tgatggtcat gttttataac agtgaccggc cctcagggat ccctgagcga   180
ttctctggct ccatctctgg gaacacggcc accctgacca tcagcagggt cgaagccggg   240
gatgaggccg actattactg tcaggtgtgg gatactagta gtgatcatcc ggagttcggc   300
ggagggacca agctgaccgt ccta                                          324
```

<210> SEQ ID NO 57
<211> LENGTH: 108
<212> TYPE: PRT
<213> ORGANISM: Artificial Sequence
<220> FEATURE:
<223> OTHER INFORMATION: ILT70080.3 VL

<400> SEQUENCE: 57

```
Ser Tyr Val Leu Thr Gln Pro Pro Ser Val Ser Val Ala Pro Gly Lys
1               5                   10                  15

Thr Ala Arg Ile Thr Cys Gly Gly Asp Ser Val Gly Ser Thr Ser Val
            20                  25                  30

His Trp Tyr Gln Gln Lys Pro Gly Gln Ala Pro Val Met Val Met Phe
        35                  40                  45

Tyr Asn Ser Asp Arg Pro Ser Gly Ile Pro Glu Arg Phe Ser Gly Ser
    50                  55                  60

Ile Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Pro Glu Phe Gly Gly Gly Thr Lys Leu Thr Val Leu
            100                 105
```

<210> SEQ ID NO 58
<211> LENGTH: 11
<212> TYPE: PRT
<213> ORGANISM: Artificial Sequence
<220> FEATURE:
<223> OTHER INFORMATION: ILT70080.3 VLCDR1

<400> SEQUENCE: 58

```
Gly Gly Asp Ser Val Gly Ser Thr Ser Val His
1               5                   10
```

<210> SEQ ID NO 59
<211> LENGTH: 7
<212> TYPE: PRT
<213> ORGANISM: Artificial Sequence
<220> FEATURE:
<223> OTHER INFORMATION: ILT70080.3 VLCDR2

<400> SEQUENCE: 59

```
Tyr Asn Ser Asp Arg Pro Ser
1               5
```

<210> SEQ ID NO 60
<211> LENGTH: 11
<212> TYPE: PRT
<213> ORGANISM: Artificial Sequence
<220> FEATURE:
<223> OTHER INFORMATION: ILT70080.3 VLCDR3

<400> SEQUENCE: 60

Gln Val Trp Asp Thr Ser Ser Asp His Pro Glu
1               5                   10

<210> SEQ ID NO 61
<211> LENGTH: 375
<212> TYPE: DNA
<213> ORGANISM: Artificial Sequence
<220> FEATURE:
<223> OTHER INFORMATION: ILT70080.4 VH

<400> SEQUENCE: 61
caggtgcagc tggtgcaatc tgggctgag gtgaaggcgc ctgggacttc ggtgaaagtc      60
tcctgcaagg catctggaga cagcttcagg aactatgctg tcagttgggt gcgacaggcc     120
ccaggacaag gtcttgagtg gatgggagcg atgatgccta gttttggaac aagggagcac     180
tcacagcagt tccagggcag agtcacccct tccgcggacg aatccacgag cacagcctac     240
atggaactga gcagtctaag atctgaggac acggccgtct attactgtgc gggtagtcgg     300
gactacaatg cttaccattt ttggactggt ccccctgact ctggggccg aggaaccctg      360 gtcaccgtct cctca                                                     375

<210> SEQ ID NO 62
<211> LENGTH: 125
<212> TYPE: PRT
<213> ORGANISM: Artificial Sequence
<220> FEATURE:
<223> OTHER INFORMATION: ILT70080.4 VH

<400> SEQUENCE: 62

Gln Val Gln Leu Val Gln Ser Gly Ala Glu Val Lys Ala Pro Gly Thr
1               5                   10                  15

Ser Val Lys Val Ser Cys Lys Ala Ser Gly Asp Ser Phe Arg Asn Tyr
            20                  25                  30

Ala Val Ser Trp Val Arg Gln Ala Pro Gly Gln Gly Leu Glu Trp Met
        35                  40                  45

Gly Ala Met Met Pro Ser Phe Gly Thr Arg Glu His Ser Gln Gln Phe
    50                  55                  60

Gln Gly Arg Val Thr Leu Ser Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ser Arg Asp Tyr Asn Ala Tyr His Phe Trp Thr Gly Pro Pro
            100                 105                 110

Asp Phe Trp Gly Arg Gly Thr Leu Val Thr Val Ser Ser
        115                 120                 125

<210> SEQ ID NO 63
<211> LENGTH: 5
<212> TYPE: PRT
<213> ORGANISM: Artificial Sequence
<220> FEATURE:
<223> OTHER INFORMATION: ILT70080.4 VHCDR1

<400> SEQUENCE: 63

Asn Tyr Ala Val Ser
1               5

<210> SEQ ID NO 64
<211> LENGTH: 17
<212> TYPE: PRT

```
<213> ORGANISM: Artificial Sequence
<220> FEATURE:
<223> OTHER INFORMATION: ILT70080.4 VHCDR2

<400> SEQUENCE: 64

Ala Met Met Pro Ser Phe Gly Thr Arg Glu His Ser Gln Gln Phe Gln
1               5                   10                  15

Gly

<210> SEQ ID NO 65
<211> LENGTH: 16
<212> TYPE: PRT
<213> ORGANISM: Artificial Sequence
<220> FEATURE:
<223> OTHER INFORMATION: ILT70080.4 VHCDR3

<400> SEQUENCE: 65

Ser Arg Asp Tyr Asn Ala Tyr His Phe Trp Thr Gly Pro Pro Asp Phe
1               5                   10                  15

<210> SEQ ID NO 66
<211> LENGTH: 324
<212> TYPE: DNA
<213> ORGANISM: Artificial Sequence
<220> FEATURE:
<223> OTHER INFORMATION: ILT70080.4 VL

<400> SEQUENCE: 66
tcctatgagc tgactcagcc accctcagtg tcagtggccc caggaaagac ggccaagatt      60
tcctgtgggg gagacagcgt tggcagtaca agtgtccact ggtaccagca gaagccgggc     120
caggcccctg tgatggtcat gttttataac agtgaccggc cctcagggat ccctgagcga     180
ttctctggct ccatctctgg gaacacggcc accctgacca tcagcagggt cgaagccggg     240
gatgaggccg actattactg tcaggtgtgg gatactagta gtgatcatcc ggagttcggc     300
ggagggacca agctgaccgt ccta                                             324

<210> SEQ ID NO 67
<211> LENGTH: 108
<212> TYPE: PRT
<213> ORGANISM: Artificial Sequence
<220> FEATURE:
<223> OTHER INFORMATION: ILT70080.4 VL

<400> SEQUENCE: 67

Ser Tyr Glu Leu Thr Gln Pro Pro Ser Val Ser Val Ala Pro Gly Lys
1               5                   10                  15

Thr Ala Lys Ile Ser Cys Gly Gly Asp Ser Val Gly Ser Thr Ser Val
                20                  25                  30

His Trp Tyr Gln Gln Lys Pro Gly Gln Ala Pro Val Met Val Met Phe
            35                  40                  45

Tyr Asn Ser Asp Arg Pro Ser Gly Ile Pro Glu Arg Phe Ser Gly Ser
        50                  55                  60

Ile Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Pro Glu Phe Gly Gly Gly Thr Lys Leu Thr Val Leu
                100                 105

<210> SEQ ID NO 68
```

```
<210> SEQ ID NO 68
<211> LENGTH: 11
<212> TYPE: PRT
<213> ORGANISM: Artificial Sequence
<220> FEATURE:
<223> OTHER INFORMATION: ILT70080.4 VLCDR1

<400> SEQUENCE: 68

Gly Gly Asp Ser Val Gly Ser Thr Ser Val His
1               5                   10

<210> SEQ ID NO 69
<211> LENGTH: 7
<212> TYPE: PRT
<213> ORGANISM: Artificial Sequence
<220> FEATURE:
<223> OTHER INFORMATION: ILT70080.4 VLCDR2

<400> SEQUENCE: 69

Tyr Asn Ser Asp Arg Pro Ser
1               5

<210> SEQ ID NO 70
<211> LENGTH: 11
<212> TYPE: PRT
<213> ORGANISM: Artificial Sequence
<220> FEATURE:
<223> OTHER INFORMATION: ILT70080.4 VLCDR3

<400> SEQUENCE: 70

Gln Val Trp Asp Thr Ser Ser Asp His Pro Glu
1               5                   10

<210> SEQ ID NO 71
<211> LENGTH: 375
<212> TYPE: DNA
<213> ORGANISM: Artificial Sequence
<220> FEATURE:
<223> OTHER INFORMATION: ILT70080.5 VH

<400> SEQUENCE: 71
caggtgcagc tggtgcaatc tggggctgag gtgaagaagc ctgggtcttc ggtgaaagtc      60
tcctgcaagg catctggaga cagcttcagg aactatgctg tcagttgggt gcgacaggcc     120
ccaggacaag gtcttgagtg gatgggagcg atgatgccta gttttggaac aagggagcac     180
tcacagcagt tccagggcag agtcacccct taccgcgacg aatccacgag cacagcctac     240
atggaactga gcagtctaag atctgaggac acggccgtct attactgtgc gggtagtcgg     300
gactacaatg cttaccattt ttggactggt ccccctgact ctggggccg aggaaccctg      360 gtcaccgtct cctca                                                      375

<210> SEQ ID NO 72
<211> LENGTH: 125
<212> TYPE: PRT
<213> ORGANISM: Artificial Sequence
<220> FEATURE:
<223> OTHER INFORMATION: ILT70080.5 VH

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ser Phe Arg Asn Tyr
            20                  25                  30

Ala Val Ser Trp Val Arg Gln Ala Pro Gly Gln Gly Leu Glu Trp Met
        35                  40                  45
```

```
Gly Ala Met Met Pro Ser Phe Gly Thr Arg Glu His Ser Gln Gln Phe
        50                  55                  60

Gln Gly Arg Val Thr Leu Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Gly Ser Arg Asp Tyr Asn Ala Tyr His Phe Trp Thr Gly Pro Pro
            100                 105                 110

Asp Phe Trp Gly Arg Gly Thr Leu Val Thr Val Ser Ser
        115                 120                 125

<210> SEQ ID NO 73
<211> LENGTH: 5
<212> TYPE: PRT
<213> ORGANISM: Artificial Sequence
<220> FEATURE:
<223> OTHER INFORMATION: ILT70080.5 VHCDR1

<400> SEQUENCE: 73

Asn Tyr Ala Val Ser
1               5

<210> SEQ ID NO 74
<211> LENGTH: 17
<212> TYPE: PRT
<213> ORGANISM: Artificial Sequence
<220> FEATURE:
<223> OTHER INFORMATION: ILT70080.5 VHCDR2

<400> SEQUENCE: 74

Ala Met Met Pro Ser Phe Gly Thr Arg Glu His Ser Gln Gln Phe Gln
1               5                   10                  15

Gly

<210> SEQ ID NO 75
<211> LENGTH: 16
<212> TYPE: PRT
<213> ORGANISM: Artificial Sequence
<220> FEATURE:
<223> OTHER INFORMATION: ILT70080.5 VHCDR3

<400> SEQUENCE: 75

Ser Arg Asp Tyr Asn Ala Tyr His Phe Trp Thr Gly Pro Pro Asp Phe
1               5                   10                  15

<210> SEQ ID NO 76
<211> LENGTH: 324
<212> TYPE: DNA
<213> ORGANISM: Artificial Sequence
<220> FEATURE:
<223> OTHER INFORMATION: ILT70080.5 VL

<400> SEQUENCE: 76
tcctatgtgc tgactcagcc accctcagtg tcagtggccc caggaaagac ggccaggatt      60
acctgtgggg agacagcgt tggcagtaca agtgtccact ggtaccagca gaagccgggc     120
caggcccctg tgatggtcat gttttataac agtgaccggc cctcagggat ccctgagcga     180
ttctctggct ccaactctgg aacacggcc accctgacca tcagcagggt cgaagccggg     240
gatgaggccg actattactg tcaggtgtgg gatactagta gtgatcatcc ggagttcggc     300
ggagggacca agctgaccgt ccta                                            324
```

<210> SEQ ID NO 77
<211> LENGTH: 108
<212> TYPE: PRT
<213> ORGANISM: Artificial Sequence
<220> FEATURE:
<223> OTHER INFORMATION: ILT70080.5 VL

<400> SEQUENCE: 77

Ser Tyr Val Leu Thr Gln Pro Pro Ser Val Ser Val Ala Pro Gly Lys
1               5                   10                  15

Thr Ala Arg Ile Thr Cys Gly Gly Asp Ser Val Gly Ser Thr Ser Val
            20                  25                  30

His Trp Tyr Gln Gln Lys Pro Gly Gln Ala Pro Val Met Val Met Phe
        35                  40                  45

Tyr Asn Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Pro Glu Phe Gly Gly Gly Thr Lys Leu Thr Val Leu
            100                 105

<210> SEQ ID NO 78
<211> LENGTH: 11
<212> TYPE: PRT
<213> ORGANISM: Artificial Sequence
<220> FEATURE:
<223> OTHER INFORMATION: ILT70080.5 VLCDR1

<400> SEQUENCE: 78

Gly Gly Asp Ser Val Gly Ser Thr Ser Val His
1               5                   10

<210> SEQ ID NO 79
<211> LENGTH: 7
<212> TYPE: PRT
<213> ORGANISM: Artificial Sequence
<220> FEATURE:
<223> OTHER INFORMATION: ILT70080.5 VLCDR2

<400> SEQUENCE: 79

Tyr Asn Ser Asp Arg Pro Ser
1               5

<210> SEQ ID NO 80
<211> LENGTH: 11
<212> TYPE: PRT
<213> ORGANISM: Artificial Sequence
<220> FEATURE:
<223> OTHER INFORMATION: ILT70080.5 VLCDR3

<400> SEQUENCE: 80

Gln Val Trp Asp Thr Ser Ser Asp His Pro Glu
1               5                   10

<210> SEQ ID NO 81
<211> LENGTH: 375
<212> TYPE: DNA
<213> ORGANISM: Artificial Sequence
<220> FEATURE:
<223> OTHER INFORMATION: ILT70080.6 VH

<400> SEQUENCE: 81

```
caggtgcagc tggtgcaatc tggggctgag gtgaagaagc ctgggtcttc ggtgaaagtc    60
tcctgcaagg catctggaga cagcttcagg aactatgctg tcagttgggt gcgacaggcc   120
ccaggacaag gtcttgagtg gatgggagcg atgatgccta gttttggaac aagggagcac   180
tcacagcagt tccagggcag agtcacccctt accgcgacg aatccacgag cacagcctac   240
atggaactga gcagtctaag atctgaggac acggccgtct attactgtgc gggtagtcgg   300
gactacaatg cttaccattt ttggactggt ccccctgact tctggggccg aggaaccctg   360
gtcaccgtct cctca                                                    375
```

\<210\> SEQ ID NO 82
\<211\> LENGTH: 125
\<212\> TYPE: PRT
\<213\> ORGANISM: Artificial Sequence
\<220\> FEATURE:
\<223\> OTHER INFORMATION: ILT70080.6 VH

\<400\> SEQUENCE: 82

```
Gln Val Gln Leu Val Gln Ser Gly Ala Glu Val Lys Lys Pro Gly Ser
1               5                   10                  15

Ser Val Lys Val Ser Cys Lys Ala Ser Gly Asp Ser Phe Arg Asn Tyr
            20                  25                  30

Ala Val Ser Trp Val Arg Gln Ala Pro Gly Gln Gly Leu Glu Trp Met
        35                  40                  45

Gly Ala Met Met Pro Ser Phe Gly Thr Arg Glu His Ser Gln Gln Phe
    50                  55                  60

Gln Gly Arg Val Thr Leu Thr Ala Asp Glu Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Gly Ser Arg Asp Tyr Asn Ala Tyr His Phe Trp Thr Gly Pro Pro
            100                 105                 110

Asp Phe Trp Gly Arg Gly Thr Leu Val Thr Val Ser Ser
        115                 120                 125
```

\<210\> SEQ ID NO 83
\<211\> LENGTH: 5
\<212\> TYPE: PRT
\<213\> ORGANISM: Artificial Sequence
\<220\> FEATURE:
\<223\> OTHER INFORMATION: ILT70080.6 VHCDR1

\<400\> SEQUENCE: 83

```
Asn Tyr Ala Val Ser
1               5
```

\<210\> SEQ ID NO 84
\<211\> LENGTH: 17
\<212\> TYPE: PRT
\<213\> ORGANISM: Artificial Sequence
\<220\> FEATURE:
\<223\> OTHER INFORMATION: ILT70080.6 VHCDR2

\<400\> SEQUENCE: 84

```
Ala Met Met Pro Ser Phe Gly Thr Arg Glu His Ser Gln Gln Phe Gln
1               5                   10                  15

Gly
```

\<210\> SEQ ID NO 85

```
<211> LENGTH: 16
<212> TYPE: PRT
<213> ORGANISM: Artificial Sequence
<220> FEATURE:
<223> OTHER INFORMATION: ILT70080.6 VHCDR3

<400> SEQUENCE: 85

Ser Arg Asp Tyr Asn Ala Tyr His Phe Trp Thr Gly Pro Pro Asp Phe
1               5                   10                  15

<210> SEQ ID NO 86
<211> LENGTH: 324
<212> TYPE: DNA
<213> ORGANISM: Artificial Sequence
<220> FEATURE:
<223> OTHER INFORMATION: ILT70080.6 VL

<400> SEQUENCE: 86
tcctatgtgc tgactcagcc accctcagtg tcagtggccc caggaaagac ggccaggatt      60
acctgtgggg agacagcgt tggcagtaca agtgtccact ggtaccagca gaagccgggc     120
caggcccctg tgctggtcat ttattataac agtgaccggc cctcagggat ccctgagcga     180
ttctctggct ccaactctgg gaacacggcc accctgacca tcagcagggt cgaagccggg     240
gatgaggccg actattactg tcaggtgtgg gatactagta gtgatcatcc ggagttcggc     300
ggagggacca agctgaccgt ccta                                            324

<210> SEQ ID NO 87
<211> LENGTH: 108
<212> TYPE: PRT
<213> ORGANISM: Artificial Sequence
<220> FEATURE:
<223> OTHER INFORMATION: ILT70080.6 VL

<400> SEQUENCE: 87

Ser Tyr Val Leu Thr Gln Pro Pro Ser Val Ser Val Ala Pro Gly Lys
1               5                   10                  15

Thr Ala Arg Ile Thr Cys Gly Gly Asp Ser Val Gly Ser Thr Ser Val
                20                  25                  30

His Trp Tyr Gln Gln Lys Pro Gly Gln Ala Pro Val Leu Val Ile Tyr
            35                  40                  45

Tyr Asn Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Pro Glu Phe Gly Gly Gly Thr Lys Leu Thr Val Leu
            100                 105

<210> SEQ ID NO 88
<211> LENGTH: 11
<212> TYPE: PRT
<213> ORGANISM: Artificial Sequence
<220> FEATURE:
<223> OTHER INFORMATION: ILT70080.6 VLCDR1

<400> SEQUENCE: 88

Gly Gly Asp Ser Val Gly Ser Thr Ser Val His
1               5                   10

<210> SEQ ID NO 89
```

```
<211> LENGTH: 7
<212> TYPE: PRT
<213> ORGANISM: Artificial Sequence
<220> FEATURE:
<223> OTHER INFORMATION: ILT70080.6 VLCDR2

<400> SEQUENCE: 89

Tyr Asn Ser Asp Arg Pro Ser
1               5

<210> SEQ ID NO 90
<211> LENGTH: 11
<212> TYPE: PRT
<213> ORGANISM: Artificial Sequence
<220> FEATURE:
<223> OTHER INFORMATION: ILT70080.6 VLCDR3

<400> SEQUENCE: 90

Gln Val Trp Asp Thr Ser Ser Asp His Pro Glu
1               5                   10

<210> SEQ ID NO 91
<211> LENGTH: 375
<212> TYPE: DNA
<213> ORGANISM: Artificial Sequence
<220> FEATURE:
<223> OTHER INFORMATION: ILT70080.7 VH

<400> SEQUENCE: 91
caggtgcagc tggtgcaatc tggggctgag gtgaagaagc ctgggtcttc ggtgaaagtc    60
tcctgcaagg catctggaga cagcttcagg aactatgctg tcagttgggt gcgacaggcc   120
ccaggacaag gtcttgagtg gatgggagcg atgatgccta gttttggaac aagggagcac   180
tcacagcagt tccagggcag agtcaccctt accgcggacg aatccacgag cacagcctac   240
atggaactga gcagtctaag atctgaggac acggccgtct attactgtgc gggtagtcgg   300
gactacaatg cttaccattt ttggactggt cccccctgact tctggggccg aggaaccctg   360
gtcaccgtct cctca                                                    375

<210> SEQ ID NO 92
<211> LENGTH: 125
<212> TYPE: PRT
<213> ORGANISM: Artificial Sequence
<220> FEATURE:
<223> OTHER INFORMATION: ILT70080.7 VH

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ser Phe Arg Asn Tyr
            20                  25                  30

Ala Val Ser Trp Val Arg Gln Ala Pro Gly Gln Gly Leu Glu Trp Met
        35                  40                  45

Gly Ala Met Met Pro Ser Phe Gly Thr Arg Glu His Ser Gln Gln Phe
    50                  55                  60

Gln Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ser Arg Asp Tyr Asn Ala Tyr His Phe Trp Thr Gly Pro Pro
            100                 105                 110
```

Asp Phe Trp Gly Arg Gly Thr Leu Val Thr Val Ser Ser
        115                 120                 125

<210> SEQ ID NO 93
<211> LENGTH: 5
<212> TYPE: PRT
<213> ORGANISM: Artificial Sequence
<220> FEATURE:
<223> OTHER INFORMATION: ILT70080.7 VHCDR1

<400> SEQUENCE: 93

Asn Tyr Ala Val Ser
1               5

<210> SEQ ID NO 94
<211> LENGTH: 17
<212> TYPE: PRT
<213> ORGANISM: Artificial Sequence
<220> FEATURE:
<223> OTHER INFORMATION: ILT70080.7 VHCDR2

<400> SEQUENCE: 94

Ala Met Met Pro Ser Phe Gly Thr Arg Glu His Ser Gln Gln Phe Gln
1               5                   10                  15

Gly

<210> SEQ ID NO 95
<211> LENGTH: 16
<212> TYPE: PRT
<213> ORGANISM: Artificial Sequence
<220> FEATURE:
<223> OTHER INFORMATION: ILT70080.7 VHCDR3

<400> SEQUENCE: 95

Ser Arg Asp Tyr Asn Ala Tyr His Phe Trp Thr Gly Pro Pro Asp Phe
1               5                   10                  15

<210> SEQ ID NO 96
<211> LENGTH: 324
<212> TYPE: DNA
<213> ORGANISM: Artificial Sequence
<220> FEATURE:
<223> OTHER INFORMATION: ILT70080.7 VL

<400> SEQUENCE: 96
tcctatgtgc tgactcagcc accctcagtg tcagtggccc caggaaagac ggccaggatt     60
acctgtgggg gagacagcgt tggcagtaca agtgtccact ggtaccagca gaagccgggc    120
caggcccctg tgctggtcat gttttataac agtgaccggc cctcagggat ccctgagcga    180
ttctctggct ccaactctgg gaacacggcc accctgacca tcagcagggt cgaagccggg    240
gatgaggccg actattactg tcaggtgtgg gatactagta gtgatcatcc ggagttcggc    300
ggagggacca agctgaccgt ccta                                           324

<210> SEQ ID NO 97
<211> LENGTH: 108
<212> TYPE: PRT
<213> ORGANISM: Artificial Sequence
<220> FEATURE:
<223> OTHER INFORMATION: ILT70080.7 VL

<400> SEQUENCE: 97

Ser Tyr Val Leu Thr Gln Pro Pro Ser Val Ser Val Ala Pro Gly Lys
1               5                   10                  15

```
Thr Ala Arg Ile Thr Cys Gly Gly Asp Ser Val Gly Ser Thr Ser Val
                20                  25                  30

His Trp Tyr Gln Gln Lys Pro Gly Gln Ala Pro Val Leu Val Met Phe
            35                  40                  45

Tyr Asn Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Pro Glu Phe Gly Gly Gly Thr Lys Leu Thr Val Leu
            100                 105
```

<210> SEQ ID NO 98
<211> LENGTH: 11
<212> TYPE: PRT
<213> ORGANISM: Artificial Sequence
<220> FEATURE:
<223> OTHER INFORMATION: ILT70080.7 VLCDR1

<400> SEQUENCE: 98

```
Gly Gly Asp Ser Val Gly Ser Thr Ser Val His
1               5                   10
```

<210> SEQ ID NO 99
<211> LENGTH: 7
<212> TYPE: PRT
<213> ORGANISM: Artificial Sequence
<220> FEATURE:
<223> OTHER INFORMATION: ILT70080.7 VLCDR2

<400> SEQUENCE: 99

```
Tyr Asn Ser Asp Arg Pro Ser
1               5
```

<210> SEQ ID NO 100
<211> LENGTH: 11
<212> TYPE: PRT
<213> ORGANISM: Artificial Sequence
<220> FEATURE:
<223> OTHER INFORMATION: ILT70080.7 VLCDR3

<400> SEQUENCE: 100

```
Gln Val Trp Asp Thr Ser Ser Asp His Pro Glu
1               5                   10
```

<210> SEQ ID NO 101
<211> LENGTH: 375
<212> TYPE: DNA
<213> ORGANISM: Artificial Sequence
<220> FEATURE:
<223> OTHER INFORMATION: ILT70083 VH

<400> SEQUENCE: 101

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggctg gttcaccatc tccagagaca attccaagaa cacgctgtat     240
ctgcaaatga acagcctgag agccgaggac acggccgtgt attactgtgc gaggcggaca     300
tattactatg atagtgatgg tcactcggat gttttgata tttggggccg gggcaccctg     360
```

```
gtcaccgtct cgagt                                                    375
```

<210> SEQ ID NO 102
<211> LENGTH: 125
<212> TYPE: PRT
<213> ORGANISM: Artificial Sequence
<220> FEATURE:
<223> OTHER INFORMATION: ILT70083 VH

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Trp Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Tyr Tyr Tyr Asp Ser Asp Gly His Ser Asp Val Phe
            100                 105                 110

Asp Ile Trp Gly Arg Gly Thr Leu Val Thr Val Ser Ser
        115                 120                 125

<210> SEQ ID NO 103
<211> LENGTH: 5
<212> TYPE: PRT
<213> ORGANISM: Artificial Sequence
<220> FEATURE:
<223> OTHER INFORMATION: ILT70083 VHCDR1

<400> SEQUENCE: 103

Ser Tyr Ala Met Ser
1               5

<210> SEQ ID NO 104
<211> LENGTH: 17
<212> TYPE: PRT
<213> ORGANISM: Artificial Sequence
<220> FEATURE:
<223> OTHER INFORMATION: ILT70083 VHCDR2

<400> SEQUENCE: 104

Ala Ile Ser Gly Ser Gly Gly Ser Thr Tyr Tyr Ala Asp Ser Val Lys
1               5                   10                  15

Gly

<210> SEQ ID NO 105
<211> LENGTH: 16
<212> TYPE: PRT
<213> ORGANISM: Artificial Sequence
<220> FEATURE:
<223> OTHER INFORMATION: ILT70083 VHCDR3

<400> SEQUENCE: 105

Arg Thr Tyr Tyr Tyr Asp Ser Asp Gly His Ser Asp Val Phe Asp Ile
1               5                   10                  15

<210> SEQ ID NO 106

<211> LENGTH: 330
<212> TYPE: DNA
<213> ORGANISM: Artificial Sequence
<220> FEATURE:
<223> OTHER INFORMATION: ILT70083 VL

<400> SEQUENCE: 106

```
cagtctgtcg tgacgcagcc gccctcagtg tctgcggccc caggacagaa ggtcaccatc    60
tcctgttctg gaagcgcctc caatattggg agtaattttg tgtcctggta ccaacaactc   120
cccggagag ccccccaaact cctcatttat gacaatgata aacgagactt agggattcct   180
gaccgcttct ctgcctccat ctcttccacg tcagccgccc tggccatcac cggactccag   240
actgaggacg aggccgatta ttactgcgga acatgggaca ccagtctgac tgttgggggtt   300
ttcggcggag ggaccaagct gaccgtccta                                    330
```

<210> SEQ ID NO 107
<211> LENGTH: 110
<212> TYPE: PRT
<213> ORGANISM: Artificial Sequence
<220> FEATURE:
<223> OTHER INFORMATION: ILT70083 VL

<400> SEQUENCE: 107

Gln Ser Val Val Thr Gln Pro Pro Ser Val Ser Ala Ala Pro Gly Gln
1               5                   10                  15

Lys Val Thr Ile Ser Cys Ser Gly Ser Ala Ser Asn Ile Gly Ser Asn
            20                  25                  30

Phe Val Ser Trp Tyr Gln Gln Leu Pro Gly Arg Ala Pro Lys Leu Leu
        35                  40                  45

Ile Tyr Asp Asn Asp Lys Arg Asp Leu Gly Ile Pro Asp Arg Phe Ser
    50                  55                  60

Ala Ser Ile Ser Ser Thr Ser Ala Ala Leu Ala Ile Thr Gly Leu Gln
65                  70                  75                  80

Thr Glu Asp Glu Ala Asp Tyr Tyr Cys Gly Thr Trp Asp Thr Ser Leu
                85                  90                  95

Thr Val Gly Val Phe Gly Gly Gly Thr Lys Leu Thr Val Leu
            100                 105                 110

<210> SEQ ID NO 108
<211> LENGTH: 13
<212> TYPE: PRT
<213> ORGANISM: Artificial Sequence
<220> FEATURE:
<223> OTHER INFORMATION: ILT70083 VLCDR1

<400> SEQUENCE: 108

Ser Gly Ser Ala Ser Asn Ile Gly Ser Asn Phe Val Ser
1               5                   10

<210> SEQ ID NO 109
<211> LENGTH: 7
<212> TYPE: PRT
<213> ORGANISM: Artificial Sequence
<220> FEATURE:
<223> OTHER INFORMATION: ILT70083 VLCDR2

<400> SEQUENCE: 109

Asp Asn Asp Lys Arg Asp Leu
1               5

<210> SEQ ID NO 110

```
<211> LENGTH: 11
<212> TYPE: PRT
<213> ORGANISM: Artificial Sequence
<220> FEATURE:
<223> OTHER INFORMATION: ILT70083 VLCDR3

<400> SEQUENCE: 110

Gly Thr Trp Asp Thr Ser Leu Thr Val Gly Val
1               5                   10

<210> SEQ ID NO 111
<211> LENGTH: 375
<212> TYPE: DNA
<213> ORGANISM: Artificial Sequence
<220> FEATURE:
<223> OTHER INFORMATION: ILT70083.1 VH

<400> SEQUENCE: 111
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggctg gttcaccatc tccagagaca attccaagaa cacgctgtat     240
ctgcaaatga acagcctgag agccgaggac acggccgtgt attactgtgc gaggcggaca     300
tattactatg atagtgatgg tcactcggat gtttttgata tttggggccg gggcaccctg     360
gtcaccgtct cgagt                                                      375

<210> SEQ ID NO 112
<211> LENGTH: 125
<212> TYPE: PRT
<213> ORGANISM: Artificial Sequence
<220> FEATURE:
<223> OTHER INFORMATION: ILT70083.1 VH

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Trp Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Tyr Tyr Tyr Asp Ser Asp Gly His Ser Asp Val Phe
            100                 105                 110

Asp Ile Trp Gly Arg Gly Thr Leu Val Thr Val Ser Ser
        115                 120                 125

<210> SEQ ID NO 113
<211> LENGTH: 5
<212> TYPE: PRT
<213> ORGANISM: Artificial Sequence
<220> FEATURE:
<223> OTHER INFORMATION: ILT70083.1 VHCDR1

<400> SEQUENCE: 113
```

```
Ser Tyr Ala Met Ser
1               5
```

```
<210> SEQ ID NO 114
<211> LENGTH: 17
<212> TYPE: PRT
<213> ORGANISM: Artificial Sequence
<220> FEATURE:
<223> OTHER INFORMATION: ILT70083.1 VHCDR2

<400> SEQUENCE: 114
```

```
Ala Ile Ser Gly Ser Gly Gly Ser Thr Tyr Tyr Ala Asp Ser Val Lys
1               5                   10                  15

Gly
```

```
<210> SEQ ID NO 115
<211> LENGTH: 16
<212> TYPE: PRT
<213> ORGANISM: Artificial Sequence
<220> FEATURE:
<223> OTHER INFORMATION: ILT70083.1 VHCDR3

<400> SEQUENCE: 115
```

```
Arg Thr Tyr Tyr Tyr Asp Ser Asp Gly His Ser Asp Val Phe Asp Ile
1               5                   10                  15
```

```
<210> SEQ ID NO 116
<211> LENGTH: 330
<212> TYPE: DNA
<213> ORGANISM: Artificial Sequence
<220> FEATURE:
<223> OTHER INFORMATION: ILT70083.1 VL

<400> SEQUENCE: 116
```

```
cagtctgtcg tgacgcagcc gccctcagtg tctgcggccc caggacagaa ggtcaccatc      60
tcctgttctg gaagcgcctc caatattggg agtaattttg tgtcctggta ccaacaactc     120
cccgggacag cccccaaact cctcatttat gacaatgata acagagactt agggattcct     180
gaccgcttct ctgcctccat ctcttccacg tcagccaccc tgggcatcac cggactccag     240
actggggacg aggccgatta ttactgcgga acatgggaca ccagtctgac tgttggggtt     300
ttcggcggag ggaccaagct gaccgtccta                                      330
```

```
<210> SEQ ID NO 117
<211> LENGTH: 110
<212> TYPE: PRT
<213> ORGANISM: Artificial Sequence
<220> FEATURE:
<223> OTHER INFORMATION: ILT70083.1 VL

<400> SEQUENCE: 117
```

```
Gln Ser Val Val Thr Gln Pro Pro Ser Val Ser Ala Ala Pro Gly Gln
1               5                   10                  15

Lys Val Thr Ile Ser Cys Ser Gly Ser Ala Ser Asn Ile Gly Ser Asn
            20                  25                  30

Phe Val Ser Trp Tyr Gln Gln Leu Pro Gly Thr Ala Pro Lys Leu Leu
        35                  40                  45

Ile Tyr Asp Asn Asp Lys Arg Asp Leu Gly Ile Pro Asp Arg Phe Ser
    50                  55                  60

Ala Ser Ile Ser Ser Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
```

```
                    85                  90                  95
Thr Val Gly Val Phe Gly Gly Gly Thr Lys Leu Thr Val Leu
            100                 105                 110

<210> SEQ ID NO 118
<211> LENGTH: 13
<212> TYPE: PRT
<213> ORGANISM: Artificial Sequence
<220> FEATURE:
<223> OTHER INFORMATION: ILT70083.1 VLCDR1

<400> SEQUENCE: 118

Ser Gly Ser Ala Ser Asn Ile Gly Ser Asn Phe Val Ser
1               5                   10

<210> SEQ ID NO 119
<211> LENGTH: 7
<212> TYPE: PRT
<213> ORGANISM: Artificial Sequence
<220> FEATURE:
<223> OTHER INFORMATION: ILT70083.1 VLCDR2

<400> SEQUENCE: 119

Asp Asn Asp Lys Arg Asp Leu
1               5

<210> SEQ ID NO 120
<211> LENGTH: 11
<212> TYPE: PRT
<213> ORGANISM: Artificial Sequence
<220> FEATURE:
<223> OTHER INFORMATION: ILT70083.1 VLCDR3

<400> SEQUENCE: 120

Gly Thr Trp Asp Thr Ser Leu Thr Val Gly Val
1               5                   10

<210> SEQ ID NO 121
<211> LENGTH: 375
<212> TYPE: DNA
<213> ORGANISM: Artificial Sequence
<220> FEATURE:
<223> OTHER INFORMATION: ILT70083.2 VH

<400> SEQUENCE: 121
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggctg gttcaccatc tccagagaca attccaagaa cacgctgtat    240
ctgcaaatga acagcctgag agccgaggac acggccgtgt attactgtgc gaggcggaca    300
tattactatg atagtgatgg tcactcggat gttttgata tttggggccg gggcaccctg     360
gtcaccgtct cgagt                                                     375

<210> SEQ ID NO 122
<211> LENGTH: 125
<212> TYPE: PRT
<213> ORGANISM: Artificial Sequence
<220> FEATURE:
<223> OTHER INFORMATION: ILT70083.2 VH

<400> SEQUENCE: 122

Glu Val Gln Leu Leu Glu Ser Gly Gly Gly Leu Val Gln Pro Gly Gly
```

```
                1               5                  10                 15
            Ser Leu Arg Leu Ser Cys Ala Ala Ser Gly Phe Thr Phe Ser Ser Tyr
                        20                  25                  30

Ala Met Ser Trp Val Arg Gln Ala Pro Gly Lys Gly Leu Glu Trp Val
                        35                  40                  45

Ser Ala Ile Ser Gly Ser Gly Gly Ser Thr Tyr Tyr Ala Asp Ser Val
                        50                  55                  60

Lys Gly Trp Phe Thr Ile Ser Arg Asp Asn Ser Lys Asn Thr Leu Tyr
            65                      70                  75                  80

Leu Gln Met Asn Ser Leu Arg Ala Glu Asp Thr Ala Val Tyr Tyr Cys
                        85                  90                  95

Ala Arg Arg Thr Tyr Tyr Tyr Asp Ser Asp Gly His Ser Asp Val Phe
                        100                 105                 110

Asp Ile Trp Gly Arg Gly Thr Leu Val Thr Val Ser Ser
                        115                 120                 125

<210> SEQ ID NO 123
<211> LENGTH: 5
<212> TYPE: PRT
<213> ORGANISM: Artificial Sequence
<220> FEATURE:
<223> OTHER INFORMATION: ILT70083.2 VHCDR1

<400> SEQUENCE: 123

Ser Tyr Ala Met Ser
1               5

<210> SEQ ID NO 124
<211> LENGTH: 17
<212> TYPE: PRT
<213> ORGANISM: Artificial Sequence
<220> FEATURE:
<223> OTHER INFORMATION: ILT70083.2 VHCDR2

<400> SEQUENCE: 124

Ala Ile Ser Gly Ser Gly Gly Ser Thr Tyr Tyr Ala Asp Ser Val Lys
1               5                   10                  15

Gly

<210> SEQ ID NO 125
<211> LENGTH: 16
<212> TYPE: PRT
<213> ORGANISM: Artificial Sequence
<220> FEATURE:
<223> OTHER INFORMATION: ILT70083.2 VHCDR3

<400> SEQUENCE: 125

Arg Thr Tyr Tyr Tyr Asp Ser Asp Gly His Ser Asp Val Phe Asp Ile
1               5                   10                  15

<210> SEQ ID NO 126
<211> LENGTH: 330
<212> TYPE: DNA
<213> ORGANISM: Artificial Sequence
<220> FEATURE:
<223> OTHER INFORMATION: ILT70083.2 VL

<400> SEQUENCE: 126
cagtctgtcc tgacgcagcc gccctcagtg tctgcggccc caggacagaa ggtcaccatc    60
tcctgttctg gaagcgcctc caatattggg agtaattttg tgtcctggta ccaacaactc   120
cccgggacag cccccaaact cctcatttat gacaatgata acgagactt agggattcct   180
```

-continued

```
gaccgcttct ctgcctccat ctcttccacg tcagccaccc tgggcatcac cggactccag    240
actggggacg aggccgatta ttactgcgga acatgggaca ccagtctgac tgttggggtt    300
ttcggcggag ggaccaagct gaccgtccta                                     330
```

<210> SEQ ID NO 127
<211> LENGTH: 110
<212> TYPE: PRT
<213> ORGANISM: Artificial Sequence
<220> FEATURE:
<223> OTHER INFORMATION: ILT70083.2 VL

<400> SEQUENCE: 127

```
Gln Ser Val Leu Thr Gln Pro Pro Ser Val Ser Ala Ala Pro Gly Gln
1               5                   10                  15

Lys Val Thr Ile Ser Cys Ser Gly Ser Ala Ser Asn Ile Gly Ser Asn
            20                  25                  30

Phe Val Ser Trp Tyr Gln Gln Leu Pro Gly Thr Ala Pro Lys Leu Leu
        35                  40                  45

Ile Tyr Asp Asn Asp Lys Arg Asp Leu Gly Ile Pro Asp Arg Phe Ser
    50                  55                  60

Ala Ser Ile Ser Ser Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Thr Val Gly Val Phe Gly Gly Gly Thr Lys Leu Thr Val Leu
            100                 105                 110
```

<210> SEQ ID NO 128
<211> LENGTH: 13
<212> TYPE: PRT
<213> ORGANISM: Artificial Sequence
<220> FEATURE:
<223> OTHER INFORMATION: ILT70083.2 VLCDR1

<400> SEQUENCE: 128

```
Ser Gly Ser Ala Ser Asn Ile Gly Ser Asn Phe Val Ser
1               5                   10
```

<210> SEQ ID NO 129
<211> LENGTH: 7
<212> TYPE: PRT
<213> ORGANISM: Artificial Sequence
<220> FEATURE:
<223> OTHER INFORMATION: ILT70083.2 VLCDR2

<400> SEQUENCE: 129

```
Asp Asn Asp Lys Arg Asp Leu
1               5
```

<210> SEQ ID NO 130
<211> LENGTH: 11
<212> TYPE: PRT
<213> ORGANISM: Artificial Sequence
<220> FEATURE:
<223> OTHER INFORMATION: ILT70083.2 VLCDR3

<400> SEQUENCE: 130

```
Gly Thr Trp Asp Thr Ser Leu Thr Val Gly Val
1               5                   10
```

<210> SEQ ID NO 131

<211> LENGTH: 375
<212> TYPE: DNA
<213> ORGANISM: Artificial Sequence
<220> FEATURE:
<223> OTHER INFORMATION: ILT70083.3 VH

<400> SEQUENCE: 131

```
gaggtgcagc tgttggagtc tgggggaggc ttggtacagc ctggggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggctg gttcaccatc tccagagaca attccaagaa cacgctgtat    240
ctgcaaatga acagcctgag agccgaggac acggccgtgt attactgtgc gaggcggaca    300
tattactatg atagtgatgg tcactcggat gttttttgata tttgggggccg gggcaccctg    360
gtcaccgtct cgagt                                                     375
```

<210> SEQ ID NO 132
<211> LENGTH: 125
<212> TYPE: PRT
<213> ORGANISM: Artificial Sequence
<220> FEATURE:
<223> OTHER INFORMATION: ILT70083.3 VH

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Trp Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Tyr Tyr Tyr Asp Ser Asp Gly His Ser Asp Val Phe
            100                 105                 110

Asp Ile Trp Gly Arg Gly Thr Leu Val Thr Val Ser Ser
        115                 120                 125

<210> SEQ ID NO 133
<211> LENGTH: 5
<212> TYPE: PRT
<213> ORGANISM: Artificial Sequence
<220> FEATURE:
<223> OTHER INFORMATION: ILT70083.3 VHCDR1

<400> SEQUENCE: 133

Ser Tyr Ala Met Ser
1               5

<210> SEQ ID NO 134
<211> LENGTH: 17
<212> TYPE: PRT
<213> ORGANISM: Artificial Sequence
<220> FEATURE:
<223> OTHER INFORMATION: ILT70083.3 VHCDR2

<400> SEQUENCE: 134

Ala Ile Ser Gly Ser Gly Gly Ser Thr Tyr Tyr Ala Asp Ser Val Lys
1               5                   10                  15

Gly

<210> SEQ ID NO 135
<211> LENGTH: 16
<212> TYPE: PRT
<213> ORGANISM: Artificial Sequence
<220> FEATURE:
<223> OTHER INFORMATION: ILT70083.3 VHCDR3

<400> SEQUENCE: 135

Arg Thr Tyr Tyr Tyr Asp Ser Asp Gly His Ser Asp Val Phe Asp Ile
1               5                   10                  15

<210> SEQ ID NO 136
<211> LENGTH: 330
<212> TYPE: DNA
<213> ORGANISM: Artificial Sequence
<220> FEATURE:
<223> OTHER INFORMATION: ILT70083.3 VL

<400> SEQUENCE: 136
cagtctgtcg tgacgcagcc gccctcagtg tctgcggccc caggacagaa ggtcaccatc      60
tcctgttctg gaagcgcctc caatattggg agtaattttg tgtcctggta ccaacaactc     120
cccgggacag cccccaaact cctcatttat gacaatgata aacgagactt agggattcct     180
gaccgcttct ctggctccaa atctggcacg tcagccaccc tgggcatcac cggactccag     240
actggggacg aggccgatta ttactgcgga acatgggaca ccagtctgac tgttggggtt     300
ttcggcggag ggaccaagct gaccgtccta                                      330

<210> SEQ ID NO 137
<211> LENGTH: 110
<212> TYPE: PRT
<213> ORGANISM: Artificial Sequence
<220> FEATURE:
<223> OTHER INFORMATION: ILT70083.3 VL

<400> SEQUENCE: 137

Gln Ser Val Val Thr Gln Pro Pro Ser Val Ser Ala Ala Pro Gly Gln
1               5                   10                  15

Lys Val Thr Ile Ser Cys Ser Gly Ser Ala Ser Asn Ile Gly Ser Asn
                20                  25                  30

Phe Val Ser Trp Tyr Gln Gln Leu Pro Gly Thr Ala Pro Lys Leu Leu
            35                  40                  45

Ile Tyr Asp Asn Asp Lys Arg Asp Leu Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Thr Val Gly Val Phe Gly Gly Gly Thr Lys Leu Thr Val Leu
            100                 105                 110

<210> SEQ ID NO 138
<211> LENGTH: 13
<212> TYPE: PRT
<213> ORGANISM: Artificial Sequence
<220> FEATURE:
<223> OTHER INFORMATION: ILT70083.3 VLCDR1

<400> SEQUENCE: 138

Ser Gly Ser Ala Ser Asn Ile Gly Ser Asn Phe Val Ser
1               5                   10

<210> SEQ ID NO 139
<211> LENGTH: 7
<212> TYPE: PRT
<213> ORGANISM: Artificial Sequence
<220> FEATURE:
<223> OTHER INFORMATION: ILT70083.3 VLCDR2

<400> SEQUENCE: 139

Asp Asn Asp Lys Arg Asp Leu
1               5

<210> SEQ ID NO 140
<211> LENGTH: 11
<212> TYPE: PRT
<213> ORGANISM: Artificial Sequence
<220> FEATURE:
<223> OTHER INFORMATION: ILT70083.3 VLCDR3

<400> SEQUENCE: 140

Gly Thr Trp Asp Thr Ser Leu Thr Val Gly Val
1               5                   10

<210> SEQ ID NO 141
<211> LENGTH: 375
<212> TYPE: DNA
<213> ORGANISM: Artificial Sequence
<220> FEATURE:
<223> OTHER INFORMATION: ILT70083.4 VH

<400> SEQUENCE: 141

```
gaggtgcagc tgttggagtc tgggggaggc ttggtacagc ctgggggtc cctgagactc        60 tcctgtgcag cctctggatt cacctttagc agctatgcca tgagctgggt ccgccaggct       120
ccagggaagg ggctggagtg ggtctcagct attagtggta gtggtggtag cacatactac       180
gcagactccg tgaagggctg gttcaccatc tccagagaca attccaagaa cacgctgtat       240
ctgcaaatga acagcctgag agccgaggac acggccgtgt attactgtgc gaggcggaca       300
tattactatg atagtgatgg tcactcggat gttttttgata tttggggccg gggcaccctg       360
gtcaccgtct cgagt                                                        375
```

<210> SEQ ID NO 142
<211> LENGTH: 125
<212> TYPE: PRT
<213> ORGANISM: Artificial Sequence
<220> FEATURE:
<223> OTHER INFORMATION: ILT70083.4 VH

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Trp Phe Thr Ile Ser Arg Asp Asn Ser Lys Asn Thr Leu Tyr
65                  70                  75                  80

-continued

Leu Gln Met Asn Ser Leu Arg Ala Glu Asp Thr Ala Val Tyr Tyr Cys
                85                  90                  95

Ala Arg Arg Thr Tyr Tyr Tyr Asp Ser Asp Gly His Ser Asp Val Phe
            100                 105                 110

Asp Ile Trp Gly Arg Gly Thr Leu Val Thr Val Ser Ser
        115                 120                 125

<210> SEQ ID NO 143
<211> LENGTH: 5
<212> TYPE: PRT
<213> ORGANISM: Artificial Sequence
<220> FEATURE:
<223> OTHER INFORMATION: ILT70083.4 VHCDR1

<400> SEQUENCE: 143

Ser Tyr Ala Met Ser
1               5

<210> SEQ ID NO 144
<211> LENGTH: 17
<212> TYPE: PRT
<213> ORGANISM: Artificial Sequence
<220> FEATURE:
<223> OTHER INFORMATION: ILT70083.4 VHCDR2

<400> SEQUENCE: 144

Ala Ile Ser Gly Ser Gly Gly Ser Thr Tyr Tyr Ala Asp Ser Val Lys
1               5                   10                  15

Gly

<210> SEQ ID NO 145
<211> LENGTH: 16
<212> TYPE: PRT
<213> ORGANISM: Artificial Sequence
<220> FEATURE:
<223> OTHER INFORMATION: ILT70083.4 VHCDR3

<400> SEQUENCE: 145

Arg Thr Tyr Tyr Tyr Asp Ser Asp Gly His Ser Asp Val Phe Asp Ile
1               5                   10                  15

<210> SEQ ID NO 146
<211> LENGTH: 330
<212> TYPE: DNA
<213> ORGANISM: Artificial Sequence
<220> FEATURE:
<223> OTHER INFORMATION: ILT70083.4 VL

<400> SEQUENCE: 146
cagtctgtcc tgacgcagcc gccctcagtg tctgcggccc caggacagaa ggtcaccatc      60
tcctgttctg gaagcgcctc caatattggg agtaattttg tgtcctggta ccaacaactc     120
cccgggacag cccccaaact cctcatttat gacaatgata acgagactt agggattcct      180 gaccgcttct ctggctccaa gtctggcacg tcagccaccc tgggcatcac cggactccag     240
actggggacg aggccgatta ttactgcgga acatgggaca ccagtctgac tgttggggtt     300
ttcggcggag ggaccaagct gaccgtccta                                      330

<210> SEQ ID NO 147
<211> LENGTH: 110
<212> TYPE: PRT
<213> ORGANISM: Artificial Sequence
<220> FEATURE:

<223> OTHER INFORMATION: ILT70083.4 VL

<400> SEQUENCE: 147

Gln Ser Val Leu Thr Gln Pro Pro Ser Val Ser Ala Ala Pro Gly Gln
1               5                   10                  15

Lys Val Thr Ile Ser Cys Ser Gly Ser Ala Ser Asn Ile Gly Ser Asn
            20                  25                  30

Phe Val Ser Trp Tyr Gln Gln Leu Pro Gly Thr Ala Pro Lys Leu Leu
        35                  40                  45

Ile Tyr Asp Asn Asp Lys Arg Asp Leu Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Thr Val Gly Val Phe Gly Gly Gly Thr Lys Leu Thr Val Leu
            100                 105                 110

<210> SEQ ID NO 148
<211> LENGTH: 13
<212> TYPE: PRT
<213> ORGANISM: Artificial Sequence
<220> FEATURE:
<223> OTHER INFORMATION: ILT70083.4 VLCDR1

<400> SEQUENCE: 148

Ser Gly Ser Ala Ser Asn Ile Gly Ser Asn Phe Val Ser
1               5                   10

<210> SEQ ID NO 149
<211> LENGTH: 7
<212> TYPE: PRT
<213> ORGANISM: Artificial Sequence
<220> FEATURE:
<223> OTHER INFORMATION: ILT70083.4 VLCDR2

<400> SEQUENCE: 149

Asp Asn Asp Lys Arg Asp Leu
1               5

<210> SEQ ID NO 150
<211> LENGTH: 11
<212> TYPE: PRT
<213> ORGANISM: Artificial Sequence
<220> FEATURE:
<223> OTHER INFORMATION: ILT70083.4 VLCDR3

<400> SEQUENCE: 150

Gly Thr Trp Asp Thr Ser Leu Thr Val Gly Val
1               5                   10

<210> SEQ ID NO 151
<211> LENGTH: 375
<212> TYPE: DNA
<213> ORGANISM: Artificial Sequence
<220> FEATURE:
<223> OTHER INFORMATION: ILT70083.5 VH

<400> SEQUENCE: 151
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180

```
gcagactccg tgaagggccg gttcaccatc tccagagaca attccaagaa cacgctgtat    240
ctgcaaatga acagcctgag agccgaggac acggccgtgt attactgtgc gaggcggaca    300
tattactatg atagtgatgg tcactcggat gttttgata tttggggccg gggcaccctg     360
gtcaccgtct cctca                                                     375
```

```
<210> SEQ ID NO 152
<211> LENGTH: 125
<212> TYPE: PRT
<213> ORGANISM: Artificial Sequence
<220> FEATURE:
<223> OTHER INFORMATION: ILT70083.5 VH

<400> SEQUENCE: 152
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Tyr Tyr Tyr Asp Ser Asp Gly His Ser Asp Val Phe
            100                 105                 110

Asp Ile Trp Gly Arg Gly Thr Leu Val Thr Val Ser Ser
        115                 120                 125

```
<210> SEQ ID NO 153
<211> LENGTH: 5
<212> TYPE: PRT
<213> ORGANISM: Artificial Sequence
<220> FEATURE:
<223> OTHER INFORMATION: ILT70083.5 VHCDR1

<400> SEQUENCE: 153
```

Ser Tyr Ala Met Ser
1               5

```
<210> SEQ ID NO 154
<211> LENGTH: 17
<212> TYPE: PRT
<213> ORGANISM: Artificial Sequence
<220> FEATURE:
<223> OTHER INFORMATION: ILT70083.5 VHCDR2

<400> SEQUENCE: 154
```

Ala Ile Ser Gly Ser Gly Gly Ser Thr Tyr Tyr Ala Asp Ser Val Lys
1               5                   10                  15

Gly

```
<210> SEQ ID NO 155
<211> LENGTH: 16
<212> TYPE: PRT
<213> ORGANISM: Artificial Sequence
<220> FEATURE:
<223> OTHER INFORMATION: ILT70083.5 VHCDR3
```

-continued

<400> SEQUENCE: 155

Arg Thr Tyr Tyr Tyr Asp Ser Asp Gly His Ser Asp Val Phe Asp Ile
1               5                   10                  15

<210> SEQ ID NO 156
<211> LENGTH: 330
<212> TYPE: DNA
<213> ORGANISM: Artificial Sequence
<220> FEATURE:
<223> OTHER INFORMATION: ILT70083.5 VL

<400> SEQUENCE: 156

```
cagtctgtcg tgacgcagcc gccctcagtg tctgcggccc caggacagaa ggtcaccatc    60
tcctgttctg gaagcgcctc caatattggg agtaattttg tgtcctggta ccaacaactc   120
cccgggagag cccccaaact cctcatttat gacaatgata aacgagactt agggattcct   180
gaccgcttct ctgcctccat ctcttccacg tcagccgccc tggccatcac cggactccag   240
actgaggacg aggccgatta ttactgcgga acatgggaca ccagtctgac tgttggggtt   300
ttcggcggag ggaccaagct gaccgtccta                                    330
```

<210> SEQ ID NO 157
<211> LENGTH: 110
<212> TYPE: PRT
<213> ORGANISM: Artificial Sequence
<220> FEATURE:
<223> OTHER INFORMATION: ILT70083.5 VL

<400> SEQUENCE: 157

Gln Ser Val Val Thr Gln Pro Pro Ser Val Ser Ala Ala Pro Gly Gln
1               5                   10                  15

Lys Val Thr Ile Ser Cys Ser Gly Ser Ala Ser Asn Ile Gly Ser Asn
                20                  25                  30

Phe Val Ser Trp Tyr Gln Gln Leu Pro Gly Arg Ala Pro Lys Leu Leu
            35                  40                  45

Ile Tyr Asp Asn Asp Lys Arg Asp Leu Gly Ile Pro Asp Arg Phe Ser
        50                  55                  60

Ala Ser Ile Ser Ser Thr Ser Ala Ala Leu Ala Ile Thr Gly Leu Gln
65                  70                  75                  80

Thr Glu Asp Glu Ala Asp Tyr Tyr Cys Gly Thr Trp Asp Thr Ser Leu
                85                  90                  95

Thr Val Gly Val Phe Gly Gly Gly Thr Lys Leu Thr Val Leu
            100                 105                 110

<210> SEQ ID NO 158
<211> LENGTH: 13
<212> TYPE: PRT
<213> ORGANISM: Artificial Sequence
<220> FEATURE:
<223> OTHER INFORMATION: ILT70083.5 VLCDR1

<400> SEQUENCE: 158

Ser Gly Ser Ala Ser Asn Ile Gly Ser Asn Phe Val Ser
1               5                   10

<210> SEQ ID NO 159
<211> LENGTH: 7
<212> TYPE: PRT
<213> ORGANISM: Artificial Sequence
<220> FEATURE:
<223> OTHER INFORMATION: ILT70083.5 VLCDR2

<400> SEQUENCE: 159

Asp Asn Asp Lys Arg Asp Leu
1               5

<210> SEQ ID NO 160
<211> LENGTH: 11
<212> TYPE: PRT
<213> ORGANISM: Artificial Sequence
<220> FEATURE:
<223> OTHER INFORMATION: ILT70083.5 VLCDR3

<400> SEQUENCE: 160

Gly Thr Trp Asp Thr Ser Leu Thr Val Gly Val
1               5                   10

<210> SEQ ID NO 161
<211> LENGTH: 375
<212> TYPE: DNA
<213> ORGANISM: Artificial Sequence
<220> FEATURE:
<223> OTHER INFORMATION: ILT70083.6 VH

<400> SEQUENCE: 161
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaggcggaca     300
tattactatg atagtgatgg tcactcggat gttttttgata tttggggccg gggcaccctg     360
gtcaccgtct cctca                                                      375

<210> SEQ ID NO 162
<211> LENGTH: 125
<212> TYPE: PRT
<213> ORGANISM: Artificial Sequence
<220> FEATURE:
<223> OTHER INFORMATION: ILT70083.6 VH

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Tyr Tyr Tyr Asp Ser Asp Gly His Ser Asp Val Phe
            100                 105                 110

Asp Ile Trp Gly Arg Gly Thr Leu Val Thr Val Ser Ser
        115                 120                 125

<210> SEQ ID NO 163
<211> LENGTH: 5

-continued

<210> SEQ ID NO 163
<211> LENGTH: 
<212> TYPE: PRT
<213> ORGANISM: Artificial Sequence
<220> FEATURE:
<223> OTHER INFORMATION: ILT70083.6 VHCDR1

<400> SEQUENCE: 163

Ser Tyr Ala Met Ser
1               5

<210> SEQ ID NO 164
<211> LENGTH: 17
<212> TYPE: PRT
<213> ORGANISM: Artificial Sequence
<220> FEATURE:
<223> OTHER INFORMATION: ILT70083.6 VHCDR2

<400> SEQUENCE: 164

Ala Ile Ser Gly Ser Gly Gly Ser Thr Tyr Tyr Ala Asp Ser Val Lys
1               5                   10                  15

Gly

<210> SEQ ID NO 165
<211> LENGTH: 16
<212> TYPE: PRT
<213> ORGANISM: Artificial Sequence
<220> FEATURE:
<223> OTHER INFORMATION: ILT70083.6 VHCDR3

<400> SEQUENCE: 165

Arg Thr Tyr Tyr Tyr Asp Ser Asp Gly His Ser Asp Val Phe Asp Ile
1               5                   10                  15

<210> SEQ ID NO 166
<211> LENGTH: 330
<212> TYPE: DNA
<213> ORGANISM: Artificial Sequence
<220> FEATURE:
<223> OTHER INFORMATION: ILT70083.6 VL

<400> SEQUENCE: 166
cagtctgtcg tgacgcagcc gcccctcagtg tctgcggccc caggacagaa ggtcaccatc      60
tcctgttctg gaagcgcctc caatattggg agtaattttg tgtcctggta ccaacaactc     120
cccgggacag cccccaaact cctcatttat gacaatgata aacgagactt agggattcct     180
gaccgcttct ctgcctccat ctcttccacg tcagccaccc tgggcatcac cggactccag     240
actggggacg aggccgatta ttactgcgga acatgggaca ccagtctgac tgttggggtt     300
ttcggcggag ggaccaagct gaccgtccta                                       330

<210> SEQ ID NO 167
<211> LENGTH: 110
<212> TYPE: PRT
<213> ORGANISM: Artificial Sequence
<220> FEATURE:
<223> OTHER INFORMATION: ILT70083.6 VL

<400> SEQUENCE: 167

Gln Ser Val Val Thr Gln Pro Pro Ser Val Ser Ala Ala Pro Gly Gln
1               5                   10                  15

Lys Val Thr Ile Ser Cys Ser Gly Ser Ala Ser Asn Ile Gly Ser Asn
                20                  25                  30

Phe Val Ser Trp Tyr Gln Gln Leu Pro Gly Thr Ala Pro Lys Leu Leu
            35                  40                  45

```
Ile Tyr Asp Asn Asp Lys Arg Asp Leu Gly Ile Pro Asp Arg Phe Ser
    50                  55                  60

Ala Ser Ile Ser Ser Thr Ser Ala Thr Leu Gly Ile Thr Gly Leu Gln
 65                  70                  75                  80

Thr Gly Asp Glu Ala Asp Tyr Tyr Cys Gly Thr Trp Asp Thr Ser Leu
                 85                  90                  95

Thr Val Gly Val Phe Gly Gly Gly Thr Lys Leu Thr Val Leu
            100                 105                 110
```

<210> SEQ ID NO 168
<211> LENGTH: 13
<212> TYPE: PRT
<213> ORGANISM: Artificial Sequence
<220> FEATURE:
<223> OTHER INFORMATION: ILT70083.6 VLCDR1

<400> SEQUENCE: 168

```
Ser Gly Ser Ala Ser Asn Ile Gly Ser Asn Phe Val Ser
1               5                   10
```

<210> SEQ ID NO 169
<211> LENGTH: 7
<212> TYPE: PRT
<213> ORGANISM: Artificial Sequence
<220> FEATURE:
<223> OTHER INFORMATION: ILT70083.6 VLCDR2

<400> SEQUENCE: 169

```
Asp Asn Asp Lys Arg Asp Leu
1               5
```

<210> SEQ ID NO 170
<211> LENGTH: 11
<212> TYPE: PRT
<213> ORGANISM: Artificial Sequence
<220> FEATURE:
<223> OTHER INFORMATION: ILT70083.6 VLCDR3

<400> SEQUENCE: 170

```
Gly Thr Trp Asp Thr Ser Leu Thr Val Gly Val
1               5                   10
```

<210> SEQ ID NO 171
<211> LENGTH: 375
<212> TYPE: DNA
<213> ORGANISM: Artificial Sequence
<220> FEATURE:
<223> OTHER INFORMATION: ILT70083.7 VH

<400> SEQUENCE: 171

```
gaggtgcagc tgttggagtc tgggggaggc ttggtacagc ctgggggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaggcggaca     300
tattactatg atagtgatgg tcactcggat gttttttgata tttggggccg gggcaccctg     360
gtcaccgtct cctca                                                       375
```

<210> SEQ ID NO 172
<211> LENGTH: 125
<212> TYPE: PRT

```
<213> ORGANISM: Artificial Sequence
<220> FEATURE:
<223> OTHER INFORMATION: ILT70083.7 VH

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Tyr Tyr Tyr Asp Ser Asp Gly His Ser Asp Val Phe
            100                 105                 110

Asp Ile Trp Gly Arg Gly Thr Leu Val Thr Val Ser Ser
        115                 120                 125

<210> SEQ ID NO 173
<211> LENGTH: 5
<212> TYPE: PRT
<213> ORGANISM: Artificial Sequence
<220> FEATURE:
<223> OTHER INFORMATION: ILT70083.7 VHCDR1

<400> SEQUENCE: 173

Ser Tyr Ala Met Ser
1               5

<210> SEQ ID NO 174
<211> LENGTH: 17
<212> TYPE: PRT
<213> ORGANISM: Artificial Sequence
<220> FEATURE:
<223> OTHER INFORMATION: ILT70083.7 VHCDR2

<400> SEQUENCE: 174

Ala Ile Ser Gly Ser Gly Gly Ser Thr Tyr Tyr Ala Asp Ser Val Lys
1               5                   10                  15

Gly

<210> SEQ ID NO 175
<211> LENGTH: 16
<212> TYPE: PRT
<213> ORGANISM: Artificial Sequence
<220> FEATURE:
<223> OTHER INFORMATION: ILT70083.7 VHCDR3

<400> SEQUENCE: 175

Arg Thr Tyr Tyr Tyr Asp Ser Asp Gly His Ser Asp Val Phe Asp Ile
1               5                   10                  15

<210> SEQ ID NO 176
<211> LENGTH: 330
<212> TYPE: DNA
<213> ORGANISM: Artificial Sequence
<220> FEATURE:
<223> OTHER INFORMATION: ILT70083.7 VL
```

<400> SEQUENCE: 176

```
cagtctgtcc tgacgcagcc gccctcagtg tctgcggccc caggacagaa ggtcaccatc      60
tcctgttctg gaagcgcctc caatattggg agtaattttg tgtcctggta ccaacaactc     120
cccgggacag ccccccaaact cctcatttat gacaatgata aacgagactt agggattcct    180
gaccgcttct ctgcctccat ctcttccacg tcagccaccc tgggcatcac cggactccag     240
actggggacg aggccgatta ttactgcgga acatgggaca ccagtctgac tgttggggtt     300
ttcggcggag ggaccaagct gaccgtccta                                      330
```

<210> SEQ ID NO 177
<211> LENGTH: 110
<212> TYPE: PRT
<213> ORGANISM: Artificial Sequence
<220> FEATURE:
<223> OTHER INFORMATION: ILT70083.7 VL

<400> SEQUENCE: 177

Gln Ser Val Leu Thr Gln Pro Pro Ser Val Ala Ala Pro Gly Gln
1               5                   10                  15

Lys Val Thr Ile Ser Cys Ser Gly Ser Ala Ser Asn Ile Gly Ser Asn
            20                  25                  30

Phe Val Ser Trp Tyr Gln Gln Leu Pro Gly Thr Ala Pro Lys Leu Leu
        35                  40                  45

Ile Tyr Asp Asn Asp Lys Arg Asp Leu Gly Ile Pro Asp Arg Phe Ser
    50                  55                  60

Ala Ser Ile Ser Ser Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Thr Val Gly Val Phe Gly Gly Gly Thr Lys Leu Thr Val Leu
            100                 105                 110

<210> SEQ ID NO 178
<211> LENGTH: 13
<212> TYPE: PRT
<213> ORGANISM: Artificial Sequence
<220> FEATURE:
<223> OTHER INFORMATION: ILT70083.7 VLCDR1

<400> SEQUENCE: 178

Ser Gly Ser Ala Ser Asn Ile Gly Ser Asn Phe Val Ser
1               5                   10

<210> SEQ ID NO 179
<211> LENGTH: 7
<212> TYPE: PRT
<213> ORGANISM: Artificial Sequence
<220> FEATURE:
<223> OTHER INFORMATION: ILT70083.7 VLCDR2

<400> SEQUENCE: 179

Asp Asn Asp Lys Arg Asp Leu
1               5

<210> SEQ ID NO 180
<211> LENGTH: 11
<212> TYPE: PRT
<213> ORGANISM: Artificial Sequence
<220> FEATURE:
<223> OTHER INFORMATION: ILT70083.7 VLCDR3

<400> SEQUENCE: 180

Gly Thr Trp Asp Thr Ser Leu Thr Val Gly Val
1               5                   10

<210> SEQ ID NO 181
<211> LENGTH: 375
<212> TYPE: DNA
<213> ORGANISM: Artificial Sequence
<220> FEATURE:
<223> OTHER INFORMATION: ILT70083.8 VH

<400> SEQUENCE: 181

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gaggcggaca    300
tattactatg atagtgatgg tcactcggat gtttttgata tttggggccg gggcaccctg    360
gtcaccgtct cctca                                                    375
```

<210> SEQ ID NO 182
<211> LENGTH: 125
<212> TYPE: PRT
<213> ORGANISM: Artificial Sequence
<220> FEATURE:
<223> OTHER INFORMATION: ILT70083.8 VH

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Tyr Tyr Tyr Asp Ser Asp Gly His Ser Asp Val Phe
            100                 105                 110

Asp Ile Trp Gly Arg Gly Thr Leu Val Thr Val Ser Ser
        115                 120                 125

<210> SEQ ID NO 183
<211> LENGTH: 5
<212> TYPE: PRT
<213> ORGANISM: Artificial Sequence
<220> FEATURE:
<223> OTHER INFORMATION: ILT70083.8 VHCDR1

<400> SEQUENCE: 183

Ser Tyr Ala Met Ser
1               5

<210> SEQ ID NO 184
<211> LENGTH: 17

```
<212> TYPE: PRT
<213> ORGANISM: Artificial Sequence
<220> FEATURE:
<223> OTHER INFORMATION: ILT70083.8 VHCDR2

<400> SEQUENCE: 184

Ala Ile Ser Gly Ser Gly Gly Ser Thr Tyr Tyr Ala Asp Ser Val Lys
1               5                   10                  15

Gly

<210> SEQ ID NO 185
<211> LENGTH: 16
<212> TYPE: PRT
<213> ORGANISM: Artificial Sequence
<220> FEATURE:
<223> OTHER INFORMATION: ILT70083.8 VHCDR3

<400> SEQUENCE: 185

Arg Thr Tyr Tyr Tyr Asp Ser Asp Gly His Ser Asp Val Phe Asp Ile
1               5                   10                  15

<210> SEQ ID NO 186
<211> LENGTH: 330
<212> TYPE: DNA
<213> ORGANISM: Artificial Sequence
<220> FEATURE:
<223> OTHER INFORMATION: ILT70083.8 VL

<400> SEQUENCE: 186
cagtctgtcg tgacgcagcc gcccctcagtg tctgcggccc caggacagaa ggtcaccatc      60
tcctgttctg gaagcgcctc caatattggg agtaattttg tgtcctggta ccaacaactc     120
cccgggacag ccccccaaact cctcatttat gacaatgata acgagacttt agggattcct     180
gaccgcttct ctggctccaa atctggcacg tcagccaccc tgggcatcac cggactccag     240
actggggacg aggccgatta ttactgcgga acatgggaca ccagtctgac tgttggggtt     300
ttcggcggag ggaccaagct gaccgtccta                                       330

<210> SEQ ID NO 187
<211> LENGTH: 110
<212> TYPE: PRT
<213> ORGANISM: Artificial Sequence
<220> FEATURE:
<223> OTHER INFORMATION: ILT70083.8 VL

<400> SEQUENCE: 187

Gln Ser Val Val Thr Gln Pro Pro Ser Val Ser Ala Ala Pro Gly Gln
1               5                   10                  15

Lys Val Thr Ile Ser Cys Ser Gly Ser Ala Ser Asn Ile Gly Ser Asn
                20                  25                  30

Phe Val Ser Trp Tyr Gln Gln Leu Pro Gly Thr Ala Pro Lys Leu Leu
            35                  40                  45

Ile Tyr Asp Asn Asp Lys Arg Asp Leu Gly Ile Pro Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Thr Val Gly Val Phe Gly Gly Gly Thr Lys Leu Thr Val Leu
            100                 105                 110
```

<210> SEQ ID NO 188
<211> LENGTH: 13
<212> TYPE: PRT
<213> ORGANISM: Artificial Sequence
<220> FEATURE:
<223> OTHER INFORMATION: ILT70083.8 VLCDR1

<400> SEQUENCE: 188

Ser Gly Ser Ala Ser Asn Ile Gly Ser Asn Phe Val Ser
1               5                   10

<210> SEQ ID NO 189
<211> LENGTH: 7
<212> TYPE: PRT
<213> ORGANISM: Artificial Sequence
<220> FEATURE:
<223> OTHER INFORMATION: ILT70083.8 VLCDR2

<400> SEQUENCE: 189

Asp Asn Asp Lys Arg Asp Leu
1               5

<210> SEQ ID NO 190
<211> LENGTH: 11
<212> TYPE: PRT
<213> ORGANISM: Artificial Sequence
<220> FEATURE:
<223> OTHER INFORMATION: ILT70083.8 VLCDR3

<400> SEQUENCE: 190

Gly Thr Trp Asp Thr Ser Leu Thr Val Gly Val
1               5                   10

<210> SEQ ID NO 191
<211> LENGTH: 375
<212> TYPE: DNA
<213> ORGANISM: Artificial Sequence
<220> FEATURE:
<223> OTHER INFORMATION: ILT70083.9 VH

<400> SEQUENCE: 191
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtgt attactgtgc gaggcggaca     300
tattactatg atagtgatgg tcactcggat gttttttgata tttggggccg gggcaccctg     360
gtcaccgtct cctca                                                     375

<210> SEQ ID NO 192
<211> LENGTH: 125
<212> TYPE: PRT
<213> ORGANISM: Artificial Sequence
<220> FEATURE:
<223> OTHER INFORMATION: ILT70083.9 VH

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
            35                  40                  45
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Arg Thr Tyr Tyr Tyr Asp Ser Asp Gly His Ser Asp Val Phe
            100                 105                 110
Asp Ile Trp Gly Arg Gly Thr Leu Val Thr Val Ser Ser
        115                 120                 125

<210> SEQ ID NO 193
<211> LENGTH: 5
<212> TYPE: PRT
<213> ORGANISM: Artificial Sequence
<220> FEATURE:
<223> OTHER INFORMATION: ILT70083.9 VHCDR1

<400> SEQUENCE: 193

Ser Tyr Ala Met Ser
1               5

<210> SEQ ID NO 194
<211> LENGTH: 17
<212> TYPE: PRT
<213> ORGANISM: Artificial Sequence
<220> FEATURE:
<223> OTHER INFORMATION: ILT70083.9 VHCDR2

<400> SEQUENCE: 194

Ala Ile Ser Gly Ser Gly Gly Ser Thr Tyr Tyr Ala Asp Ser Val Lys
1               5                   10                  15
Gly

<210> SEQ ID NO 195
<211> LENGTH: 16
<212> TYPE: PRT
<213> ORGANISM: Artificial Sequence
<220> FEATURE:
<223> OTHER INFORMATION: ILT70083.9 VHCDR3

<400> SEQUENCE: 195

Arg Thr Tyr Tyr Tyr Asp Ser Asp Gly His Ser Asp Val Phe Asp Ile
1               5                   10                  15

<210> SEQ ID NO 196
<211> LENGTH: 330
<212> TYPE: DNA
<213> ORGANISM: Artificial Sequence
<220> FEATURE:
<223> OTHER INFORMATION: ILT70083.9 VL

<400> SEQUENCE: 196
cagtctgtcc tgacgcagcc gccctcagtg tctgcggccc caggacagaa ggtcaccatc      60
tcctgttctg gaagcgcctc caatattggg agtaattttg tgtcctggta ccaacaactc     120
cccgggacag cccccaaact cctcatttat gacaatgata acgagacttt agggattcct     180
gaccgcttct ctggctccaa gtctggcacg tcagccaccc tgggcatcac cggactccag     240
actggggacg aggccgatta ttactgcgga acatgggaca ccagtctgac tgttggggtt     300
ttcggcggag ggaccaagct gaccgtccta                                       330
```

<210> SEQ ID NO 197
<211> LENGTH: 110
<212> TYPE: PRT
<213> ORGANISM: Artificial Sequence
<220> FEATURE:
<223> OTHER INFORMATION: ILT70083.9 VL

<400> SEQUENCE: 197

Gln Ser Val Leu Thr Gln Pro Pro Ser Val Ser Ala Ala Pro Gly Gln
1               5                   10                  15

Lys Val Thr Ile Ser Cys Ser Gly Ser Ala Ser Asn Ile Gly Ser Asn
            20                  25                  30

Phe Val Ser Trp Tyr Gln Gln Leu Pro Gly Thr Ala Pro Lys Leu Leu
        35                  40                  45

Ile Tyr Asp Asn Asp Lys Arg Asp Leu Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Thr Val Gly Val Phe Gly Gly Gly Thr Lys Leu Thr Val Leu
            100                 105                 110

<210> SEQ ID NO 198
<211> LENGTH: 13
<212> TYPE: PRT
<213> ORGANISM: Artificial Sequence
<220> FEATURE:
<223> OTHER INFORMATION: ILT70083.9 VLCDR1

<400> SEQUENCE: 198

Ser Gly Ser Ala Ser Asn Ile Gly Ser Asn Phe Val Ser
1               5                   10

<210> SEQ ID NO 199
<211> LENGTH: 7
<212> TYPE: PRT
<213> ORGANISM: Artificial Sequence
<220> FEATURE:
<223> OTHER INFORMATION: ILT70083.9 VLCDR2

<400> SEQUENCE: 199

Asp Asn Asp Lys Arg Asp Leu
1               5

<210> SEQ ID NO 200
<211> LENGTH: 11
<212> TYPE: PRT
<213> ORGANISM: Artificial Sequence
<220> FEATURE:
<223> OTHER INFORMATION: ILT70083.9 VLCDR3

<400> SEQUENCE: 200

Gly Thr Trp Asp Thr Ser Leu Thr Val Gly Val
1               5                   10

<210> SEQ ID NO 201
<211> LENGTH: 366
<212> TYPE: DNA
<213> ORGANISM: Artificial Sequence
<220> FEATURE:
<223> OTHER INFORMATION: ILT70137 VH

<400> SEQUENCE: 201

```
caggtacagc tgcagcagtc aggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagaaatggc     300
ctctgggggt gggactctga tgcttttgat atctggggcc aggaacccct ggtcaccgtc     360
tcctca                                                                 366
```

<210> SEQ ID NO 202
<211> LENGTH: 122
<212> TYPE: PRT
<213> ORGANISM: Artificial Sequence
<220> FEATURE:
<223> OTHER INFORMATION: ILT70137 VH

<400> SEQUENCE: 202

```
Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Leu Trp Gly Trp Asp Ser Asp Ala Phe Asp Ile Trp
            100                 105                 110

Gly Arg Gly Thr Leu Val Thr Val Ser Ser
        115                 120
```

<210> SEQ ID NO 203
<211> LENGTH: 5
<212> TYPE: PRT
<213> ORGANISM: Artificial Sequence
<220> FEATURE:
<223> OTHER INFORMATION: ILT70137 VHCDR1

<400> SEQUENCE: 203

```
Ser Tyr Gly Ile Ser
1               5
```

<210> SEQ ID NO 204
<211> LENGTH: 17
<212> TYPE: PRT
<213> ORGANISM: Artificial Sequence
<220> FEATURE:
<223> OTHER INFORMATION: ILT70137 VHCDR2

<400> SEQUENCE: 204

```
Trp Ile Ser Ala Tyr Asn Gly Asn Thr Asn Tyr Ala Gln Lys Leu Gln
1               5                   10                  15

Gly
```

```
<210> SEQ ID NO 205
<211> LENGTH: 13
<212> TYPE: PRT
<213> ORGANISM: Artificial Sequence
<220> FEATURE:
<223> OTHER INFORMATION: ILT70137 VHCDR3

<400> SEQUENCE: 205

Asn Gly Leu Trp Gly Trp Asp Ser Asp Ala Phe Asp Ile
1               5                   10

<210> SEQ ID NO 206
<211> LENGTH: 330
<212> TYPE: DNA
<213> ORGANISM: Artificial Sequence
<220> FEATURE:
<223> OTHER INFORMATION: ILT70137 VL

<400> SEQUENCE: 206
cagtctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca aagcccccaa actcatgatt tatgatgtca gtaatcggcc ctcaggggtt     180
tctaatcgct tctctggctc caagtctggc aacacggcct ccctgaccat ctctgggctc     240
caggctgagg acgaggctga ttattactgc agctcatata caagcagcag cactgtggta     300
ttcggcggag ggaccaaggt caccgtccta                                      330

<210> SEQ ID NO 207
<211> LENGTH: 110
<212> TYPE: PRT
<213> ORGANISM: Artificial Sequence
<220> FEATURE:
<223> OTHER INFORMATION: ILT70137 VL

<400> SEQUENCE: 207

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Val Thr Val Leu
            100                 105                 110

<210> SEQ ID NO 208
<211> LENGTH: 14
<212> TYPE: PRT
<213> ORGANISM: Artificial Sequence
<220> FEATURE:
<223> OTHER INFORMATION: ILT70137 VLCDR1

<400> SEQUENCE: 208

Thr Gly Thr Ser Ser Asp Val Gly Gly Tyr Asn Tyr Val Ser
1               5                   10
```

-continued

```
<210> SEQ ID NO 209
<211> LENGTH: 7
<212> TYPE: PRT
<213> ORGANISM: Artificial Sequence
<220> FEATURE:
<223> OTHER INFORMATION: ILT70137 VLCDR2

<400> SEQUENCE: 209

Asp Val Ser Asn Arg Pro Ser
1               5

<210> SEQ ID NO 210
<211> LENGTH: 10
<212> TYPE: PRT
<213> ORGANISM: Artificial Sequence
<220> FEATURE:
<223> OTHER INFORMATION: ILT70137 VLCDR3

<400> SEQUENCE: 210

Ser Ser Tyr Thr Ser Ser Ser Thr Val Val
1               5                   10

<210> SEQ ID NO 211
<211> LENGTH: 360
<212> TYPE: DNA
<213> ORGANISM: Artificial Sequence
<220> FEATURE:
<223> OTHER INFORMATION: ILT70052 VH

<400> SEQUENCE: 211
gaggtgcagc tggtggagtc tgggggaggc ttggtcaagc ctggagggtc cctgagactc      60
tcctgtgaag cctccggatt caccttcact gactactaca tgaactggat ccgccaggct     120
ccagggaagg ggctggagtg gatttcatac attagtcctg ggggtactac cgtatactac     180
gcagactctg tgaagggccg attcaccatc tccagggaca acgccaagaa ctcattatat     240
ctccaaatga acagcctgag agtcgaggac acggccgtct attactgtgc gagagacatt     300
agtggttatg gcgactggtt cgaccctggg ggcaagggca ccctggtcac cgtctcgagt     360

<210> SEQ ID NO 212
<211> LENGTH: 120
<212> TYPE: PRT
<213> ORGANISM: Artificial Sequence
<220> FEATURE:
<223> OTHER INFORMATION: ILT70052 VH

<400> SEQUENCE: 212

Glu Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Thr Asp Tyr
            20                  25                  30

Tyr Met Asn Trp Ile Arg Gln Ala Pro Gly Lys Gly Leu Glu Trp Ile
        35                  40                  45

Ser Tyr Ile Ser Pro Gly Gly Thr Thr Val Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Ile Ser Gly Tyr Gly Asp Trp Phe Asp Pro Trp Gly Lys
            100                 105                 110

Gly Thr Leu Val Thr Val Ser Ser
```

<210> SEQ ID NO 213
<211> LENGTH: 5
<212> TYPE: PRT
<213> ORGANISM: Artificial Sequence
<220> FEATURE:
<223> OTHER INFORMATION: ILT70052 VHCDR1

<400> SEQUENCE: 213

Asp Tyr Tyr Met Asn
1               5

<210> SEQ ID NO 214
<211> LENGTH: 17
<212> TYPE: PRT
<213> ORGANISM: Artificial Sequence
<220> FEATURE:
<223> OTHER INFORMATION: ILT70052 VHCDR2

<400> SEQUENCE: 214

Tyr Ile Ser Pro Gly Gly Thr Thr Val Tyr Tyr Ala Asp Ser Val Lys
1               5                   10                  15

Gly

<210> SEQ ID NO 215
<211> LENGTH: 11
<212> TYPE: PRT
<213> ORGANISM: Artificial Sequence
<220> FEATURE:
<223> OTHER INFORMATION: ILT70052 VHCDR3

<400> SEQUENCE: 215

Asp Ile Ser Gly Tyr Gly Asp Trp Phe Asp Pro
1               5                   10

<210> SEQ ID NO 216
<211> LENGTH: 330
<212> TYPE: DNA
<213> ORGANISM: Artificial Sequence
<220> FEATURE:
<223> OTHER INFORMATION: ILT70052 VL

<400> SEQUENCE: 216
cagtctgtcg tgacgcagcc gccctcagcg tctgggaccc ccgggcagag ggtcaccatc        60
tcttgttctg gaagcagctc aacatcgga agtaataccg taaactggta ccagctgctc       120
ccagctacgg cccccagaat cctcatctat aataataatc agcggccgtc aggggtccca       180
gaccgattcg ctggctccaa gtctggcacc tcagcctccc tggccatcag tgggctccag       240
tctgaggatg aggctgatta ttactgtgga gcatgggatg acagcctgaa tagtccggtg       300
ttcggcggag ggaccaagct gaccgtccta                                        330

<210> SEQ ID NO 217
<211> LENGTH: 110
<212> TYPE: PRT
<213> ORGANISM: Artificial Sequence
<220> FEATURE:
<223> OTHER INFORMATION: ILT70052 VL

<400> SEQUENCE: 217

Gln Ser Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn

```
                        20                  25                  30
Thr Val Asn Trp Tyr Gln Leu Leu Pro Ala Thr Ala Pro Arg Ile Leu
                 35                  40                  45
Ile Tyr Asn Asn Asn Gln Arg Pro Ser Gly Val Pro Asp Arg Phe Ala
             50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Gly Ala Trp Asp Asp Ser Leu
                 85                  90                  95
Asn Ser Pro Val Phe Gly Gly Gly Thr Lys Leu Thr Val Leu
            100                 105                 110

<210> SEQ ID NO 218
<211> LENGTH: 13
<212> TYPE: PRT
<213> ORGANISM: Artificial Sequence
<220> FEATURE:
<223> OTHER INFORMATION: ILT70052 VLCDR1

<400> SEQUENCE: 218

Ser Gly Ser Ser Ser Asn Ile Gly Ser Asn Thr Val Asn
1               5                   10

<210> SEQ ID NO 219
<211> LENGTH: 7
<212> TYPE: PRT
<213> ORGANISM: Artificial Sequence
<220> FEATURE:
<223> OTHER INFORMATION: ILT70052 VLCDR2

<400> SEQUENCE: 219

Asn Asn Asn Gln Arg Pro Ser
1               5

<210> SEQ ID NO 220
<211> LENGTH: 11
<212> TYPE: PRT
<213> ORGANISM: Artificial Sequence
<220> FEATURE:
<223> OTHER INFORMATION: ILT70052 VLCDR3

<400> SEQUENCE: 220

Gly Ala Trp Asp Asp Ser Leu Asn Ser Pro Val
1               5                   10

<210> SEQ ID NO 221
<211> LENGTH: 360
<212> TYPE: DNA
<213> ORGANISM: Artificial Sequence
<220> FEATURE:
<223> OTHER INFORMATION: ILT70100 VH

<400> SEQUENCE: 221
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gaggcatagg    300
ggccggtggc taccgtactt cgatctctgg ggccagggga caatggtcac cgtctcgagt    360
```

```
<210> SEQ ID NO 222
<211> LENGTH: 120
<212> TYPE: PRT
<213> ORGANISM: Artificial Sequence
<220> FEATURE:
<223> OTHER INFORMATION: ILT70100 VH

<400> SEQUENCE: 222

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Arg Trp Leu Pro Tyr Phe Asp Leu Trp Gly Gln
            100                 105                 110

Gly Thr Met Val Thr Val Ser Ser
        115                 120

<210> SEQ ID NO 223
<211> LENGTH: 5
<212> TYPE: PRT
<213> ORGANISM: Artificial Sequence
<220> FEATURE:
<223> OTHER INFORMATION: ILT70100 VHCDR1

<400> SEQUENCE: 223

Ser Tyr Ala Met Ser
1               5

<210> SEQ ID NO 224
<211> LENGTH: 17
<212> TYPE: PRT
<213> ORGANISM: Artificial Sequence
<220> FEATURE:
<223> OTHER INFORMATION: ILT70100 VHCDR2

<400> SEQUENCE: 224

Ala Ile Ser Gly Ser Gly Gly Ser Thr Tyr Tyr Ala Asp Ser Val Lys
1               5                   10                  15

Gly

<210> SEQ ID NO 225
<211> LENGTH: 11
<212> TYPE: PRT
<213> ORGANISM: Artificial Sequence
<220> FEATURE:
<223> OTHER INFORMATION: ILT70100 VHCDR3

<400> SEQUENCE: 225

His Arg Gly Arg Trp Leu Pro Tyr Phe Asp Leu
1               5                   10

<210> SEQ ID NO 226
<211> LENGTH: 321
<212> TYPE: DNA
<213> ORGANISM: Artificial Sequence
```

<220> FEATURE:
<223> OTHER INFORMATION: ILT70100 VH

<400> SEQUENCE: 226

```
gacatccagt tgacccagtc tccatcctcc ctgtctgcat ctgtgggaga gagagtcacc    60
atcacttgcc aggcgagtca ggacattcgc agctatttaa attggtatca gcaaaaacca   120
gggaaagccc ctaaactcct gatctatgat gtatccaatt tggaaaccgg ggtcccatca   180
cggttcagtg aagtggatc tgggacagag tatactttca gcatcagcag cctgcagcct   240
gaagattttg caacatatta ttgtcaacag tatgataaag ccccgcttac tttcggcgga   300
gggaccaagg tggaaatcaa a                                             321
```

<210> SEQ ID NO 227
<211> LENGTH: 107
<212> TYPE: PRT
<213> ORGANISM: Artificial Sequence
<220> FEATURE:
<223> OTHER INFORMATION: ILT70100 VL

<400> SEQUENCE: 227

```
Asp Ile Gln Leu Thr Gln Ser Pro Ser Ser Leu Ser Ala Ser Val Gly
1               5                   10                  15

Glu Arg Val Thr Ile Thr Cys Gln Ala Ser Gln Asp Ile Arg Ser Tyr
            20                  25                  30

Leu Asn Trp Tyr Gln Gln Lys Pro Gly Lys Ala Pro Lys Leu Leu Ile
        35                  40                  45

Tyr Asp Val Ser Asn Leu Glu Thr Gly Val Pro Ser Arg Phe Ser Gly
    50                  55                  60

Ser Gly Ser Gly Thr Glu Tyr Thr Phe Ser Ile Ser Ser Leu Gln Pro
65                  70                  75                  80

Glu Asp Phe Ala Thr Tyr Tyr Cys Gln Gln Tyr Asp Lys Ala Pro Leu
                85                  90                  95

Thr Phe Gly Gly Gly Thr Lys Val Glu Ile Lys
            100                 105
```

<210> SEQ ID NO 228
<211> LENGTH: 11
<212> TYPE: PRT
<213> ORGANISM: Artificial Sequence
<220> FEATURE:
<223> OTHER INFORMATION: ILT70100 VLCDR1

<400> SEQUENCE: 228

```
Gln Ala Ser Gln Asp Ile Arg Ser Tyr Leu Asn
1               5                   10
```

<210> SEQ ID NO 229
<211> LENGTH: 7
<212> TYPE: PRT
<213> ORGANISM: Artificial Sequence
<220> FEATURE:
<223> OTHER INFORMATION: ILT70100 VLCDR2

<400> SEQUENCE: 229

```
Asp Val Ser Asn Leu Glu Thr
1               5
```

<210> SEQ ID NO 230
<211> LENGTH: 9
<212> TYPE: PRT
<213> ORGANISM: Artificial Sequence

```
<220> FEATURE:
<223> OTHER INFORMATION: ILT70100 VLCDR3

<400> SEQUENCE: 230

Gln Gln Tyr Asp Lys Ala Pro Leu Thr
1               5

<210> SEQ ID NO 231
<211> LENGTH: 366
<212> TYPE: DNA
<213> ORGANISM: Artificial Sequence
<220> FEATURE:
<223> OTHER INFORMATION: ILT70142 VH

<400> SEQUENCE: 231
caggtccagc tggtacagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaactat   180
gcacagaagc tccagggcag agtcaccatg accaggaca cgtccatcag cacagcctac   240
atggagctga gcaggctgag atctgacgac acggccgtgt attactgtgc gagaaatggc   300
ctctgggggt gggactctga tgcttttgat atctgggggc aagggaccac ggtcaccgtc   360
tcgagt                                                              366

<210> SEQ ID NO 232
<211> LENGTH: 122
<212> TYPE: PRT
<213> ORGANISM: Artificial Sequence
<220> FEATURE:
<223> OTHER INFORMATION: ILT70142 VH

<400> SEQUENCE: 232

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Gly Leu Trp Gly Trp Asp Ser Asp Ala Phe Asp Ile Trp
            100                 105                 110

Gly Gln Gly Thr Thr Val Thr Val Ser Ser
        115                 120

<210> SEQ ID NO 233
<211> LENGTH: 5
<212> TYPE: PRT
<213> ORGANISM: Artificial Sequence
<220> FEATURE:
<223> OTHER INFORMATION: ILT70142 VHCDR1

<400> SEQUENCE: 233

Ser Tyr Gly Ile Ser
1               5
```

<210> SEQ ID NO 234
<211> LENGTH: 17
<212> TYPE: PRT
<213> ORGANISM: Artificial Sequence
<220> FEATURE:
<223> OTHER INFORMATION: ILT70142 VHCDR2

<400> SEQUENCE: 234

Trp Ile Ser Ala Tyr Asn Gly Asn Thr Asn Tyr Ala Gln Lys Leu Gln
1               5                   10                  15

Gly

<210> SEQ ID NO 235
<211> LENGTH: 13
<212> TYPE: PRT
<213> ORGANISM: Artificial Sequence
<220> FEATURE:
<223> OTHER INFORMATION: ILT70142 VHCDR3

<400> SEQUENCE: 235

Asn Gly Leu Trp Gly Trp Asp Ser Asp Ala Phe Asp Ile
1               5                   10

<210> SEQ ID NO 236
<211> LENGTH: 330
<212> TYPE: DNA
<213> ORGANISM: Artificial Sequence
<220> FEATURE:
<223> OTHER INFORMATION: ILT70142 VL

<400> SEQUENCE: 236
cagtctgtgc tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata gcgaccctca gggattcct     180 gaccgattct ctggctccaa gtctggcacg tcagccaccc tgggcatcac cggactccag     240
actggggacg aggccgatta ttactgcgga acatgggata gcagcctgag tgctggcgtc     300
ttcggaactg ggacccagct caccgtttta                                      330

<210> SEQ ID NO 237
<211> LENGTH: 110
<212> TYPE: PRT
<213> ORGANISM: Artificial Sequence
<220> FEATURE:
<223> OTHER INFORMATION: ILT70142 VL

<400> SEQUENCE: 237

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Thr Gly Thr Gln Leu Thr Val Leu

<210> SEQ ID NO 238
<211> LENGTH: 13
<212> TYPE: PRT
<213> ORGANISM: Artificial Sequence
<220> FEATURE:
<223> OTHER INFORMATION: ILT70142 VLCDR1

<400> SEQUENCE: 238

Ser Gly Ser Ser Ser Asn Ile Gly Asn Asn Tyr Val Ser
1               5                   10

<210> SEQ ID NO 239
<211> LENGTH: 7
<212> TYPE: PRT
<213> ORGANISM: Artificial Sequence
<220> FEATURE:
<223> OTHER INFORMATION: ILT70142 VLCDR2

<400> SEQUENCE: 239

Asp Asn Asn Lys Arg Pro Ser
1               5

<210> SEQ ID NO 240
<211> LENGTH: 11
<212> TYPE: PRT
<213> ORGANISM: Artificial Sequence
<220> FEATURE:
<223> OTHER INFORMATION: ILT70142 VLCDR3

<400> SEQUENCE: 240

Gly Thr Trp Asp Ser Ser Leu Ser Ala Gly Val
1               5                   10

<210> SEQ ID NO 241
<211> LENGTH: 366
<212> TYPE: DNA
<213> ORGANISM: Artificial Sequence
<220> FEATURE:
<223> OTHER INFORMATION: ILT70144 VH

<400> SEQUENCE: 241
caggtccagc tggtacagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagcgctt acaatggtaa cacaaactat      180
gcacagaagc tccagggcag agtcaccatg accaggaca cgtccatcag cacagcctac      240
atggagctga gcaggctgag atctgacgac acggccgtgt attactgtgc gagaaatggc     300 ctctggggt gggactctga tgcttttgat atctgggggc aagggaccac ggtcaccgtc      360
tcgagt                                                                366

<210> SEQ ID NO 242
<211> LENGTH: 122
<212> TYPE: PRT
<213> ORGANISM: Artificial Sequence
<220> FEATURE:
<223> OTHER INFORMATION: ILT70144 VH

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                    20                  25                  30
Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Gly Leu Trp Gly Trp Asp Ser Asp Ala Phe Asp Ile Trp
            100                 105                 110

Gly Gln Gly Thr Thr Val Thr Val Ser Ser
        115                 120
```

```
<210> SEQ ID NO 243
<211> LENGTH: 5
<212> TYPE: PRT
<213> ORGANISM: Artificial Sequence
<220> FEATURE:
<223> OTHER INFORMATION: ILT70144 VHCDR1

<400> SEQUENCE: 243

Ser Tyr Gly Ile Ser
1               5
```

```
<210> SEQ ID NO 244
<211> LENGTH: 17
<212> TYPE: PRT
<213> ORGANISM: Artificial Sequence
<220> FEATURE:
<223> OTHER INFORMATION: ILT70144 VHCDR2

<400> SEQUENCE: 244

Trp Ile Ser Ala Tyr Asn Gly Asn Thr Asn Tyr Ala Gln Lys Leu Gln
1               5                   10                  15

Gly
```

```
<210> SEQ ID NO 245
<211> LENGTH: 13
<212> TYPE: PRT
<213> ORGANISM: Artificial Sequence
<220> FEATURE:
<223> OTHER INFORMATION: ILT70144 VHCDR3

<400> SEQUENCE: 245

Asn Gly Leu Trp Gly Trp Asp Ser Asp Ala Phe Asp Ile
1               5                   10
```

```
<210> SEQ ID NO 246
<211> LENGTH: 330
<212> TYPE: DNA
<213> ORGANISM: Artificial Sequence
<220> FEATURE:
<223> OTHER INFORMATION: ILT70144 VL

<400> SEQUENCE: 246
cagtctgtgc tgacgcagcc gccctcagtg tctgcggccc caggacagaa ggtcaccatc      60
tcctgctctg gaagcagctc aacattggga ataattatg tatcctggta ccagcagctc     120
ccaggaacag cccccaaact cctcatttat gacaataata agcgaccctc agggattcct    180
gaccgattct ctggctccaa gtctggcacg tcagccaccc tgggcatcac cggactccag    240
```

```
actggggacg aggccgatta ttactgcgga acatgggata gcagcctgag tgctggcgtc    300
ttcggaactg ggacccagct caccgtttta                                    330
```

<210> SEQ ID NO 247
<211> LENGTH: 110
<212> TYPE: PRT
<213> ORGANISM: Artificial Sequence
<220> FEATURE:
<223> OTHER INFORMATION: ILT70144 VL

<400> SEQUENCE: 247

```
Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Thr Gly Thr Gln Leu Thr Val Leu
            100                 105                 110
```

<210> SEQ ID NO 248
<211> LENGTH: 13
<212> TYPE: PRT
<213> ORGANISM: Artificial Sequence
<220> FEATURE:
<223> OTHER INFORMATION: ILT70144 VLCDR1

<400> SEQUENCE: 248

```
Ser Gly Ser Ser Ser Asn Ile Gly Asn Asn Tyr Val Ser
1               5                   10
```

<210> SEQ ID NO 249
<211> LENGTH: 7
<212> TYPE: PRT
<213> ORGANISM: Artificial Sequence
<220> FEATURE:
<223> OTHER INFORMATION: ILT70144 VLCDR2

<400> SEQUENCE: 249

```
Asp Asn Asn Lys Arg Pro Ser
1               5
```

<210> SEQ ID NO 250
<211> LENGTH: 11
<212> TYPE: PRT
<213> ORGANISM: Artificial Sequence
<220> FEATURE:
<223> OTHER INFORMATION: ILT70144 VLCDR3

<400> SEQUENCE: 250

```
Gly Thr Trp Asp Ser Ser Leu Ser Ala Gly Val
1               5                   10
```

<210> SEQ ID NO 251
<211> LENGTH: 351
<212> TYPE: DNA
<213> ORGANISM: Artificial Sequence -continued

<220> FEATURE:
<223> OTHER INFORMATION: ILT70019 VH

<400> SEQUENCE: 251

```
caggtccagc tggtgcagtc tgggggaggc ctggtcaagc ctgggggtc cctgagactc      60
tcctgtgcag cctctggatt caccttcagt agctatagca tgaactgggt ccgccaggct    120
ccagggaagg gctggagtg gtctcatcc attagtagta gtagttacat atactacgca      180
gactcagtga agggccgatt caccatctcc cgagacaacg ccaagaactc actgtatctg    240
caaatgaaca gcctgagagc cgaggacacg gctgtgtatt actgtgcgag agaggcacca    300
aatggtctaa ttgactaccg gggccggggg acaatggtca ccgtctcttc a             351
```

<210> SEQ ID NO 252
<211> LENGTH: 117
<212> TYPE: PRT
<213> ORGANISM: Artificial Sequence
<220> FEATURE:
<223> OTHER INFORMATION: ILT70019 VH

<400> SEQUENCE: 252

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Glu Ala Pro Asn Gly Leu Ile Asp Tyr Arg Gly Arg Gly Thr Met
            100                 105                 110

Val Thr Val Ser Ser
        115

<210> SEQ ID NO 253
<211> LENGTH: 5
<212> TYPE: PRT
<213> ORGANISM: Artificial Sequence
<220> FEATURE:
<223> OTHER INFORMATION: ILT70019 VHCDR1

<400> SEQUENCE: 253

Ser Tyr Ser Met Asn
1               5

<210> SEQ ID NO 254
<211> LENGTH: 16
<212> TYPE: PRT
<213> ORGANISM: Artificial Sequence
<220> FEATURE:
<223> OTHER INFORMATION: ILT70019 VHCDR2

<400> SEQUENCE: 254

Ser Ile Ser Ser Ser Ser Tyr Ile Tyr Tyr Ala Asp Ser Val Lys Gly
1               5                   10                  15

<210> SEQ ID NO 255

<211> LENGTH: 9
<212> TYPE: PRT
<213> ORGANISM: Artificial Sequence
<220> FEATURE:
<223> OTHER INFORMATION: ILT70019 VHCDR3

<400> SEQUENCE: 255

Glu Ala Pro Asn Gly Leu Ile Asp Tyr
1               5

<210> SEQ ID NO 256
<211> LENGTH: 321
<212> TYPE: DNA
<213> ORGANISM: Artificial Sequence
<220> FEATURE:
<223> OTHER INFORMATION: ILT70019 VL

<400> SEQUENCE: 256
gacatcgtga tgacccagtc tccttccacc ctgtctgcat ctgtaggaga cagagtcacc      60
atcacttgcc gggccagtca gggtattagt agctggttgg cctggtatca gcagaaacca     120
gggagagccc ctaaggtctt gatctataag gcatctactt tagaaagtgg ggtcccatca     180
aggttcagcg gcagtggatc tgggacagat ttcactctca ccatcagcag tctgcaacct     240
gaagattttg caacttacta ctgtcaacag agttacagta ccccgtggac gttcggccaa     300
gggaccaagc tggagatcaa a                                                321

<210> SEQ ID NO 257
<211> LENGTH: 107
<212> TYPE: PRT
<213> ORGANISM: Artificial Sequence
<220> FEATURE:
<223> OTHER INFORMATION: ILT70019 VL

<400> SEQUENCE: 257

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105

<210> SEQ ID NO 258
<211> LENGTH: 11
<212> TYPE: PRT
<213> ORGANISM: Artificial Sequence
<220> FEATURE:
<223> OTHER INFORMATION: ILT70019 VLCDR1

<400> SEQUENCE: 258

Arg Ala Ser Gln Gly Ile Ser Ser Trp Leu Ala
1               5                   10

<210> SEQ ID NO 259

```
<211> LENGTH: 7
<212> TYPE: PRT
<213> ORGANISM: Artificial Sequence
<220> FEATURE:
<223> OTHER INFORMATION: ILT70019 VLCDR2

<400> SEQUENCE: 259

Lys Ala Ser Thr Leu Glu Ser
1               5

<210> SEQ ID NO 260
<211> LENGTH: 9
<212> TYPE: PRT
<213> ORGANISM: Artificial Sequence
<220> FEATURE:
<223> OTHER INFORMATION: ILT70019 VLCDR3

<400> SEQUENCE: 260

Gln Gln Ser Tyr Ser Thr Pro Trp Thr
1               5

<210> SEQ ID NO 261
<211> LENGTH: 351
<212> TYPE: DNA
<213> ORGANISM: Artificial Sequence
<220> FEATURE:
<223> OTHER INFORMATION: ILT70028 VH

<400> SEQUENCE: 261
cagctgcagc tgcaggagtc gggcgcaaga atgttgaagc cttcggagac cctgtccctc      60
acgtgcgacg tccagaatgg gtccttcagt actcactact ggacttggat ccgccagccc     120
ccagggaagg gctggagtg gattggagac atcaatcaaa ggggaagtac caaccacaat     180
ccgtccctca ggagtcgact caccatatca gtagacccgt ccaagaatca gttctcagtg     240
aggttgactt ctgtgaccgc cgcggacacg gctgtctatt actgtgcgag attgaacgac     300
gatgatgctt ttgatatctg gggccggggg acaatggtca ccgtctcgag t             351

<210> SEQ ID NO 262
<211> LENGTH: 117
<212> TYPE: PRT
<213> ORGANISM: Artificial Sequence
<220> FEATURE:
<223> OTHER INFORMATION: ILT70028 VH

<400> SEQUENCE: 262

Gln Leu Gln Leu Gln Glu Ser Gly Ala Arg Met Leu Lys Pro Ser Glu
1               5                   10                  15

Thr Leu Ser Leu Thr Cys Asp Val Gln Asn Gly Ser Phe Ser Thr His
                20                  25                  30

Tyr Trp Thr Trp Ile Arg Gln Pro Pro Gly Lys Gly Leu Glu Trp Ile
            35                  40                  45

Gly Asp Ile Asn Gln Arg Gly Ser Thr Asn His Asn Pro Ser Leu Arg
        50                  55                  60

Ser Arg Leu Thr Ile Ser Val Asp Pro Ser Lys Asn Gln Phe Ser Val
65                  70                  75                  80

Arg Leu Thr Ser Val Thr Ala Ala Asp Thr Ala Val Tyr Tyr Cys Ala
                85                  90                  95

Arg Leu Asn Asp Asp Asp Ala Phe Asp Ile Trp Gly Arg Gly Thr Met
            100                 105                 110

Val Thr Val Ser Ser
        115
```

<210> SEQ ID NO 263
<211> LENGTH: 5
<212> TYPE: PRT
<213> ORGANISM: Artificial Sequence
<220> FEATURE:
<223> OTHER INFORMATION: ILT70028 VHCDR1

<400> SEQUENCE: 263

Thr His Tyr Trp Thr
1               5

<210> SEQ ID NO 264
<211> LENGTH: 16
<212> TYPE: PRT
<213> ORGANISM: Artificial Sequence
<220> FEATURE:
<223> OTHER INFORMATION: ILT70028 VHCDR2

<400> SEQUENCE: 264

Asp Ile Asn Gln Arg Gly Ser Thr Asn His Asn Pro Ser Leu Arg Ser
1               5                   10                  15

<210> SEQ ID NO 265
<211> LENGTH: 9
<212> TYPE: PRT
<213> ORGANISM: Artificial Sequence
<220> FEATURE:
<223> OTHER INFORMATION: ILT70028 VHCDR3

<400> SEQUENCE: 265

Leu Asn Asp Asp Asp Ala Phe Asp Ile
1               5

<210> SEQ ID NO 266
<211> LENGTH: 330
<212> TYPE: DNA
<213> ORGANISM: Artificial Sequence
<220> FEATURE:
<223> OTHER INFORMATION: ILT70028 VL

<400> SEQUENCE: 266
cagtctgtgc tgacgcagcc gccctcagcg tctgggaccc ccgggcaggg ggtcaccatc    60
tcgtgttctg gaagcagctc aacatcggg agtcatactg taaattggta ccaacatctc    120
gcaggaacgg cccccaaact cctcatctat agtaataatc agcggccctc aggggtccct    180
gaccgattct ctggctccaa gtctgcctcc tcagcctccc tggccatcag tgggctccag    240
tctgaggatg aggctgatta ttactgtgca gcctgggatg ccggtgtcga tggttatgtc    300
ttcggaaccg ggaccaaggt caccgtccta                                    330

<210> SEQ ID NO 267
<211> LENGTH: 110
<212> TYPE: PRT
<213> ORGANISM: Artificial Sequence
<220> FEATURE:
<223> OTHER INFORMATION: ILT70028 VL

<400> SEQUENCE: 267

Gln Ser Val Leu Thr Gln Pro Pro Ser Ala Ser Gly Thr Pro Gly Gln
1               5                   10                  15

Gly Val Thr Ile Ser Cys Ser Gly Ser Ser Ser Asn Ile Gly Ser His
            20                  25                  30

Thr Val Asn Trp Tyr Gln His Leu Ala Gly Thr Ala Pro Lys Leu Leu

```
                35                  40                  45

Ile Tyr Ser Asn Asn Gln Arg Pro Ser Gly Val Pro Asp Arg Phe Ser
         50                  55                  60

Gly Ser Lys Ser Ala Ser Ala Ser Leu Ala Ile Ser Gly Leu Gln
65                  70                  75                  80

Ser Glu Asp Glu Ala Asp Tyr Tyr Cys Ala Ala Trp Asp Ala Gly Val
                 85                  90                  95

Asp Gly Tyr Val Phe Gly Thr Gly Thr Lys Val Thr Val Leu
            100                 105                 110
```

<210> SEQ ID NO 268
<211> LENGTH: 13
<212> TYPE: PRT
<213> ORGANISM: Artificial Sequence
<220> FEATURE:
<223> OTHER INFORMATION: ILT70028 VLCDR1

<400> SEQUENCE: 268

```
Ser Gly Ser Ser Ser Asn Ile Gly Ser His Thr Val Asn
1               5                   10
```

<210> SEQ ID NO 269
<211> LENGTH: 7
<212> TYPE: PRT
<213> ORGANISM: Artificial Sequence
<220> FEATURE:
<223> OTHER INFORMATION: ILT70028 VLCDR2

<400> SEQUENCE: 269

```
Ser Asn Asn Gln Arg Pro Ser
1               5
```

<210> SEQ ID NO 270
<211> LENGTH: 11
<212> TYPE: PRT
<213> ORGANISM: Artificial Sequence
<220> FEATURE:
<223> OTHER INFORMATION: ILT70028 VLCDR3

<400> SEQUENCE: 270

```
Ala Ala Trp Asp Ala Gly Val Asp Gly Tyr Val
1               5                   10
```

<210> SEQ ID NO 271
<211> LENGTH: 354
<212> TYPE: DNA
<213> ORGANISM: Artificial Sequence
<220> FEATURE:
<223> OTHER INFORMATION: ILT70076 VH

<400> SEQUENCE: 271

```
gaggtgcagc tggtggagtc cggagctgag gtgaagaagc ctggggcctc agtgaaggtc    60
tcctgcaagg cttctggtta cacctttacc agctacggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagaggtccg   300
gggtggctgg gctttgacta ctggggccgg ggcaccctgg tcaccgtctc gagt         354
```

<210> SEQ ID NO 272
<211> LENGTH: 118
<212> TYPE: PRT

<213> ORGANISM: Artificial Sequence
<220> FEATURE:
<223> OTHER INFORMATION: ILT70076 VH

<400> SEQUENCE: 272

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Pro Gly Trp Leu Gly Phe Asp Tyr Trp Gly Arg Gly Thr
            100                 105                 110

Leu Val Thr Val Ser Ser
        115
```

<210> SEQ ID NO 273
<211> LENGTH: 5
<212> TYPE: PRT
<213> ORGANISM: Artificial Sequence
<220> FEATURE:
<223> OTHER INFORMATION: ILT70076 VHCDR1

<400> SEQUENCE: 273

```
Ser Tyr Gly Ile Ser
1               5
```

<210> SEQ ID NO 274
<211> LENGTH: 17
<212> TYPE: PRT
<213> ORGANISM: Artificial Sequence
<220> FEATURE:
<223> OTHER INFORMATION: ILT70076 VHCDR2

<400> SEQUENCE: 274

```
Trp Ile Ser Ala Tyr Asn Gly Asn Thr Asn Tyr Ala Gln Lys Leu Gln
1               5                   10                  15

Gly
```

<210> SEQ ID NO 275
<211> LENGTH: 9
<212> TYPE: PRT
<213> ORGANISM: Artificial Sequence
<220> FEATURE:
<223> OTHER INFORMATION: ILT70076 VHCDR3

<400> SEQUENCE: 275

```
Gly Pro Gly Trp Leu Gly Phe Asp Tyr
1               5
```

<210> SEQ ID NO 276
<211> LENGTH: 330
<212> TYPE: DNA
<213> ORGANISM: Artificial Sequence
<220> FEATURE:
<223> OTHER INFORMATION: ILT70076 VL -continued

<400> SEQUENCE: 276

```
cagtctgccc tgactcagcc tgcctccgtg tctgggtctc ctggacagtc gatcaccatc    60
tcctgcactg gaaccagcag tgacgttggt ggttataact atgtctcttg gtaccaacaa   120
gacccaggca aggcccccaa actcatgatt tataatgtca gtaatcggcc ctcagggggtt  180
tctaatcgct tctctggctc caagtctggc aatacggcct ccctgaccat ctctgggctc   240
caggctgagg acgaggctga ttattactgc agttcatata caagcagcag cacttatgtc   300
ttcggaactg ggaccaagct gaccgtccta                                    330
```

<210> SEQ ID NO 277
<211> LENGTH: 110
<212> TYPE: PRT
<213> ORGANISM: Artificial Sequence
<220> FEATURE:
<223> OTHER INFORMATION: ILT70076 VL

<400> SEQUENCE: 277

```
Gln Ser Ala Leu Thr Gln Pro Ala Ser Val Ser Gly Ser Pro Gly Gln
1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln Asp Pro Gly Lys Ala Pro Lys Leu
        35                  40                  45

Met Ile Tyr Asn Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Leu Thr Val Leu
            100                 105                 110
```

<210> SEQ ID NO 278
<211> LENGTH: 14
<212> TYPE: PRT
<213> ORGANISM: Artificial Sequence
<220> FEATURE:
<223> OTHER INFORMATION: ILT70076 VHCDR1

<400> SEQUENCE: 278

```
Thr Gly Thr Ser Ser Asp Val Gly Gly Tyr Asn Tyr Val Ser
1               5                  10
```

<210> SEQ ID NO 279
<211> LENGTH: 7
<212> TYPE: PRT
<213> ORGANISM: Artificial Sequence
<220> FEATURE:
<223> OTHER INFORMATION: ILT70076 VHCDR2

<400> SEQUENCE: 279

```
Asn Val Ser Asn Arg Pro Ser
1               5
```

<210> SEQ ID NO 280
<211> LENGTH: 10
<212> TYPE: PRT
<213> ORGANISM: Artificial Sequence
<220> FEATURE:
<223> OTHER INFORMATION: ILT70076 VHCDR3

<400> SEQUENCE: 280

Ser Ser Tyr Thr Ser Ser Ser Thr Tyr Val
1               5                   10

<210> SEQ ID NO 281
<211> LENGTH: 360
<212> TYPE: DNA
<213> ORGANISM: Artificial Sequence
<220> FEATURE:
<223> OTHER INFORMATION: ILT70089 VH

<400> SEQUENCE: 281

```
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gctcaccatc tccagagaca attccaagaa cacgctgtat    240
ctgcaaatga acagcctgag agccgaggac acggccgtgt attactgtgc gaaagattta    300
ggatatactt tagatacaag tgacttctgg ggccggggca ccctggtcac cgtctcgagt    360
```

<210> SEQ ID NO 282
<211> LENGTH: 120
<212> TYPE: PRT
<213> ORGANISM: Artificial Sequence
<220> FEATURE:
<223> OTHER INFORMATION: ILT70089 VH

<400> SEQUENCE: 282

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Tyr Thr Leu Asp Thr Ser Asp Phe Trp Gly Arg
            100                 105                 110

Gly Thr Leu Val Thr Val Ser Ser
        115                 120

<210> SEQ ID NO 283
<211> LENGTH: 5
<212> TYPE: PRT
<213> ORGANISM: Artificial Sequence
<220> FEATURE:
<223> OTHER INFORMATION: ILT70089 VHCDR1

<400> SEQUENCE: 283

Ser Tyr Ala Met Ser
1               5

<210> SEQ ID NO 284
<211> LENGTH: 17
<212> TYPE: PRT
<213> ORGANISM: Artificial Sequence

<220> FEATURE:
<223> OTHER INFORMATION: ILT70089 VHCDR2

<400> SEQUENCE: 284

Ala Ile Ser Gly Ser Gly Gly Ser Thr Tyr Tyr Ala Asp Ser Val Lys
1               5                   10                  15

Gly

<210> SEQ ID NO 285
<211> LENGTH: 11
<212> TYPE: PRT
<213> ORGANISM: Artificial Sequence
<220> FEATURE:
<223> OTHER INFORMATION: ILT70089 VHCDR3

<400> SEQUENCE: 285

Asp Leu Gly Tyr Thr Leu Asp Thr Ser Asp Phe
1               5                   10

<210> SEQ ID NO 286
<211> LENGTH: 330
<212> TYPE: DNA
<213> ORGANISM: Artificial Sequence
<220> FEATURE:
<223> OTHER INFORMATION: ILT70089 VL

<400> SEQUENCE: 286
tcctatgtgc tgactcagcc accctcagcg tctgggtccc ccgggcaggg ggtcaccatc      60
tcttgttctg gaagcagctc aacatcgga actaatactg taaactggta cctgcacgtt     120
ccaggaacgg cccccaaact cctcacttat actaataatc agcggccctc aggggtccaa     180
gatcgattct ctggctccaa gtctgacacg tcagcctccc tggccatcag tgggctccag     240
gctgaggatg agggtgatta ttactgtgcg acatgggatg acagcctgaa tggtctagcg     300
ttcggcggag ggaccaagct gaccgtccta                                      330

<210> SEQ ID NO 287
<211> LENGTH: 110
<212> TYPE: PRT
<213> ORGANISM: Artificial Sequence
<220> FEATURE:
<223> OTHER INFORMATION: ILT70089 VL

<400> SEQUENCE: 287

Ser Tyr Val Leu Thr Gln Pro Pro Ser Ala Ser Gly Ser Pro Gly Gln
1               5                   10                  15

Gly Val Thr Ile Ser Cys Ser Gly Ser Ser Asn Ile Gly Thr Asn
                20                  25                  30

Thr Val Asn Trp Tyr Leu His Val Pro Gly Thr Ala Pro Lys Leu Leu
            35                  40                  45

Thr Tyr Thr Asn Asn Gln Arg Pro Ser Gly Val Gln Asp Arg Phe Ser
        50                  55                  60

Gly Ser Lys Ser Asp Thr Ser Ala Ser Leu Ala Ile Ser Gly Leu Gln
65                  70                  75                  80

Ala Glu Asp Glu Gly Asp Tyr Tyr Cys Ala Thr Trp Asp Asp Ser Leu
                85                  90                  95

Asn Gly Leu Ala Phe Gly Gly Gly Thr Lys Leu Thr Val Leu
            100                 105                 110

<210> SEQ ID NO 288
<211> LENGTH: 13

```
<212> TYPE: PRT
<213> ORGANISM: Artificial Sequence
<220> FEATURE:
<223> OTHER INFORMATION: ILT70089 VLCDR1

<400> SEQUENCE: 288

Ser Gly Ser Ser Ser Asn Ile Gly Thr Asn Thr Val Asn
1               5                   10

<210> SEQ ID NO 289
<211> LENGTH: 7
<212> TYPE: PRT
<213> ORGANISM: Artificial Sequence
<220> FEATURE:
<223> OTHER INFORMATION: ILT70089 VLCDR2

<400> SEQUENCE: 289

Thr Asn Asn Gln Arg Pro Ser
1               5

<210> SEQ ID NO 290
<211> LENGTH: 11
<212> TYPE: PRT
<213> ORGANISM: Artificial Sequence
<220> FEATURE:
<223> OTHER INFORMATION: ILT70089 VLCDR3

<400> SEQUENCE: 290

Ala Thr Trp Asp Asp Ser Leu Asn Gly Leu Ala
1               5                   10

<210> SEQ ID NO 291
<211> LENGTH: 499
<212> TYPE: PRT
<213> ORGANISM: Homo sapiens

<400> SEQUENCE: 291

Met Thr Leu Ile Leu Thr Ser Leu Leu Phe Phe Gly Leu Ser Leu Gly
1               5                   10                  15

Pro Arg Thr Arg Val Gln Ala Glu Asn Leu Pro Lys Pro Ile Leu Trp
            20                  25                  30

Ala Glu Pro Gly Pro Val Ile Thr Trp His Asn Pro Val Thr Ile Trp
        35                  40                  45

Cys Gln Gly Thr Leu Glu Ala Gln Gly Tyr Arg Leu Asp Lys Glu Gly
    50                  55                  60

Asn Ser Met Ser Arg His Ile Leu Lys Thr Leu Glu Ser Glu Asn Lys
65                  70                  75                  80

Val Lys Leu Ser Ile Pro Ser Met Met Trp Glu His Ala Gly Arg Tyr
                85                  90                  95

His Cys Tyr Tyr Gln Ser Pro Ala Gly Trp Ser Glu Pro Ser Asp Pro
            100                 105                 110

Leu Glu Leu Val Val Thr Ala Tyr Ser Arg Pro Thr Leu Ser Ala Leu
        115                 120                 125

Pro Ser Pro Val Val Thr Ser Gly Val Asn Val Thr Leu Arg Cys Ala
    130                 135                 140

Ser Arg Leu Gly Leu Gly Arg Phe Thr Leu Ile Glu Glu Gly Asp His
145                 150                 155                 160

Arg Leu Ser Trp Thr Leu Asn Ser His Gln His Asn His Gly Lys Phe
                165                 170                 175

Gln Ala Leu Phe Pro Met Gly Pro Leu Thr Phe Ser Asn Arg Gly Thr
            180                 185                 190
```

```
Phe Arg Cys Tyr Gly Tyr Glu Asn Asn Thr Pro Tyr Val Trp Ser Glu
        195                 200                 205

Pro Ser Asp Pro Leu Gln Leu Leu Val Ser Gly Val Ser Arg Lys Pro
        210                 215                 220

Ser Leu Leu Thr Leu Gln Gly Pro Val Val Thr Pro Gly Glu Asn Leu
225                 230                 235                 240

Thr Leu Gln Cys Gly Ser Asp Val Gly Tyr Ile Arg Tyr Thr Leu Tyr
                245                 250                 255

Lys Glu Gly Ala Asp Gly Leu Pro Gln Arg Pro Gly Arg Gln Pro Gln
                260                 265                 270

Ala Gly Leu Ser Gln Ala Asn Phe Thr Leu Ser Pro Val Ser Arg Ser
                275                 280                 285

Tyr Gly Gly Gln Tyr Arg Cys Tyr Gly Ala His Asn Val Ser Ser Glu
                290                 295                 300

Trp Ser Ala Pro Ser Asp Pro Leu Asp Ile Leu Ile Ala Gly Gln Ile
305                 310                 315                 320

Ser Asp Arg Pro Ser Leu Ser Val Gln Pro Gly Pro Thr Val Thr Ser
                325                 330                 335

Gly Glu Lys Val Thr Leu Leu Cys Gln Ser Trp Asp Pro Met Phe Thr
                340                 345                 350

Phe Leu Leu Thr Lys Glu Gly Ala Ala His Pro Pro Leu Arg Leu Arg
                355                 360                 365

Ser Met Tyr Gly Ala His Lys Tyr Gln Ala Glu Phe Pro Met Ser Pro
                370                 375                 380

Val Thr Ser Ala His Ala Gly Thr Tyr Arg Cys Tyr Gly Ser Arg Ser
385                 390                 395                 400

Ser Asn Pro Tyr Leu Leu Ser His Pro Ser Glu Pro Leu Glu Leu Val
                405                 410                 415

Val Ser Gly Ala Thr Glu Thr Leu Asn Pro Ala Gln Lys Lys Ser Asp
                420                 425                 430

Ser Lys Thr Ala Pro His Leu Gln Asp Tyr Thr Val Glu Asn Leu Ile
                435                 440                 445

Arg Met Gly Val Ala Gly Leu Val Leu Leu Phe Leu Gly Ile Leu Leu
                450                 455                 460

Phe Glu Ala Gln His Ser Gln Arg Ser Pro Pro Arg Cys Ser Gln Glu
465                 470                 475                 480

Ala Asn Ser Arg Lys Asp Asn Ala Pro Phe Arg Val Val Glu Pro Trp
                485                 490                 495

Glu Gln Ile

<210> SEQ ID NO 292
<211> LENGTH: 483
<212> TYPE: PRT
<213> ORGANISM: Cynomolgus monkey

<400> SEQUENCE: 292

Pro Arg Thr His Met Gln Ala Glu Asn Leu Leu Lys Pro Ile Leu Trp
1               5                   10                  15

Ala Glu Pro Gly Pro Val Ile Ile Trp Lys Lys Pro Val Thr Ile Trp
                20                  25                  30

Cys Gln Gly Thr Leu Glu Ala Gln Glu Tyr Arg Leu Asp Lys Glu Gly
            35                  40                  45

Asn Ser Ile Ser Arg His Met Leu Lys Thr Leu Glu Ser Glu Asn Lys
        50                  55                  60
```

```
Ala Lys Phe Ser Ile Pro Ser Met Met Trp Glu His Ala Gly Arg Tyr
 65                  70                  75                  80

His Cys Tyr Tyr Gln Ser Pro Ala Gly Trp Ser Glu Pro Ser Asp Pro
                 85                  90                  95

Leu Glu Leu Val Val Thr Ala Tyr Ser Arg Pro Ser Leu Ser Ala Leu
                100                 105                 110

Pro Ser Pro Val Val Thr Ser Gly Val Asn Val Thr Leu Arg Cys Ala
                115                 120                 125

Ser Arg Leu Gly Leu Gly Arg Phe Thr Leu Ile Glu Glu Gly Asp His
        130                 135                 140

Arg Leu Ser Trp Thr Leu Asp Ser His Gln His Asn His Gly Lys Phe
145                 150                 155                 160

Gln Ala Leu Phe Pro Val Gly Pro Leu Thr Phe Ser Asn Arg Gly Thr
                165                 170                 175

Phe Arg Cys Tyr Gly Tyr Glu Asn Asn Thr Pro Tyr Val Trp Ser Glu
                180                 185                 190

Pro Ser Asp Pro Leu Gln Leu Val Ser Gly Val Ser Arg Lys Pro
        195                 200                 205

Ser Leu Leu Thr Leu Gln Gly Pro Val Val Ala Pro Gly Asp Asn Leu
210                 215                 220

Thr Leu Gln Cys Gly Ser Asp Val Gly Tyr Ile Arg Tyr Ala Leu Tyr
225                 230                 235                 240

Lys Glu Gly Gly Asp Gly Leu Pro Gln Arg Pro Gly Gln Gln Ser Gln
                245                 250                 255

Ala Gly Leu Ser Gln Ala Ser Phe Thr Leu Asn Pro Val Arg Gly Ser
                260                 265                 270

His Gly Gly Gln Tyr Arg Cys Tyr Gly Ala His Asn Val Ser Ser Lys
        275                 280                 285

Trp Ser Ala Pro Ser Asp Pro Leu Asp Ile Leu Ile Ala Gly Gln Ile
290                 295                 300

Pro Asp Arg Pro Ser Leu Ser Val Gln Leu Gly Pro Thr Val Ala Ser
305                 310                 315                 320

Gly Glu Lys Val Thr Leu Leu Cys Gln Ser Trp Gly Pro Met Phe Thr
                325                 330                 335

Phe Leu Leu Ala Lys Glu Gly Ala Ala His Pro Pro Leu Arg Leu Arg
                340                 345                 350

Ser Thr Tyr Arg Ala Gln Gln Tyr Gln Ala Glu Phe Pro Met Ser Pro
        355                 360                 365

Val Thr Ser Ala His Ala Gly Thr Tyr Arg Cys Tyr Gly Ser Arg Ser
        370                 375                 380

Ser Asp Pro Tyr Leu Leu Ser His Ser Ser Glu Pro Leu Glu Leu Val
385                 390                 395                 400

Val Ser Glu Ala Thr Glu Thr Leu Asn Pro Ala Gln Asn Lys Ser Asp
                405                 410                 415

Ser Lys Thr Ala Pro His Leu Gln Asp Tyr Thr Val Glu Asn Leu Ile
                420                 425                 430

Arg Met Gly Ile Ala Gly Leu Val Leu Val Phe Leu Gly Ile Leu Leu
                435                 440                 445

Phe Glu Ala Gln Gln Ser Gln Arg Ser Pro Thr Arg Cys Ser Gln Glu
        450                 455                 460

Val Asn Ser Arg Glu Asp Asn Ala Pro Phe Arg Val Val Glu Pro Trp
465                 470                 475                 480
```

Glu Gln Ile

<210> SEQ ID NO 293
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 10D10-VH

<400> SEQUENCE: 293

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Pro Ile Glu Trp Val Arg Gln Ala Pro Gly Gln Gly Leu Glu Trp Ile
        35                  40                  45

Gly Asn Phe His Leu Tyr Asn Asp Asp Thr Lys Tyr Asn Glu Lys Phe
    50                  55                  60

Lys Gly Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Asp Asp Tyr Gly Met Asp Tyr Trp Gly Gln Gly Thr Leu
            100                 105                 110

Val Thr Val Ser Ser
        115

<210> SEQ ID NO 294
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 10D10-VL

<400> SEQUENCE: 294

Asn Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Ala
            20                  25                  30

Val Ala Trp Tyr Gln Gln Lys Pro Gly Lys Ala Pro Lys Arg Leu Ile
        35                  40                  45

Tyr Leu Ala Ser Asn Arg His Thr Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Leu Gln His Trp Asn Tyr Pro Phe
                85                  90                  95

Thr Phe Gly Pro Gly Thr Lys Leu Glu Ile Lys
            100                 105

<210> SEQ ID NO 295
<211> LENGTH: 98
<212> TYPE: PRT
<213> ORGANISM: Artificial Sequence
<220> FEATURE:

<223> OTHER INFORMATION: Description of Artificial Sequence: Synthetic
    polypeptide
<220> FEATURE:
<223> OTHER INFORMATION: IGHV1-69*01

<400> SEQUENCE: 295

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 296
<211> LENGTH: 91
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: IGLV3-21*01

<400> SEQUENCE: 296

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp
                85                  90

<210> SEQ ID NO 297
<211> LENGTH: 98
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: IGHV3-23*01

<400> SEQUENCE: 297

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys

<210> SEQ ID NO 298
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IGLV1-51*01

<400> SEQUENCE: 298

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp
                85                  90

<210> SEQ ID NO 299
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 299

His His His His His His
 1               5
```